US009905777B2

(12) United States Patent
Kim et al.

(10) Patent No.: US 9,905,777 B2
(45) Date of Patent: Feb. 27, 2018

(54) COMPOUND AND ORGANIC ELECTROLUMINESCENCE DEVICE COMPRISING SAME

(71) Applicant: DOOSAN CORPORATION, Seoul (KR)

(72) Inventors: Tae Hyung Kim, Yongin-si (KR); In Hyuk Lee, Yongin-si (KR); Hoe Moon Kim, Suwon-si (KR); Jin Yong Shin, Yongin-si (KR); Ho Cheol Park, Suwon-si (KR); Chang Jun Lee, Ansan-si (KR); Young Mi Beak, Yongin-si (KR); Eun Jung Lee, Seoul (KR)

(73) Assignee: DOOSAN CORPORATION, Seoul (KR)

( * ) Notice: Subject to any disclaimer, the term of this patent is extended or adjusted under 35 U.S.C. 154(b) by 370 days.

(21) Appl. No.: 14/420,539

(22) PCT Filed: Aug. 7, 2013

(86) PCT No.: PCT/KR2013/007138
§ 371 (c)(1),
(2) Date: May 4, 2015

(87) PCT Pub. No.: WO2014/025209
PCT Pub. Date: Feb. 13, 2014

(65) Prior Publication Data
US 2015/0236271 A1    Aug. 20, 2015

(30) Foreign Application Priority Data

Aug. 10, 2012  (KR) .................. 10-2012-0088004
Sep. 19, 2012  (KR) .................. 10-2012-0103947

(51) Int. Cl.
*H01L 51/00* (2006.01)
*C07D 487/04* (2006.01)
*C07D 495/04* (2006.01)
*C07D 491/048* (2006.01)
*C07F 7/08* (2006.01)
*C07D 517/04* (2006.01)
*C07D 403/14* (2006.01)
*C09K 11/06* (2006.01)
*H01L 51/52* (2006.01)
*H01L 51/50* (2006.01)

(52) U.S. Cl.
CPC ........ *H01L 51/0072* (2013.01); *C07D 403/14* (2013.01); *C07D 487/04* (2013.01); *C07D 491/048* (2013.01); *C07D 495/04* (2013.01); *C07D 517/04* (2013.01); *C07F 7/0816* (2013.01); *C09K 11/06* (2013.01); *H01L 51/0052* (2013.01); *H01L 51/0058* (2013.01); *H01L 51/0067* (2013.01); *H01L 51/0094* (2013.01); *C09K 2211/107* (2013.01); *C09K 2211/1062* (2013.01); *C09K 2211/1066* (2013.01); *C09K 2211/1074* (2013.01); *H01L 51/5016* (2013.01); *H01L 51/5056* (2013.01); *H01L 51/5088* (2013.01); *H01L 51/5206* (2013.01); *H01L 51/5221* (2013.01); *H01L 2251/308* (2013.01)

(58) Field of Classification Search
None
See application file for complete search history.

(56) References Cited

U.S. PATENT DOCUMENTS

2011/0210318 A1   9/2011  Bae et al.
2012/0001165 A1*  1/2012  Komori .............. C07D 403/14
                                                    257/40

FOREIGN PATENT DOCUMENTS

| CN | 102449106 | | 5/2012 |
|---|---|---|---|
| JP | 2015502953 | A | 1/2015 |
| KP | 10-2012-0038374 | | 4/2012 |
| KR | 10-2010-0023783 | A | 3/2010 |
| KR | 10-2011-0105269 | A | 9/2011 |
| KR | 10-2012-0052879 | | 5/2012 |
| KR | 10-2012-0081539 | A | 7/2012 |
| WO | 2010107244 | A2 | 9/2010 |
| WO | 2012039561 | A1 | 3/2012 |
| WO | 2012050347 | A1 | 4/2012 |
| WO | 2012050371 | A1 | 4/2012 |
| WO | 2012067425 | A1 | 5/2012 |

OTHER PUBLICATIONS

Chinese Patent Office, Communication issued Aug. 3, 2016 in counterpart Chinese Application No. 201380052505.6.
Korean Patent Office, Communication issued Sep. 19, 2016 b in counterpart Korean Application No. 10-2015-7003313.
State Intellectual Property Office of P.R. China, Communication dated Nov. 3, 2015 issued in counterpart application No. 201380052505.6.
Vasudevan Dhayalan, et al., "A Versatile Synthesis of Annulated Carbazole Analogs Involving a Domino Reaction of Bromomethylindoles with Arenes/Heteroarenes", Eur. J. Org. Chem., 2009, pp. 531-546, vol. 2009.
Isabel C.F.R. Ferreira, et al., "Synthesis of New Methylated thieno [2,3-a] and [3,2-b] carbazoles by Reductive Cyclization of 6-(2'-Nitrophenyl)benzo[b] thiophenes Obtained by Palladium-catalyzed Cross-coupling", J. Heterocyclic Chem., 2001, pp. 749-754, vol. 38.
International Searching Authority, International Search Report of PCT/KR2013/007138, dated Nov. 29, 2013. [PCT/ISA/210].
Japanese Patent Office; Communication dated Feb. 9, 2016 in counterpart application No. 2015-526466.

* cited by examiner

*Primary Examiner* — Robert S Loewe
(74) *Attorney, Agent, or Firm* — Sughrue Mion, PLLC

(57) ABSTRACT

The present invention relates to a novel compound and an organic electroluminescence device including the same, and the compound according to the present invention may be used in an organic material layer, preferably a light-emitting layer of an organic electroluminescence device, thereby enhancing the light-emitting efficiency, driving voltage, lifespan, and the like of the organic electroluminescence device.

9 Claims, No Drawings

COMPOUND AND ORGANIC ELECTROLUMINESCENCE DEVICE COMPRISING SAME

CROSS REFERENCE TO RELATED APPLICATIONS

This application is a National Stage of International Application No. PCT/KR2013/007138 filed Aug. 7, 2013, claiming priority based on Korean Patent Application No. 10-2012-0088004 filed Aug. 10, 2012, the contents of all of which are incorporated herein by reference in their entirety.

TECHNICAL FIELD

The present invention relates to a novel compound and an organic electroluminescence device including the same.

BACKGROUND ART

When voltage is applied between two electrodes of the organic electroluminescence device, holes are injected into the organic material layer at the anode and electrons are injected into the organic material layer at the cathode, the injected holes and electrons meet each other to form an exciton, and when the formed exciton falls down to a bottom state, light is emitted. Materials used as the organic material layer may be classified into a light-emitting material, a hole injection material, a hole transporting material, an electron transporting material, an electron injection material, and the like according to the function.

The light-emitting materials may be divided into blue, green, and red light-emitting materials according to the light-emitting color, and into yellow and orange light-emitting materials required for implementing a much better natural color. Further, a host/dopant system may be used as a light-emitting material in order to enhance color purity and light-emitting efficiency through an energy transfer.

Dopant materials may be divided into a fluorescent dopant using an organic material and a phosphorescent dopant in which a metal complex compound including heavy atoms such as Ir and Pt is used. Since the development of the phosphorescent dopant may theoretically enhance light-emitting efficiency by up to 4 times compared to the development of the fluorescent dopant, studies on not only phosphorescent dopants, but also phosphorescent hosts have been conducted.

As the hole transporting material, the hole injection material, the electron transporting layer, and the like, NPB, BCP, Alq$_3$ and the like have been widely known until now, and as the light-emitting material, anthracene derivatives have been used. In particular, metal complex compounds including Ir and having a great advantage in terms of enhancing the efficiency, such as Firpic, Ir(ppy)$_3$ and (acac)Ir(btp)$_2$, are used as blue, green and red phosphorescent dopant materials, and CBP is used as a phosphorescent host material. In addition, the official gazette of Korean Patent Application Laid-Open No. 2012-0020816 discloses an organic electroluminescence device which uses an indolo benzofluoranthene derivative as the host material.

However, since light-emitting materials in the related art have good light-emitting characteristics, but have low glass transition temperature, and thus poor thermal stability, these materials fall short of a level that sufficiently satisfies the lifespan of the organic electroluminescence device.

DISCLOSURE

Technical Problem

In order to solve the aforementioned problems, an object of the present invention is to provide a novel compound which may enhance the efficiency, lifespan, stability, and the like of an organic electroluminescence device, and an organic electroluminescence device including the compound.

Technical Solution

In order to achieve the aforementioned object, the present invention provides a compound represented by the following Formula 1.

[Formula 1]

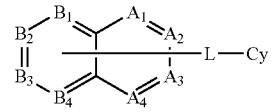

In Formula 1, $A_1$ to $A_4$ are each independently $CR_1$ or N, and here, at least one thereof is N, and $B_1$ to $B_4$ are each independently $CR_2$ or N, $R_1$ and $R_2$ are each independently selected from the group consisting of hydrogen, deuterium, halogen, a cyano group, a nitro group, an amino group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, or may form a fused ring with an adjacent group.

L is a single bond, or a $C_6$ to $C_{30}$ arylene group or a heteroarylene group having 5 to 30 nuclear atoms, Cy is a compound represented by the following Formula 2, and

[Formula 2]

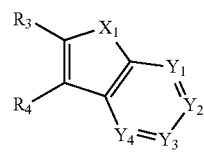

In Formula 2, $Y_1$ to $Y_4$ are each independently $CR_5$ or N, and at least one of $Y_1$ and $Y_2$, $Y_2$ and $Y_3$ or $Y_3$ and $Y_4$ forms a fused ring represented by the following Formula 3;

[Formula 3]

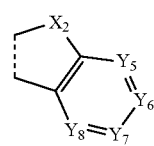

In Formula 3, the dotted line means a site where a fusion (condensation) with the compound of Formula 2 occurs, and $Y_5$ to $Y_8$ are each independently $CR_6$ or N, $X_1$ and $X_2$ are each independently selected from the group consisting of O, S, Se, $N(Ar_1)$, $C(Ar_2)(Ar_3)$ and $Si(Ar_4)(Ar_5)$, and here, at least one of $X_1$ and $X_2$ is $N(Ar_1)$, and $R_3$ to $R_6$ are each independently selected from the group consisting of hydrogen, deuterium, halogen, a cyano group, a nitro group, an amino group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, or may form a fused ring with an adjacent group, $Ar_1$ to $Ar_5$ are each independently selected from the group consisting of hydrogen, deuterium, halogen, a cyano group, a nitro group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group and the arylamine group of $R_1$ to $R_6$ and $Ar_1$ to $Ar_5$ may be each independently substituted with one or more selected from the group consisting of deuterium, halogen, a cyano group, a nitro group, an amino group, a $C_1$ to $C_{40}$ alkyl group (preferably a $C_1$ to $C_{10}$ alkyl group), a $C_2$ to $C_{40}$ alkenyl group (preferably a $C_2$ to $C_{10}$ alkenyl group), a $C_2$ to $C_{40}$ alkynyl group (preferably a $C_2$ to $C_{10}$ alkynyl group), a $C_3$ to $C_{40}$ cycloalkyl group (preferably a $C_3$ to $C_{18}$ cycloalkyl group), a heterocycloalkyl group having 3 to 40 nuclear atoms (preferably a heterocycloalkyl group having 3 to 18 nuclear atoms), a $C_6$ to $C_{40}$ aryl group (preferably a $C_6$ to $C_{18}$ aryl group), a heteroaryl group having 5 to 40 nuclear atoms (preferably a heteroaryl group having 5 to 18 nuclear atoms), $C_1$ to $C_{40}$ alkyloxy group (preferably a $C_1$ to $C_{10}$ alkyloxy group), a $C_6$ to $C_{60}$ aryloxy group (preferably a $C_6$ to $C_{18}$ aryloxy group), a $C_1$ to $C_{40}$ alkylsilyl group (preferably a $C_1$ to $C_{10}$ alkylsilyl group), a $C_6$ to $C_{60}$ arylsilyl group (preferably a $C_6$ to $C_{18}$ arylsilyl group), a $C_1$ to $C_{40}$ alkyl boron group (preferably a $C_1$ to $C_{10}$ alkyl boron group), a $C_6$ to $C_{60}$ aryl boron group (preferably a $C_6$ to $C_{18}$ aryl boron group), a $C_6$ to $C_{60}$ arylphosphone group (preferably $C_6$ to $C_{18}$ arylphosphine group), a $C_6$ to $C_{60}$ arylphosphine oxide group (preferably a $C_6$ to $C_{18}$ arylphosphine oxide group) and a $C_6$ to $C_{60}$ arylamine group (preferably a $C_6$ to $C_{20}$ arylamine group), and in this case, a plurality of substituents may be the same as or different from each other, and L is linked to any one of $A_1$ to $A_4$ and $B_1$ to $B_4$ of Formula 1, and simultaneously to any one of $X_1$, $X_2$, $R_3$, $R_4$ and $Y_1$ to $Y_8$ of Formula 2.

The alkyl used in the present invention means a monovalent functional group obtained by removing a hydrogen atom from a linear or branched, saturated hydrocarbon having 1 to 40 carbon atoms, and non-limiting examples thereof include methyl, ethyl, propyl, isobutyl, sec-butyl, pentyl, iso-amyl, hexyl, and the like.

The alkenyl used in the present invention means a monovalent functional group obtained by removing a hydrogen atom from a linear or branched, unsaturated hydrocarbon having 2 to 40 carbon atoms, which has one or more carbon-carbon double bonds. Non-limiting examples thereof include vinyl, allyl, isopropenyl, 2-butenyl, and the like.

The alkynyl used in the present invention means a monovalent functional group obtained by removing a hydrogen atom from a linear or branched, unsaturated hydrocarbon having 2 to 40 carbon atoms, which has one or more carbon-carbon triple bonds. Non-limiting examples thereof include ethynyl, 2-propynyl, and the like.

The cycloalkyl used in the present invention means a monovalent functional group obtained by removing a hydrogen atom from a monocyclic or polycyclic non-aromatic hydrocarbon (saturated cyclic hydrocarbon) having 3 to 40 carbon atoms. Non-limiting examples thereof include cyclopropyl, cyclopentyl, cyclohexyl, norbornyl, adamantine, and the like.

The heterocycloalkyl used in the present invention means a monovalent functional group obtained by removing a hydrogen atom from a non-aromatic hydrocarbon (saturated cyclic hydrocarbon) having 3 to 40 nuclear atoms, and one or more carbons in the ring, preferably 1 to 3 carbons, are substituted with a heteroatom such as N, O, or S. Non-limiting examples thereof include morpholine, piperazine, and the like.

The aryl used in the present invention means a monovalent functional group obtained by removing a hydrogen atom from an aromatic hydrocarbon having 6 to 60 carbon atoms of a single ring or a combination of two or more rings. In this case, the two or more rings may be simply pendant to each other or pendant to each other in a fused form. Non-limiting examples thereof include phenyl, biphenyl, triphenyl, terphenyl, naphthyl, fluorenyl, phenanthryl, anthracenyl, indenyl, and the like.

The heteroaryl used in the present invention is a monovalent functional group obtained by removing a hydrogen atom from a monoheterocyclic or polyheterocyclic aromatic hydrocarbon having 5 to 60 nuclear atoms, and one or more carbons in the ring, preferably 1 to 3 carbons are substituted with a heteroatom such as nitrogen (N), oxygen (O), sulfur (S), or selenium (Se). In this case, the two or more rings may be simply pendant to each other or pendant to each other in a fused form in the heteroaryl, and furthermore, the heteroaryl may also include a fused form with an aryl group. Non-limiting examples of the heteroaryl include: a six-membered monocyclic ring such as pyridyl, pyrazinyl, pyrimidinyl, pyridazinyl, and triazinyl; a polycyclic ring such as phenoxathienyl, indolizinyl, indolyl, purinyl, quinolyl, benzothiazole, and carbazolyl; and 2-furanyl, N-imidazolyl, 2-isoxazolyl, 2-pyridinyl, 2-pyrimidinyl, and the like.

The alkyloxy used in the present invention means a monovalent functional group represented by RO—, and R is an alkyl having 1 to 40 carbon atoms, and may include a linear, branched, or cyclic structure. Non-limiting examples of the alkyloxy include methoxy, ethoxy, n-propoxy, 1-propoxy, t-butoxy, n-butoxy, pentoxy, and the like.

The aryloxy used in the present invention means a monovalent functional group represented by R'O—, and R' is an aryl having 6 to 60 carbon atoms. Non-limiting examples of the aryloxy include phenyloxy, naphthyloxy, diphenyloxy, and the like.

The alkylsilyl used in the present invention means a silyl substituted with an alkyl having 1 to 40 carbon atoms, the arylsilyl means a silyl substituted with an aryl having 6 to 60 carbon atoms, and the arylamine means an amine substituted with an aryl having 6 to 60 carbon atoms.

The fused ring used in the present invention means a fused aliphatic ring, a fused aromatic ring, a fused heteroaliphatic ring, a fused heteroaromatic ring, or a combined form thereof.

Further, the present invention provides an organic electroluminescence device including: an anode; a cathode; and an organic material layer having one or more layers interposed between the anode and the cathode, in which at least one of the organic material layers having one or more layers includes the compound represented by Formula 1.

Here, the organic material layer including the compound represented by Formula 1 is selected from the group consisting of a hole injection layer, a hole transporting layer, and a light-emitting layer, and is preferably a light-emitting layer. In this case, the compound represented by Formula 1 may be used as a phosphorescent host material of the light-emitting layer.

Advantageous Effects

The compound represented by Formula 1 according to the present invention has excellent thermal stability and phosphorescent characteristics, and thus may be applied to an organic material layer, preferably a light-emitting layer of an organic electroluminescence device. Therefore, when the light-emitting layer of the organic electroluminescence device includes the compound represented by Formula 1 as a phosphorescent host material, the efficiency (light-emitting efficiency and power efficiency), lifespan, brightness, and driving voltage of the device may be enhanced as compared to the case in which a host material in the related art is included, and furthermore, performance and lifespan of a full-color organic electroluminescence panel may be greatly enhanced.

BEST MODE

Hereinafter, the present invention will be described in detail.

1. Novel Compound

A novel compound according to the present invention has a basic structure in which an indole group fusion compound is bonded to a naphthalene derivative including nitrogen (N), and is represented by Formula 1.

The compound represented by Formula 1 according to the present invention has excellent phosphorescent characteristics and excellent electron and/or hole transporting capabilities, and thus may be used as a material for any one of a hole injection layer, a hole transporting layer, a light-emitting layer, an electron transporting layer, and an electron injection layer, which are the organic material layers of an organic electroluminescence device. The compound may be used preferably as a material for any one of a hole injection layer, a hole transporting layer, and a light-emitting layer, and more preferably as a material (particularly, a phosphorescent host material) for a light-emitting layer.

Specifically, the compound represented by Formula 1 according to the present invention is a compound into which various substituents are introduced and in which a naphthalene derivative including nitrogen (N) and an indole group fusion compound are combined, and since the mobility balance between holes and electrons may be controlled by bipolar characteristics which the compound has, the recombination efficiency of holes and electrons may be enhanced, thereby exhibiting excellent phosphorescent characteristics. Furthermore, the compound represented by Formula 1 according to the present invention may have a wide energy band gap (sky blue to red) because the energy level is controlled by various substituents introduced into a basic structure composed of a naphthalene derivative and an indole group fusion compound. Therefore, when the compound of Formula 1 according to the present invention is used in an organic electroluminescence device, phosphorescent characteristics of the device are improved, and simultaneously, hole injection capabilities and/or transporting capabilities, light-emitting efficiency, driving voltage, lifespan characteristics, and the like may be improved.

Further, the molecular weight of the compound represented by Formula 1 according to the present invention is significantly increased due to various substituents introduced into the basic structure, so that the glass transition temperature is enhanced, and accordingly, the compound represented by Formula 1 according to the present invention may have higher thermal stability than that of a material (for example, CBP [4,4-dicarbazolybiphenyl]) for the organic electroluminescence device in the related art.

Therefore, the compound according to the present invention may greatly contribute to the improvement of performance and the enhancement of lifespan, of the organic electroluminescence device, and furthermore, the enhancement of lifespan of the organic electroluminescence device may maximize the performance of a full color organic light-emitting panel.

In the compound represented by Formula 1 of the present invention, $A_1$ to $A_4$ of the naphthalene derivative including nitrogen (N) are each independently $CR_1$ or N, and in this case, it is preferred that at least one thereof is nitrogen (N), and it is more preferred that two thereof are nitrogen (N). In addition, $B_1$ to $B_4$ are each independently $CR_2$ or N, and it is preferred that all of $B_1$ to $B_4$ are $CR_2$, or one of $B_1$ to $B_4$ is nitrogen (N).

Here, it is preferred that

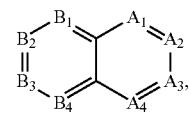

which is a naphthalene derivative including nitrogen (N), is selected from the group consisting of structures represented by the following S-1 to S-30.

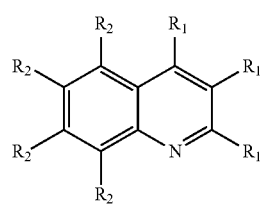

S-1

S-2 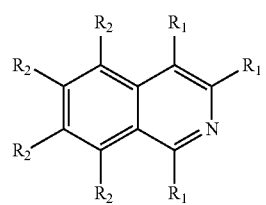
S-3 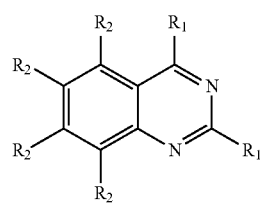
S-4 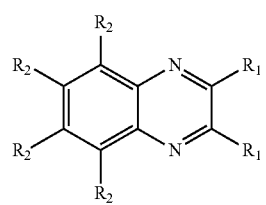
S-5 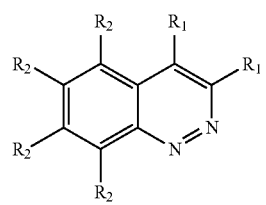
S-6 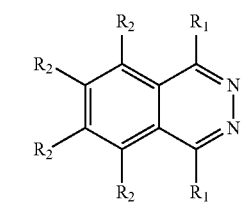
S-7 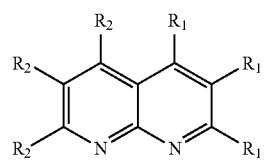
S-8 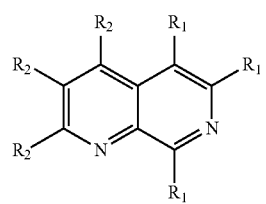
S-9 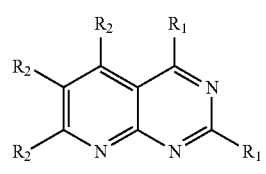
S-10 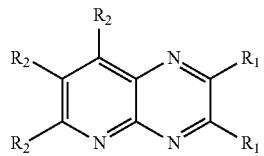
S-11 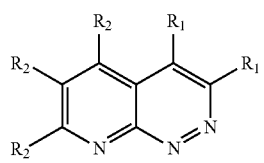
S-12 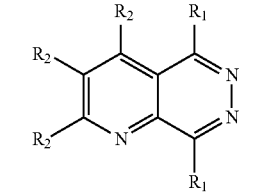
S-13 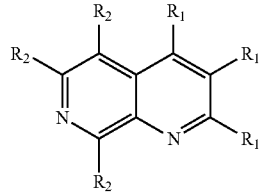
S-14 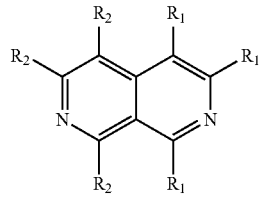
S-15 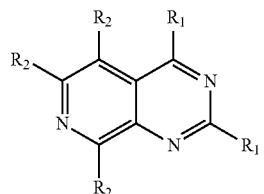
S-16 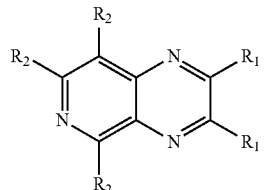
S-17 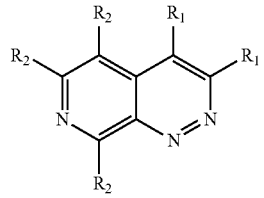

-continued

S-18
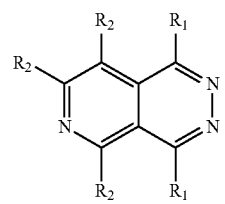

S-19
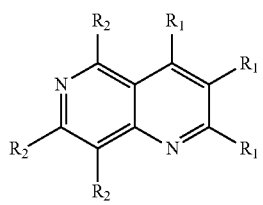

S-20
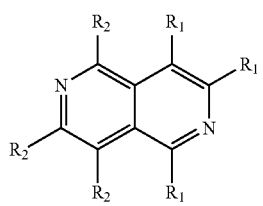

S-21
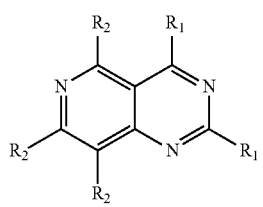

S-22
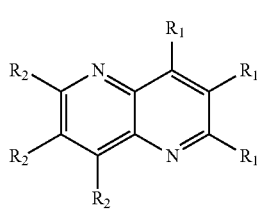

S-23
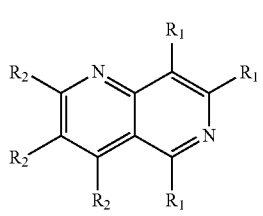

S-24
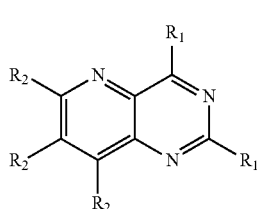

-continued

S-25
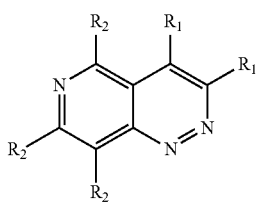

S-26
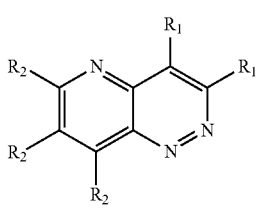

S-27
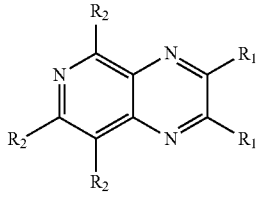

S-28
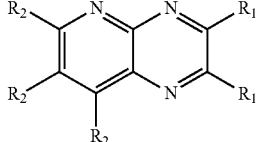

S-29
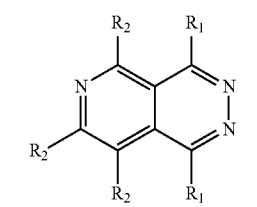

S-30
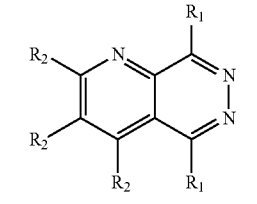

In the structures represented by S-1 to S-30, $R_1$ and $R_2$ are the same as those defined above, a plurality of $R_1$'s may be the same as or different from each other, and a plurality of $R_2$'s may also be the same as or different from each other.

In this case, in consideration of efficiency and lifespan characteristics of the organic electroluminescence device, it is preferred that $R_1$ and $R_2$ are selected from the group consisting of hydrogen, a $C_6$ to $C_{60}$ (preferably $C_6$ to $C_{25}$) aryl group, a heteroaryl group having 5 to 40 nuclear atoms (preferably 5 to 32 nuclear atoms), and a $C_6$ to $C_{60}$ (preferably $C_6$ to $C_{20}$) arylamine group.

More preferably, $R_1$ and $R_2$ may be each independently selected from the group consisting of hydrogen, or structures represented by the following A1 to A70.

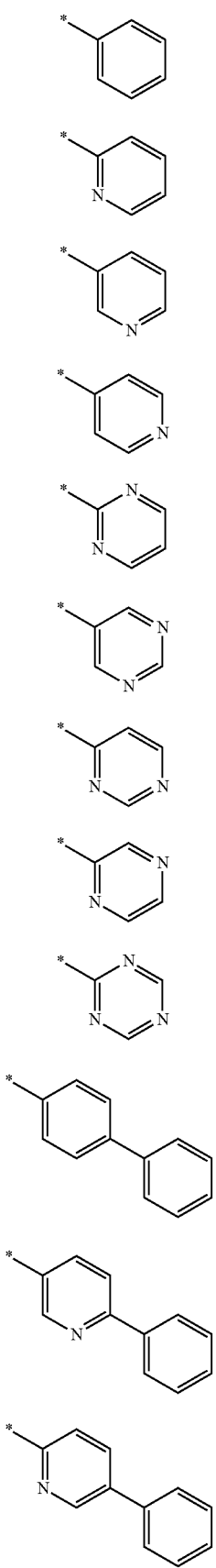
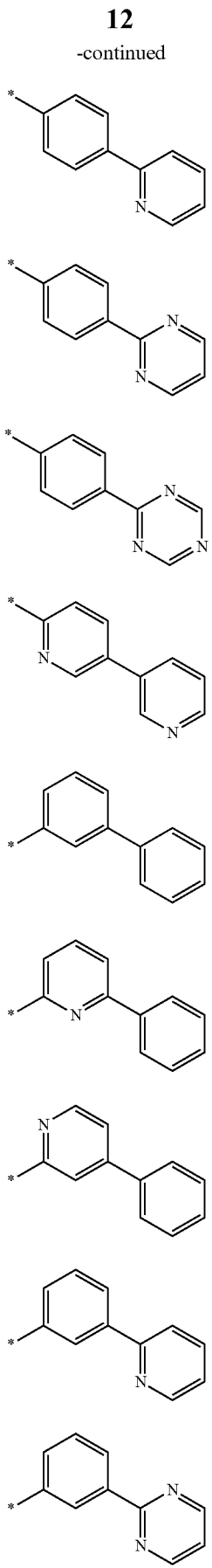

A22 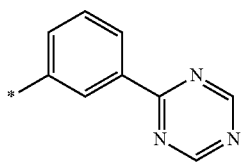
A23 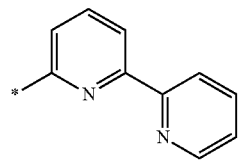
A24 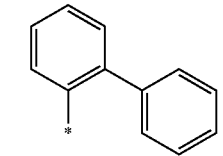
A25 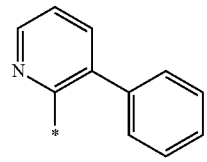
A26 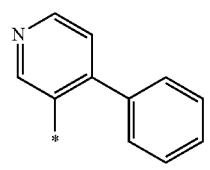
A27 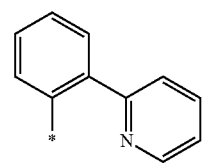
A28 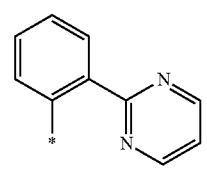
A29 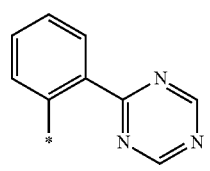
A30 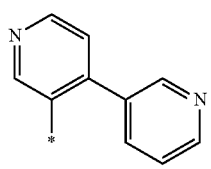
A31 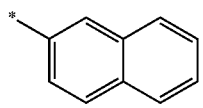
A32 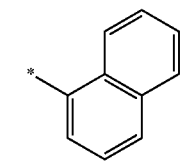
A33 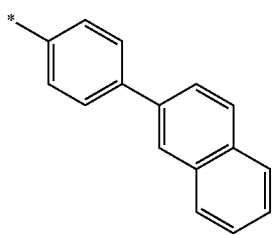
A34 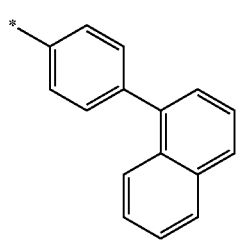
A35 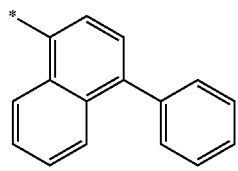
A36 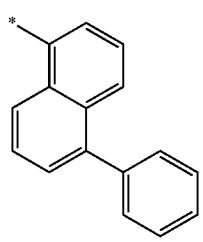
A37 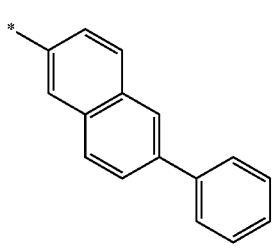
A38 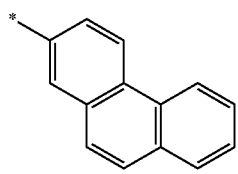

-continued

A39
A40
A41
A42
A43
A44
A45
A46
A47
A48
A49
A50
A51
A52
A53

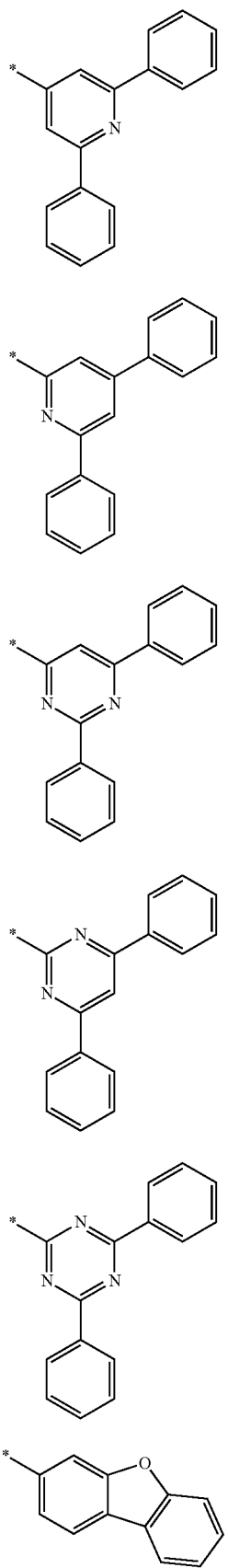
A54
A55
A56
A57
A58
A59
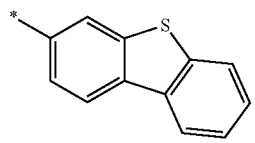
A60
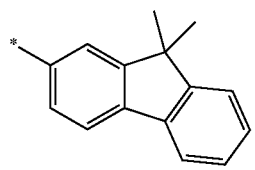
A61
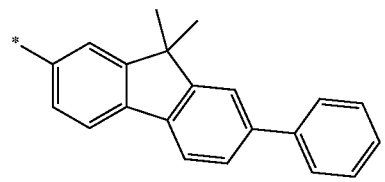
A62
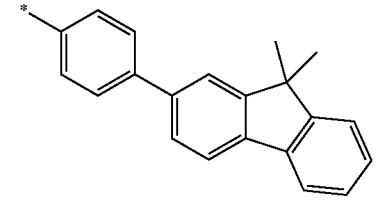
A63
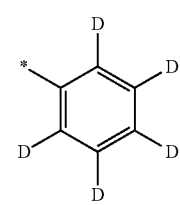
A64
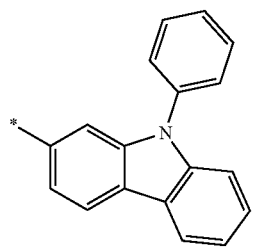
A65
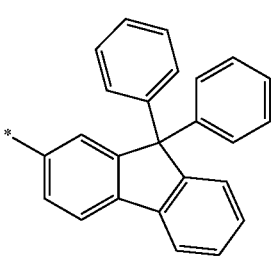
A66

-continued

A67
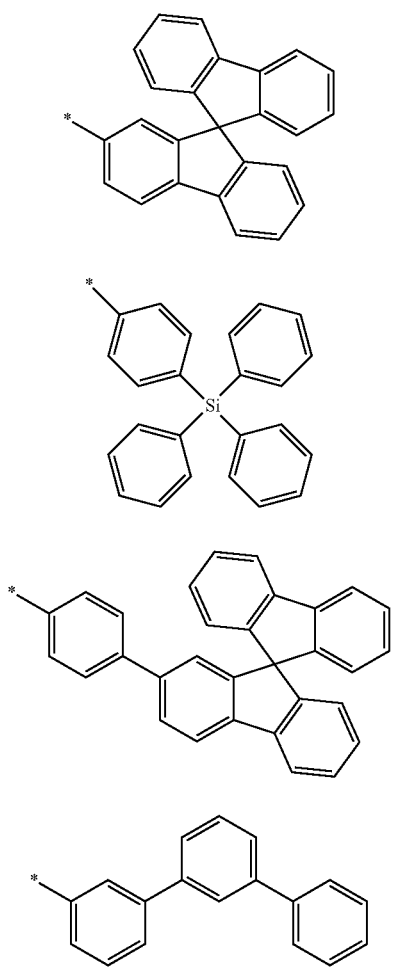

A68

A69

A70

Meanwhile, in the compound represented by Formula 1 according to the present invention, it is preferred that the compound represented by Formula 2 which corresponds to Cy is selected from the group consisting of compounds represented by the following Formulae 2a to 2f.

[Formula 2a]
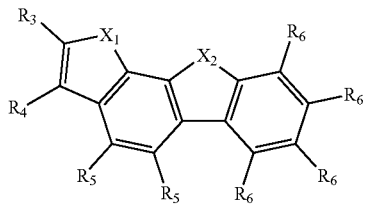

[Formula 2b]
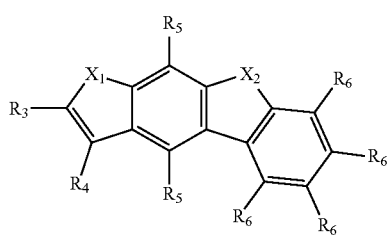

[Formula 2c]
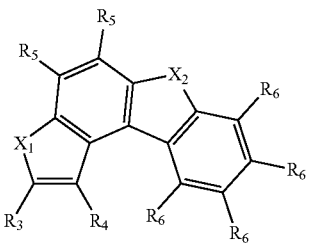

[Formula 2d]
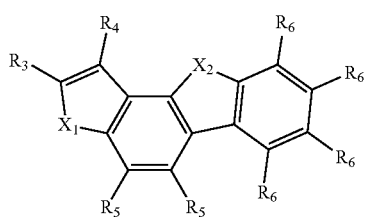

[Formula 2e]
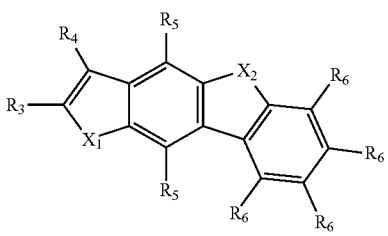

[Formula 2f]
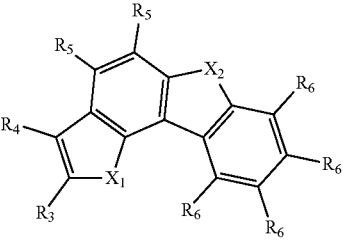

In Formulae 2a to 2f, $X_1$, $X_2$ and $R_3$ to $R_6$ are the same as those defined above. In this case, a plurality of $R_5$'s may be the same as or different from each other, and a plurality of $R_6$'s may also be the same as or different from each other.

Meanwhile, in consideration of efficiency and lifespan characteristics of the organic electroluminescence device, in the compound represented by Formula 1 according to the present invention, it is preferred that L which links the naphthalene derivative including nitrogen (N) to one compound of the compounds represented by Formulae 2a to 2f is a single bond or phenylene.

In addition, in the compounds represented by Formulae 2a to 2f, it is preferred that both $X_1$ and $X_2$ are $N(Ar_1)$. In this case, $Ar_1$ of $N(Ar_1)$ to be combined as $X_1$ and $Ar_1$ of $N(Ar_1)$ to be combined as $X_2$ may be the same as or different from each other. It is preferred that $Ar_1$ is selected from the group consisting of hydrogen, a $C_6$ to $C_{60}$ aryl group (preferably a $C_6$ to $C_{18}$ aryl group) and a heteroaryl group having 5 to 40 nuclear atoms (preferably a heteroaryl group having 5 to 18 nuclear atoms).

In the compound represented by Formula 1 according to the present invention, the linking position of L and the compound represented by Formula 2 is not particularly limited, but it is preferred that L is linked to any one of $X_1$ and $Y_5$ to $Y_8$ of Formula 2.

The compound represented by Formula 1 according to the present invention may be specifically exemplified as the following compounds (C1 to C458), but is not limited thereto.
C1
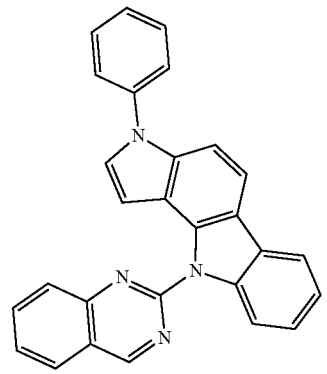
C2
C3
C4
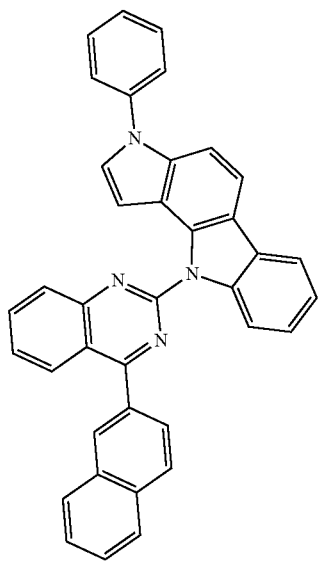
C5
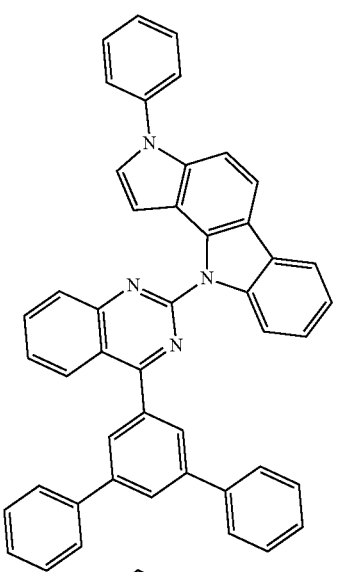
C6
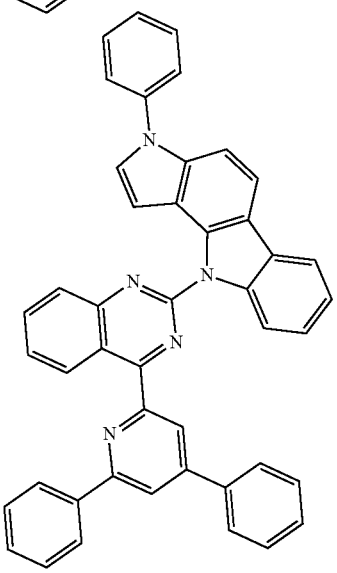

-continued
C7
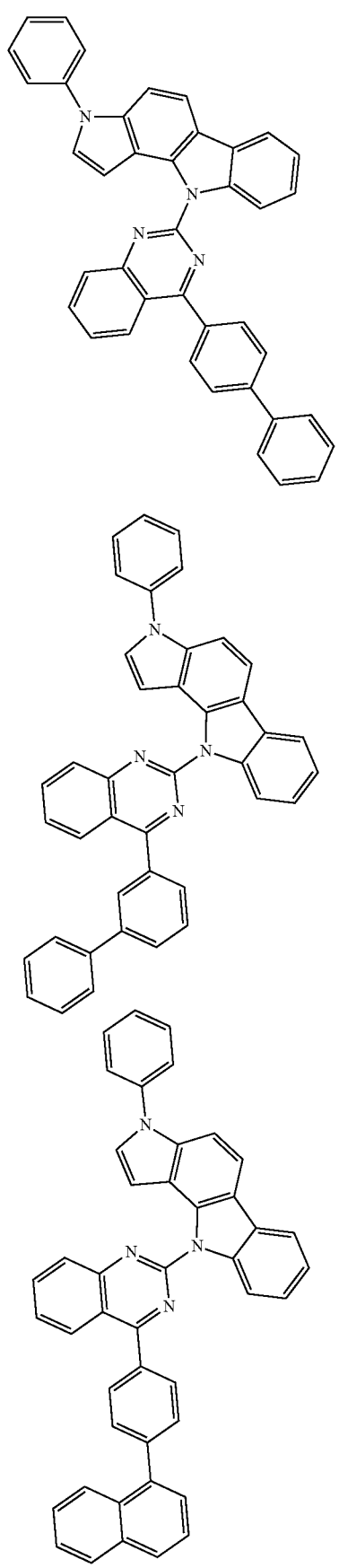
C8
C9
-continued
C10
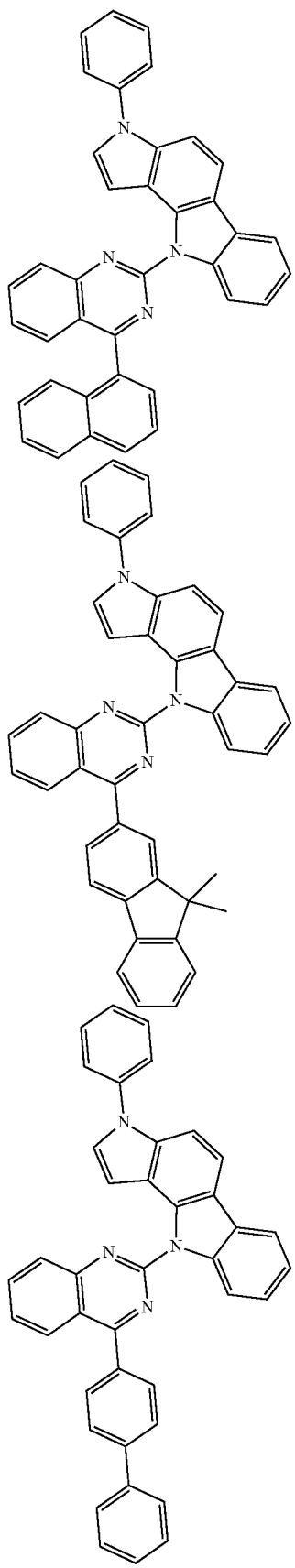
C11
C12

C13
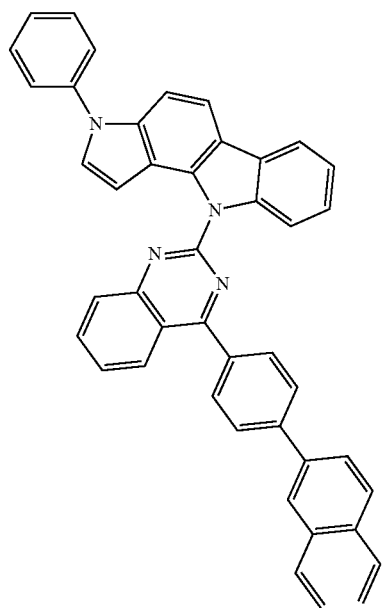
C14
C15
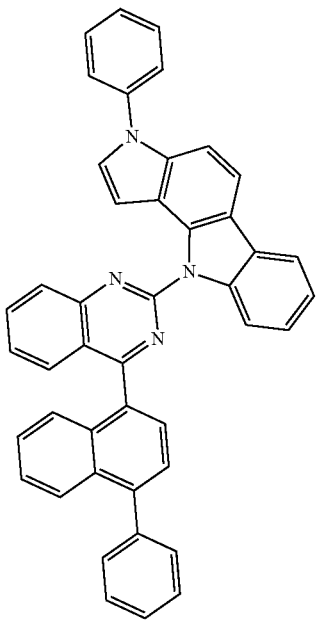
C16
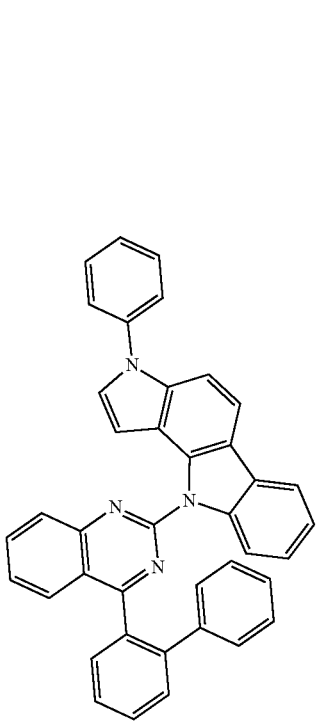

C17
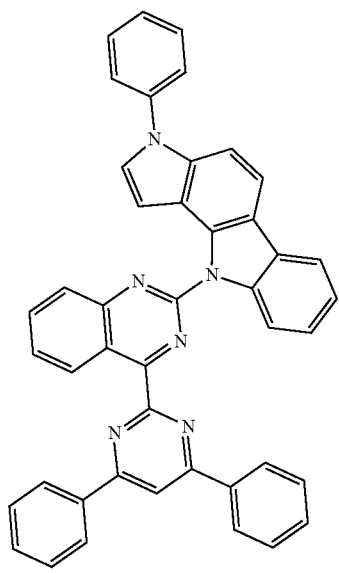
C19
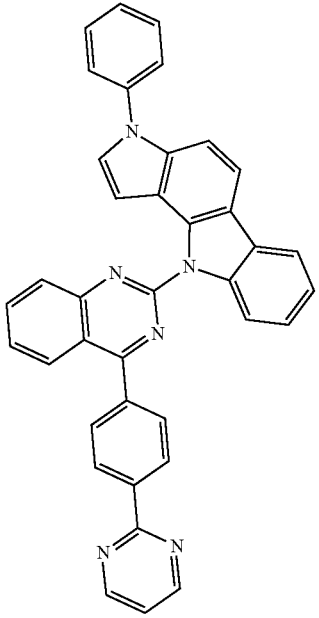
C18
C20
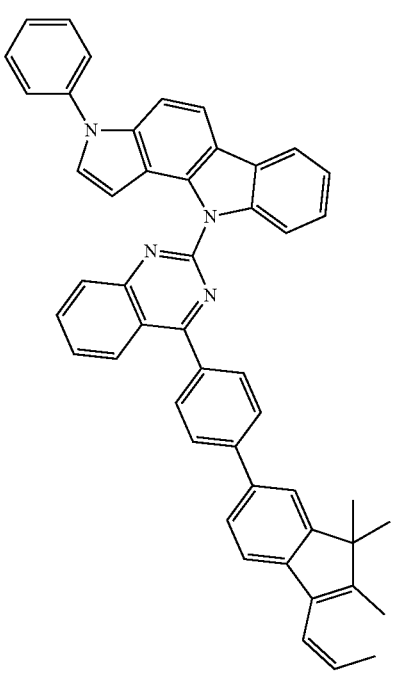

C21
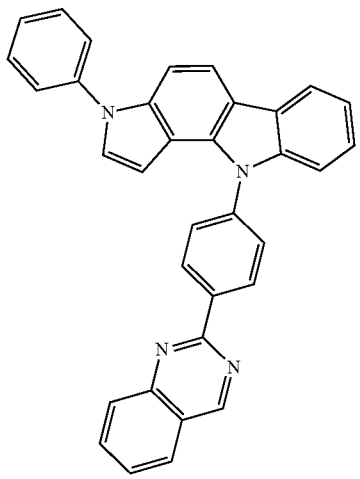
C22
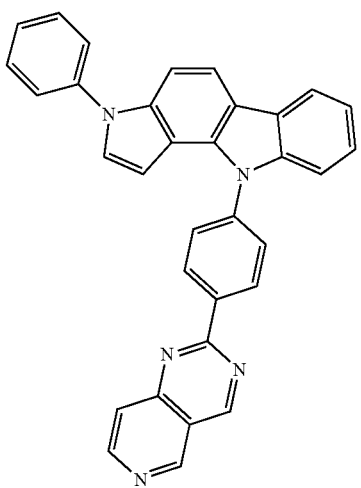
C23
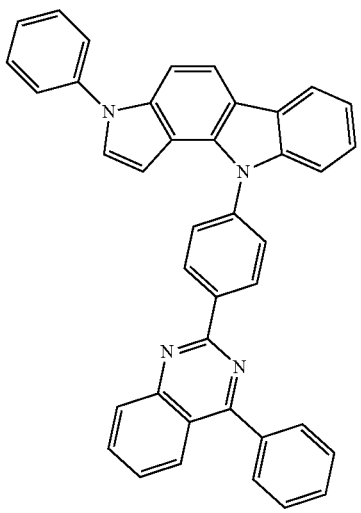
C24
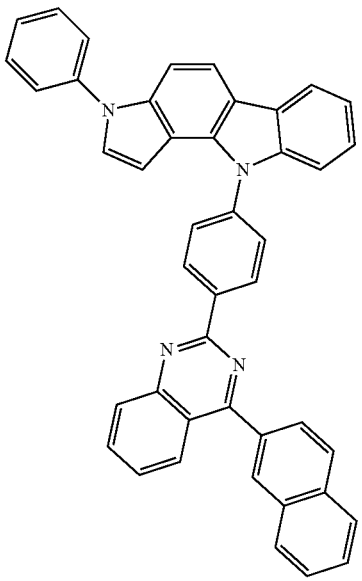
C25
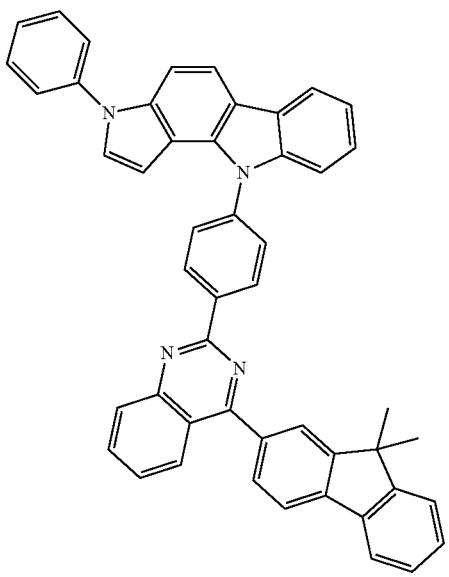

C26
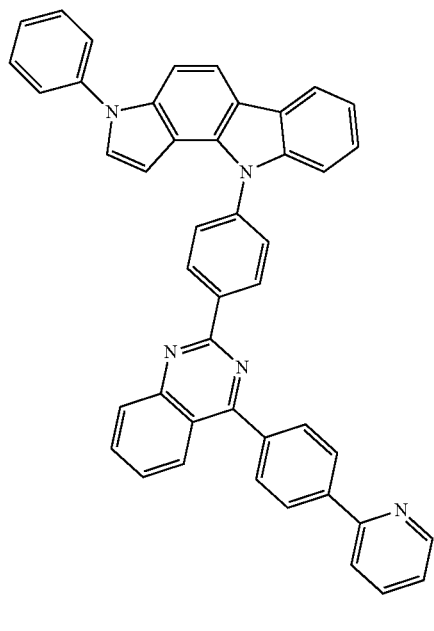
C28
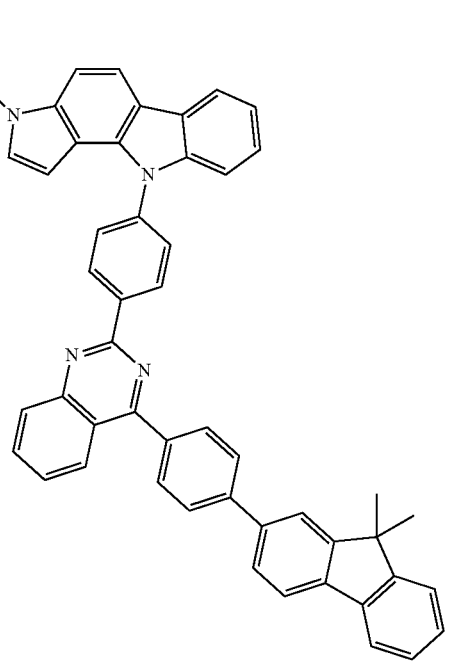
C27
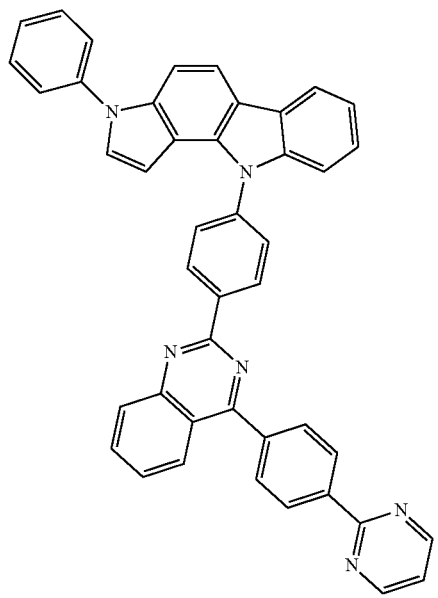
C29
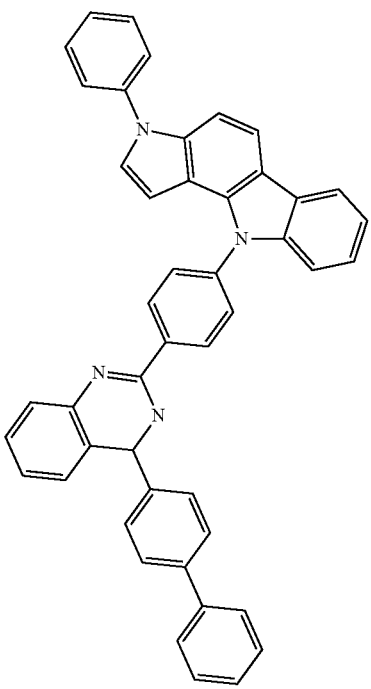

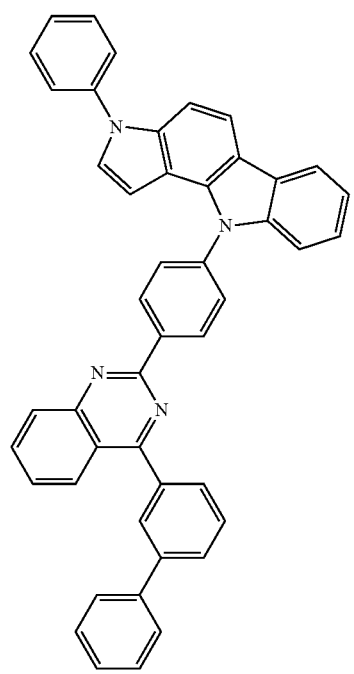
C30
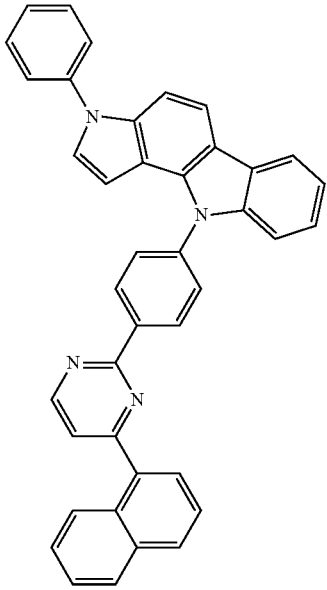
C32
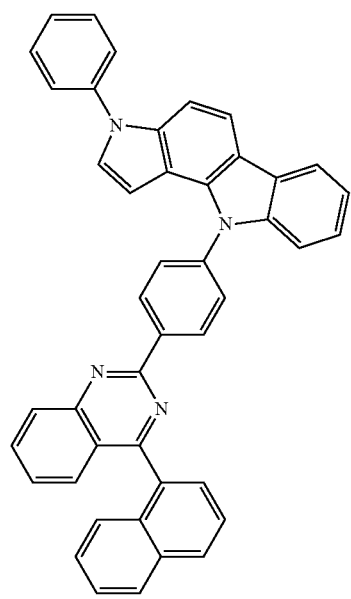
C31
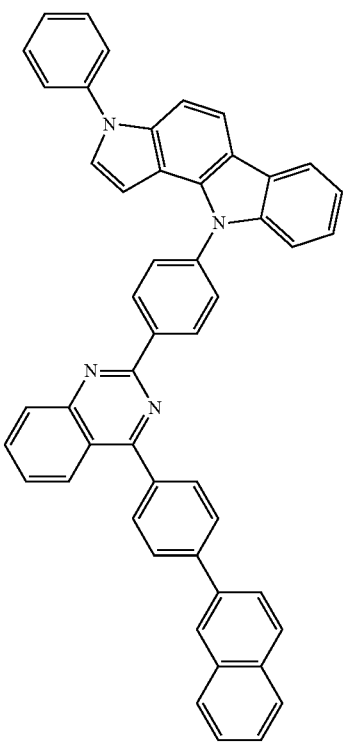
C33

C34
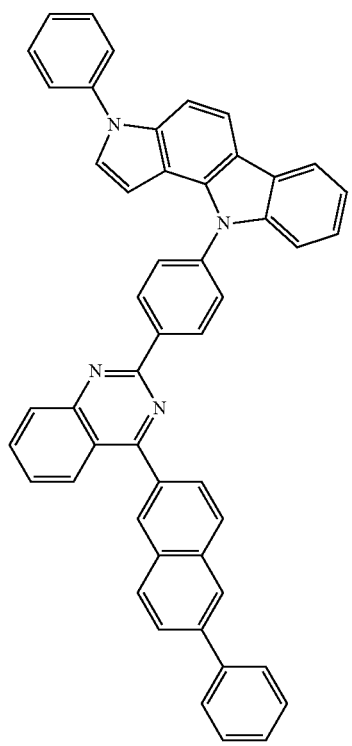
C35
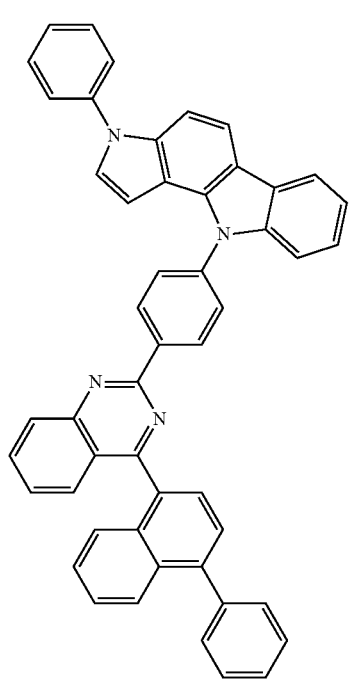
C36
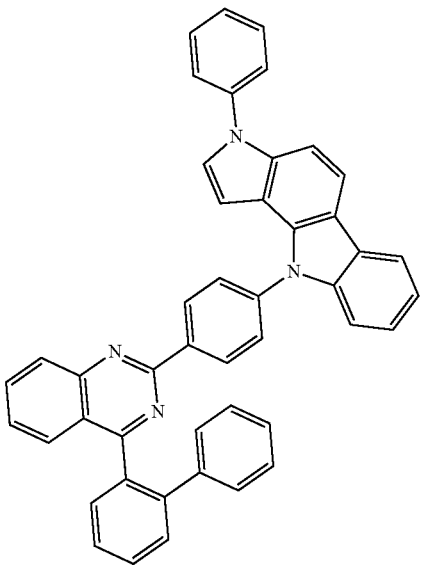
C37
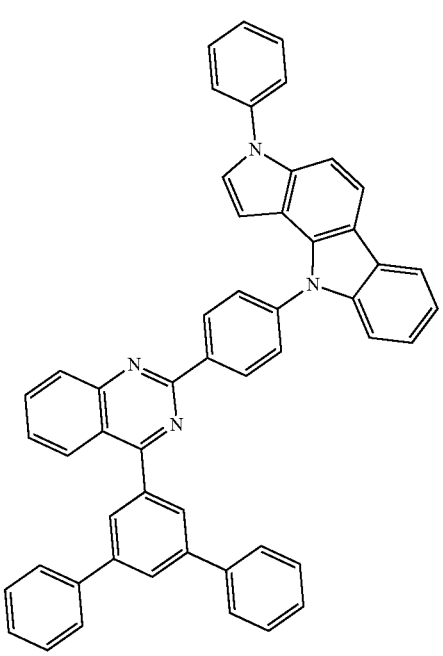

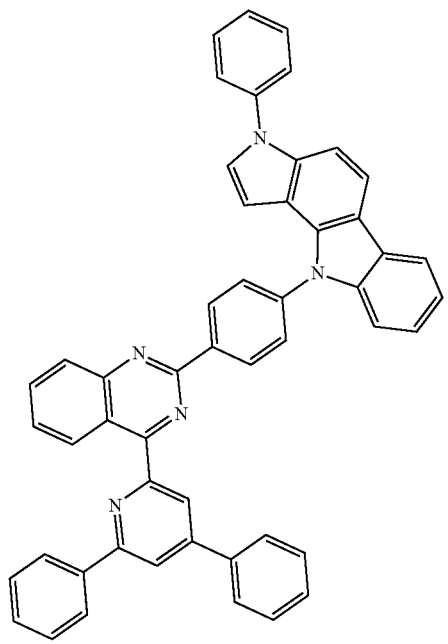
C38
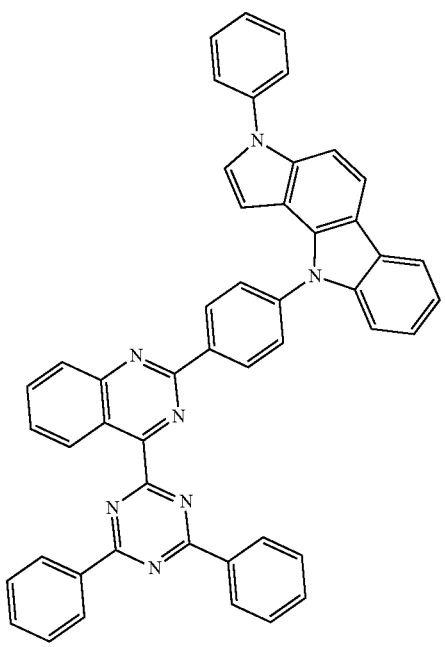
C40
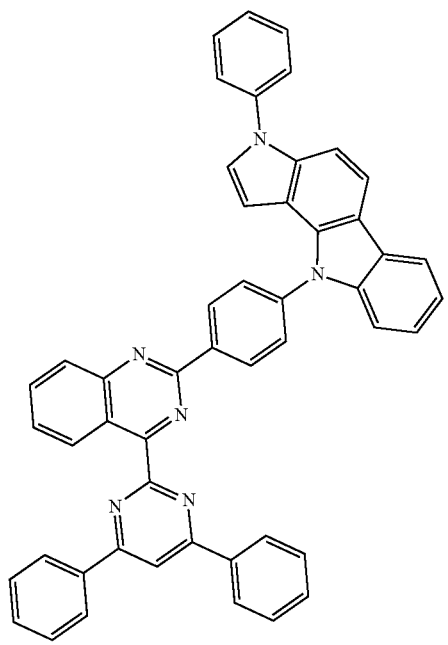
C39
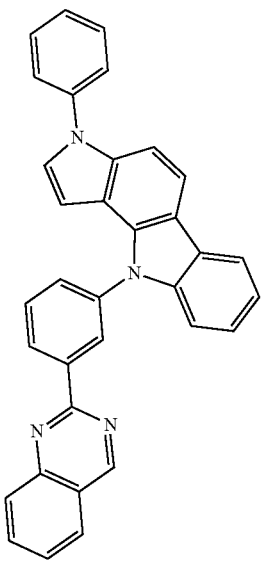
C41

C42
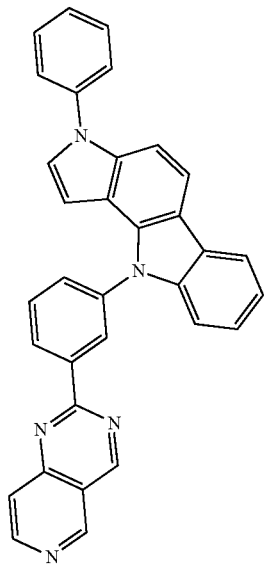
C44
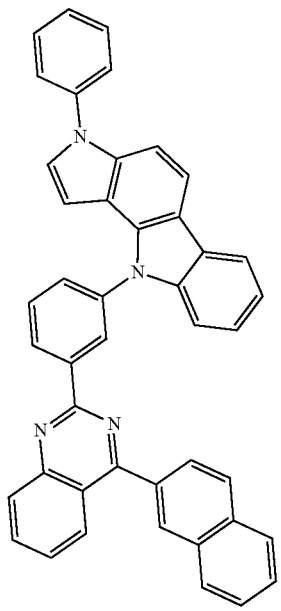
C43
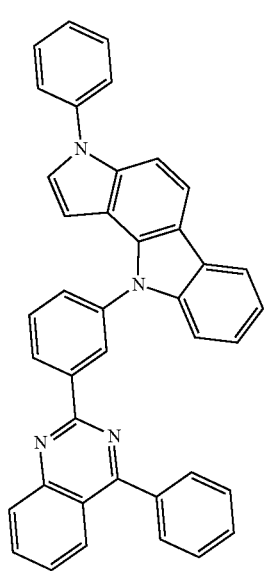
C45
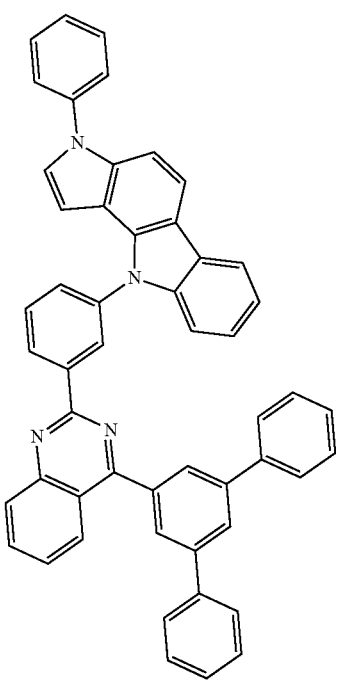

C46
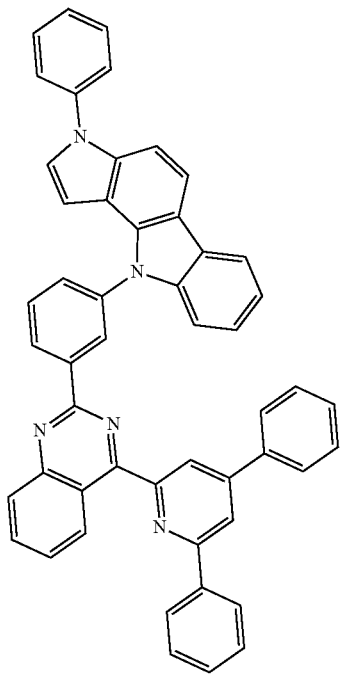
C48
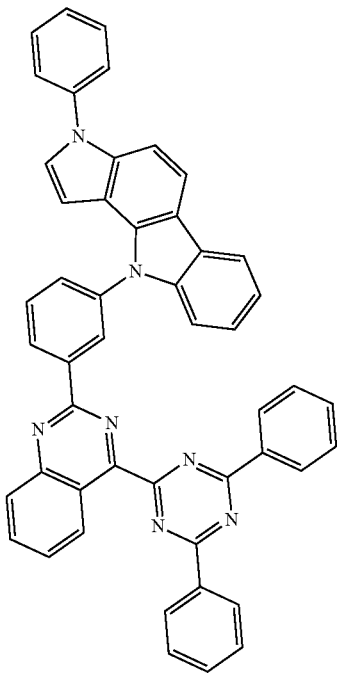
C47
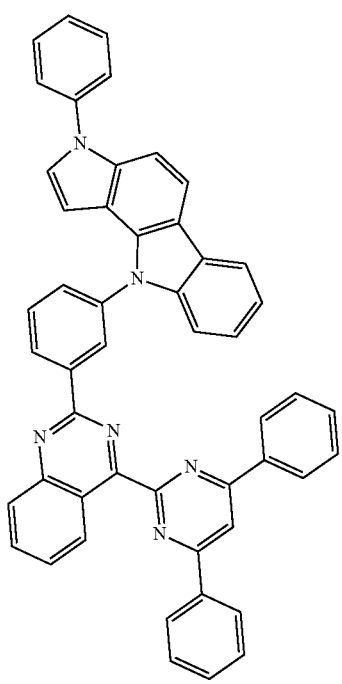
C49
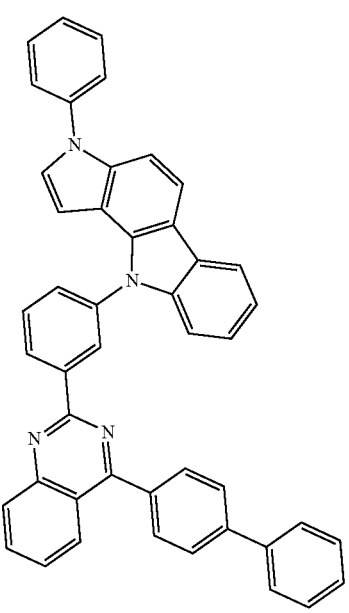

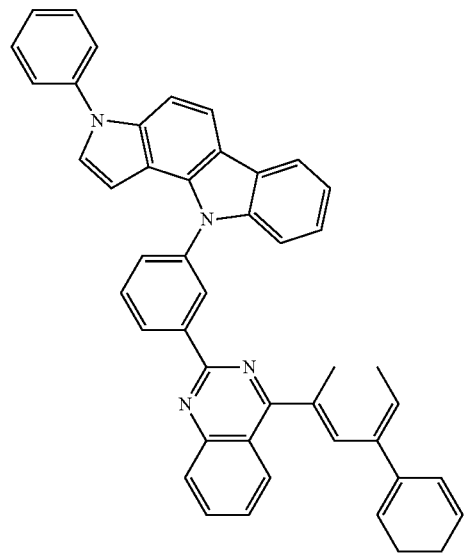
C50
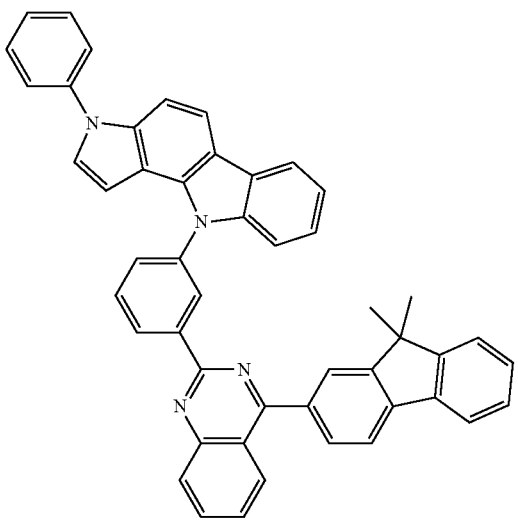
C53
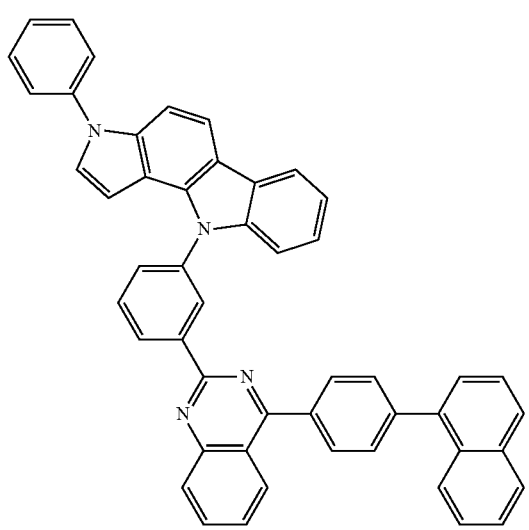
C51
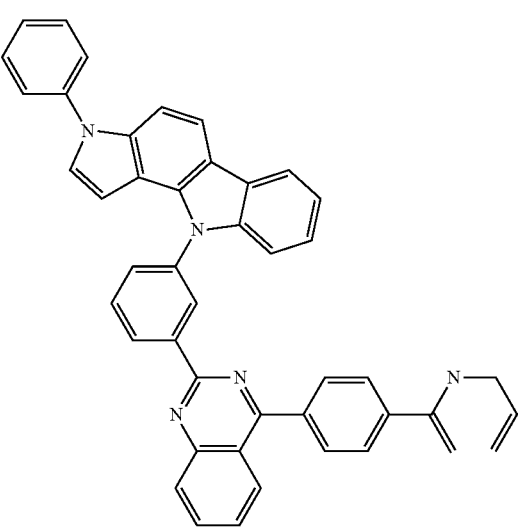
C54
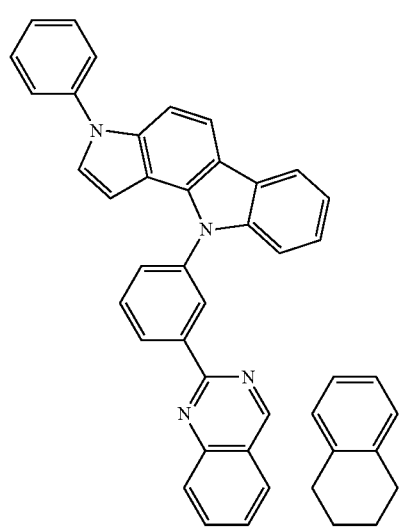
C52
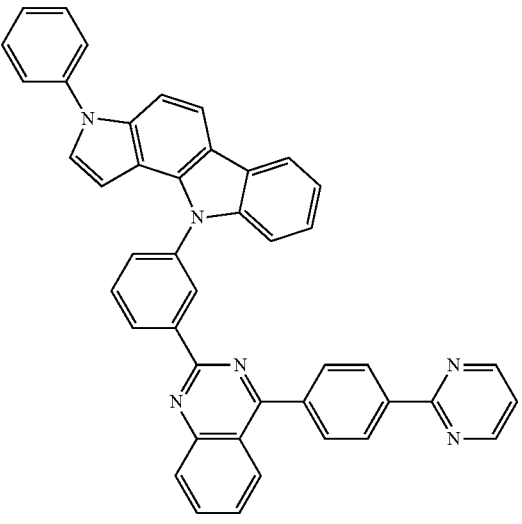
C55

C56
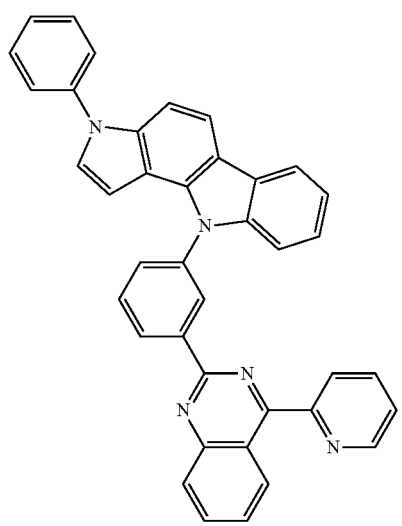
C57
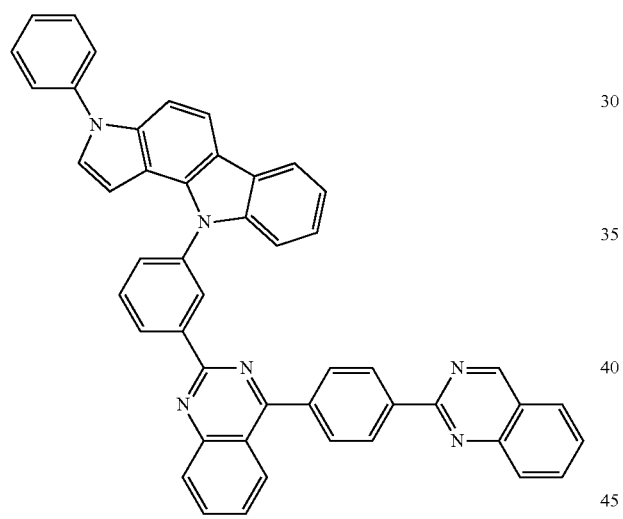
C58
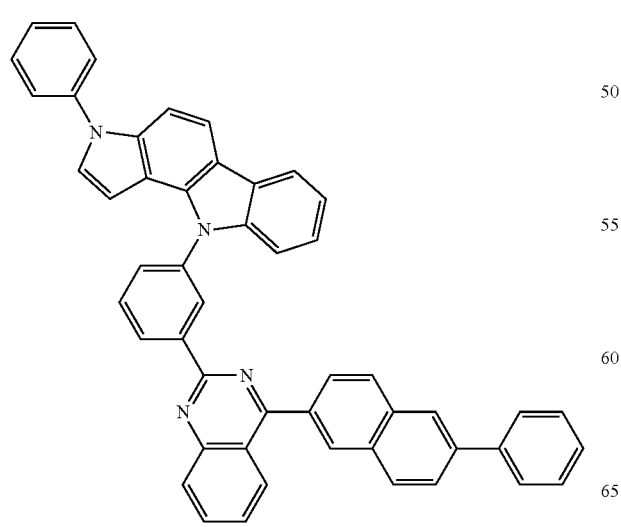
C59
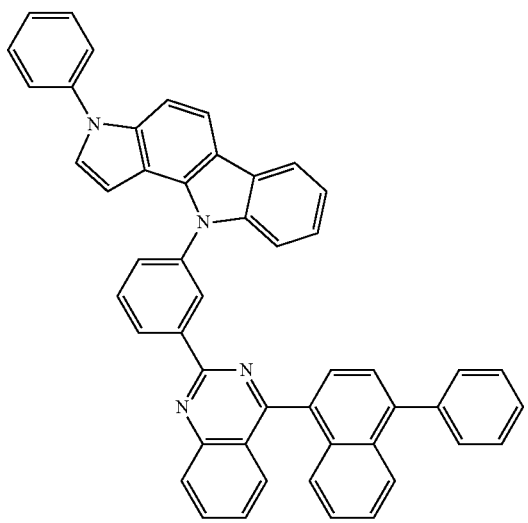
C60
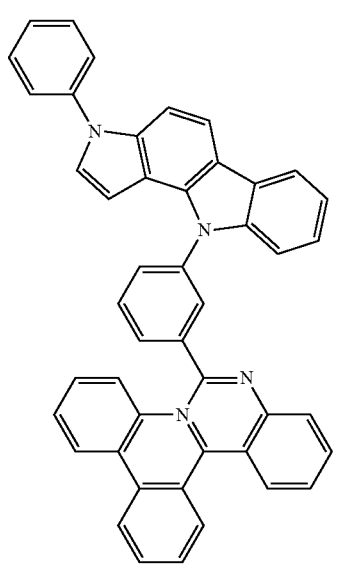
C61
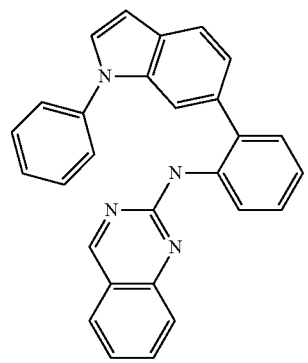

47
-continued
C62
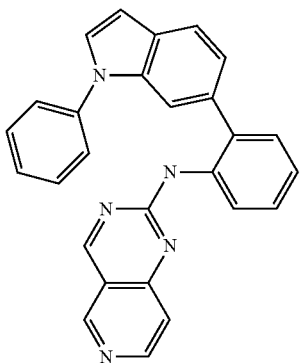
C63
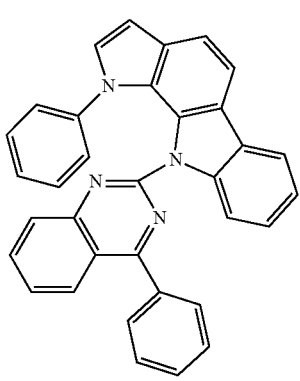
C64
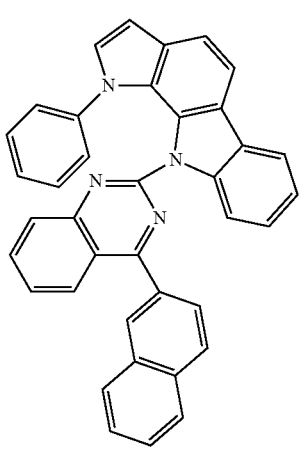
48
-continued
C65
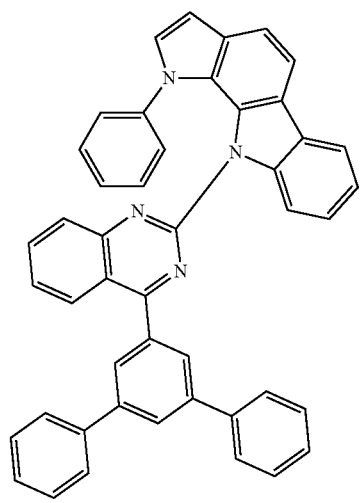
C66
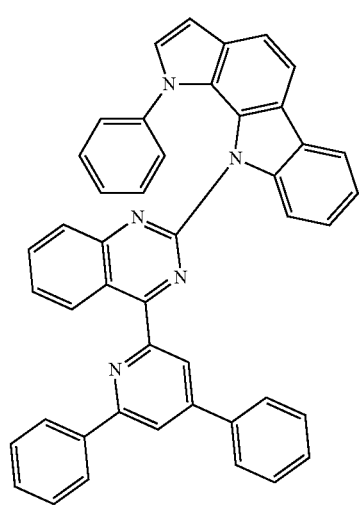
C67
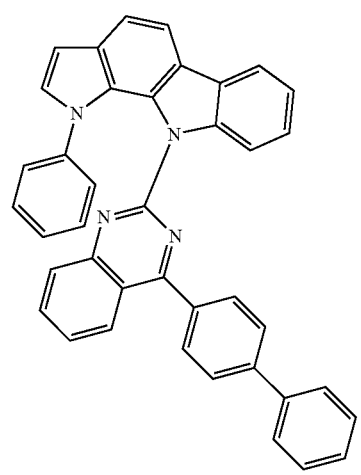

-continued
C68
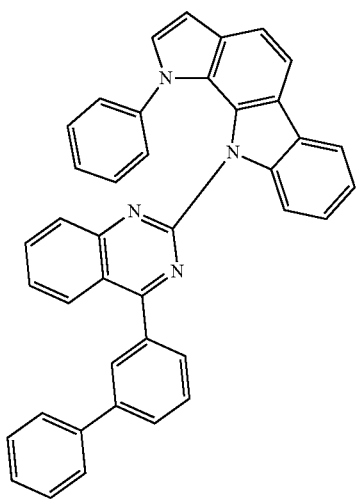
C69
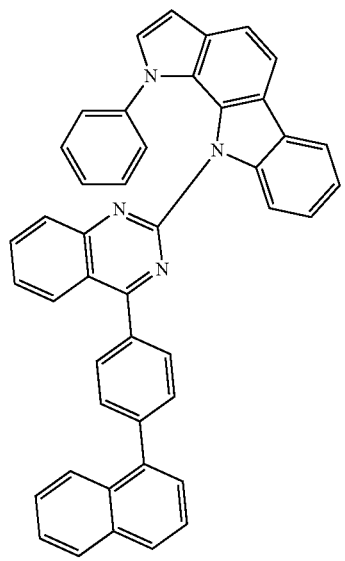
C70
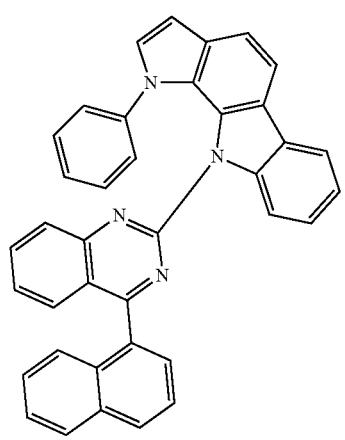
-continued
C71
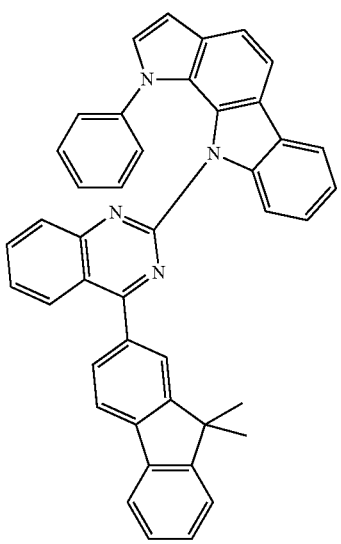
C72
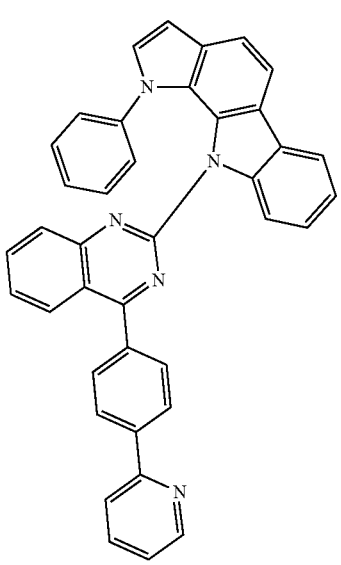
C73
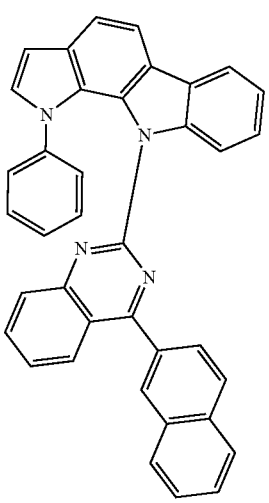

-continued
C74
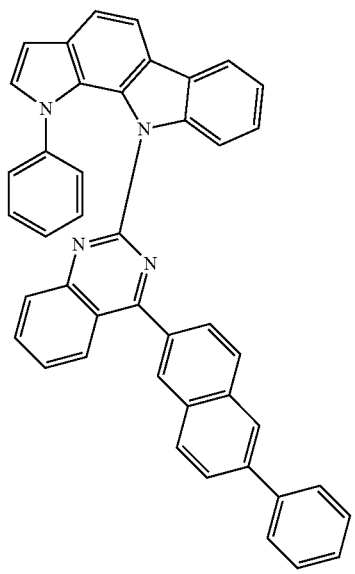
C75
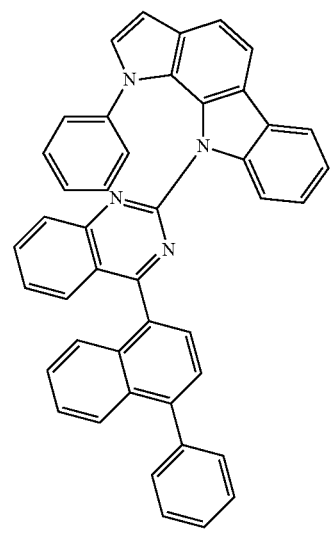
C76
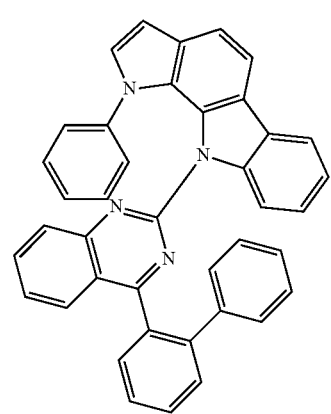
-continued
C77
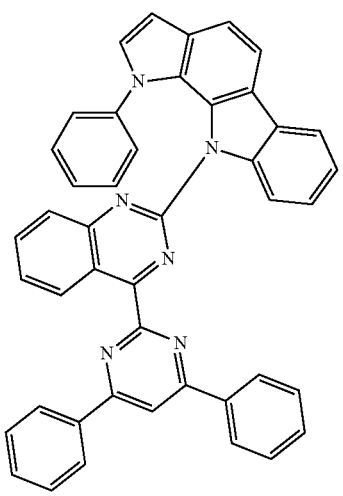
C78
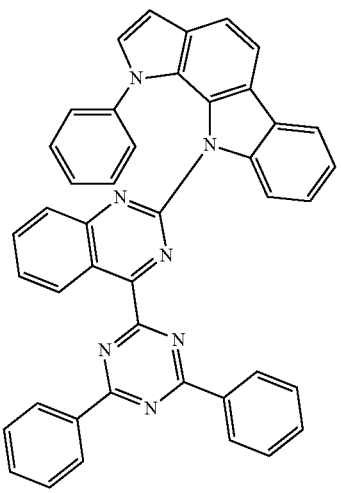
C79
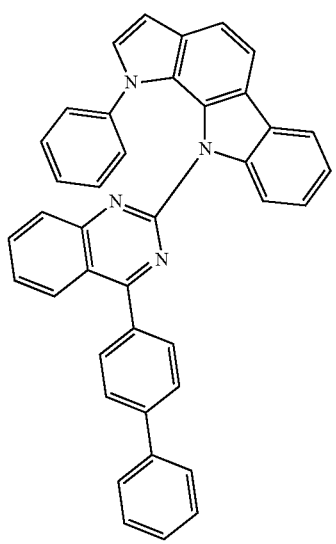

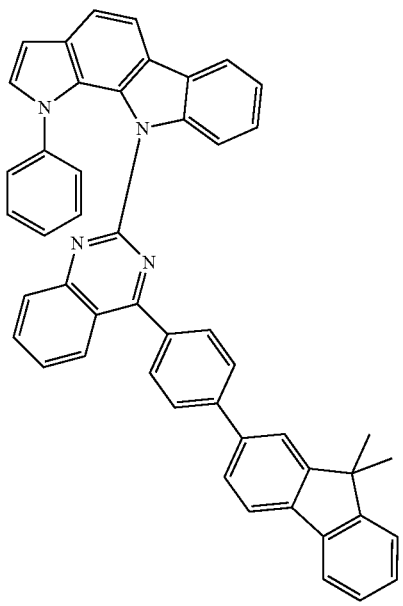
C80
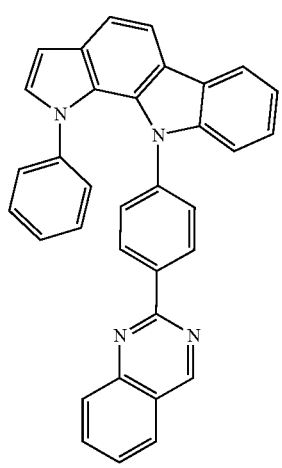
C81
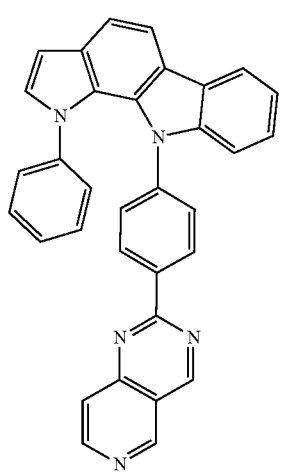
C82
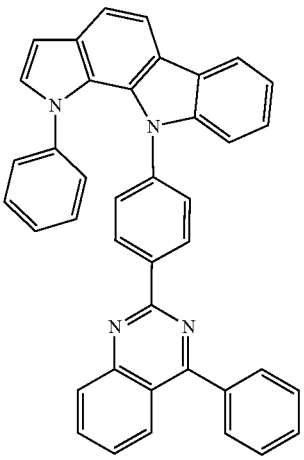
C83
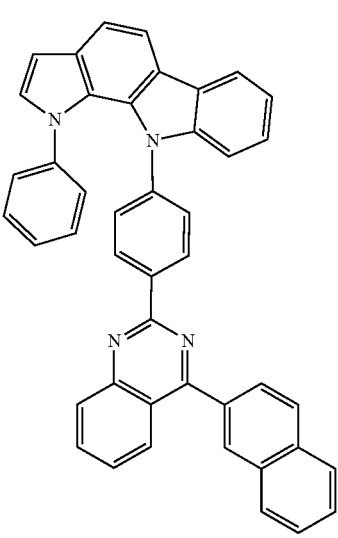
C84
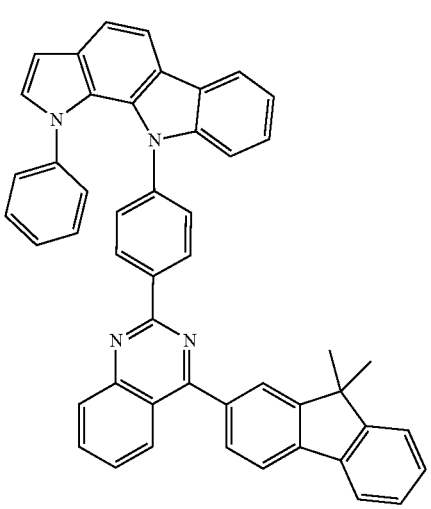
C85

C86
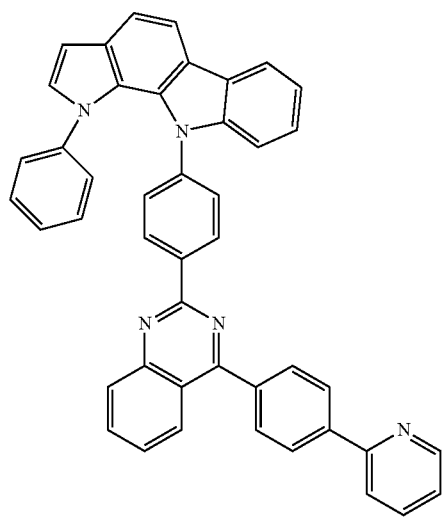
C87
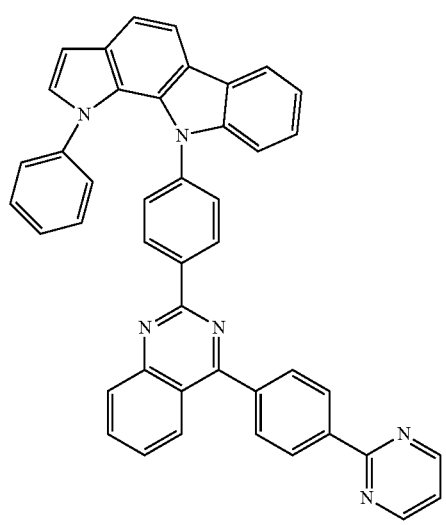
C88
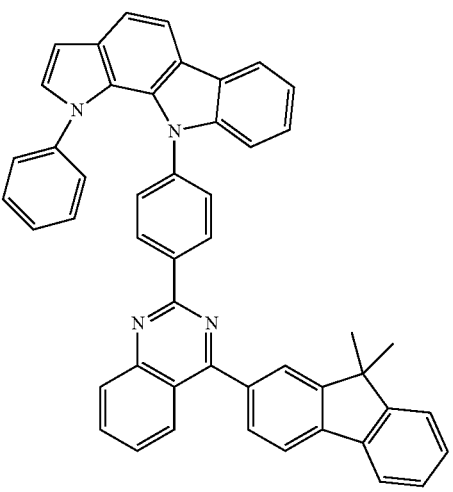
C89
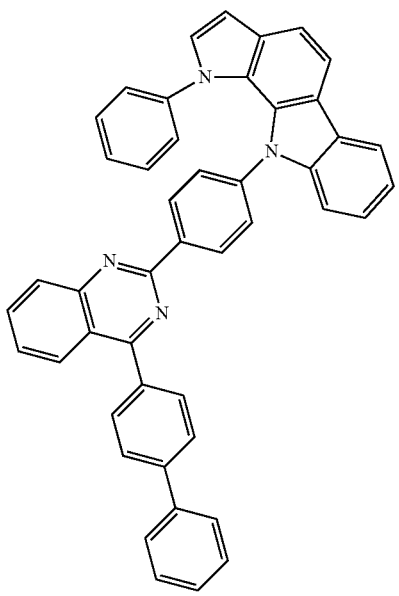
C90
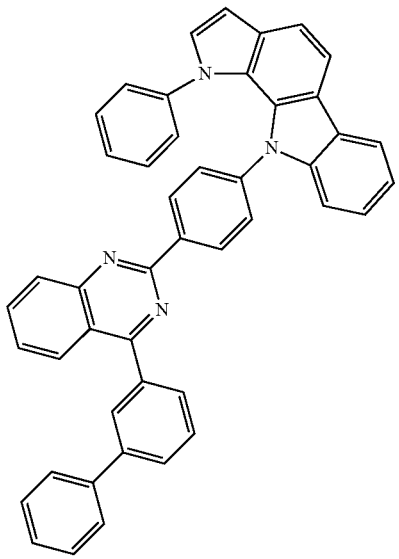
C91
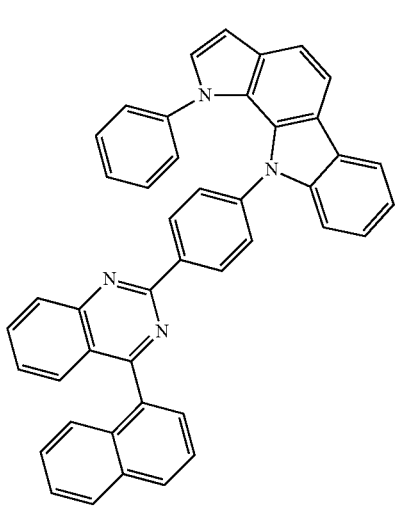

C92
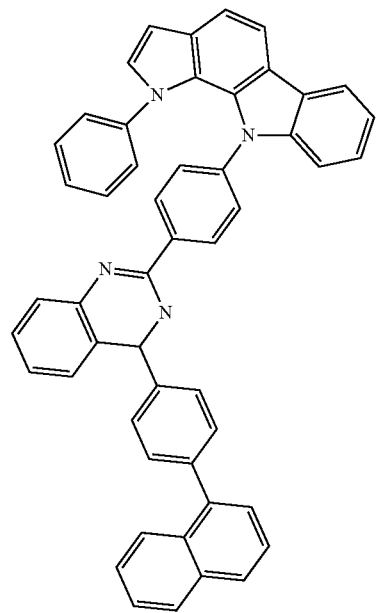
C93
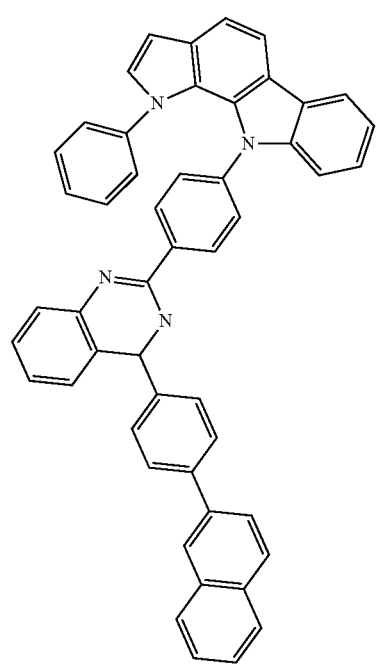
C94
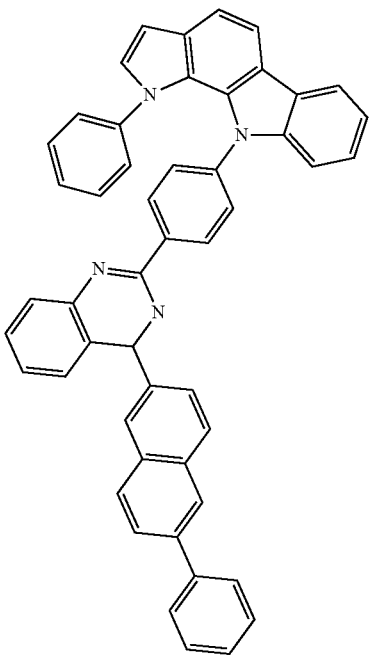
C95
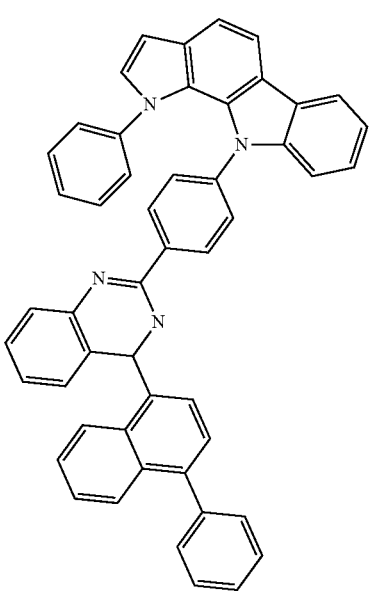
C96
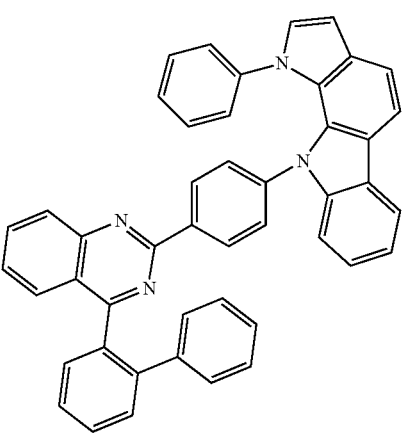

C97
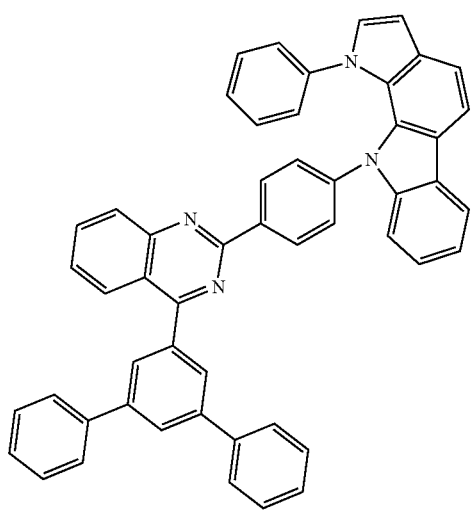
C98
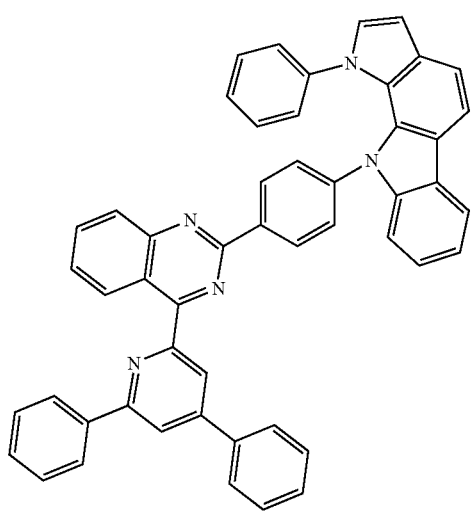
C99
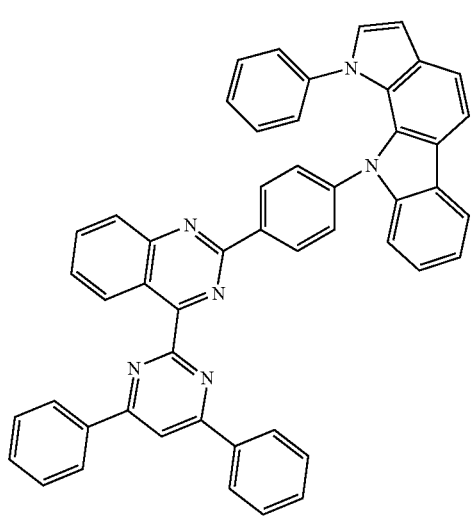
C100
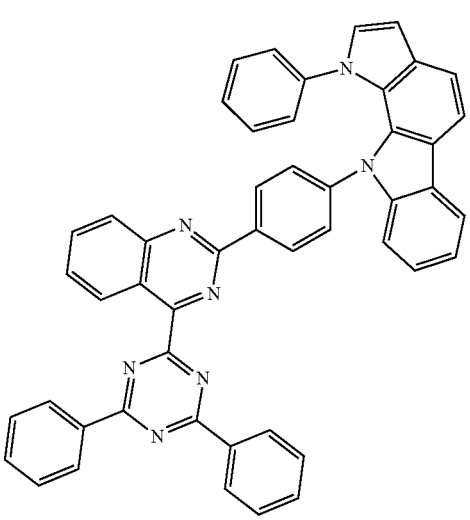
C101
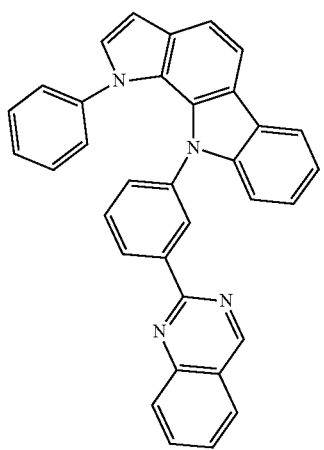
C102
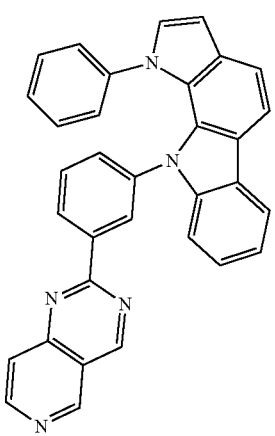

C103
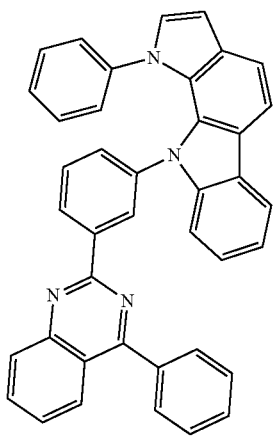
C104
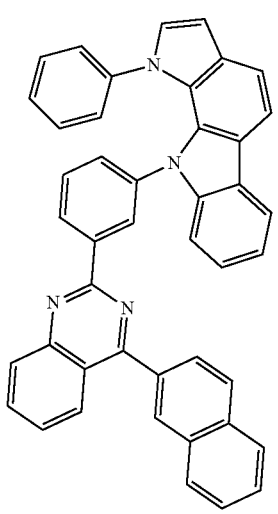
C105
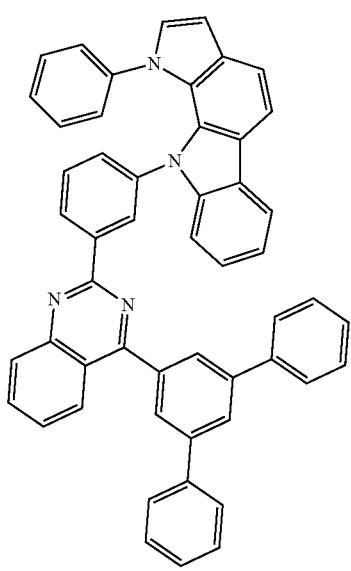
C106
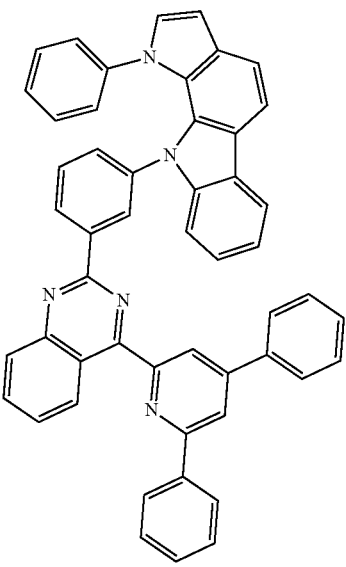
C107
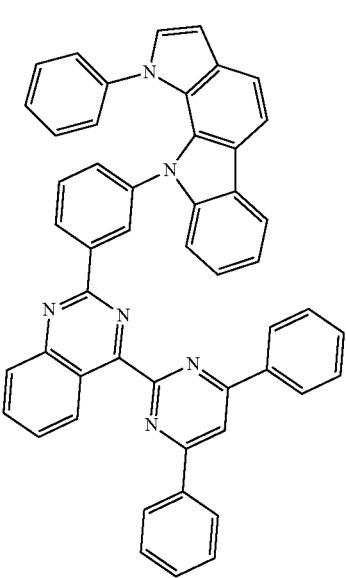

C108
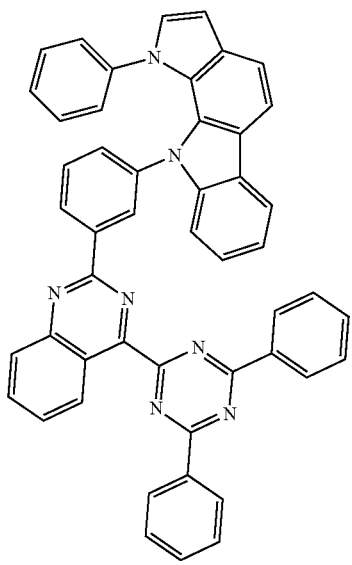
C109
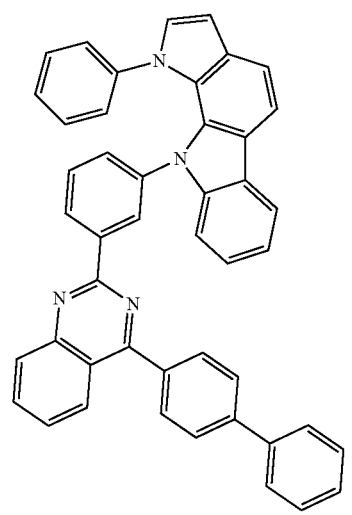
C110
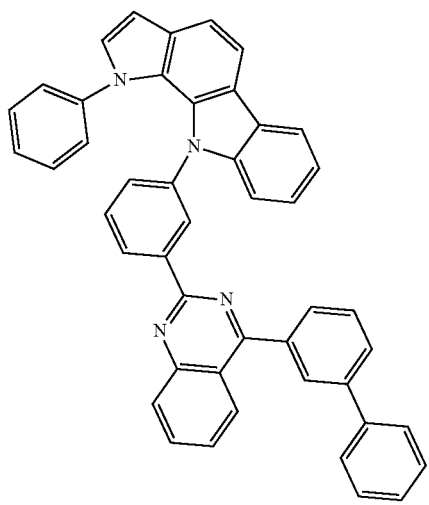
C111
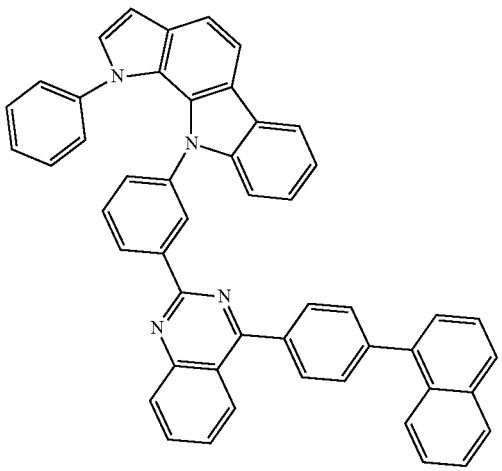
C112
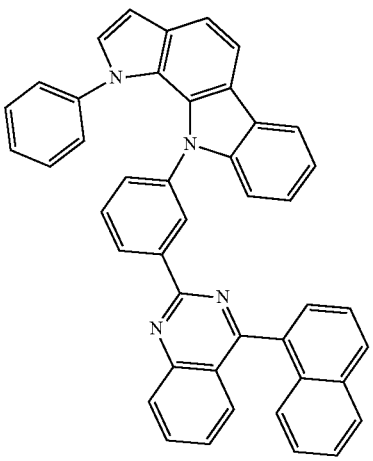
C113
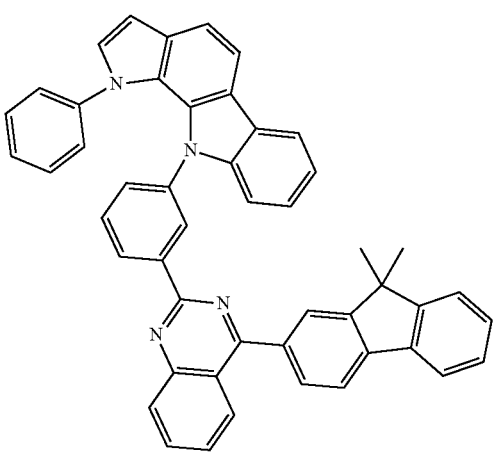

C114
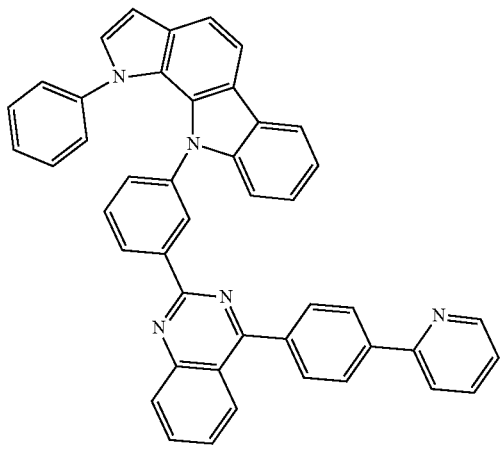
C117
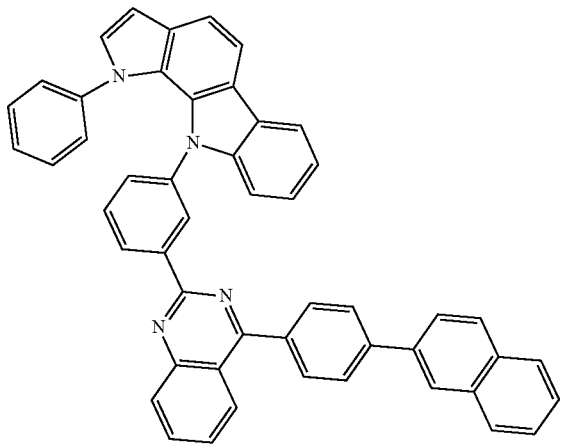
C115
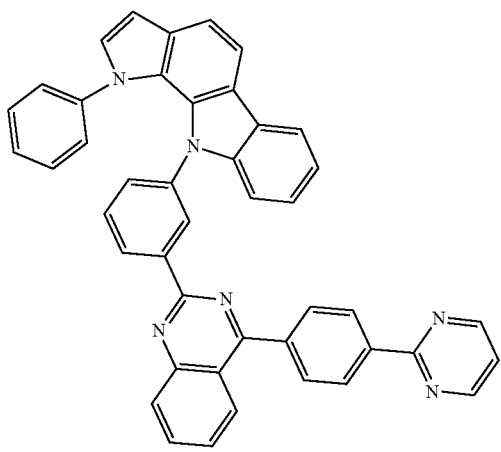
C118
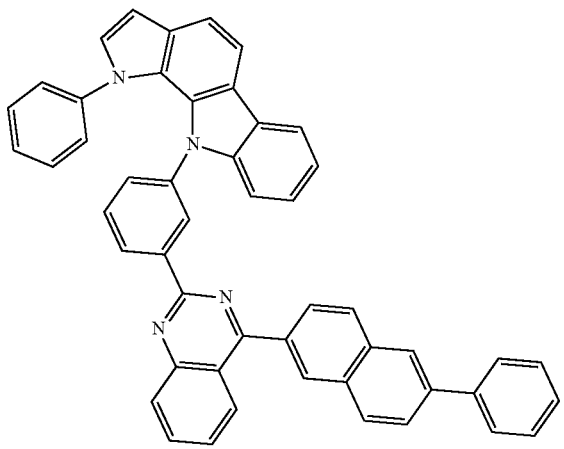
C116
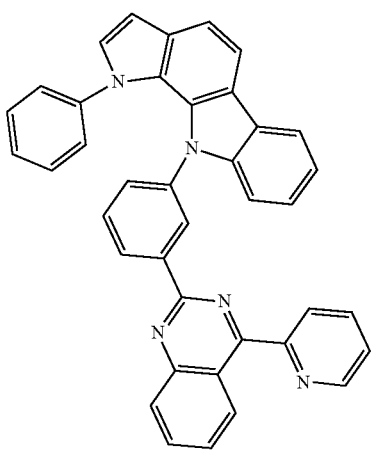
C119
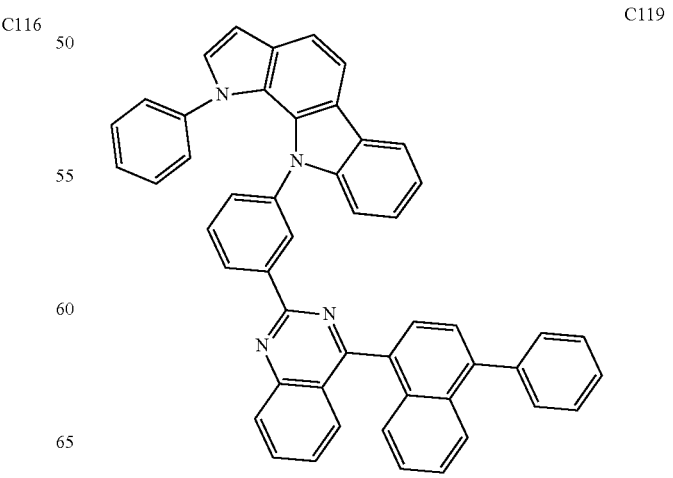

C120 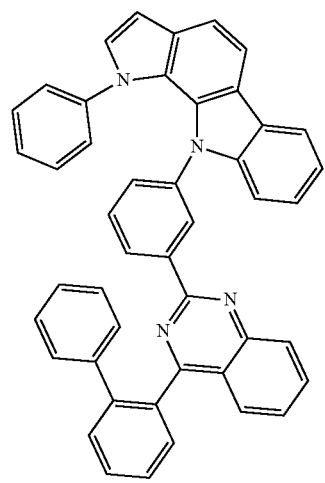
C121 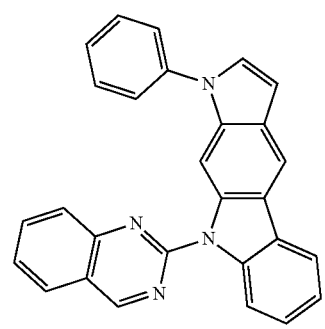
C122
C123
C124 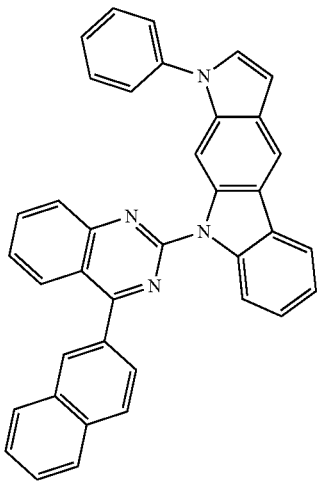
C125 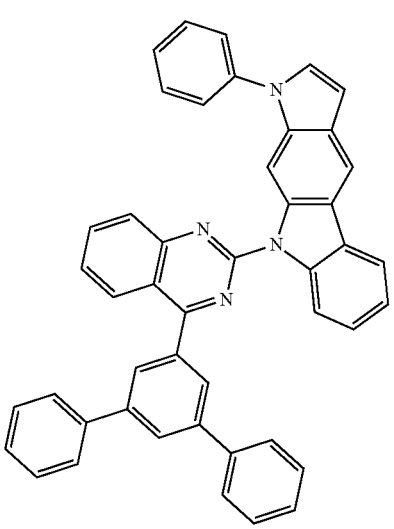
C126 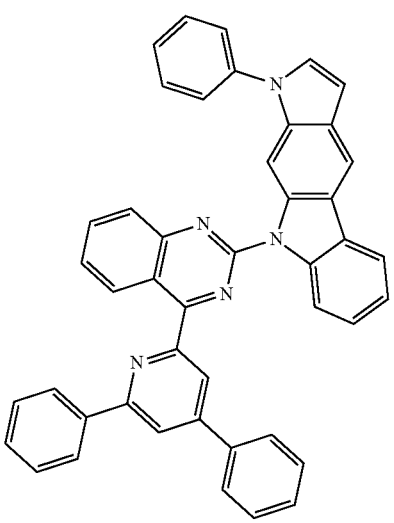

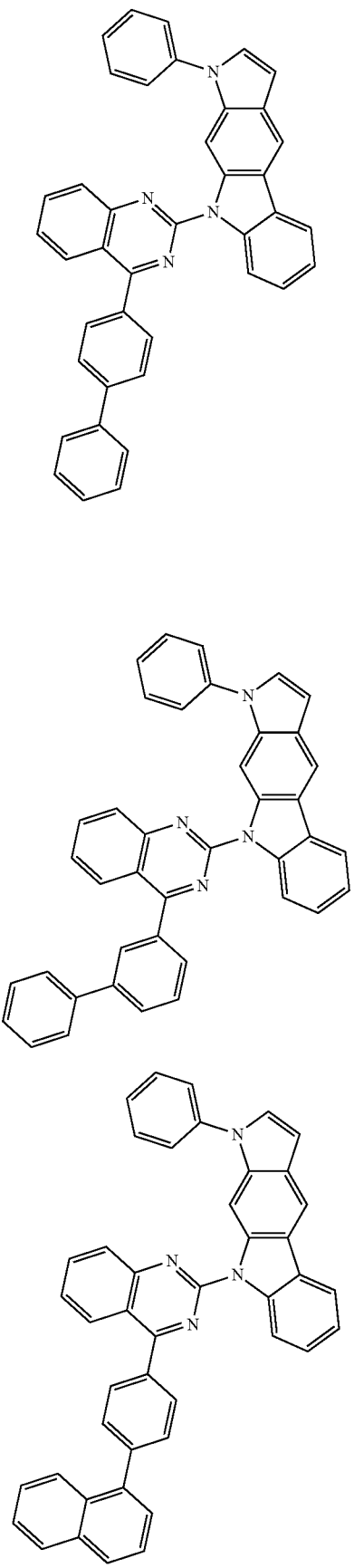
C127
C128
C129
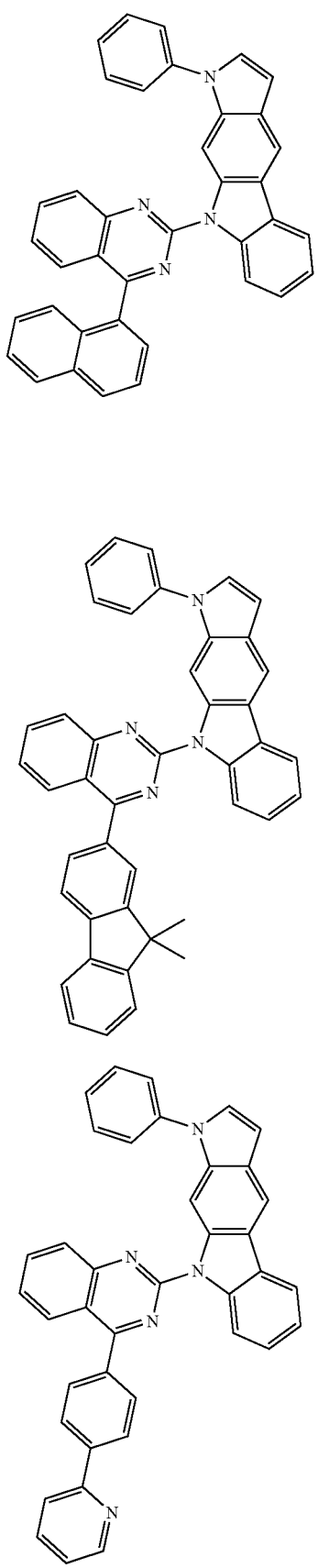
C130
C131
C132

-continued
C133
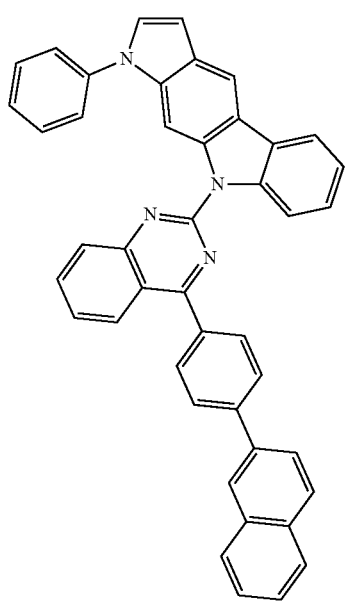
C134
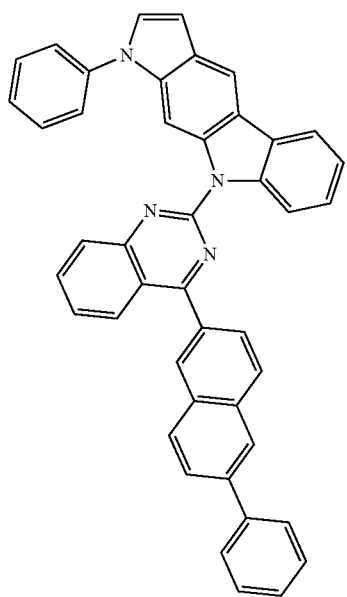
-continued
C135
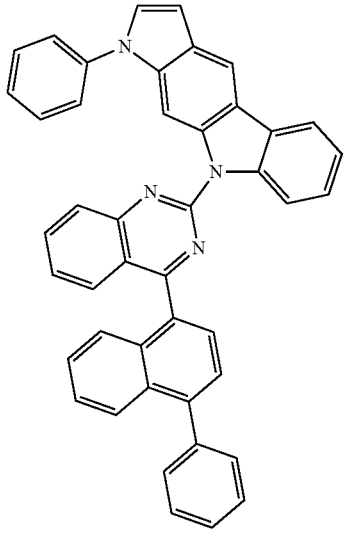
C136
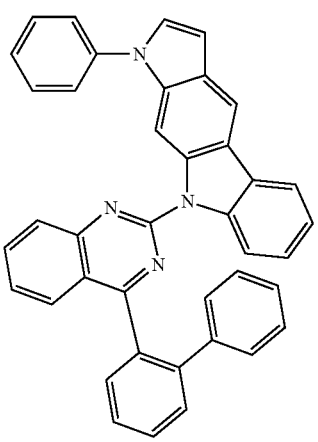
C137
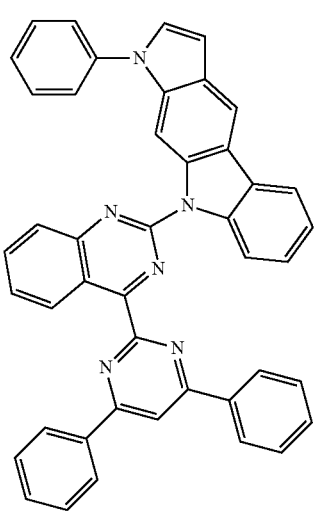

-continued
C138
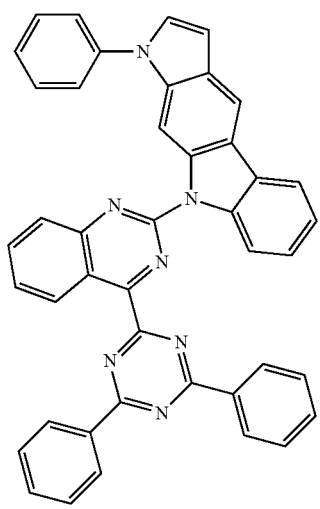
C139
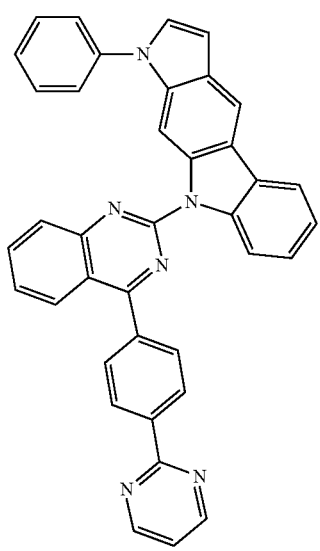
C140
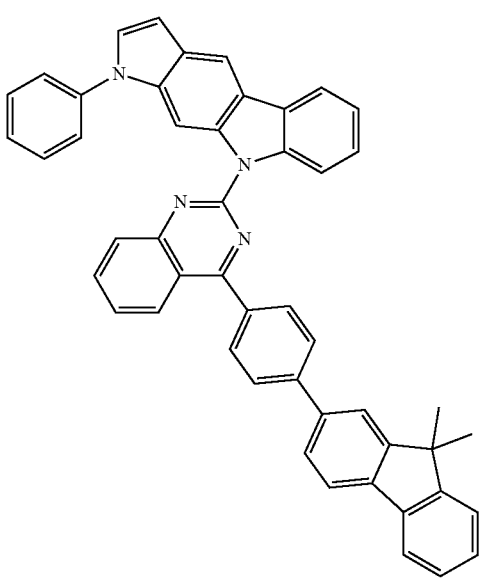
-continued
C141
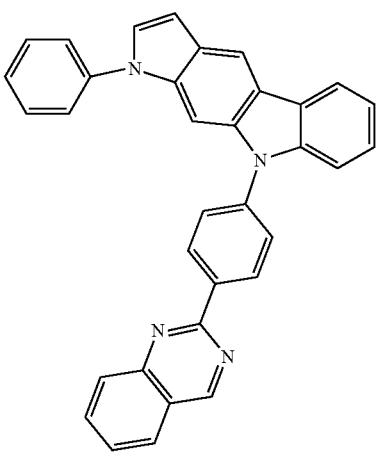
C142
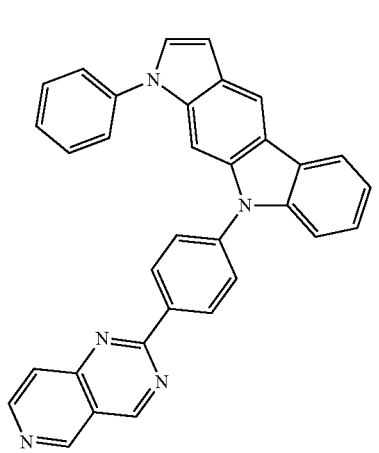
C143
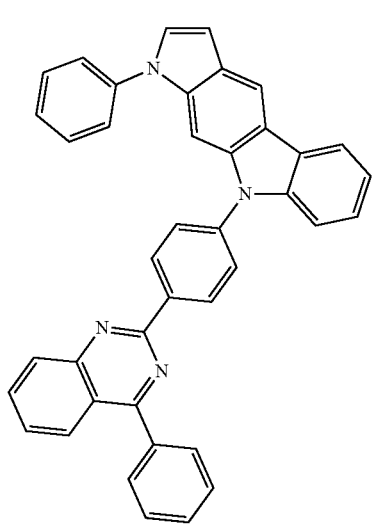

-continued
C144
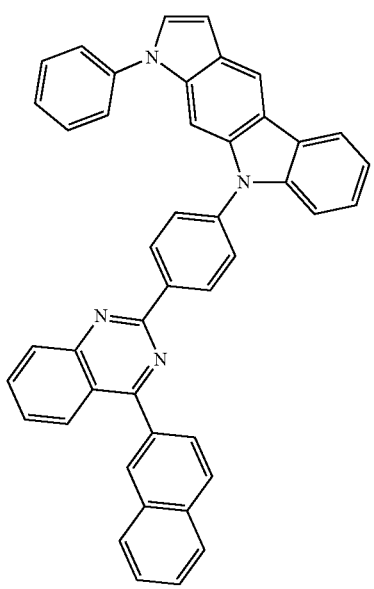
C145
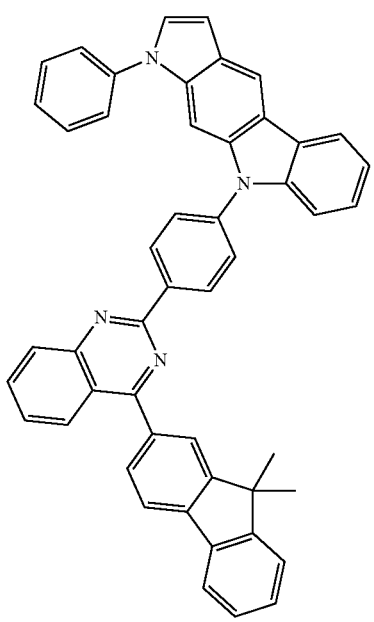
C146
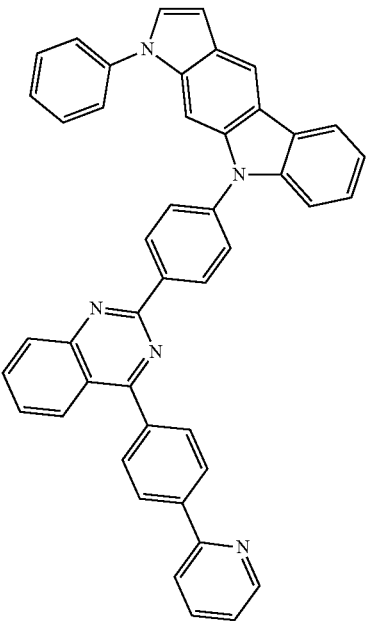
C147

C148
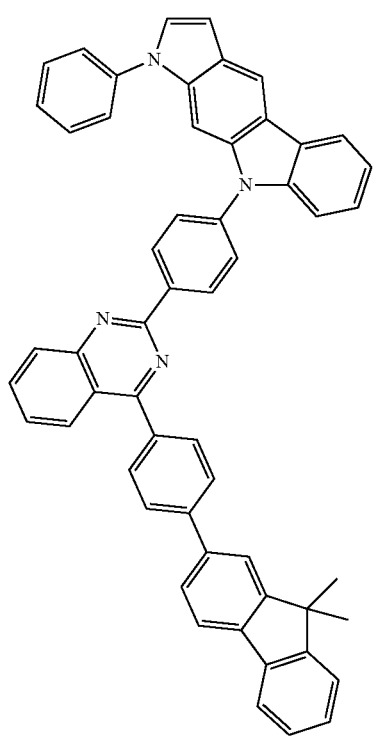
C150
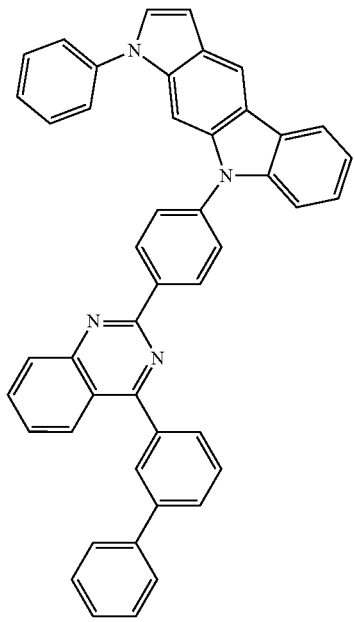
C149
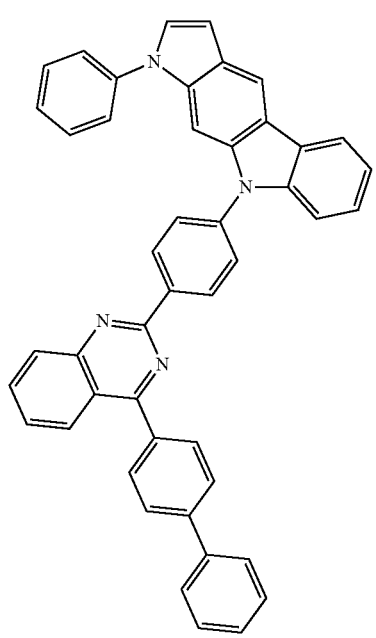
C151
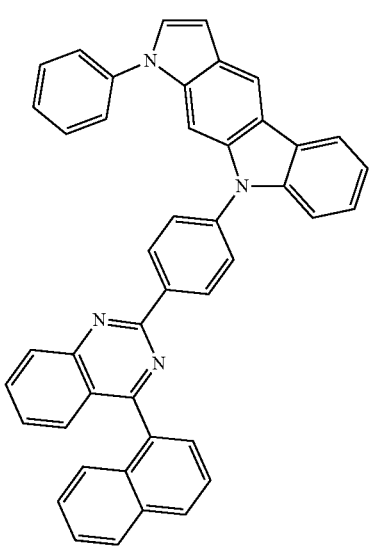

-continued
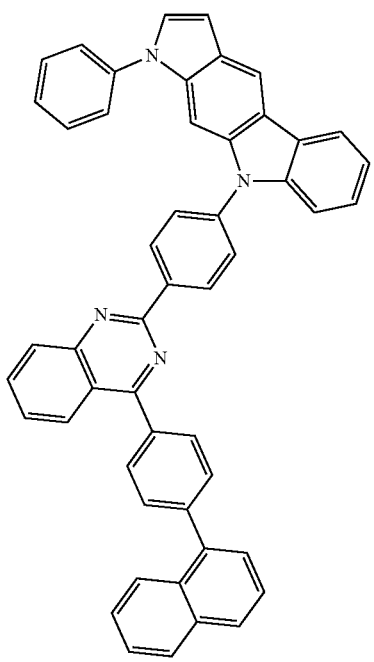
C152
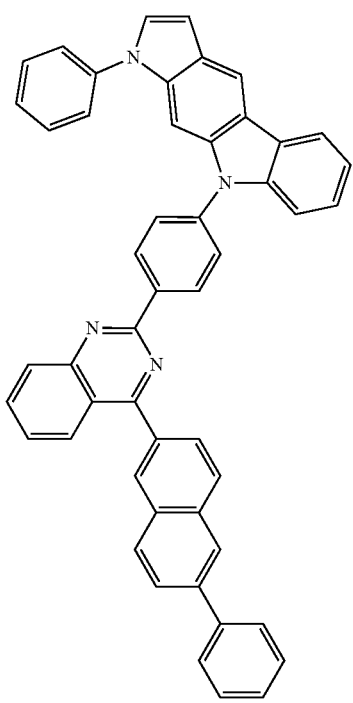
C154
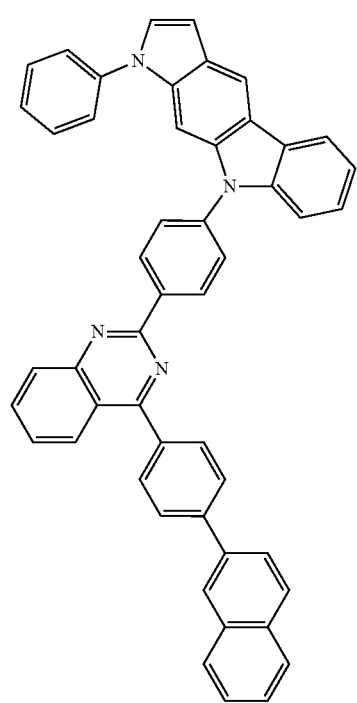
C153
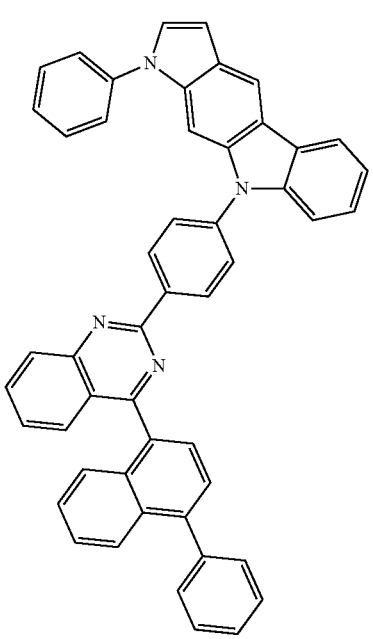
C155

C156
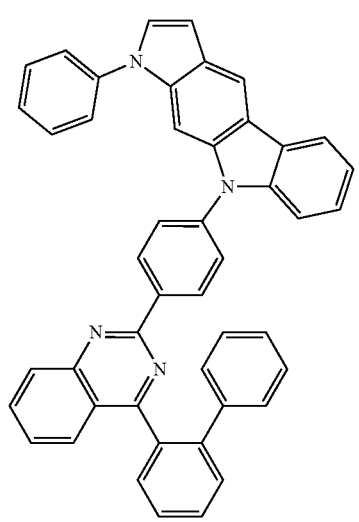
C159
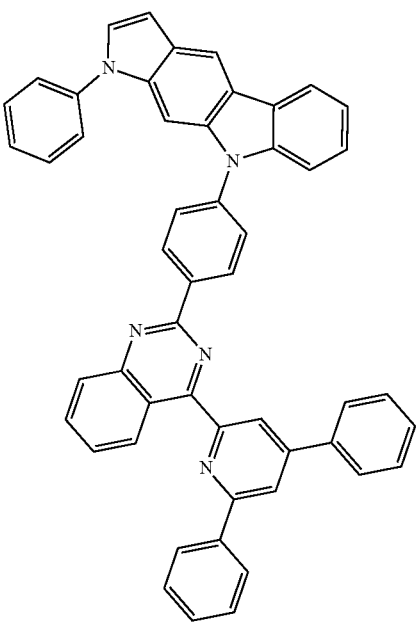
C157
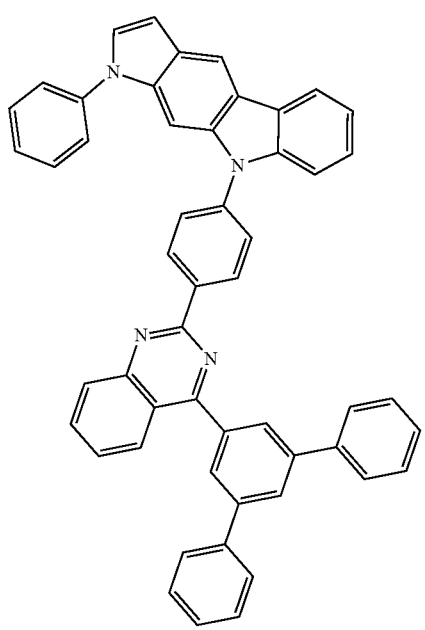
C160
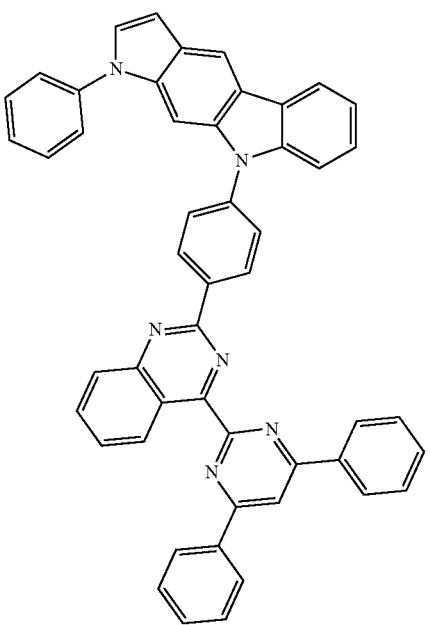

C160
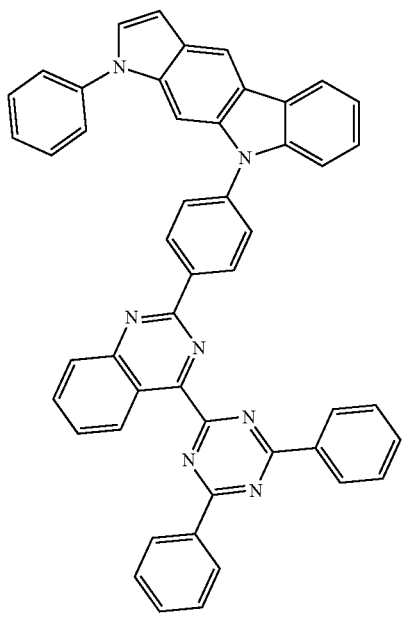
C161
C162
C163
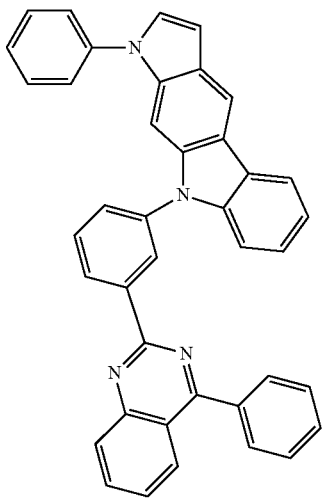
C164
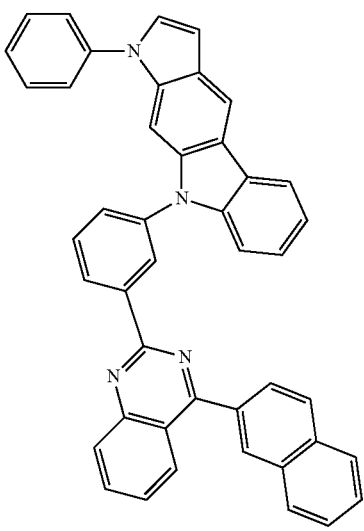
C165
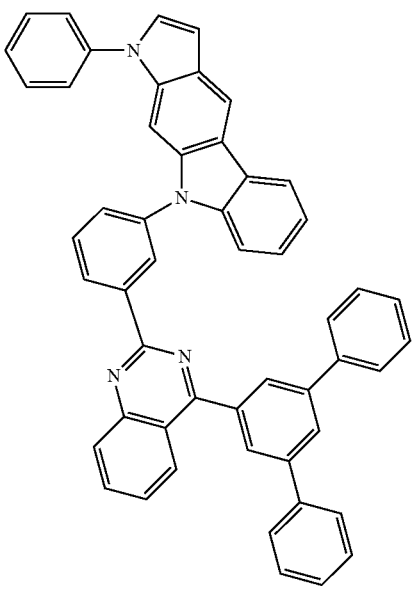

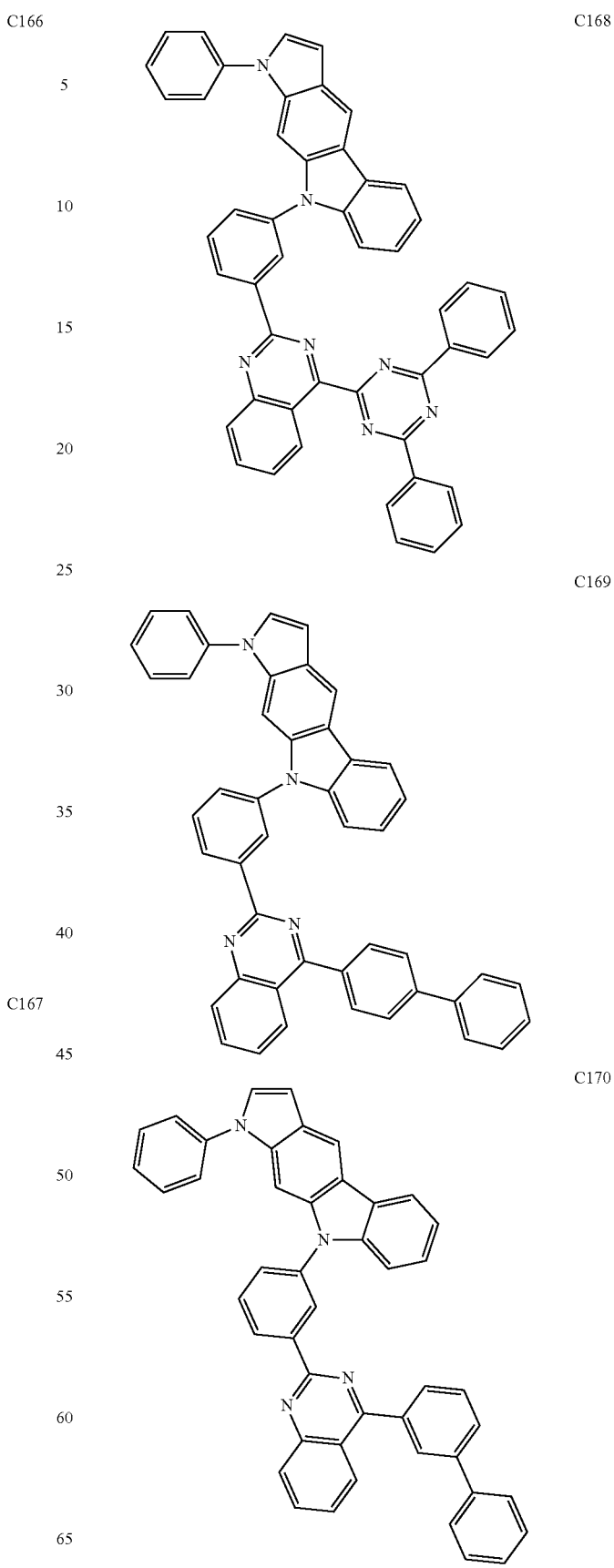

-continued
C171
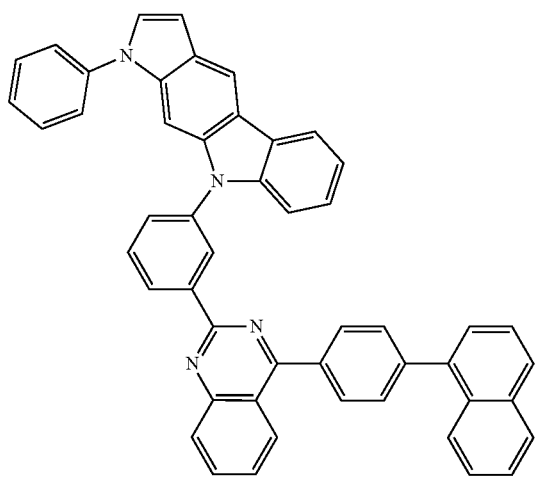
C172
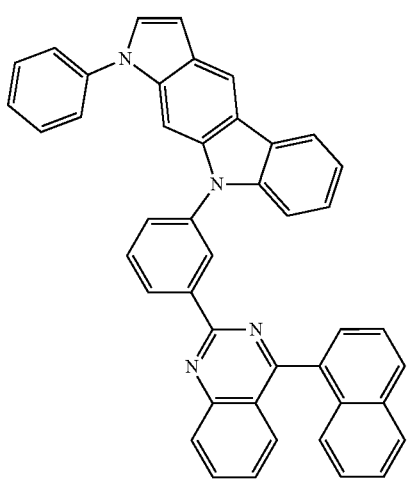
C173
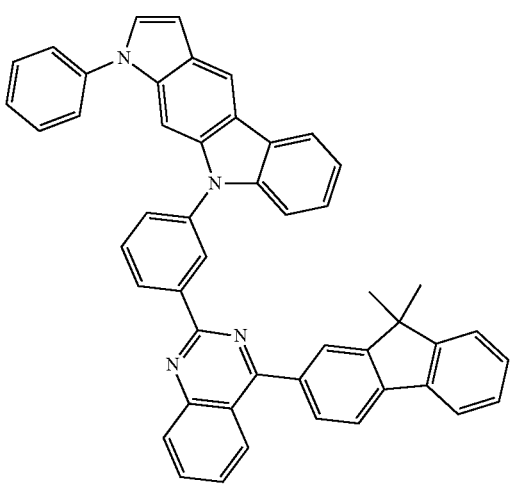
-continued
C174
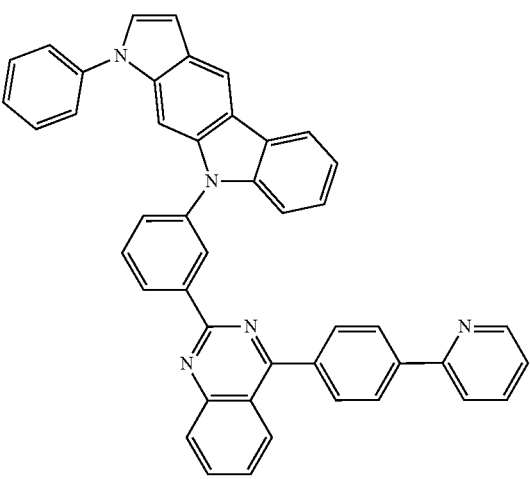
C175
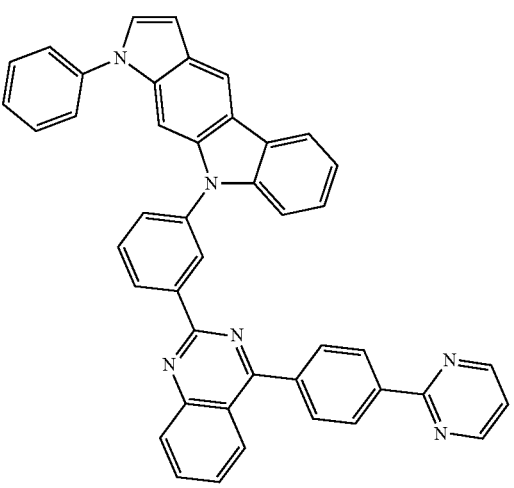
C176
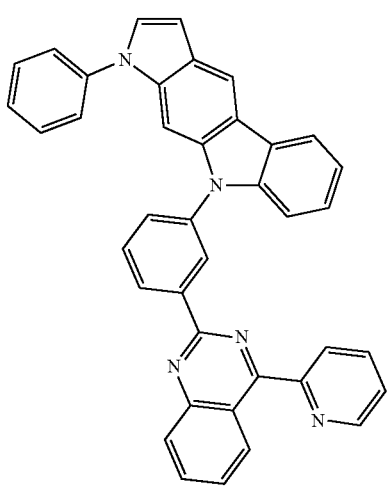

-continued
C177
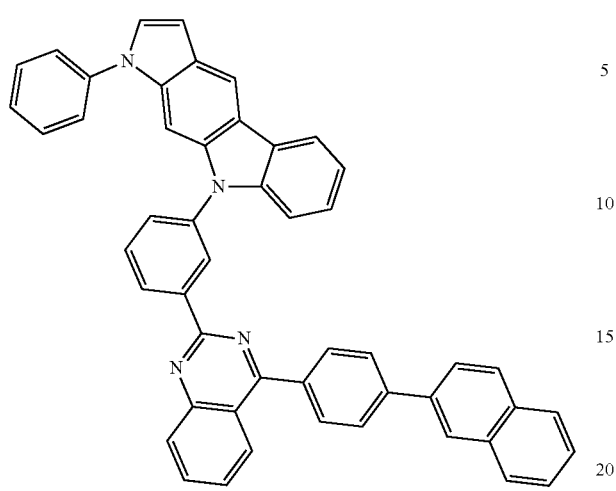
C178
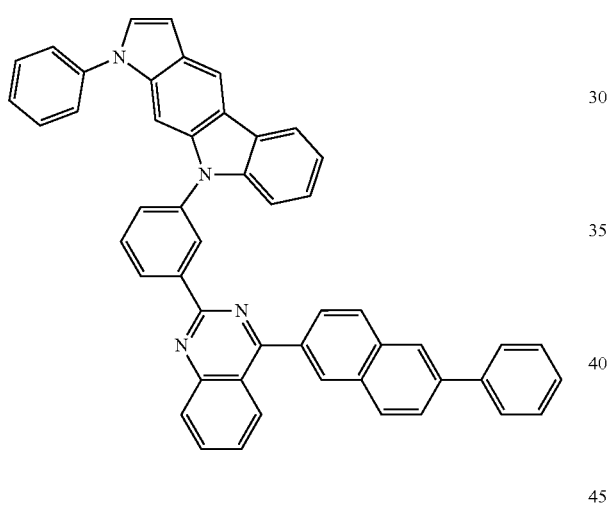
C179
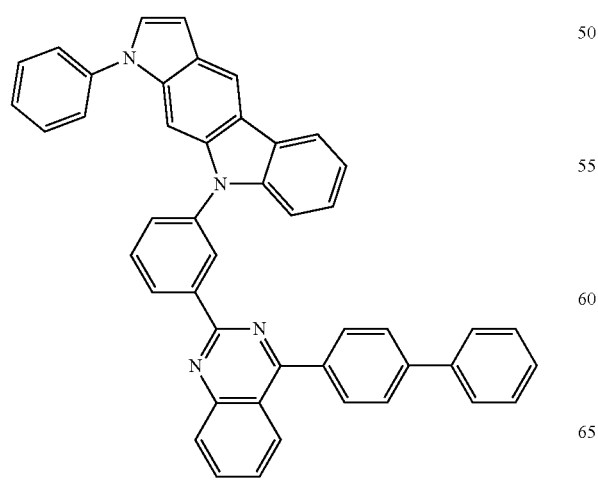
C180
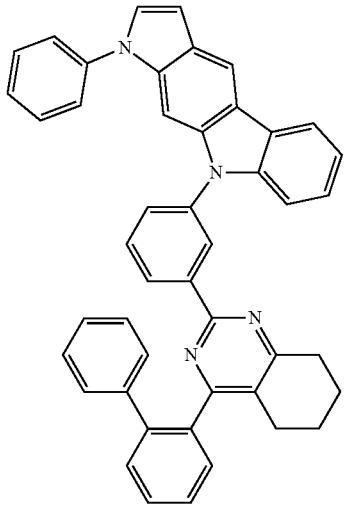
C181
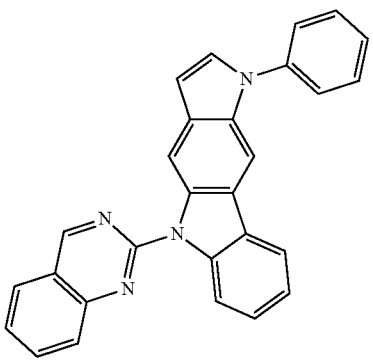
C182
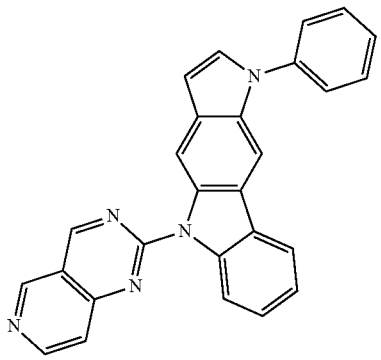

-continued
C183
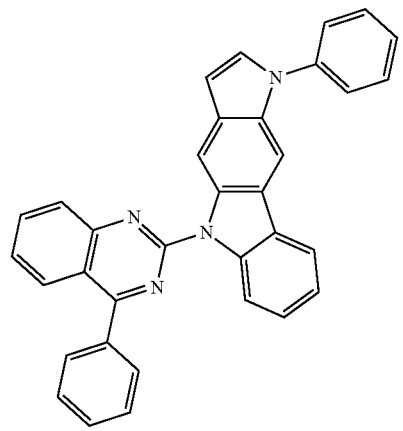
C184
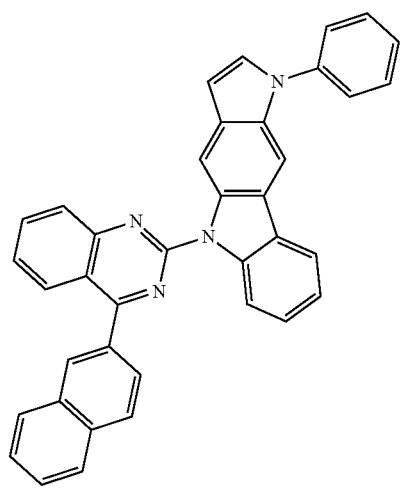
C185
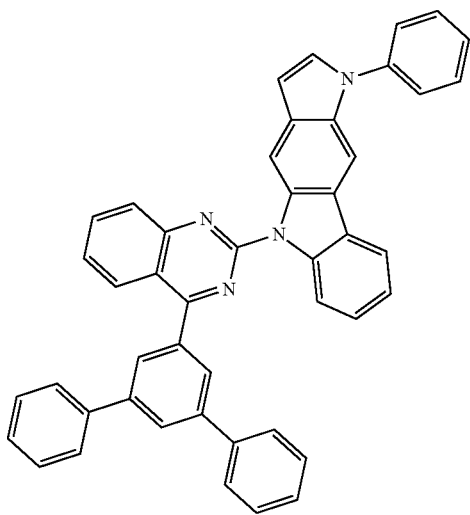
-continued
C186
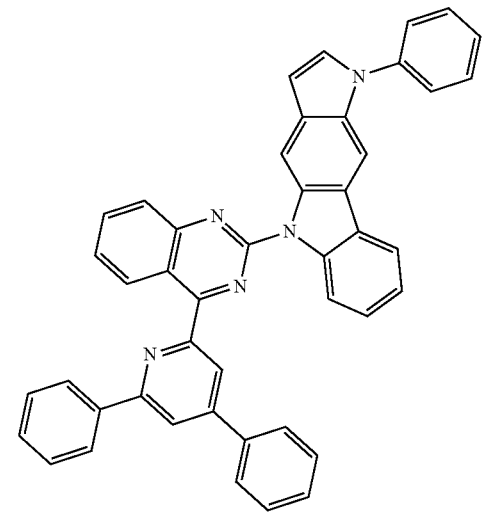
C187
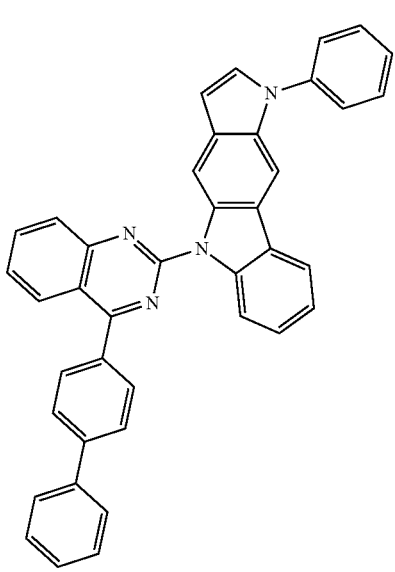
C188
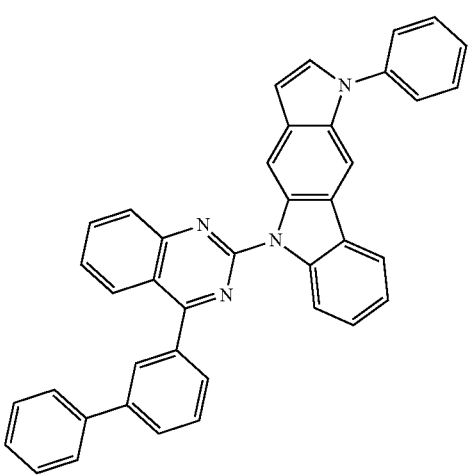

C189
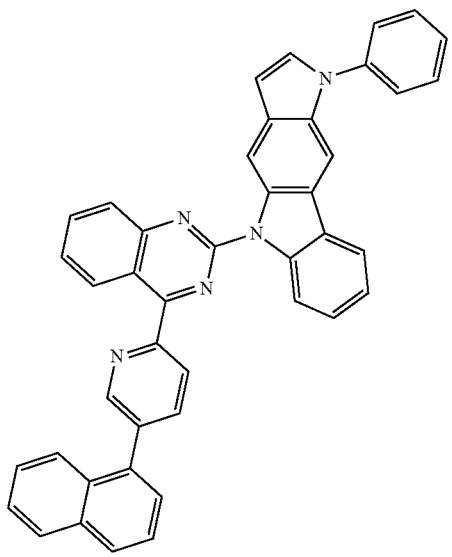
C190
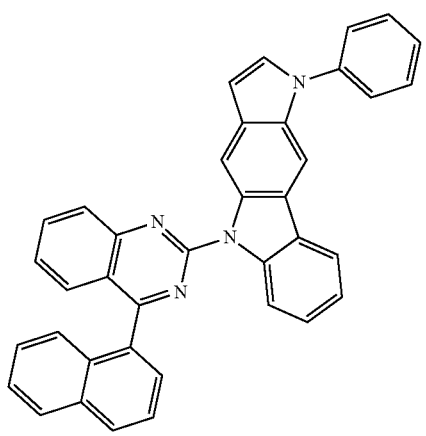
C192
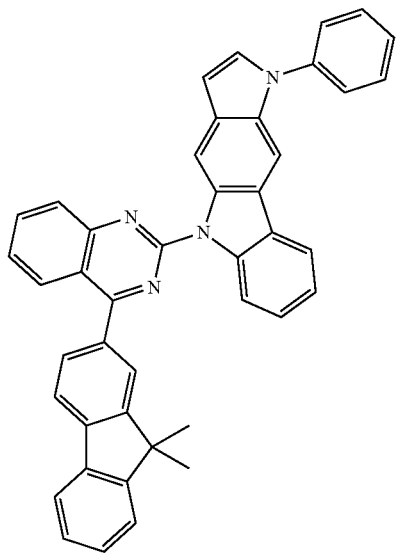
C193
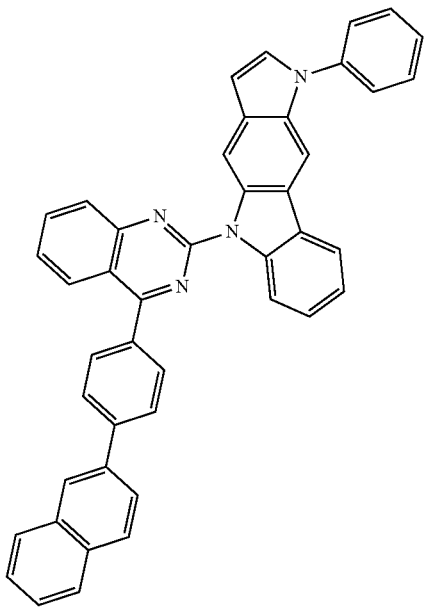
C194
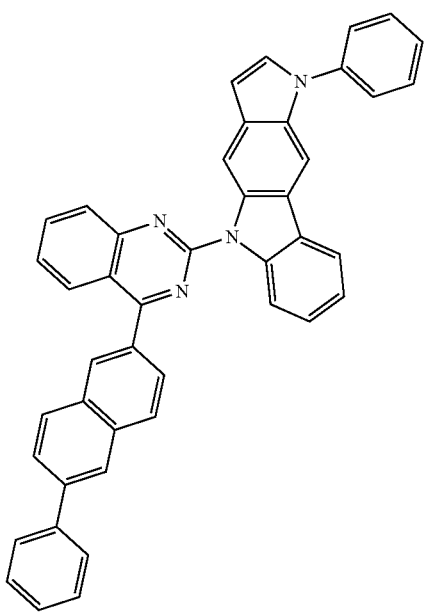

-continued
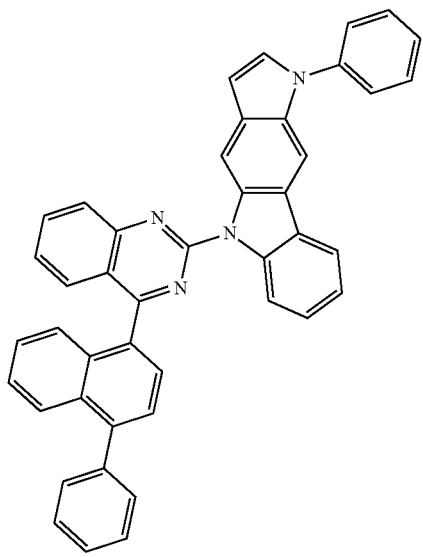
C195
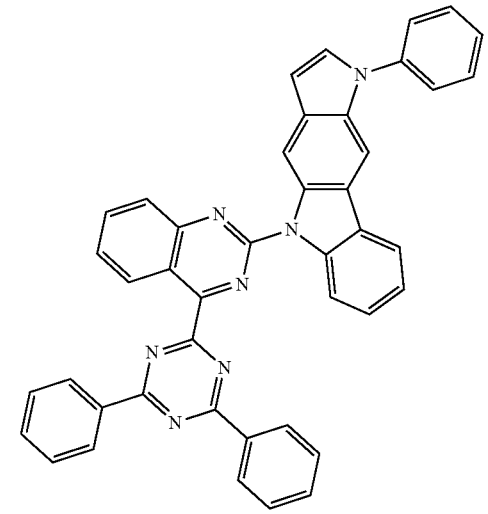
C199
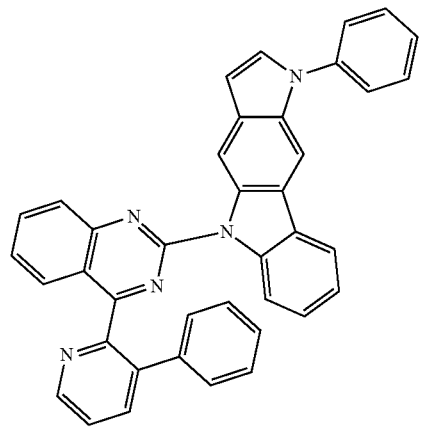
C196
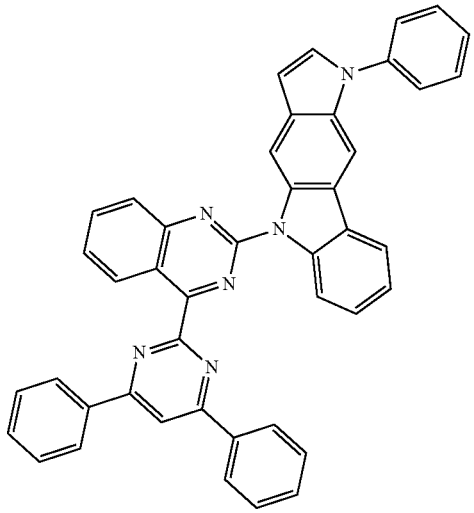
C197
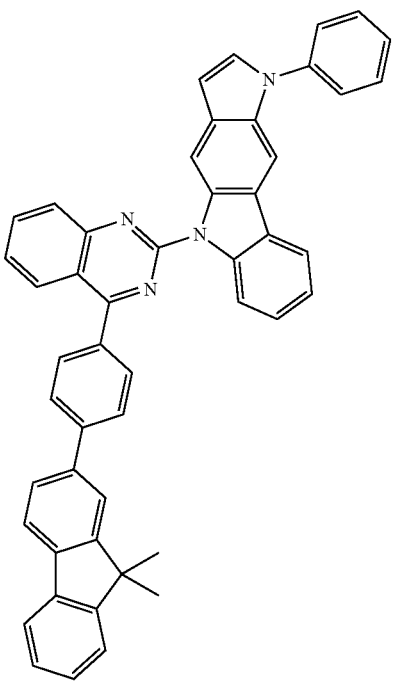
C200

C201
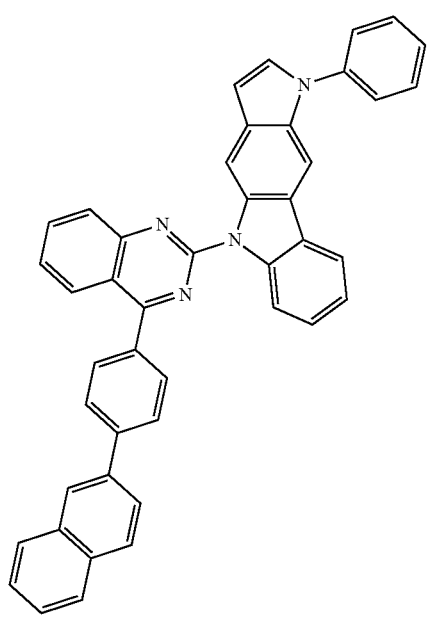
C202
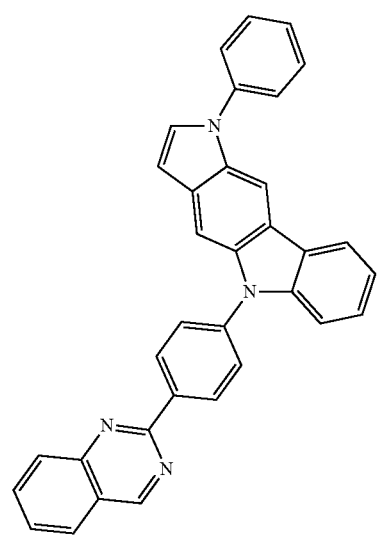
C203
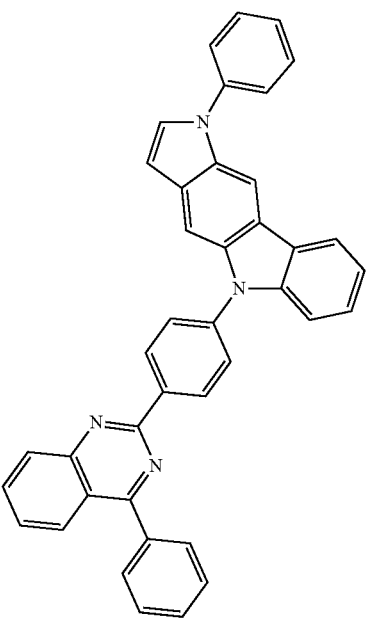
C204
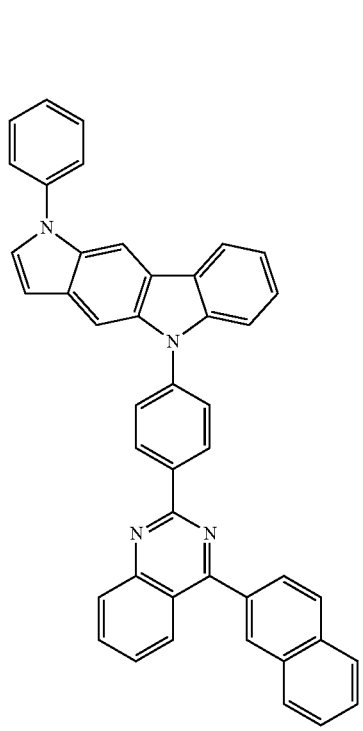

C205
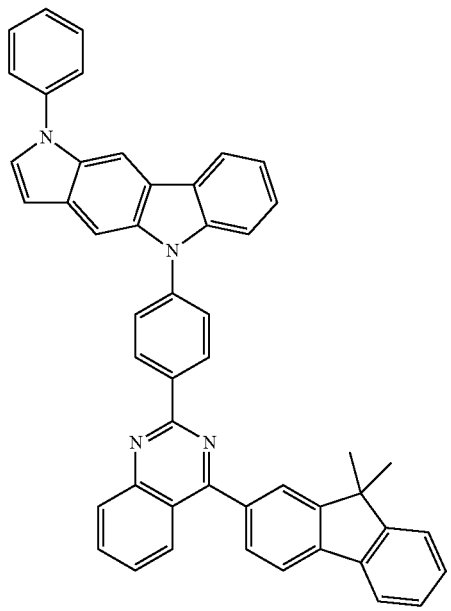
C206
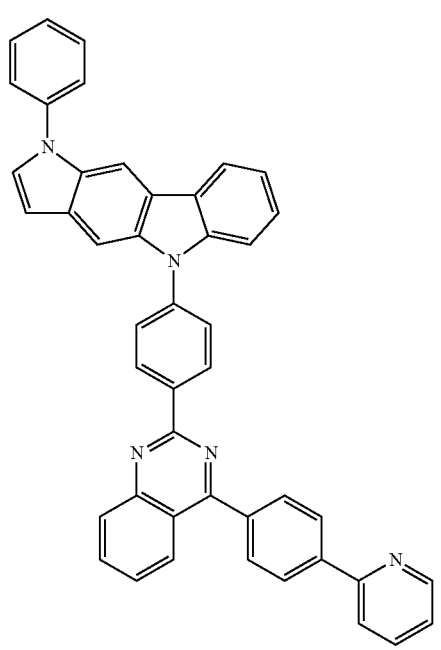
C207
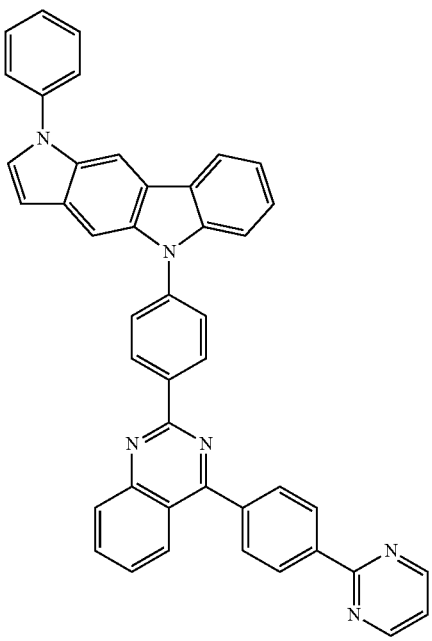
C208
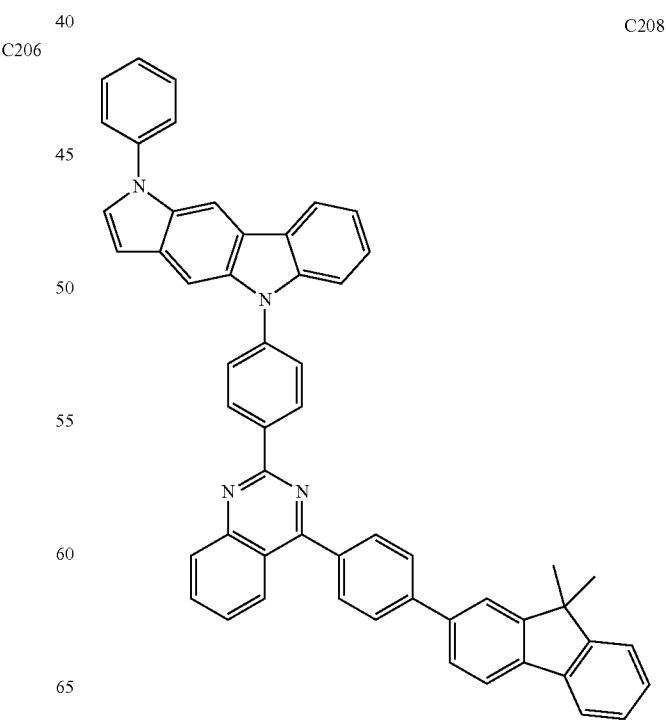

C209
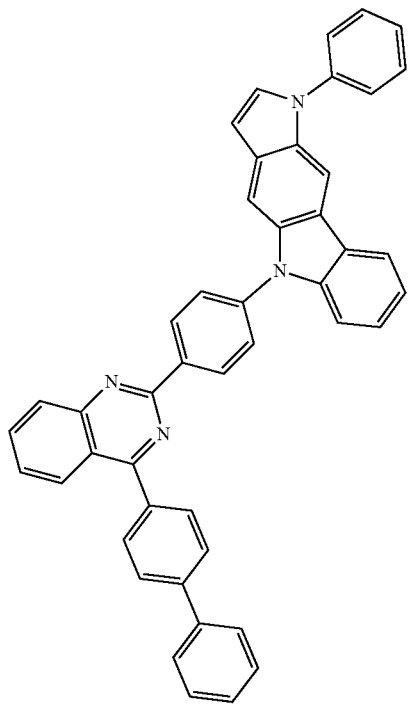
C211
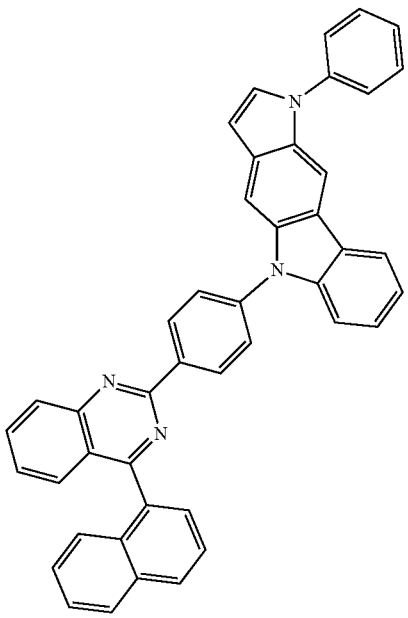
C210
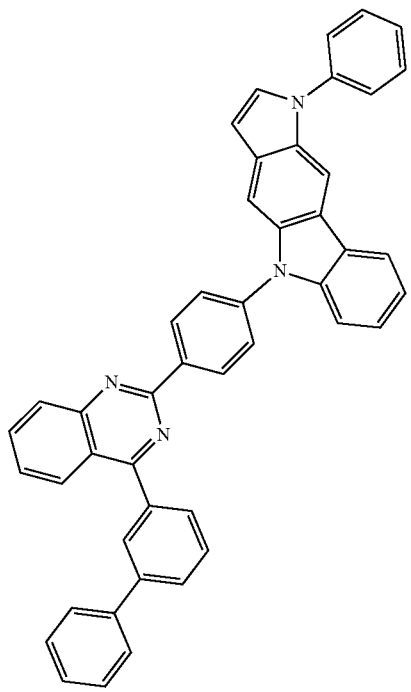
C212
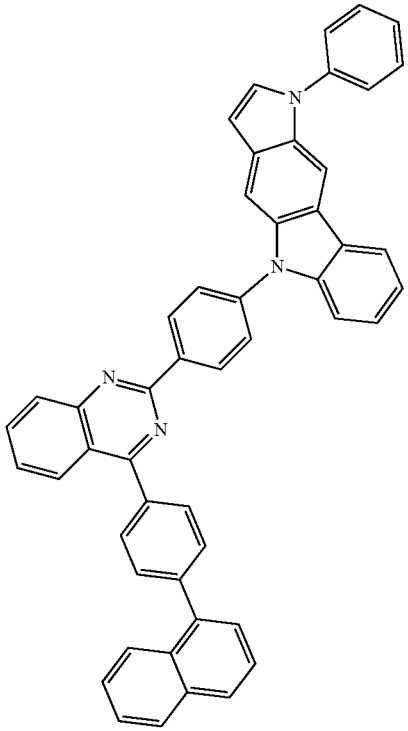

-continued
C213
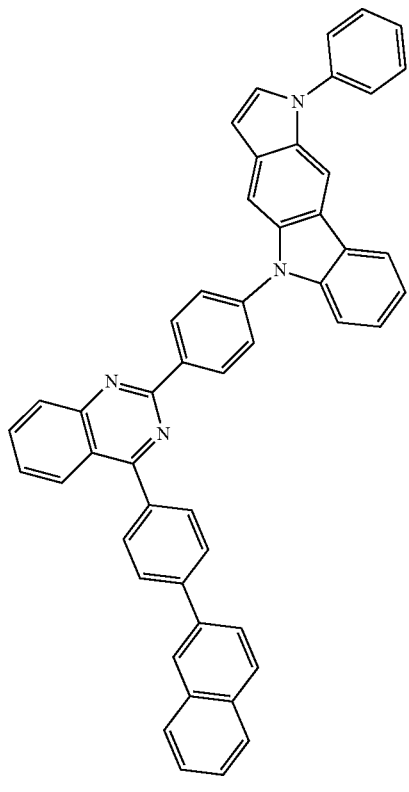
C214
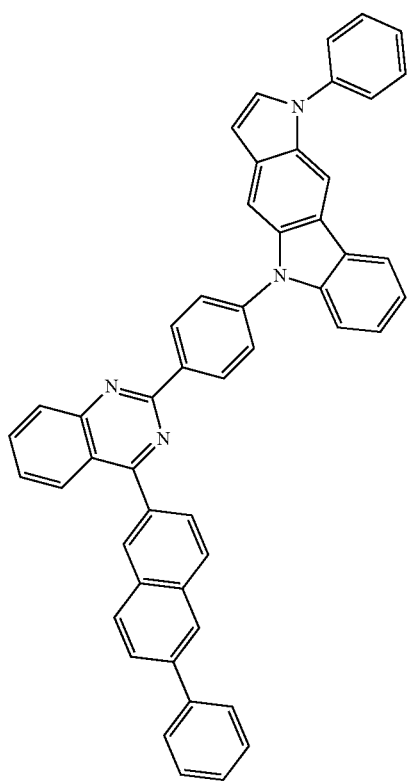
C215
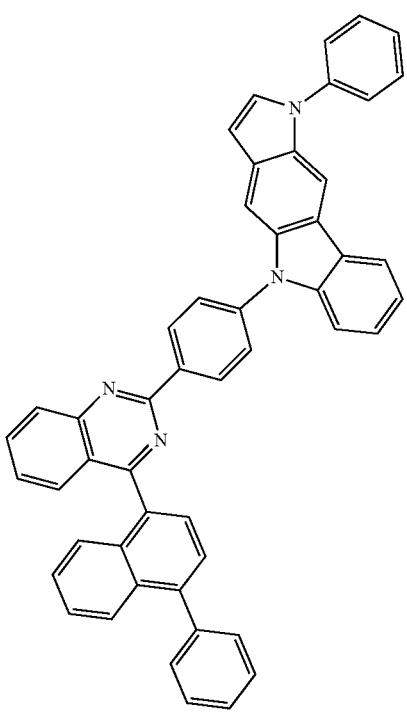
C216
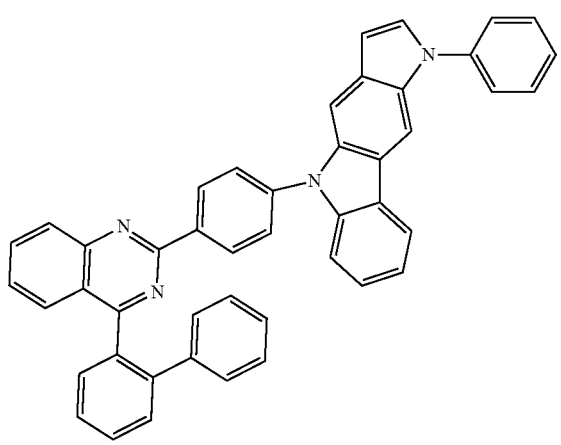
C217
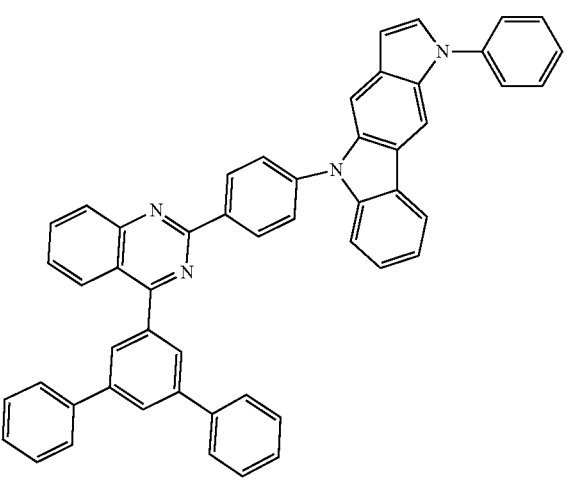

C218
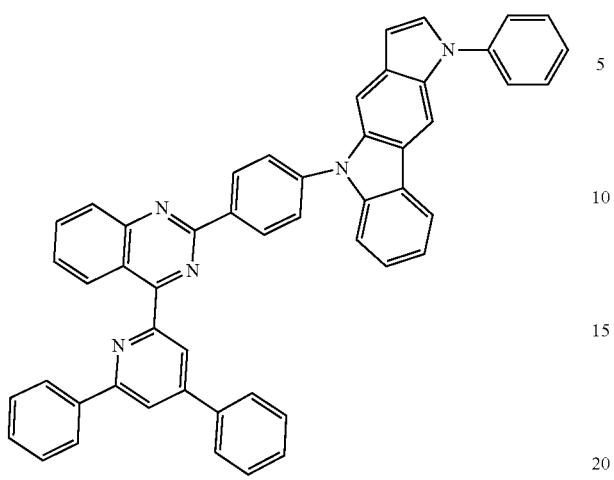
C219
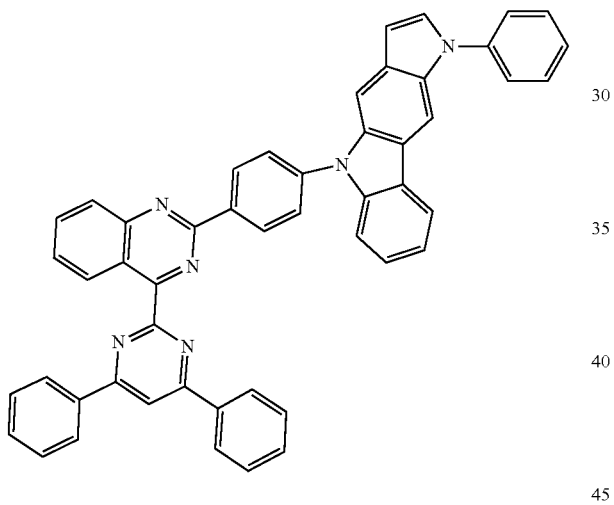
C220
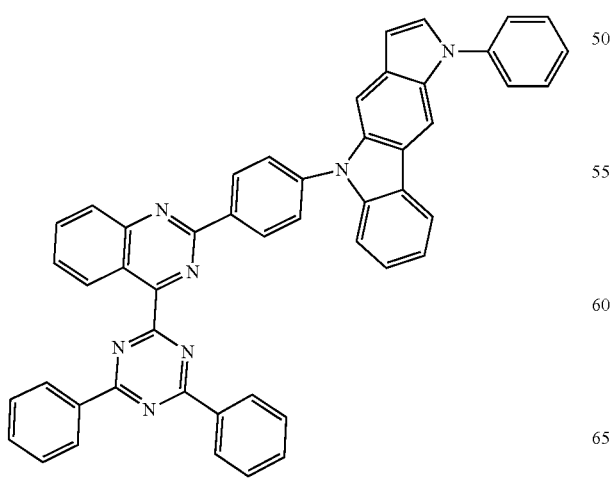
C221
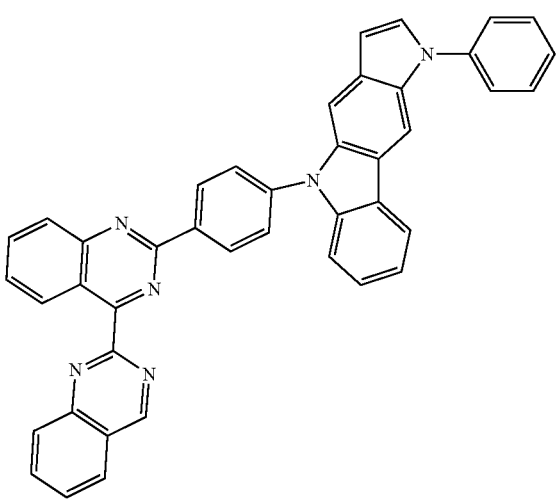
C222
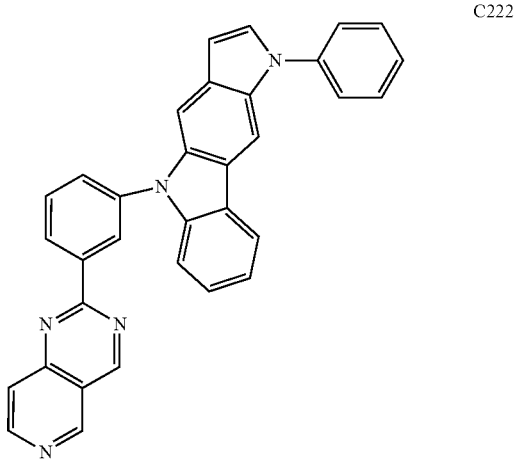
C223
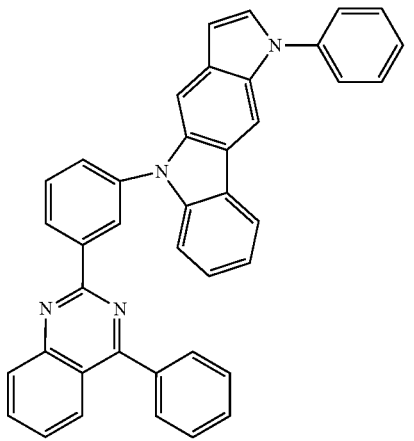

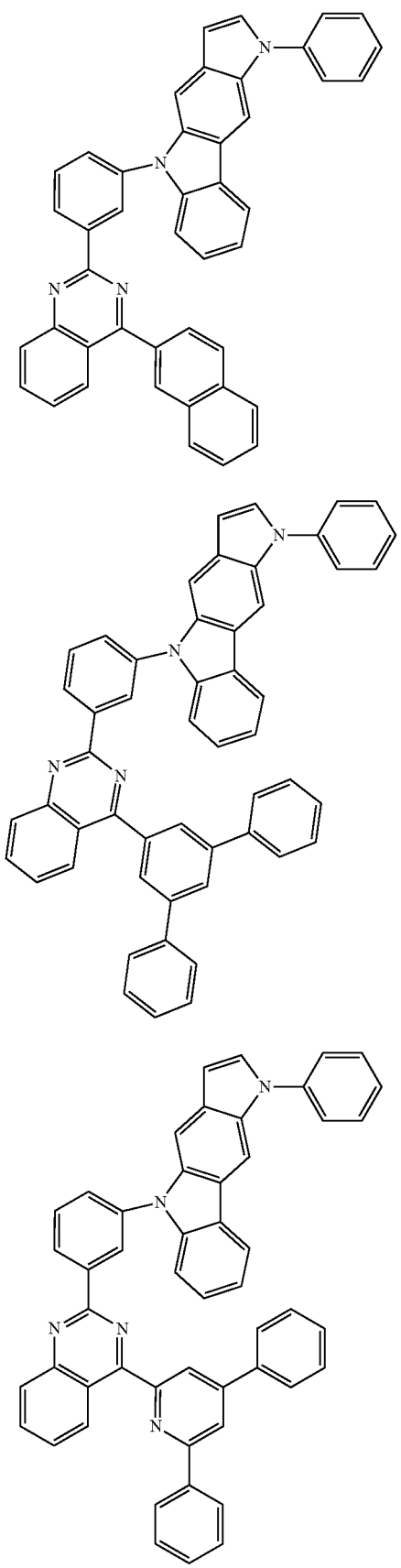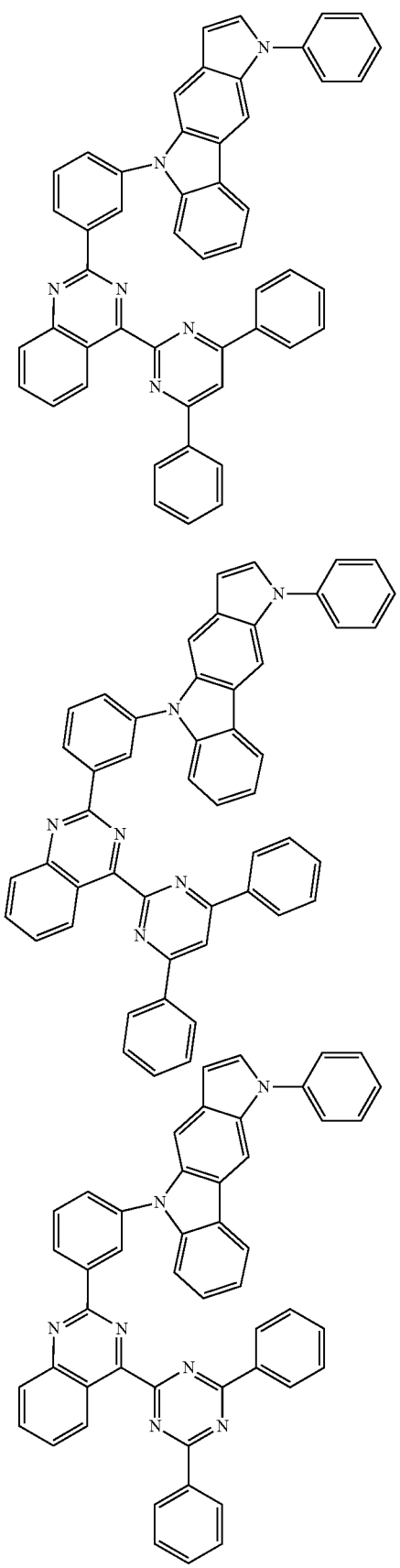

C229
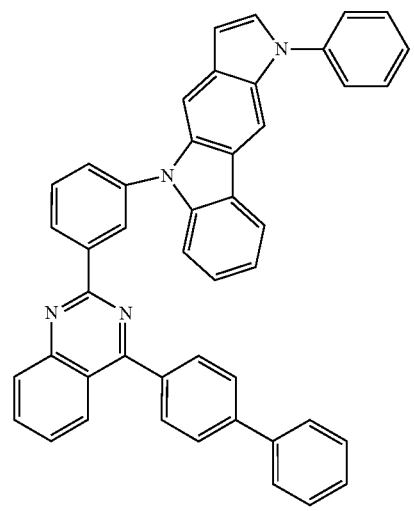
C230
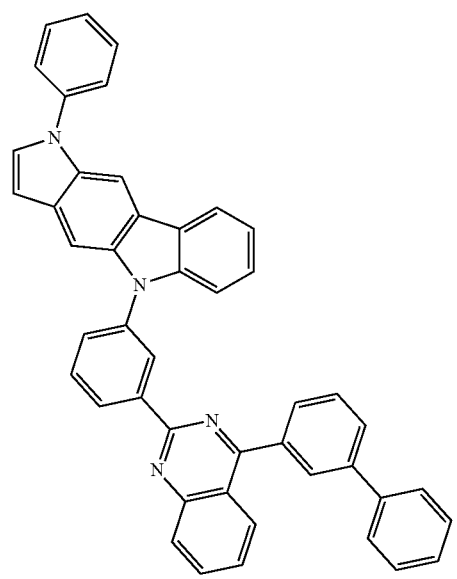
C231
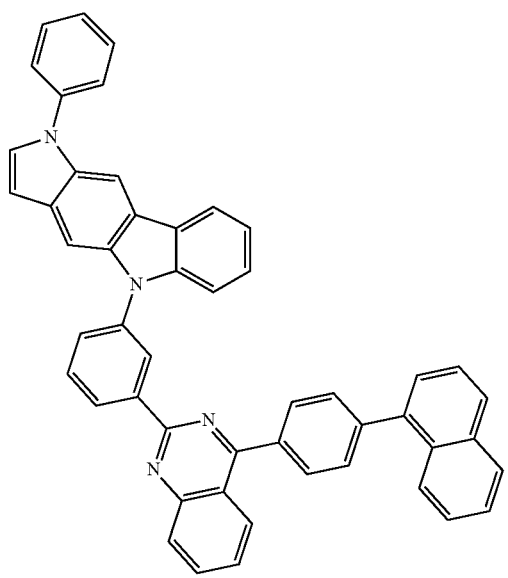
C232
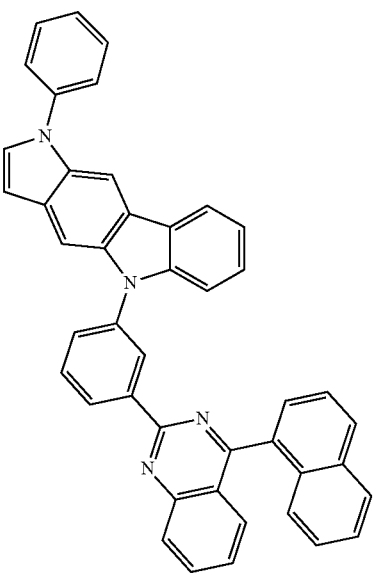
C233
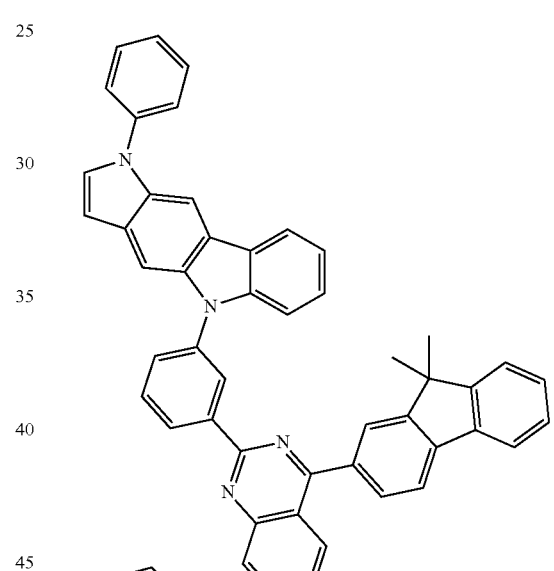
C234
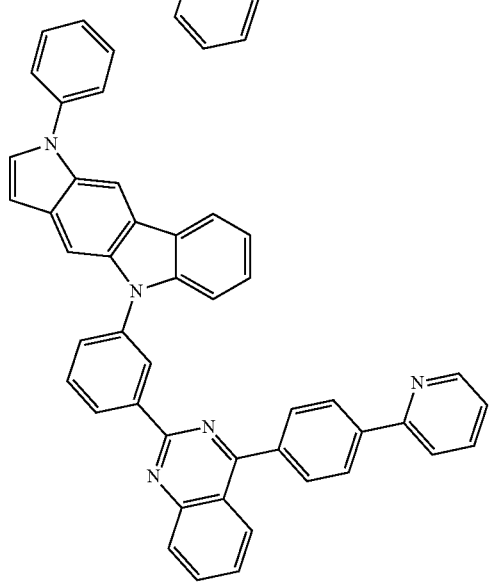

-continued
C235
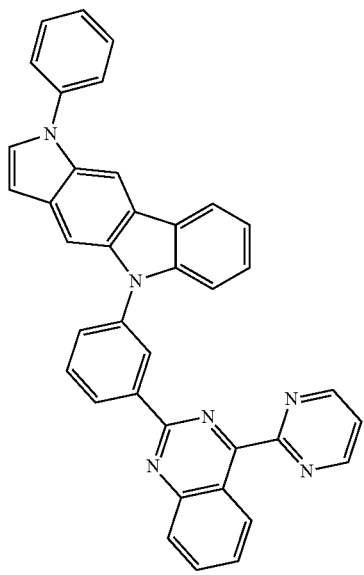
C236
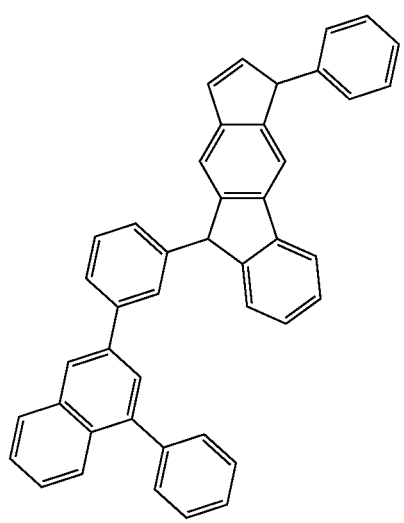
C237
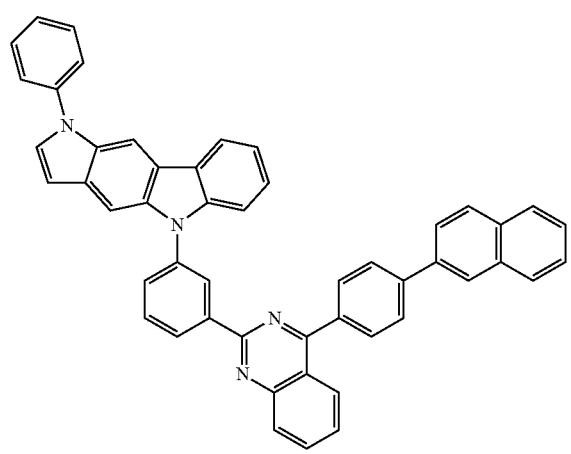
-continued
C238
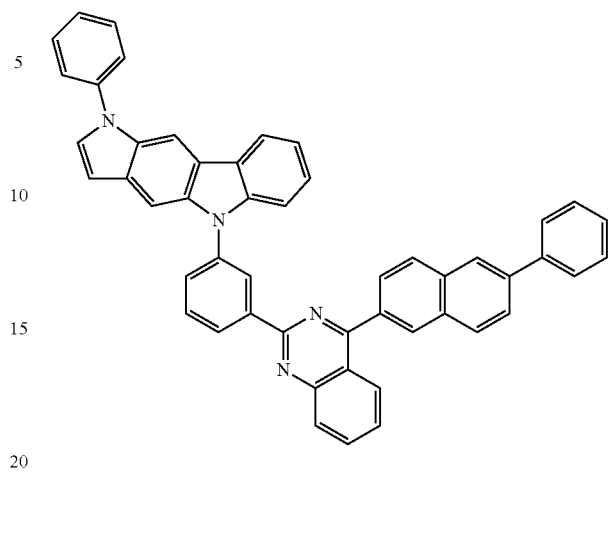
C239
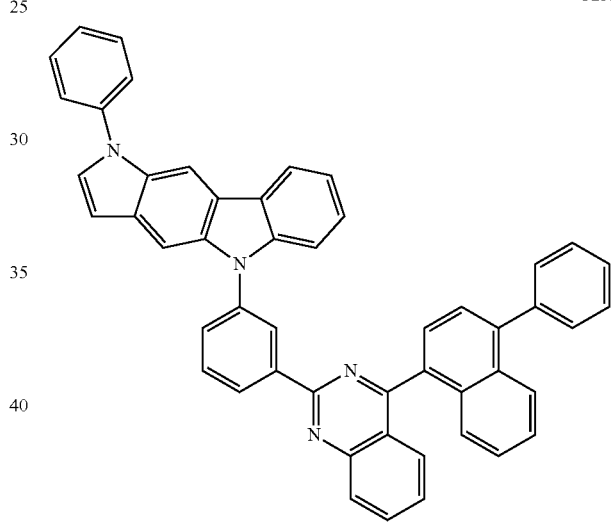
C240
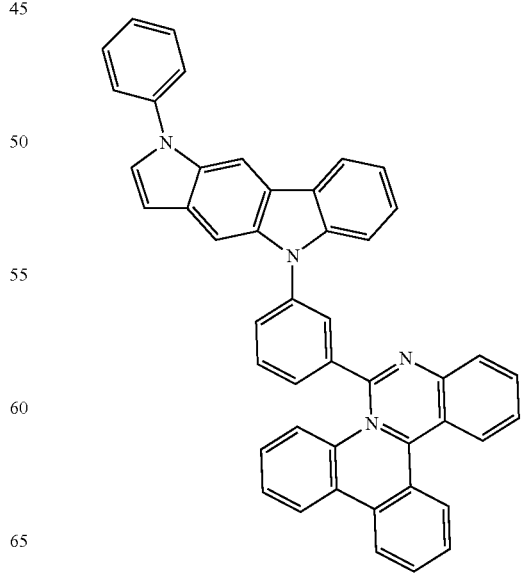

-continued
C241

C242

C243
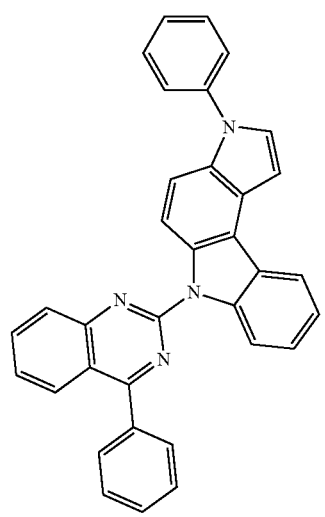
-continued
C244
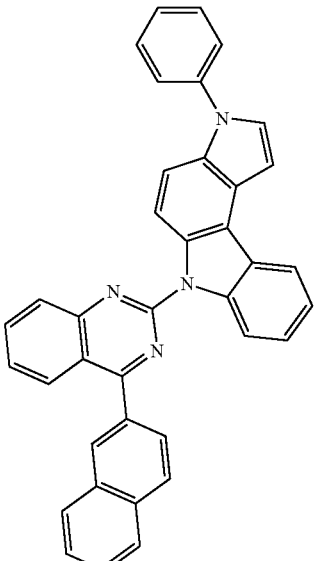
C245
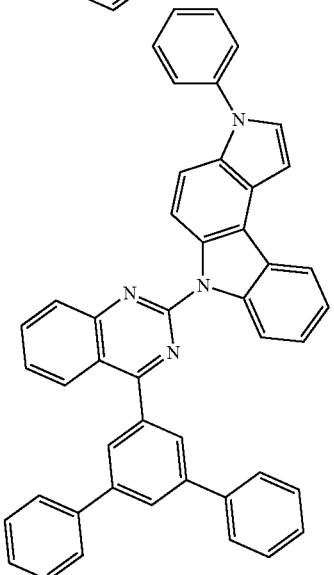
C246
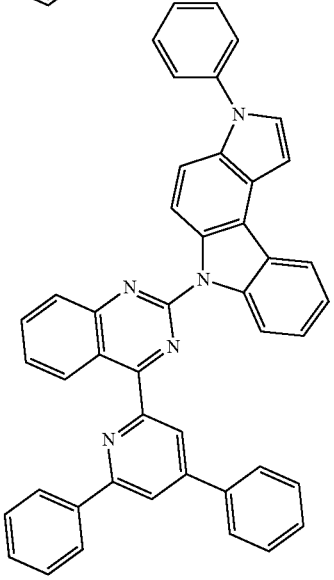

C247
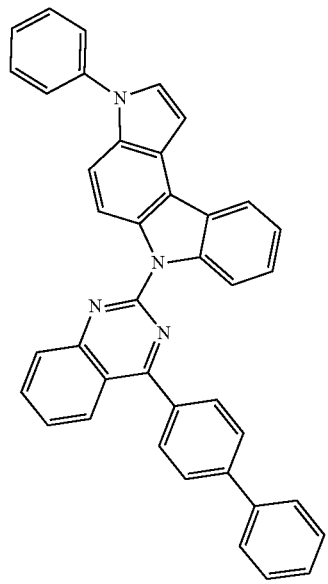
C248
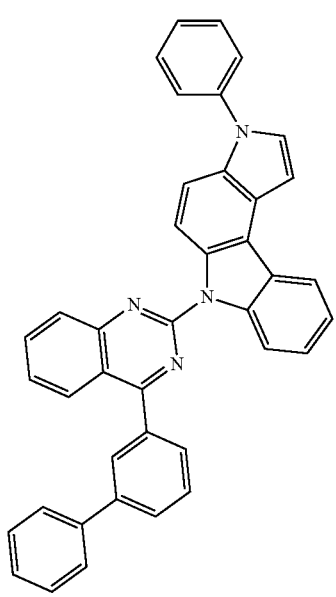
C249
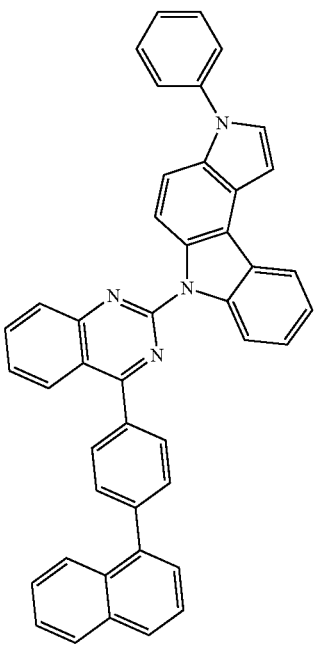
C250
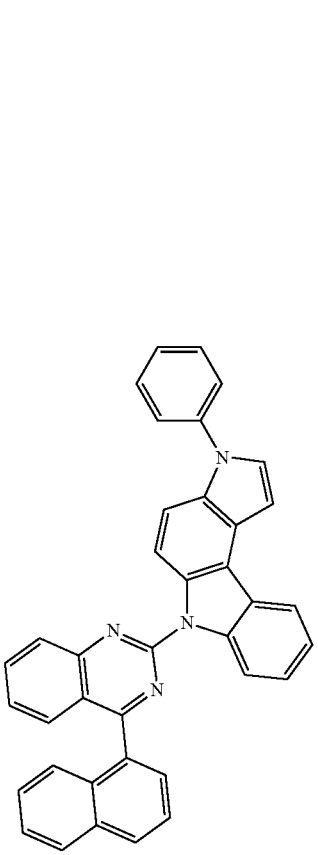

C251
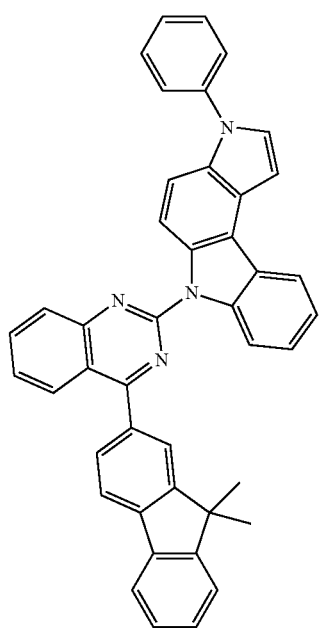
C252
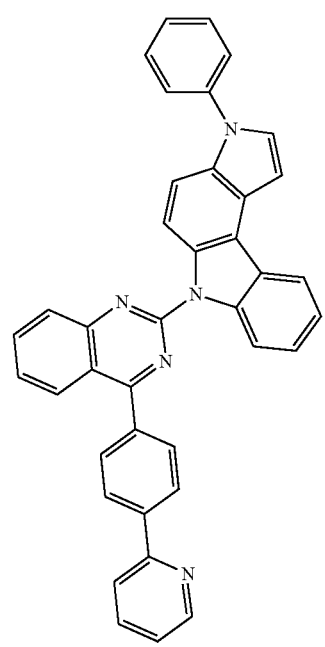
C253
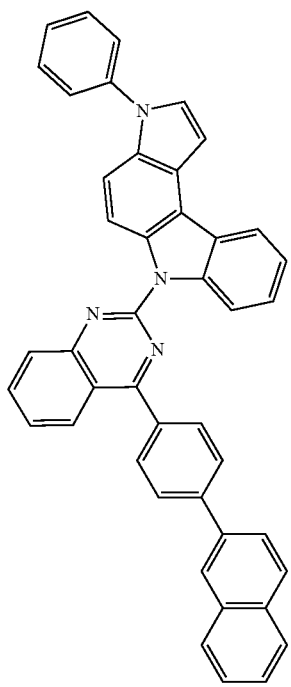
C254
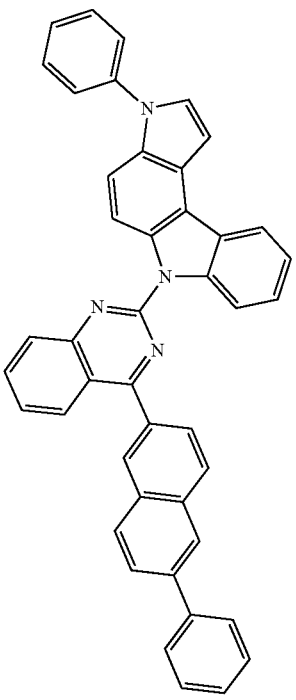

C255
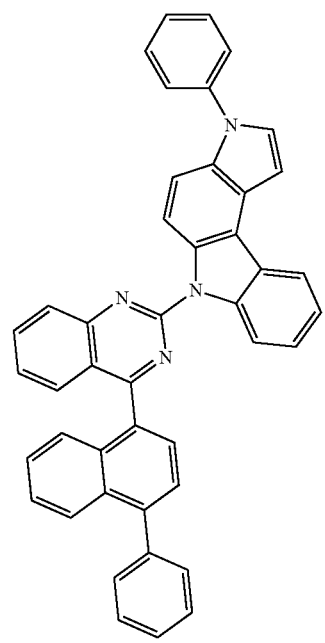
C257
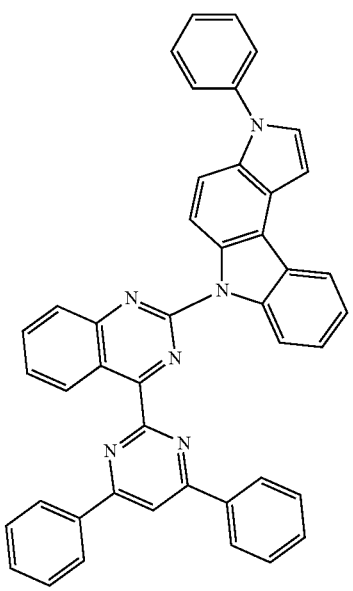
C256
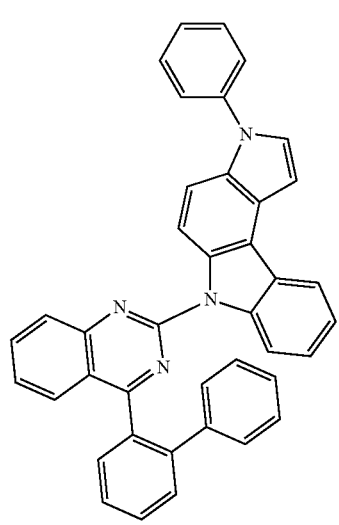
C258
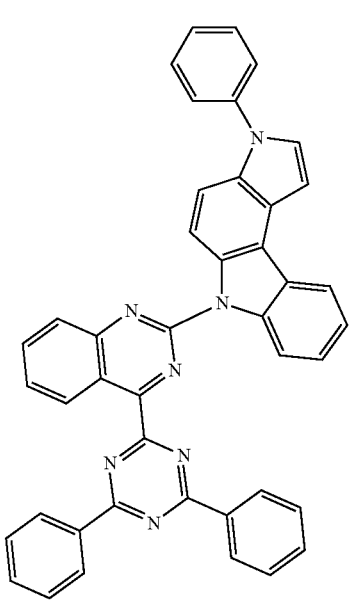

C259
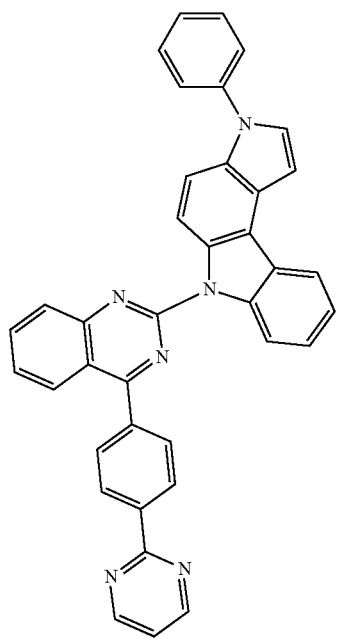
C260
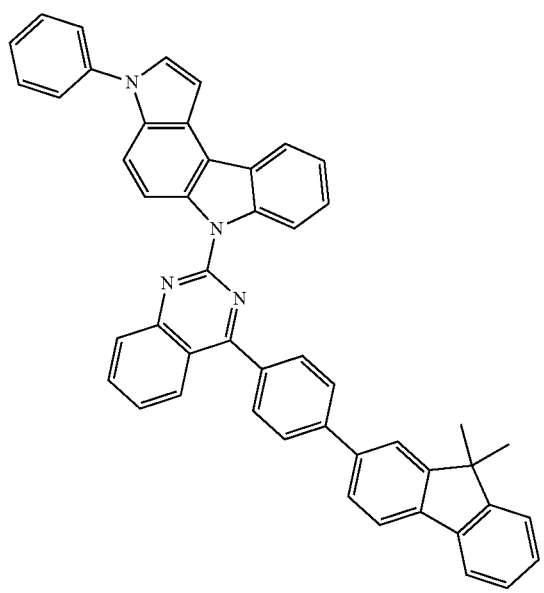
C261
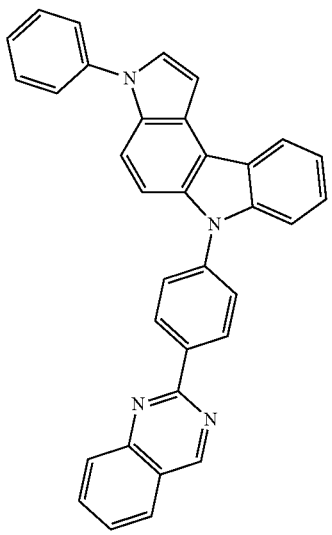
C262
C263
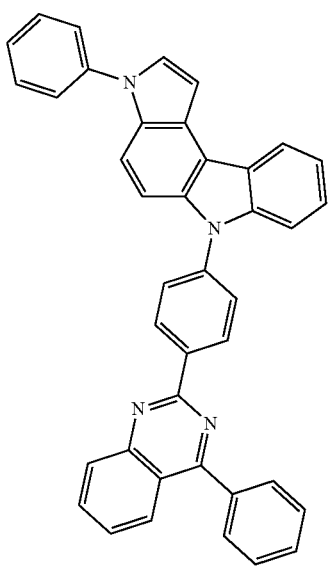

123
-continued
C264
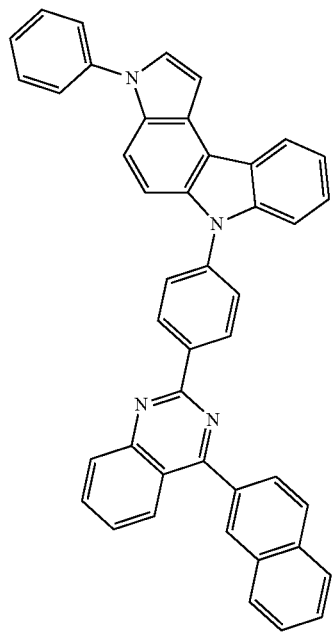
C265
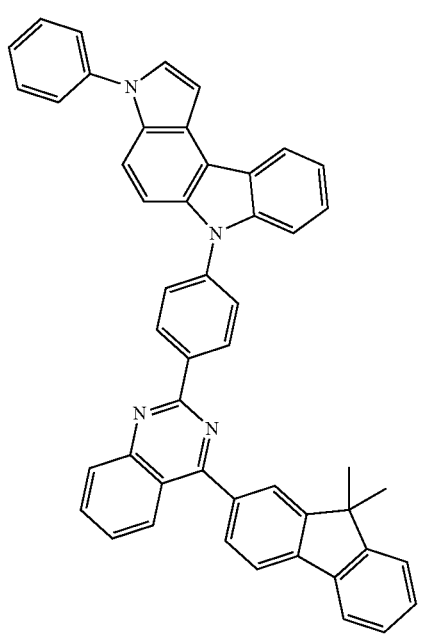
124
-continued
C266
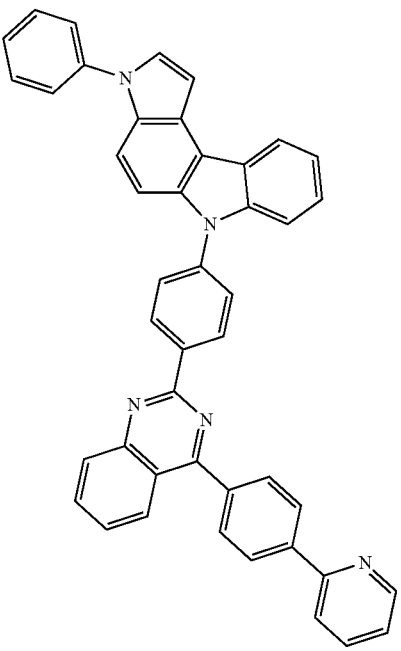
C267
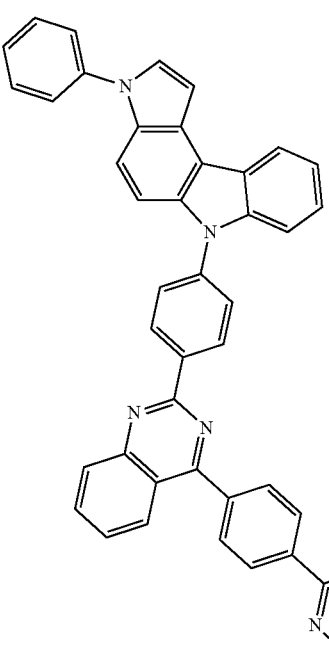

C268
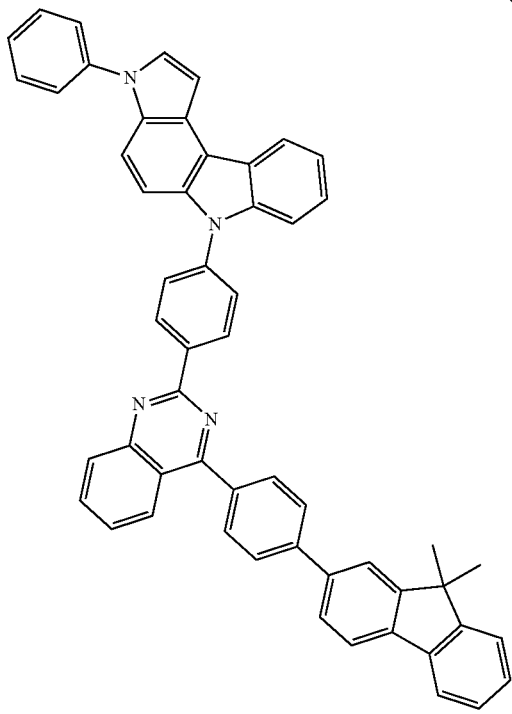
C270
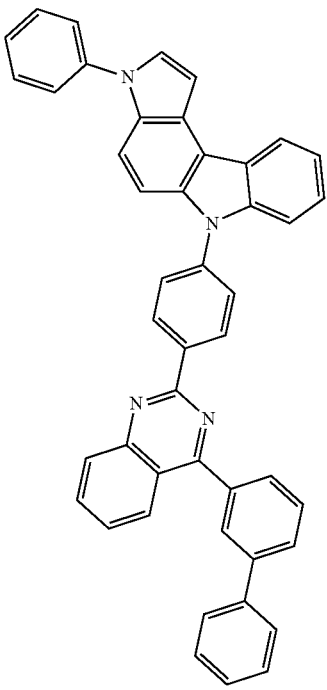
C269
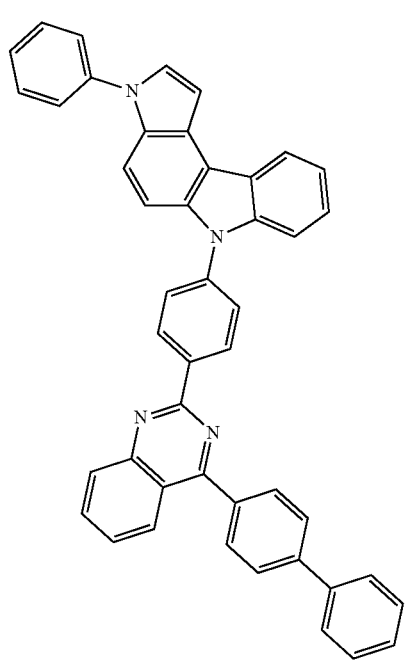
C271
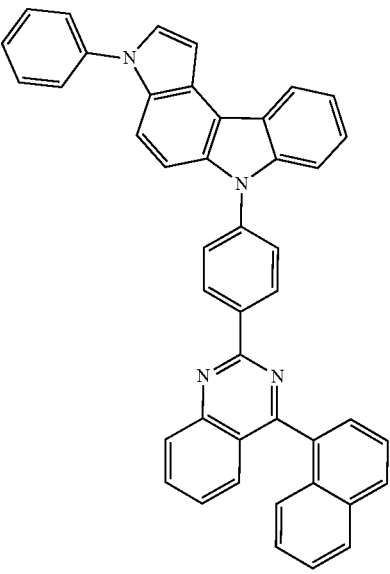

C272
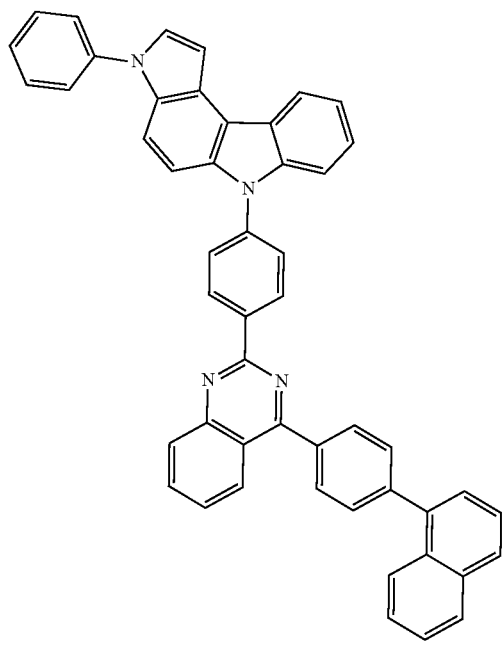
C274
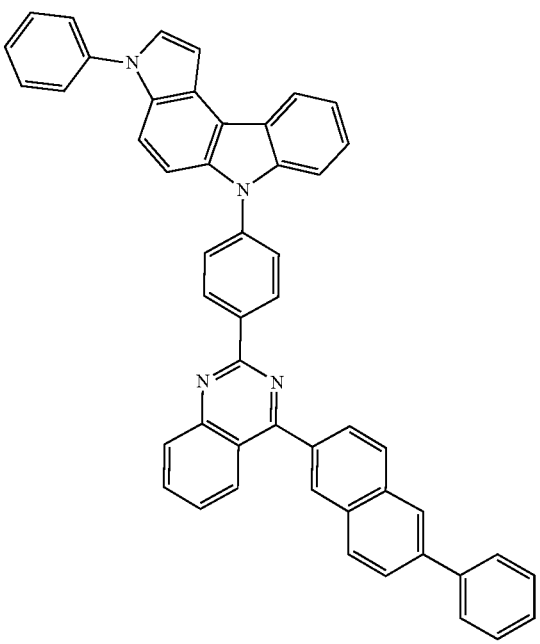
C273
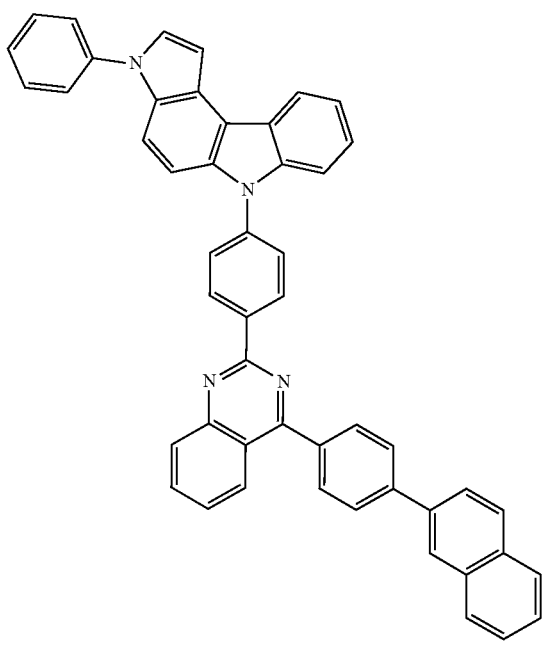
C275
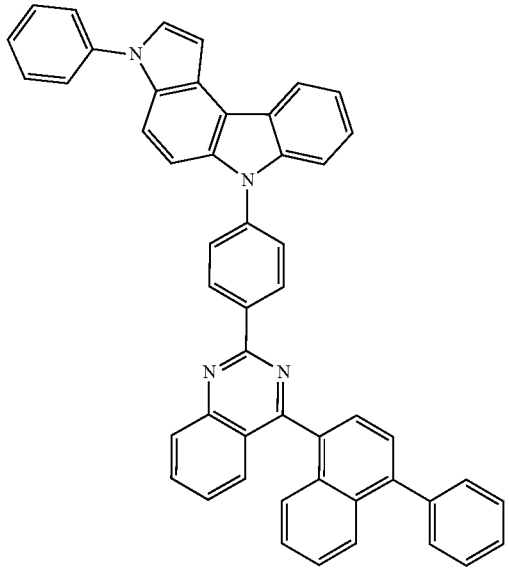

C276
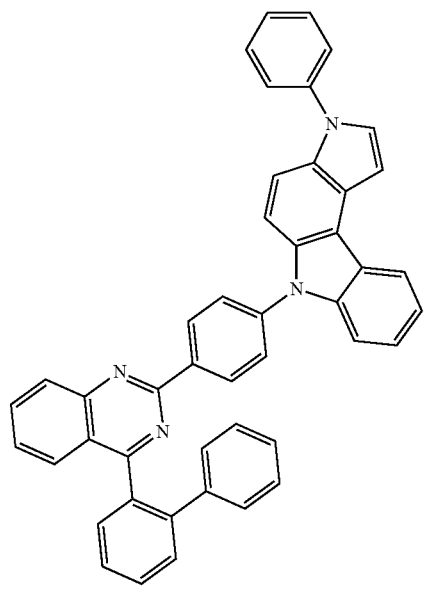
C277
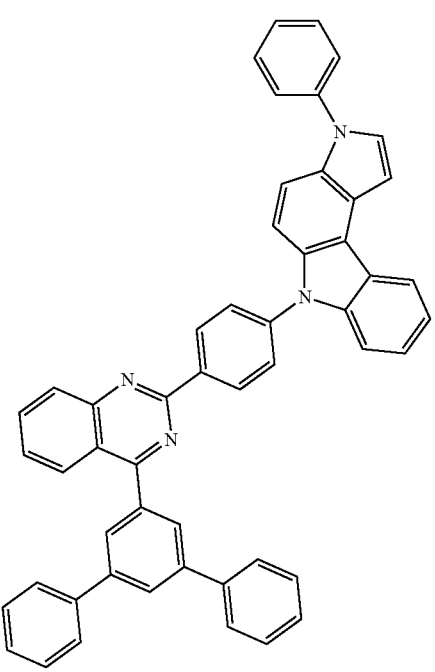
C278
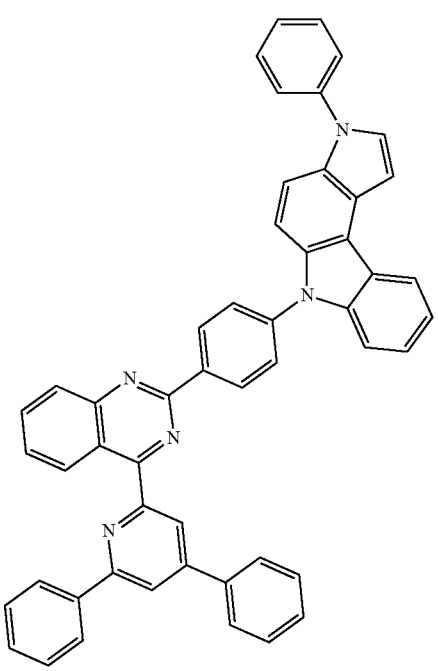
C279
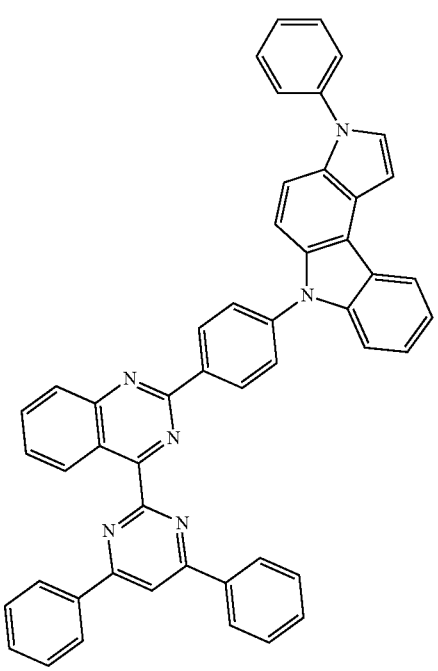

C280
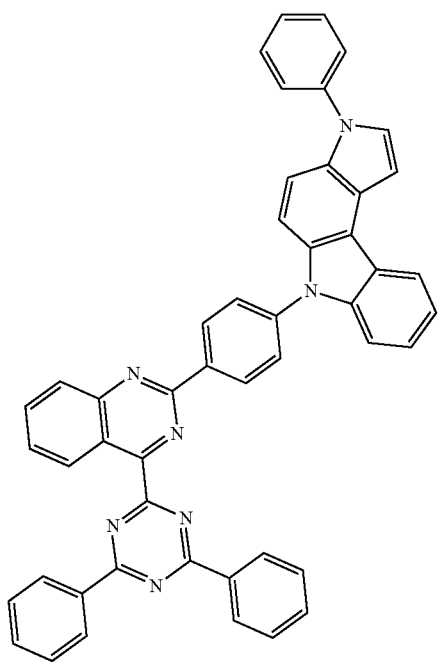
C281
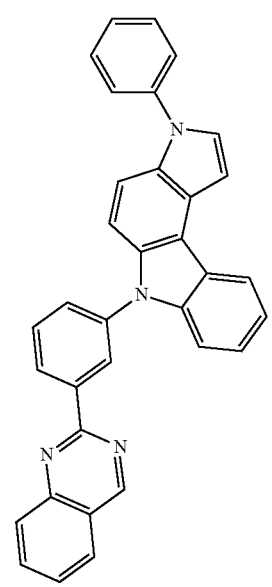
C282
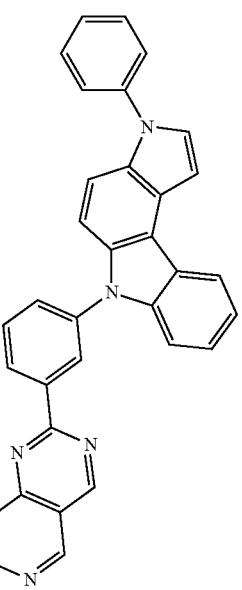
C283
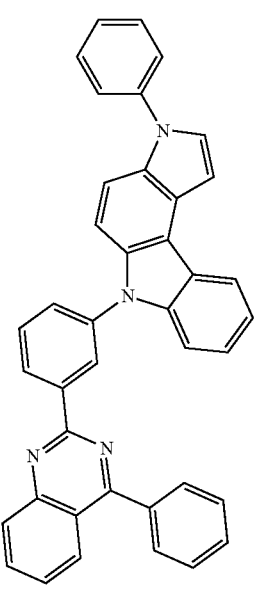

133
-continued
C284
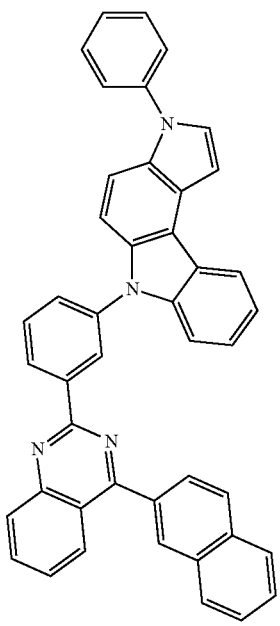
C285
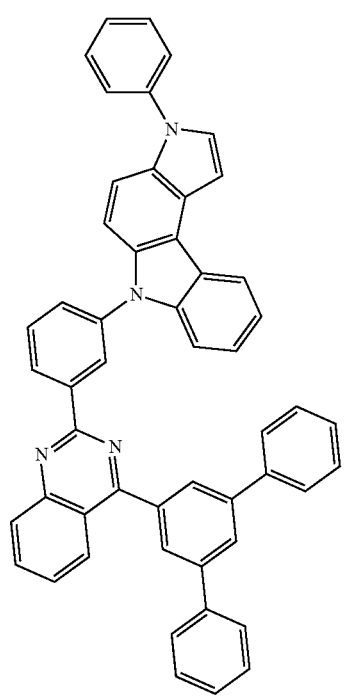
134
-continued
C286
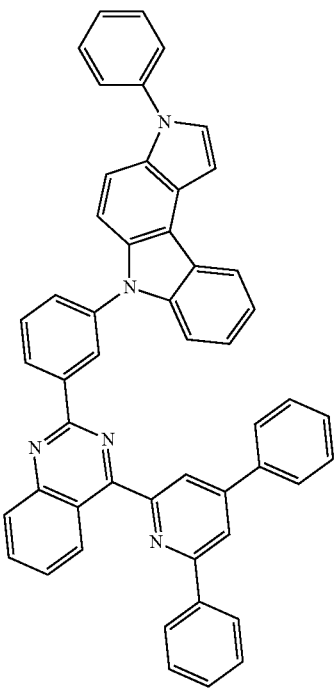
C287
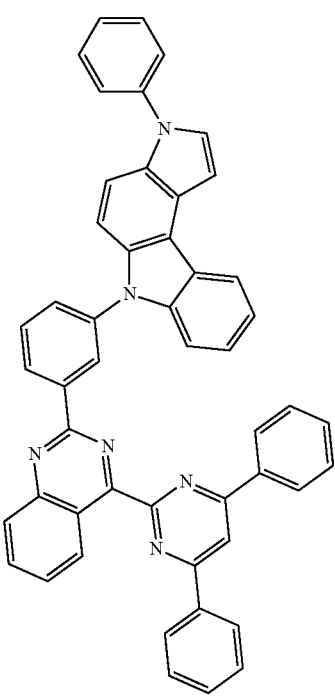

C288

C289

C290

C291

C292
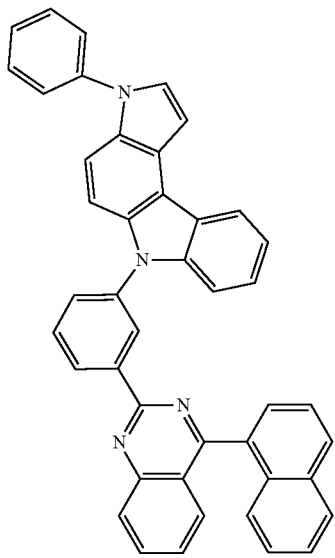
C293
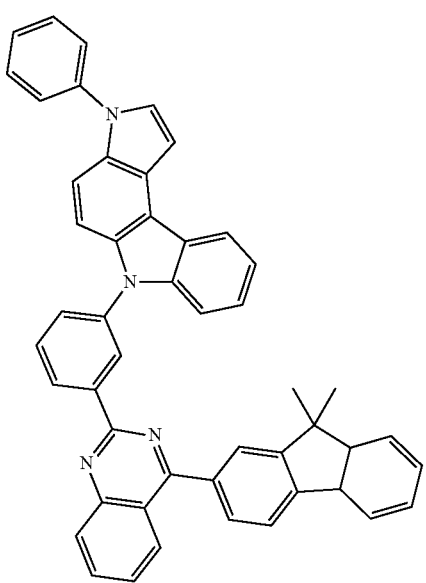
C294
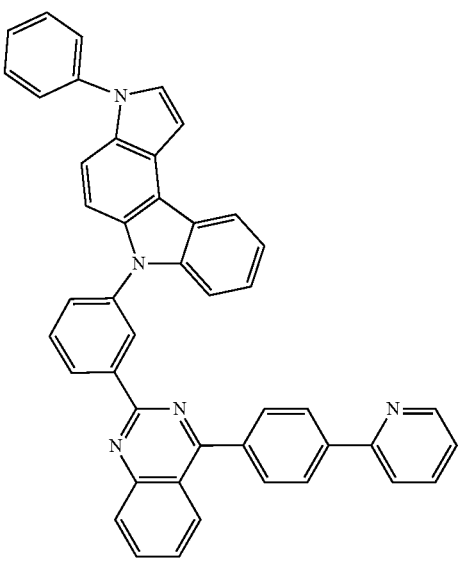
C295
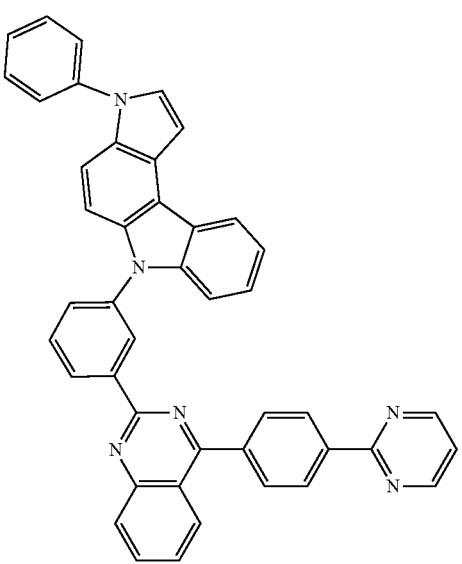

C296
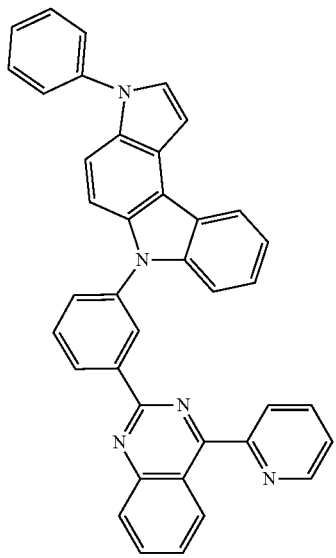
C297
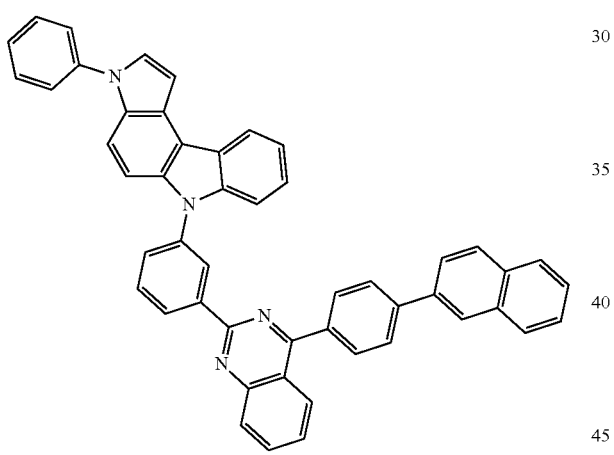
C298
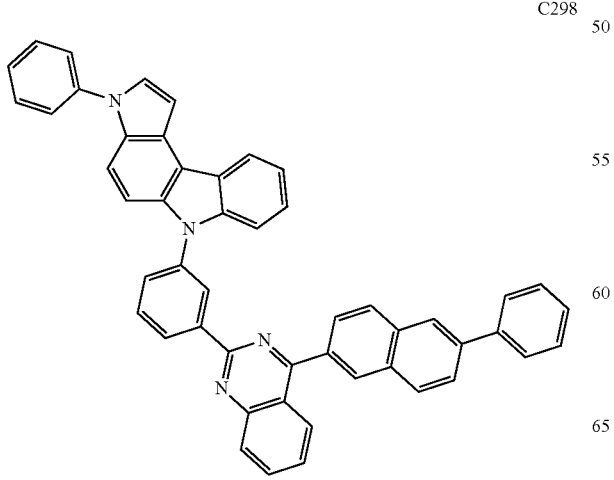
C299
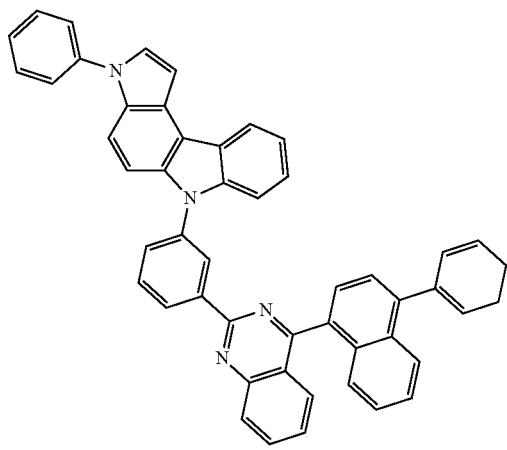
C300
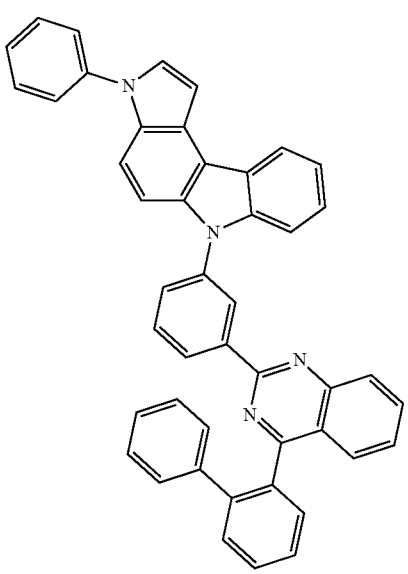
C301
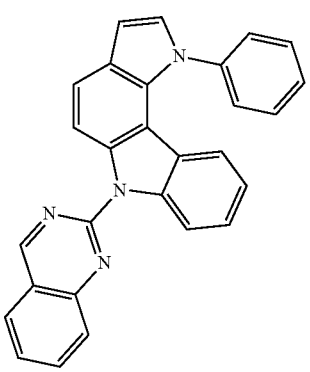

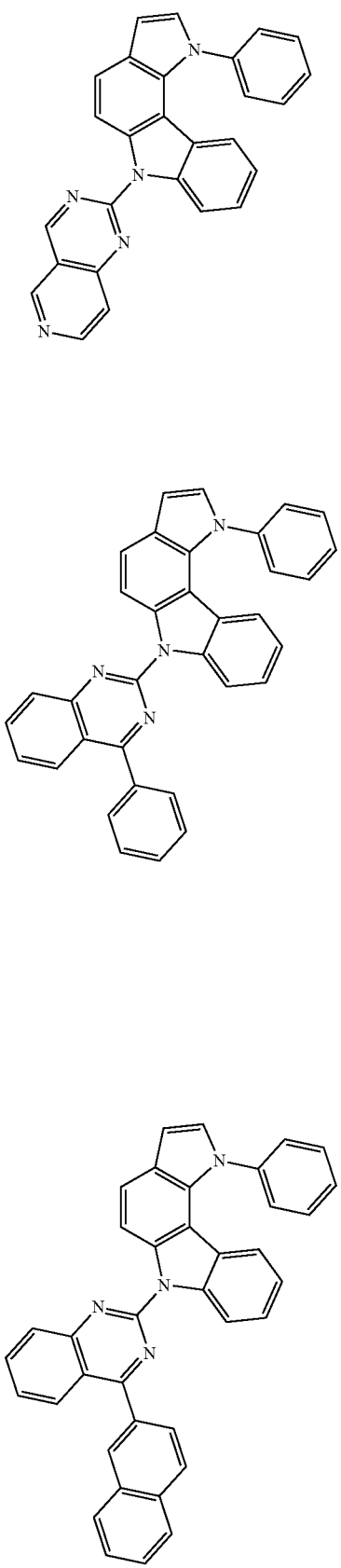
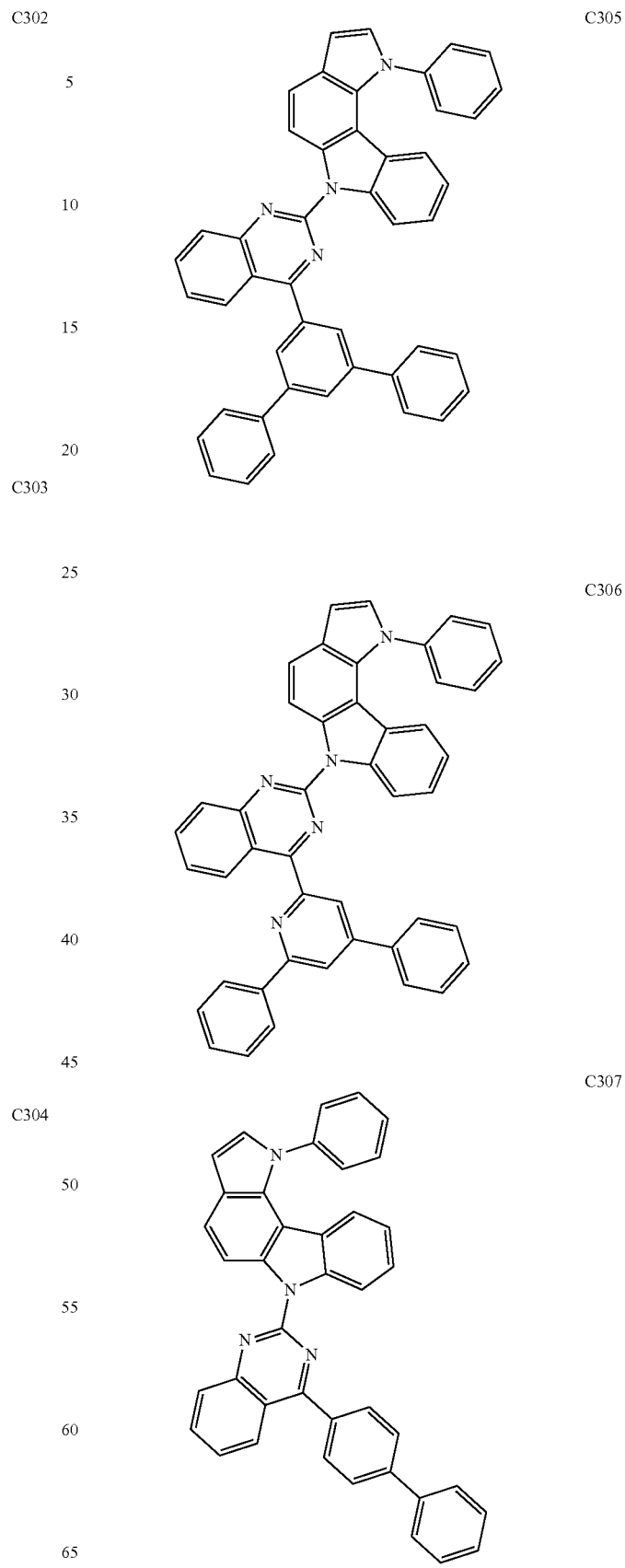

C308
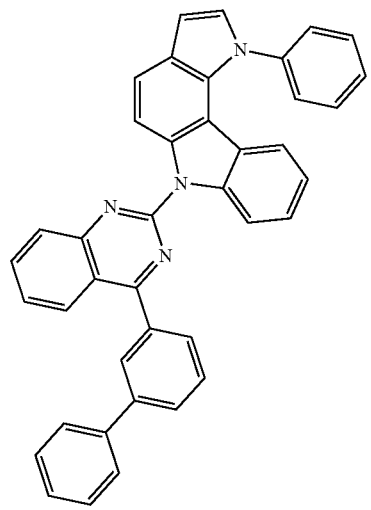
C309
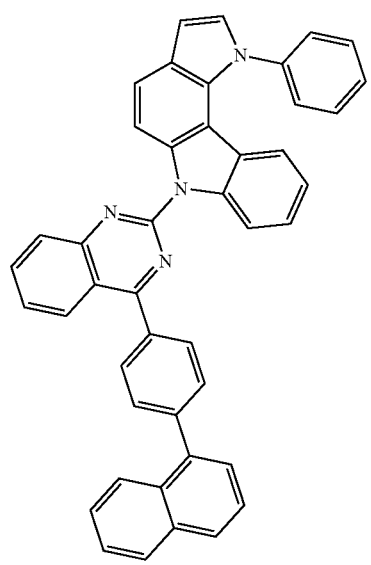
C310
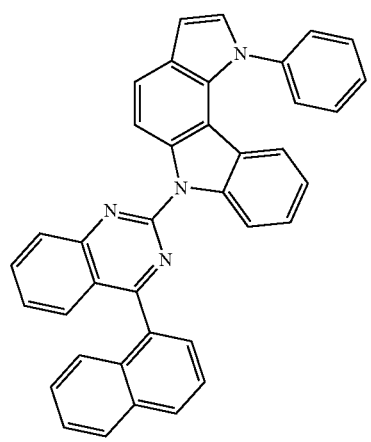
C311
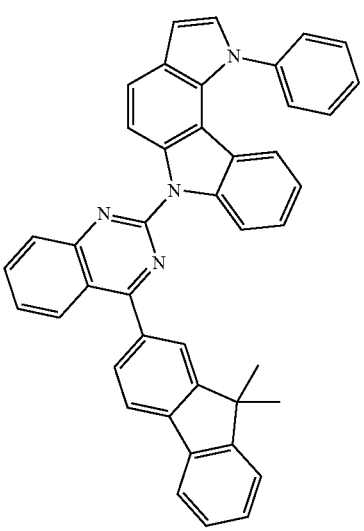
C312
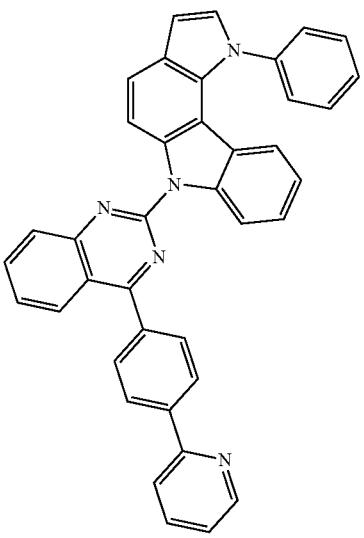
C313
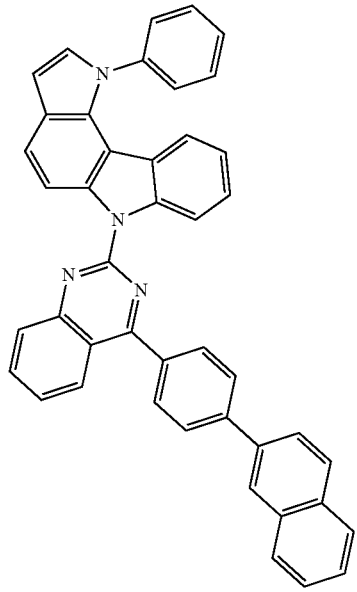

-continued
C314
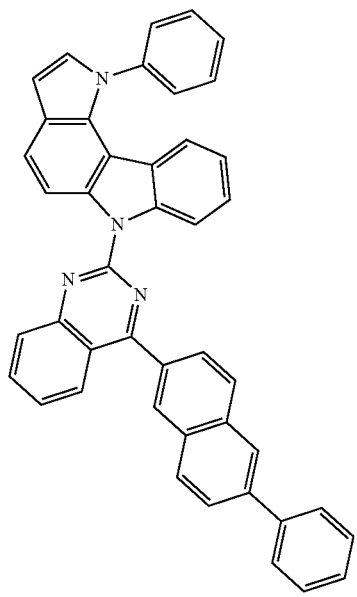
C315
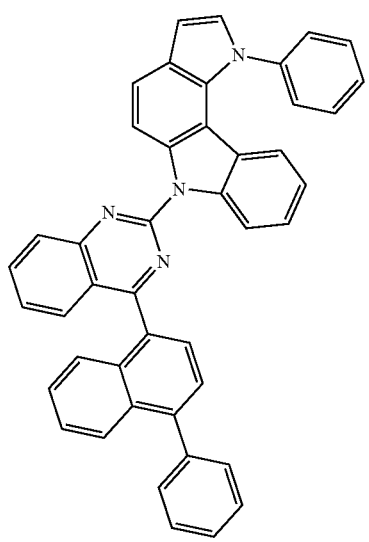
C316
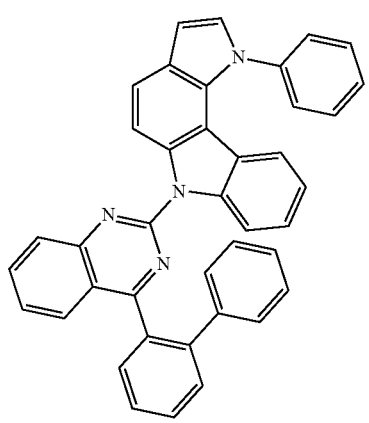
-continued
C317
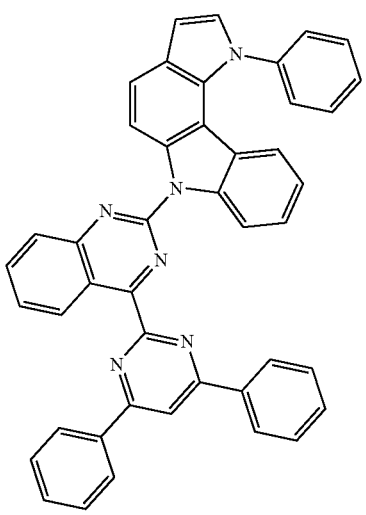
C318
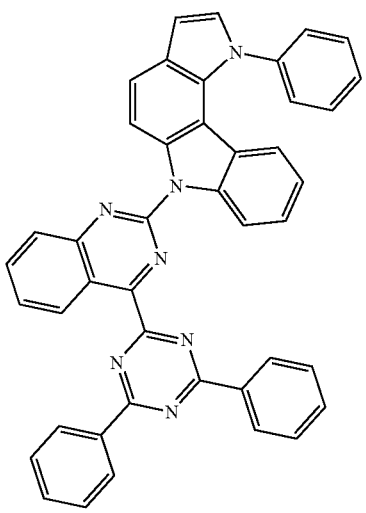
C319
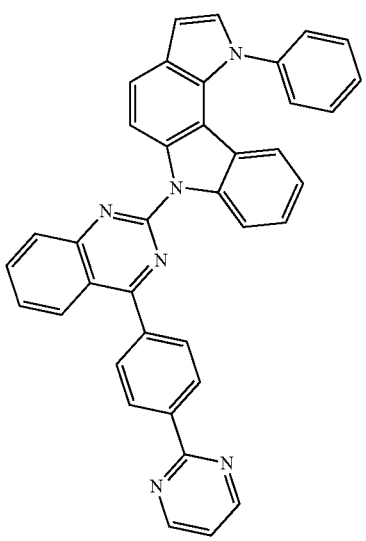

C320
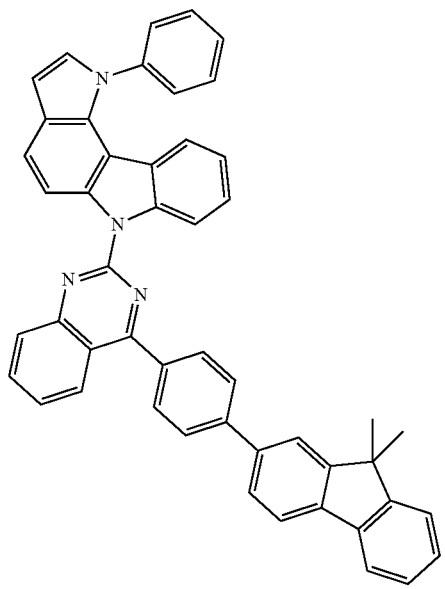
C321
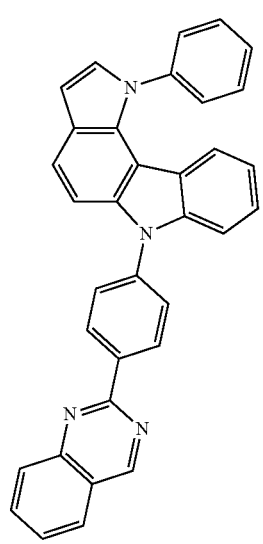
C322
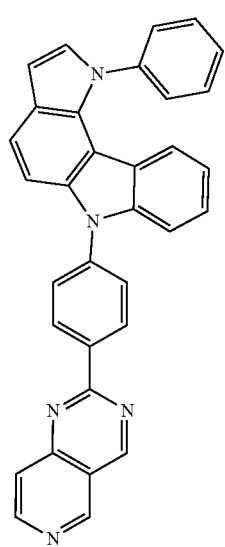
C323
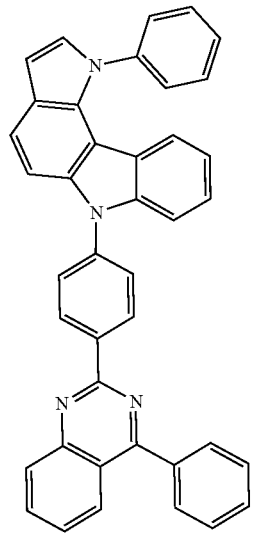
C324
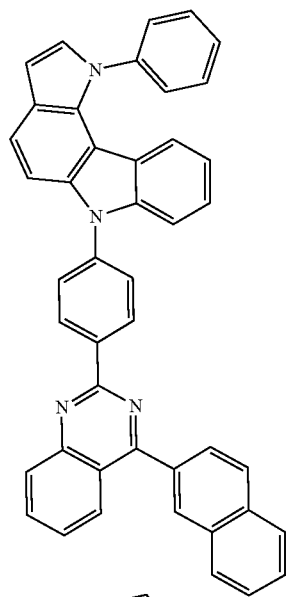
C325
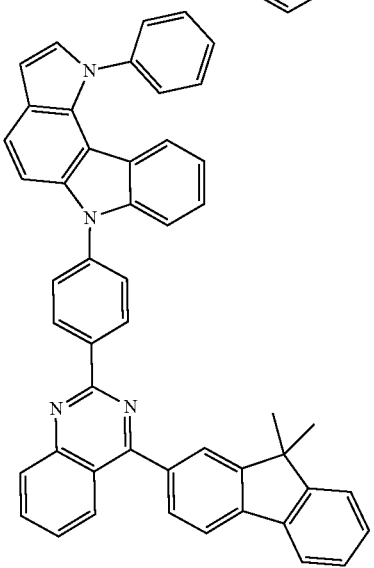

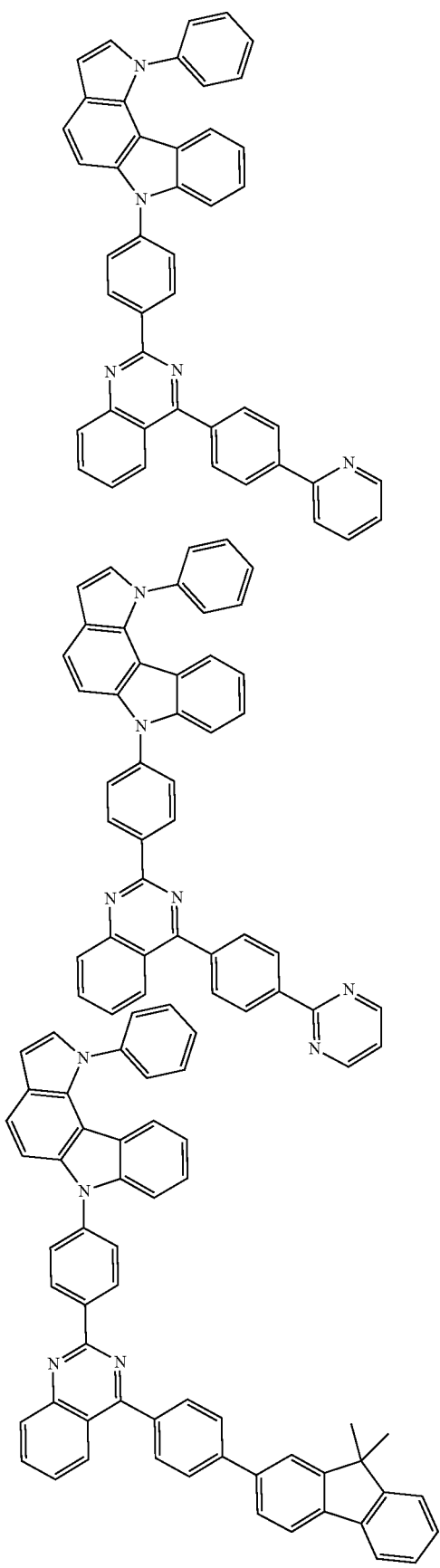
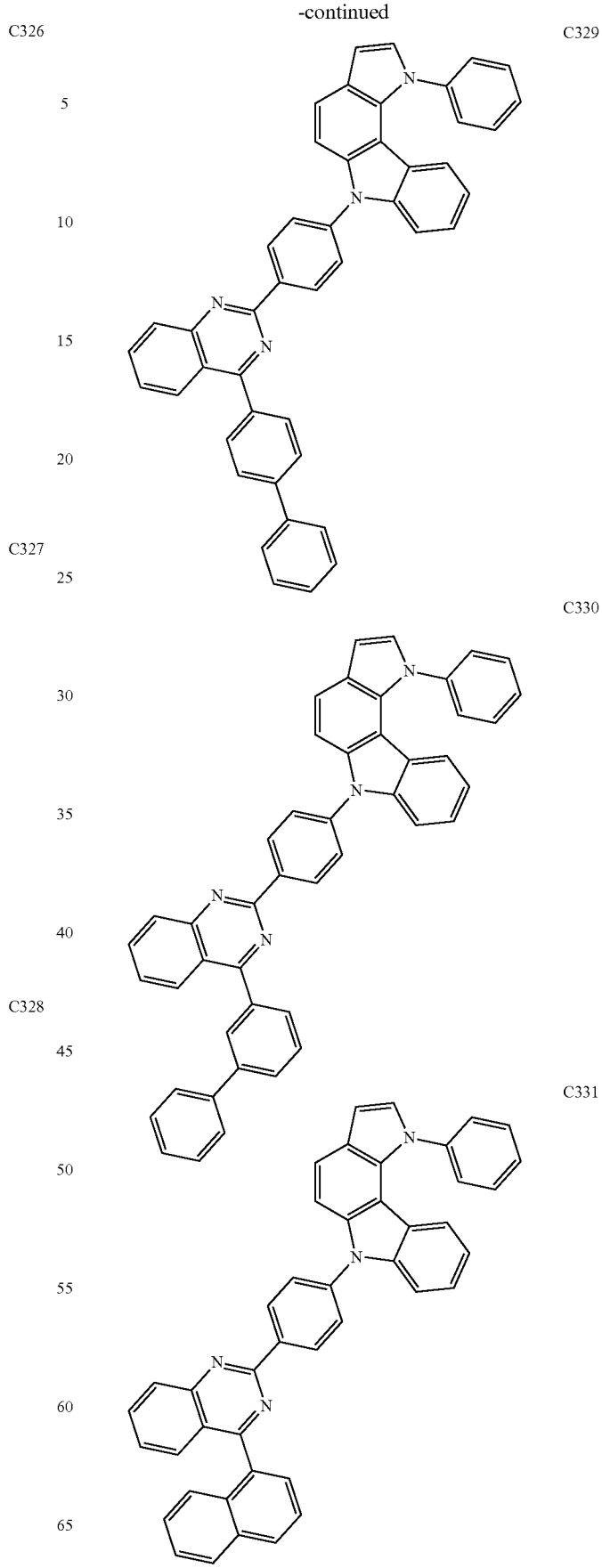

-continued
C332
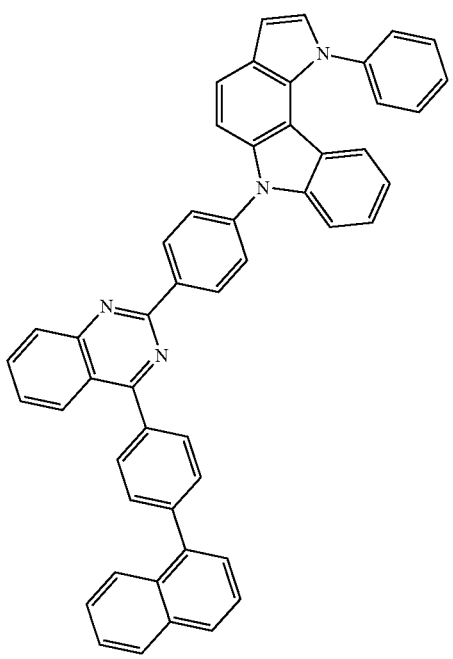
C333
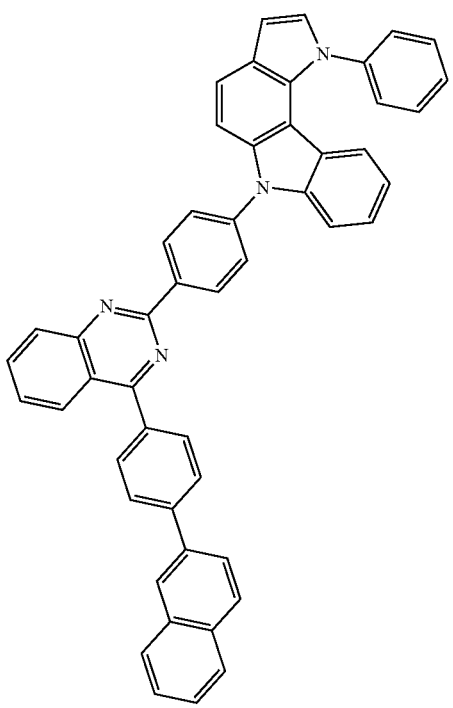
-continued
C334
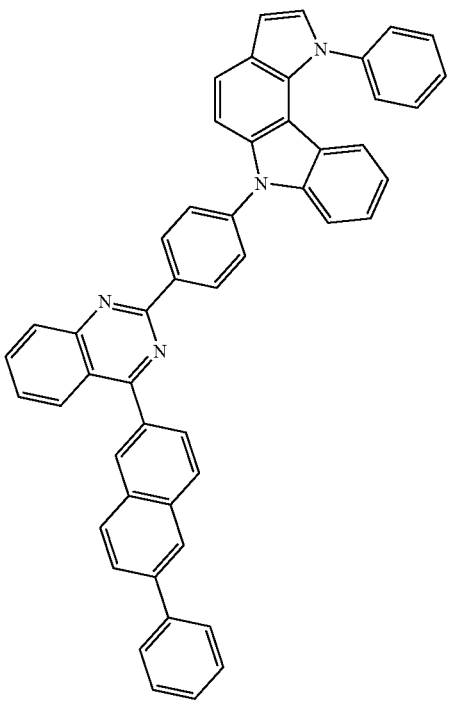
C335
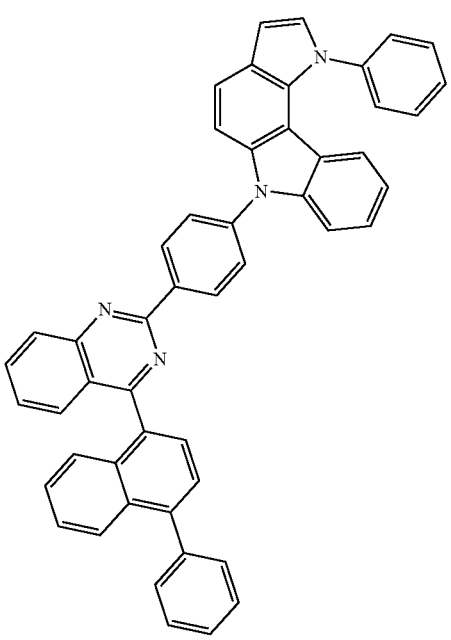

C336
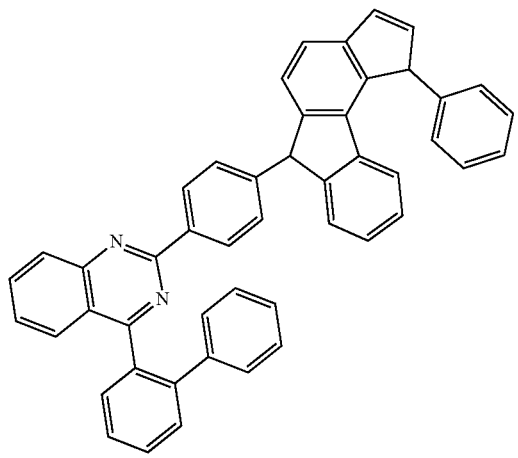
C337
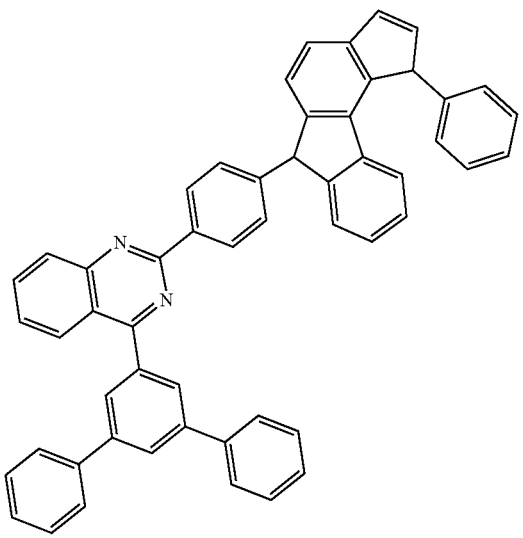
C338
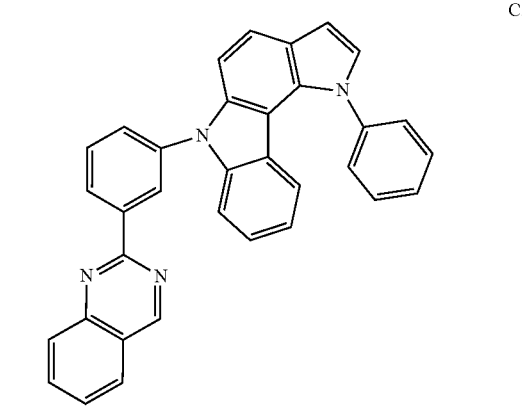
C339
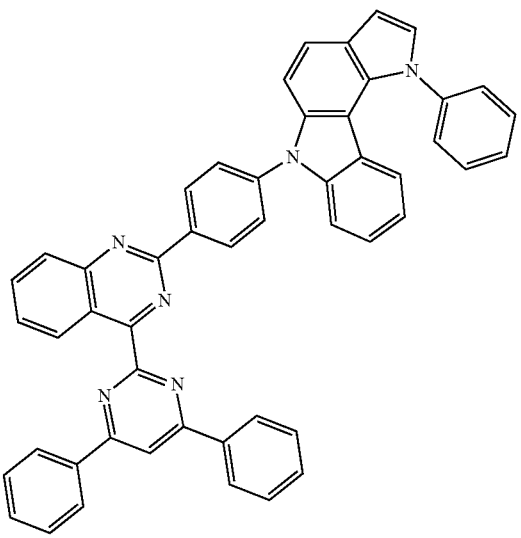
C340
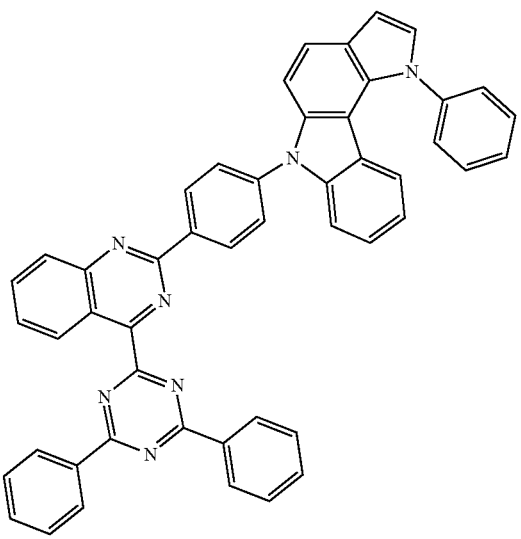
C341

C342
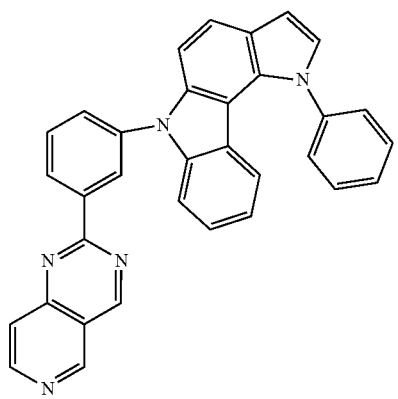
C343
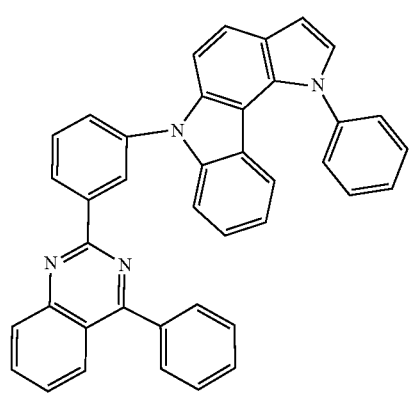
C344
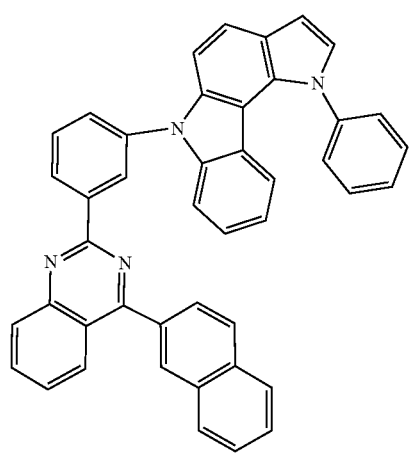
C345
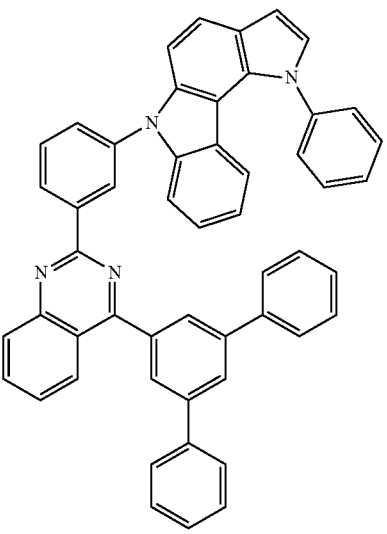
C346
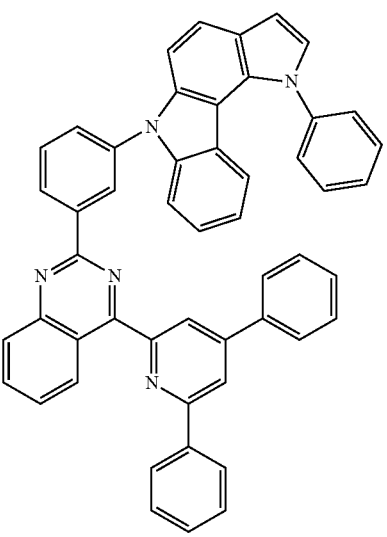
C347
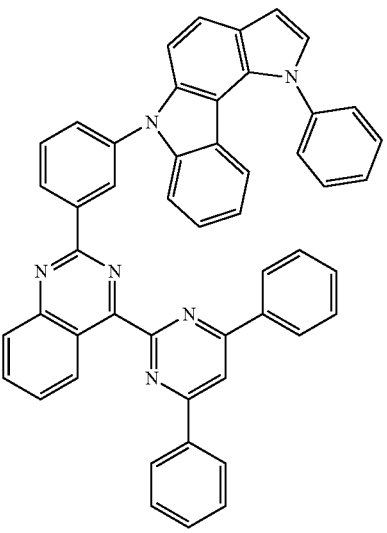

C348
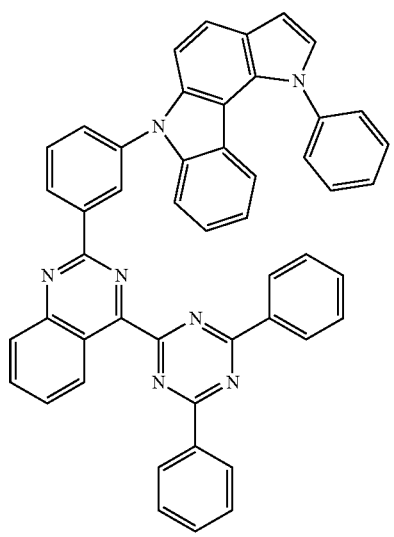
C349
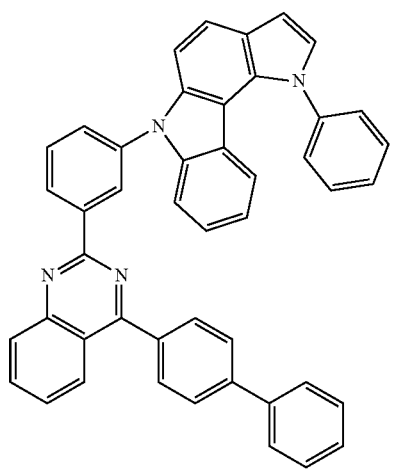
C350
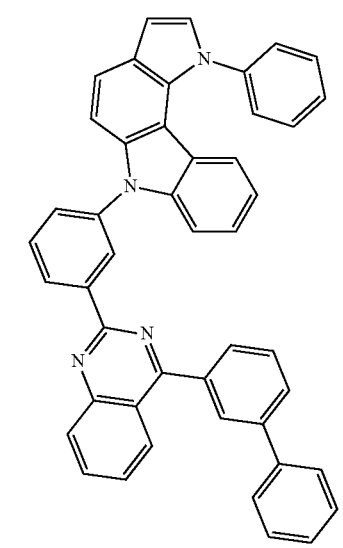
C351
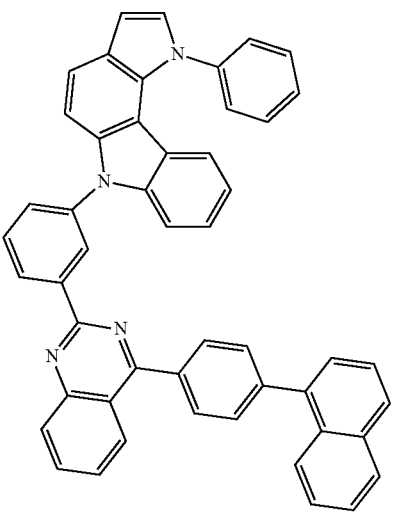
C352
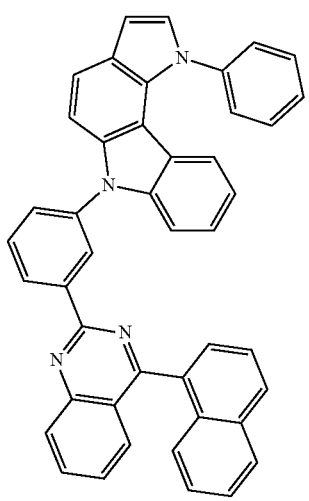
C353
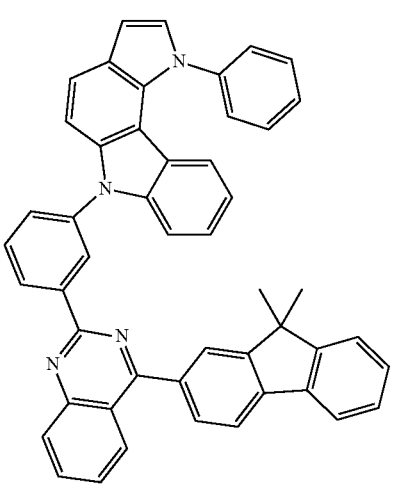

-continued
C354
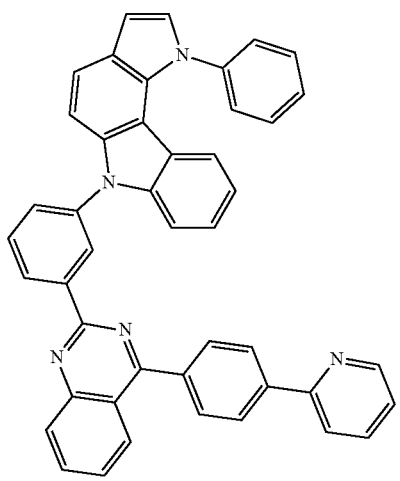
C355
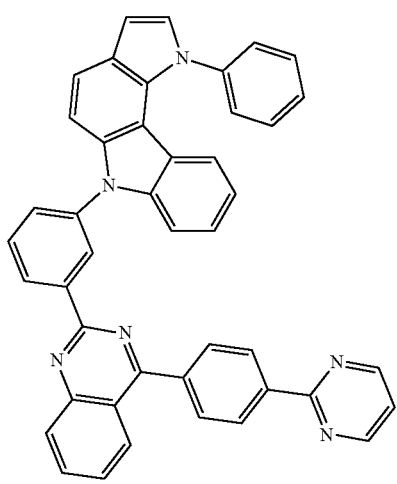
C356
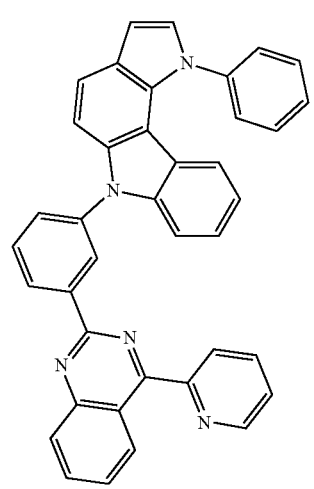
-continued
C357
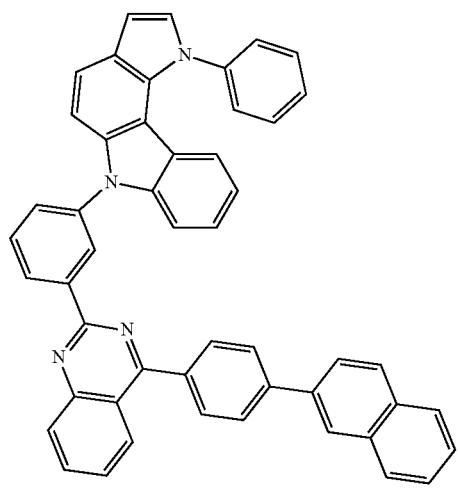
C358
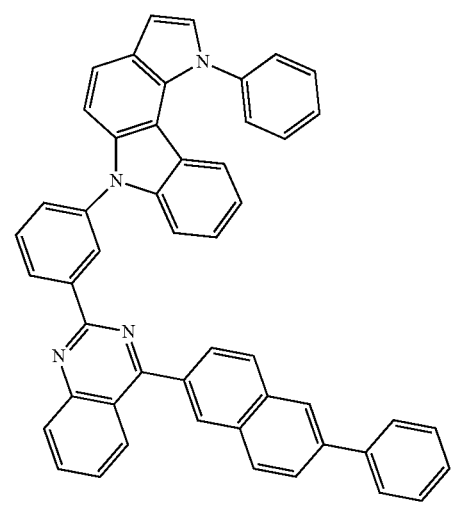
C359
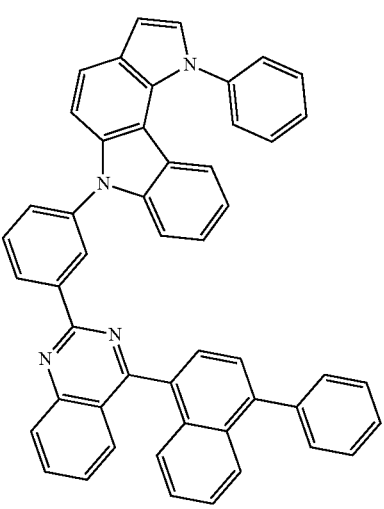

C360
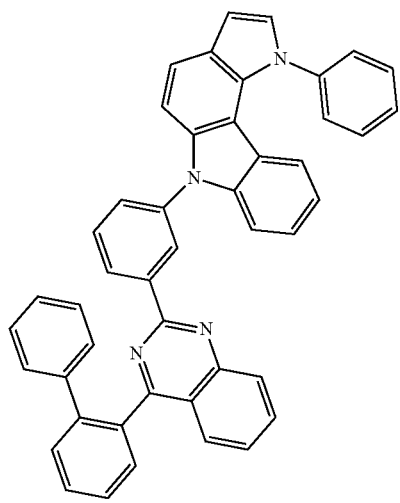
C361
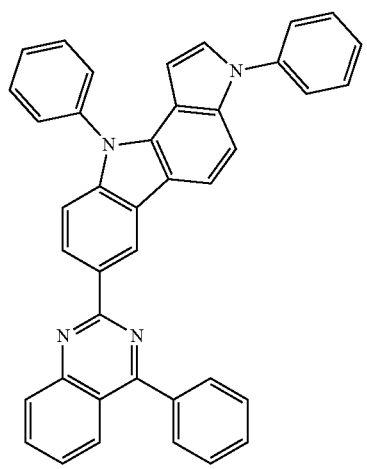
C362
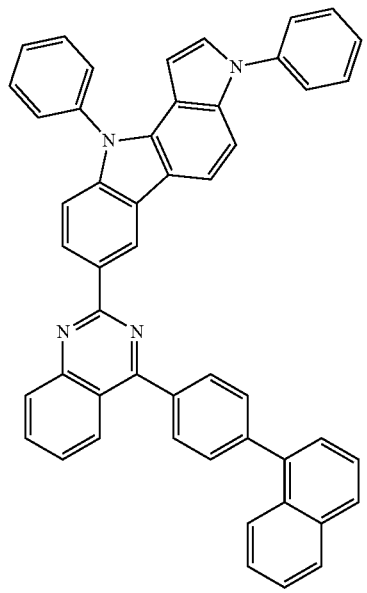
C363
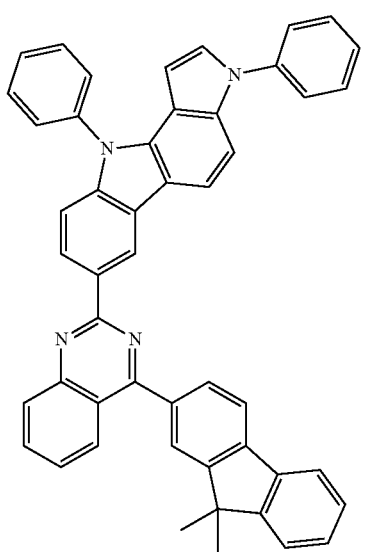
C364
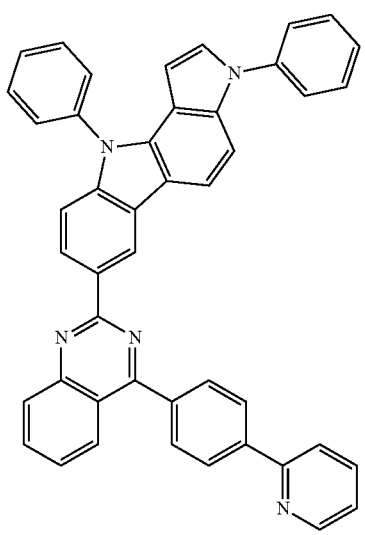
C365
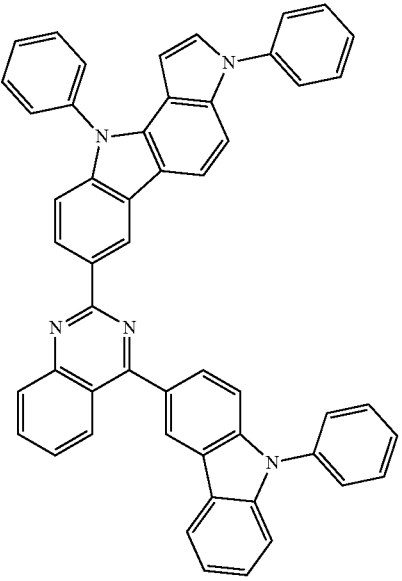

-continued
C366
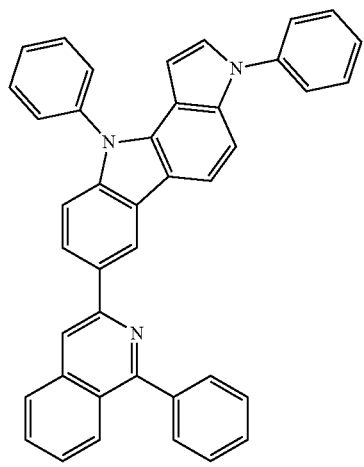
C367
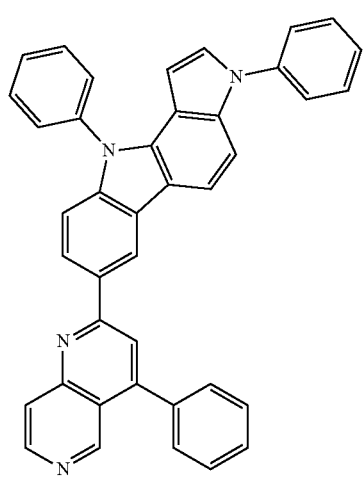
C368
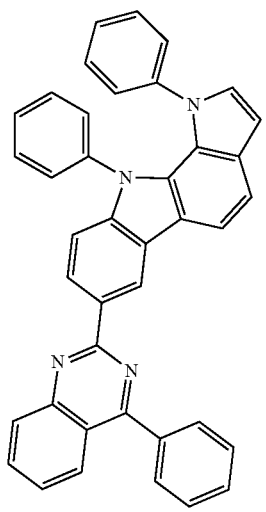
-continued
C369
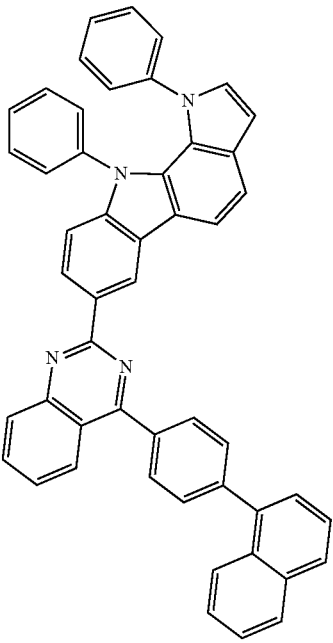
C370
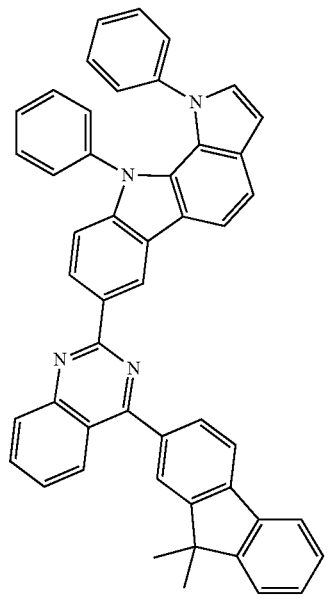

-continued
C371
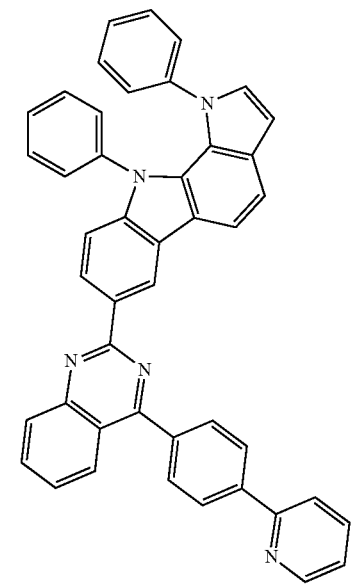
C372
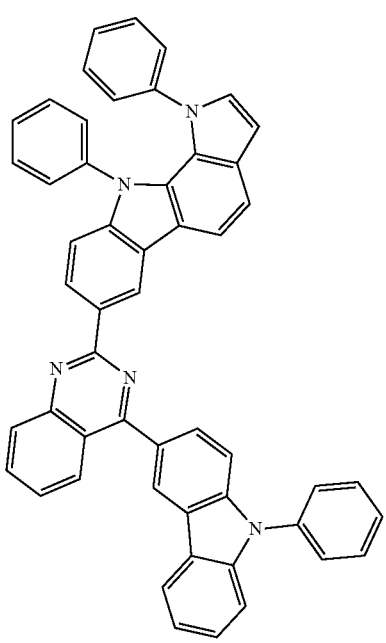
-continued
C373
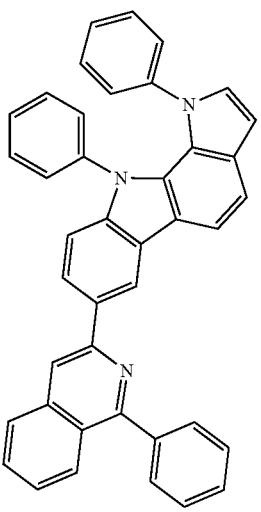
C374
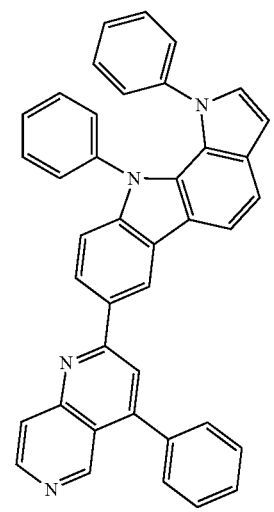
C375
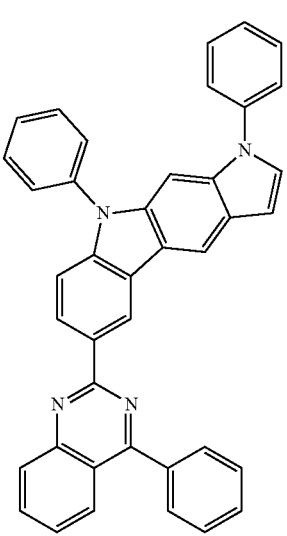

C377
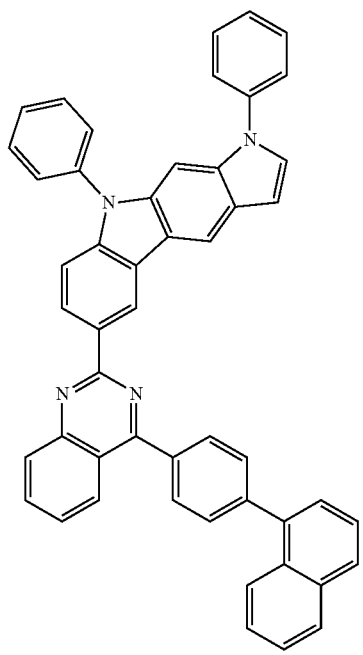
C378
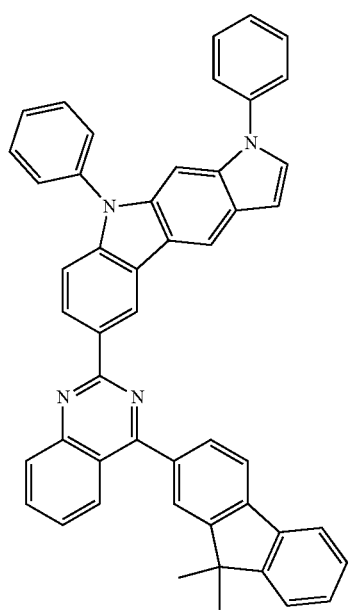
C379
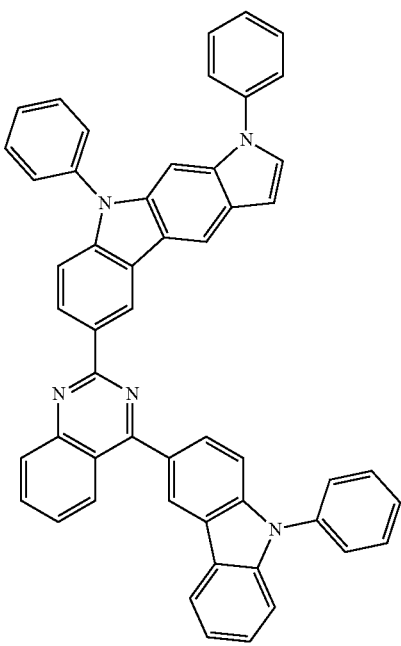
C380
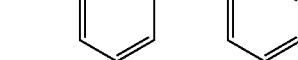

-continued
C381
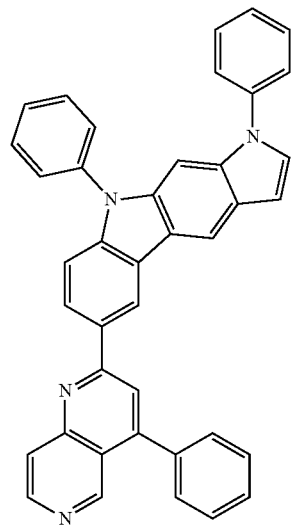
C382
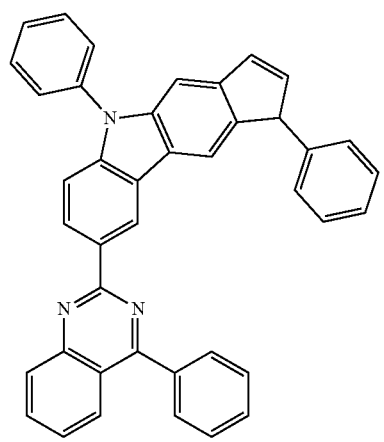
C383
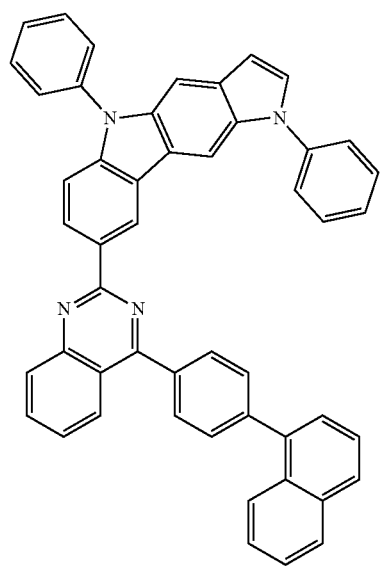
-continued
C384
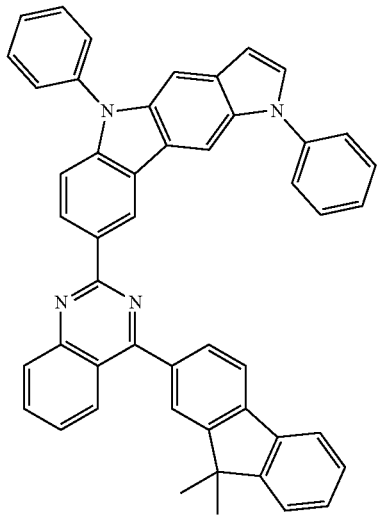
C385
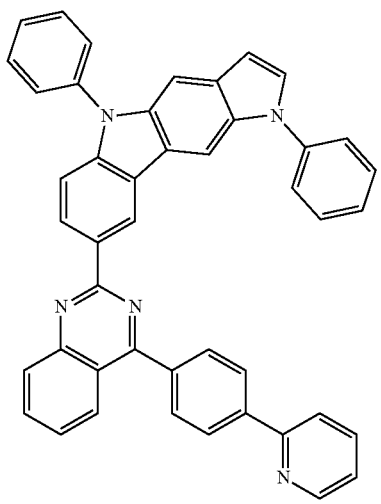
C386
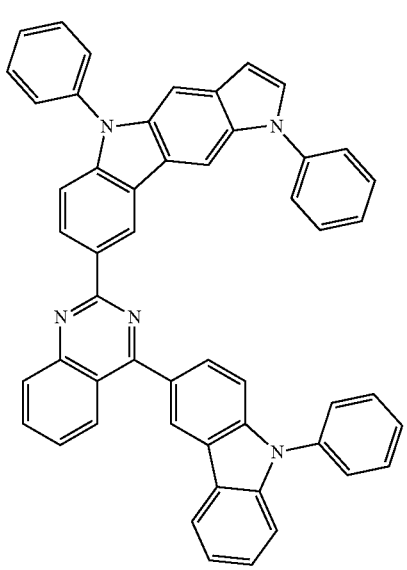

C387
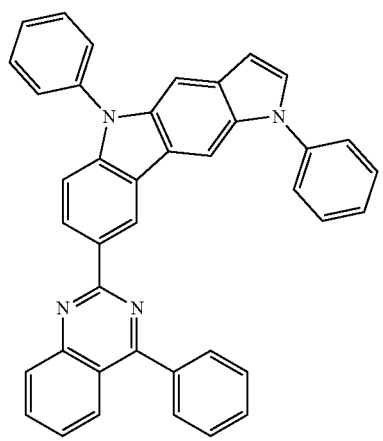
C388
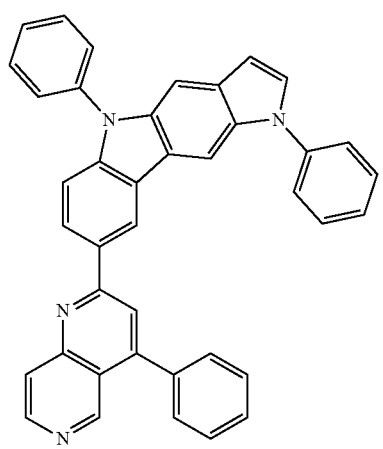
C389
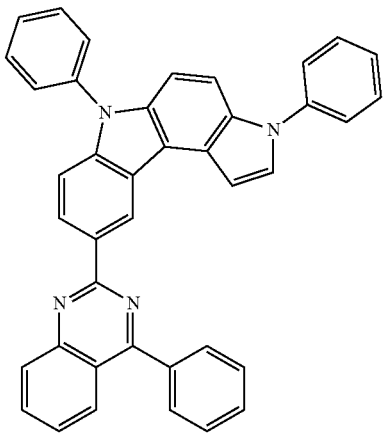
C390
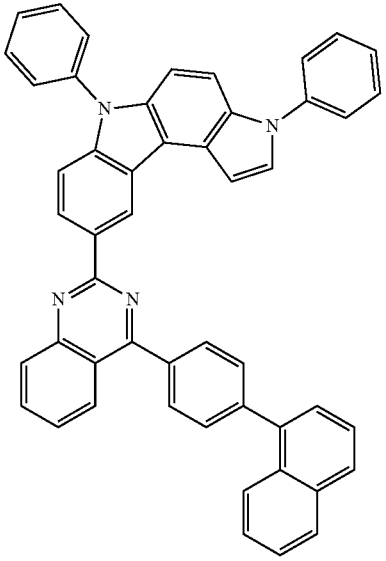
C391
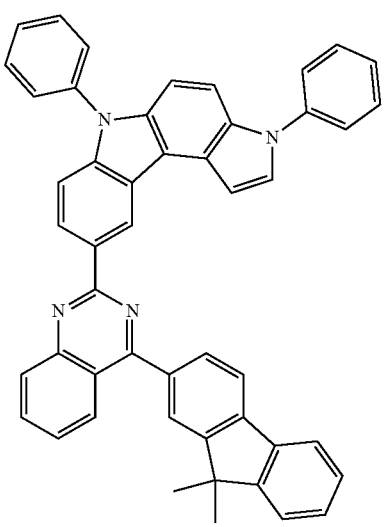
C392
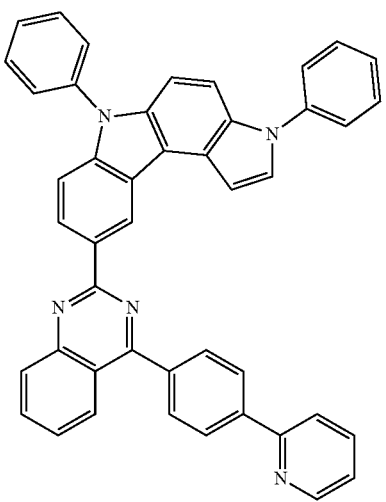

C393
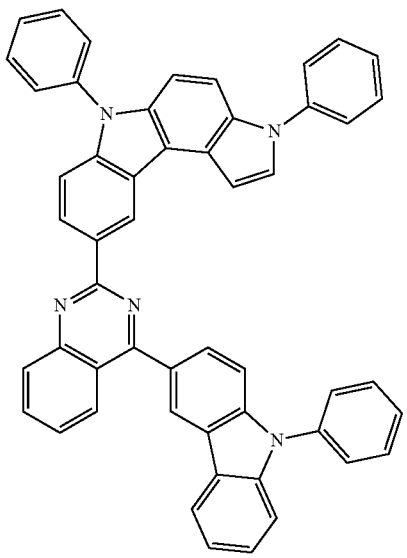
C394
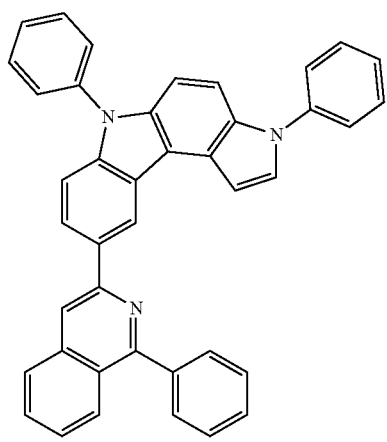
C395
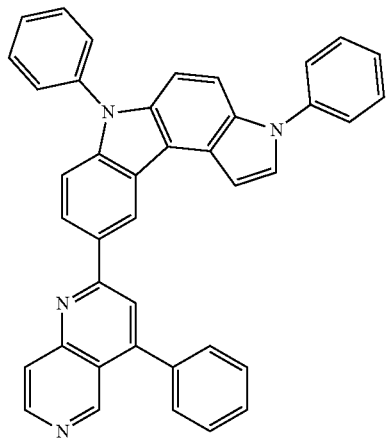
C396
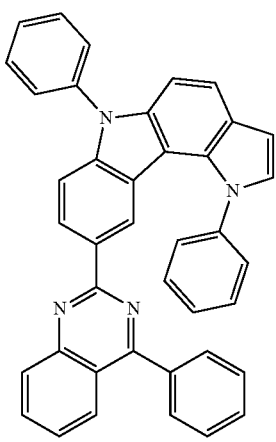
C397
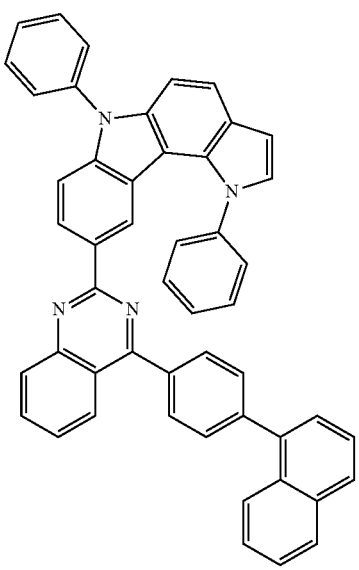
C398
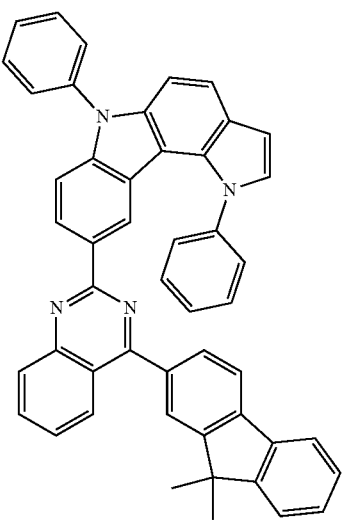

-continued
C399
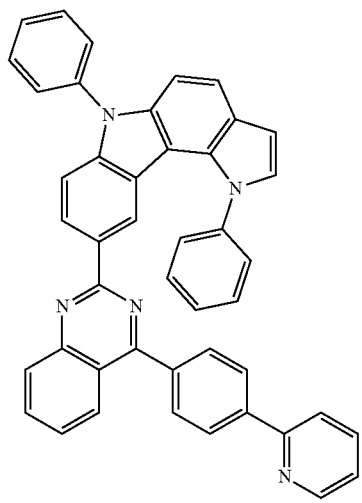
C399
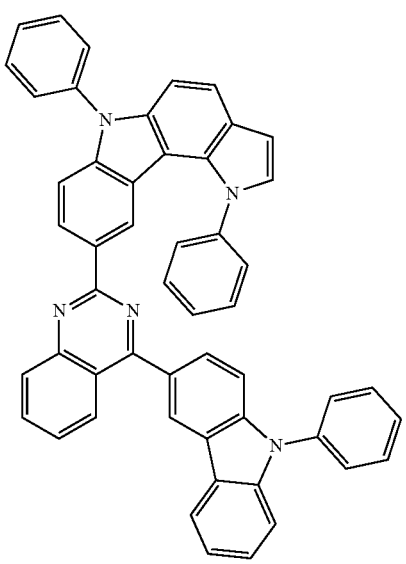
C400
-continued
C401
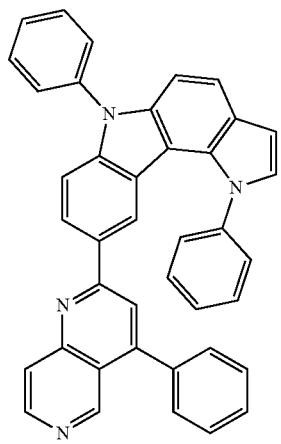
C403
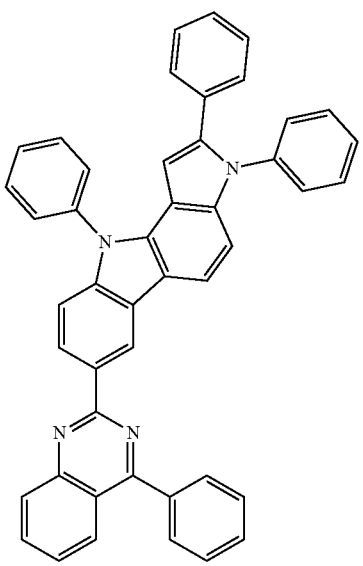
C404
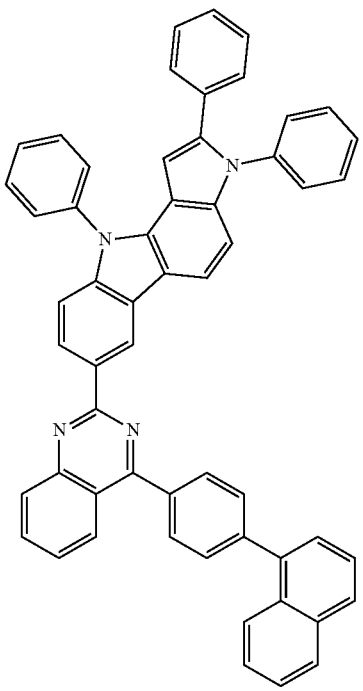

C405
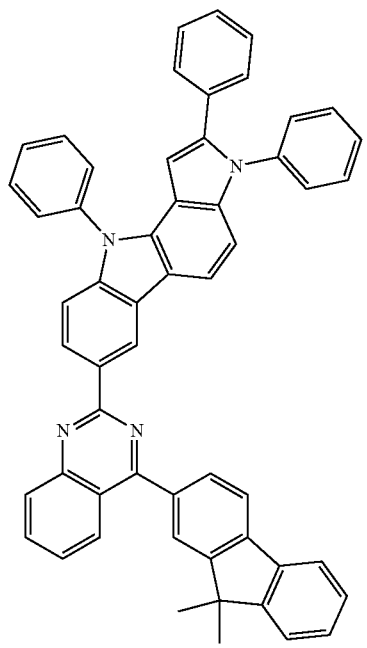
C407
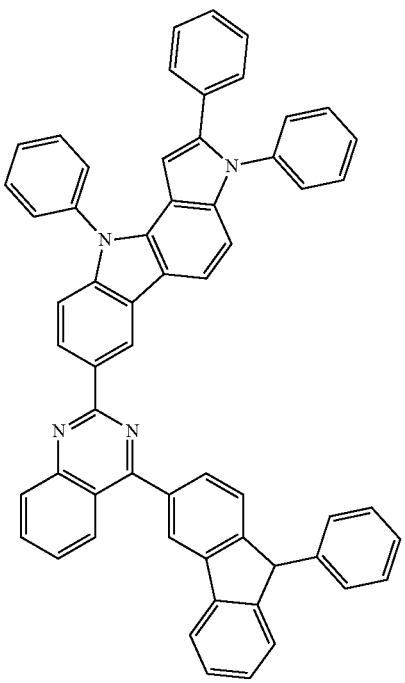
C406
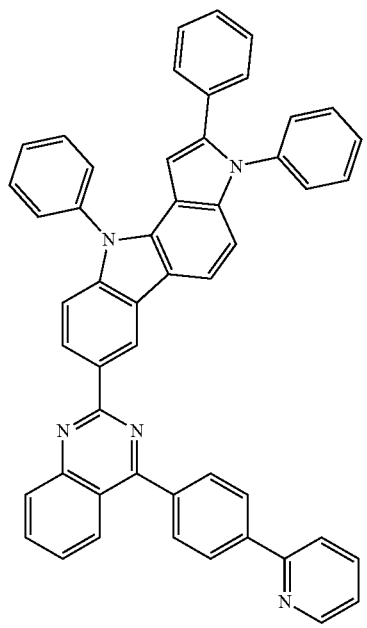
C408
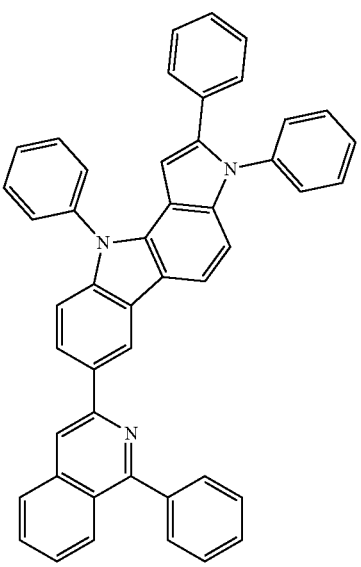

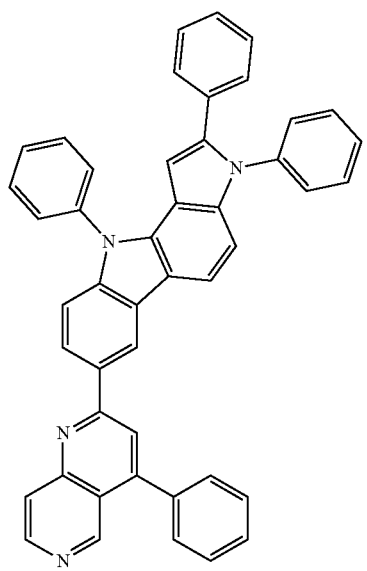
C409
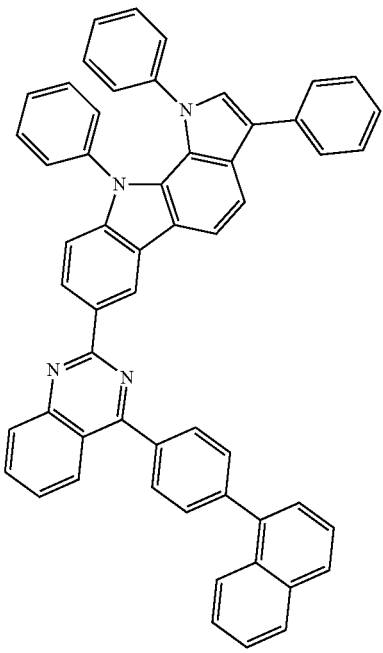
C411
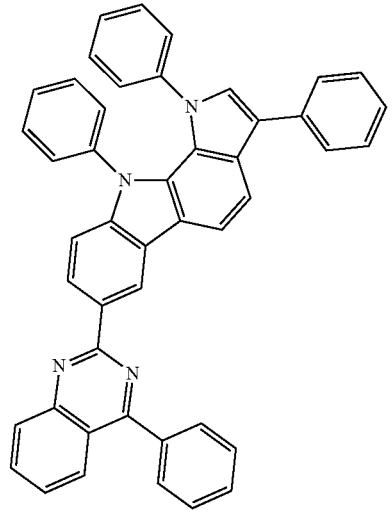
C410
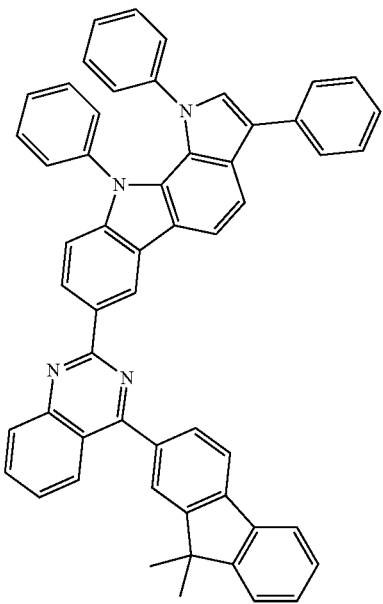
C412

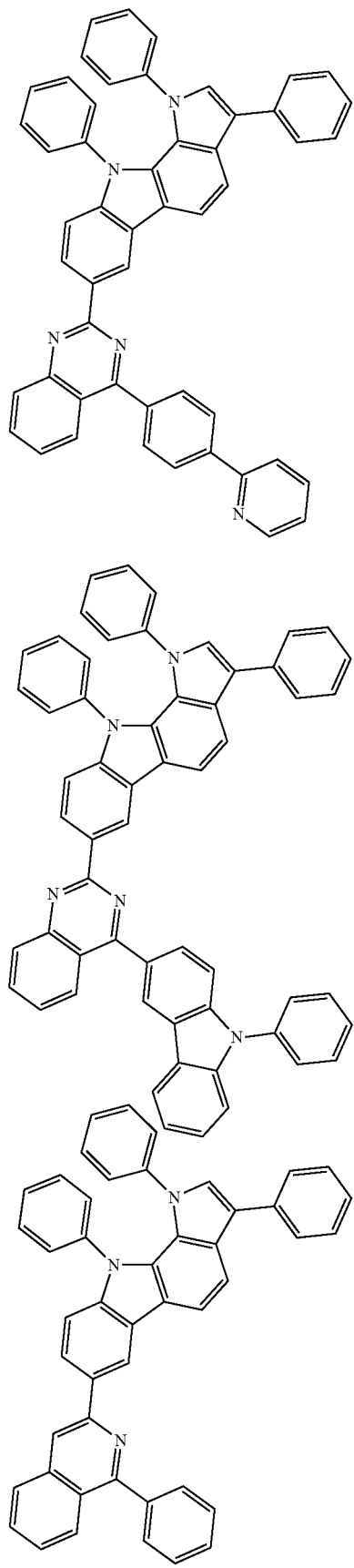
C413
C414
C415
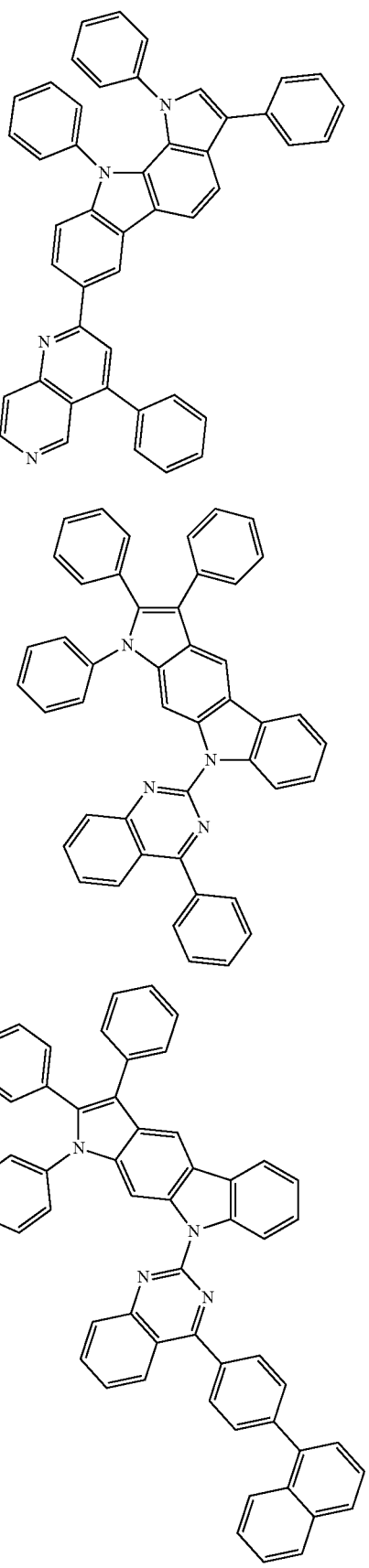
C416
C417
C418

C419
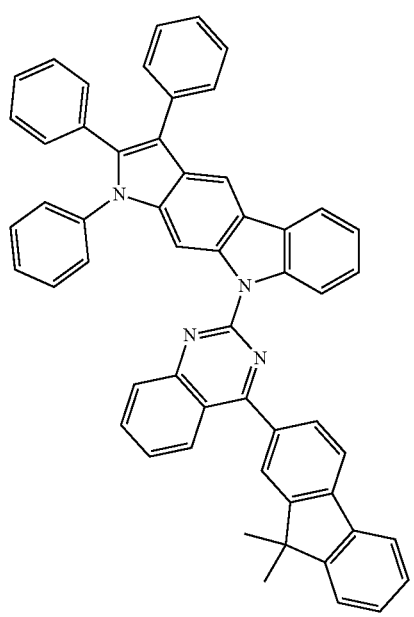
C420
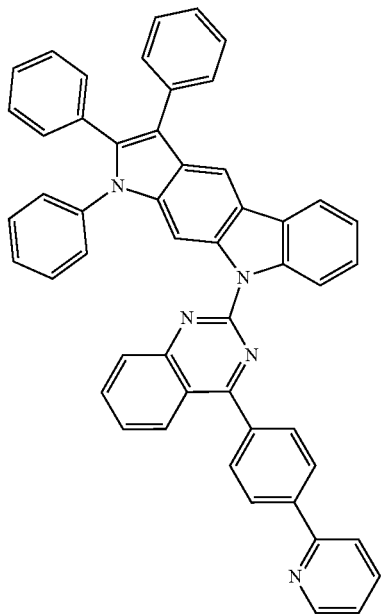
C421
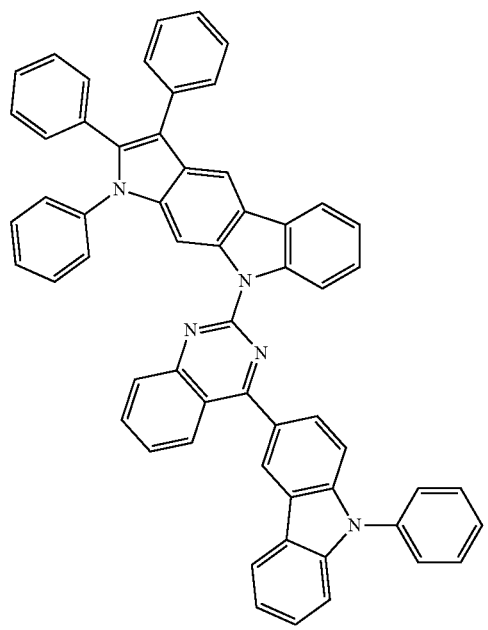
C422
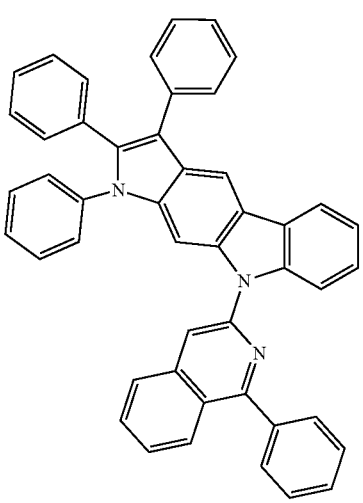
C423
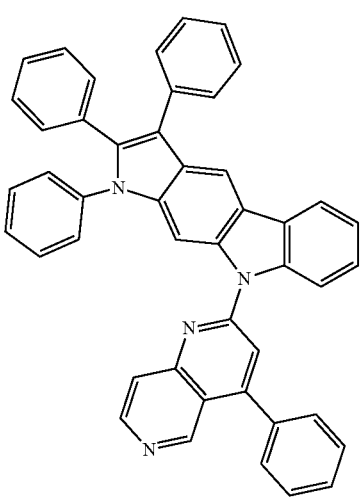

-continued
C424
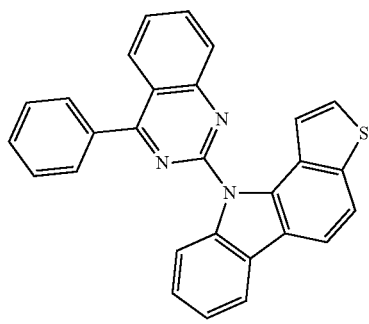
C425
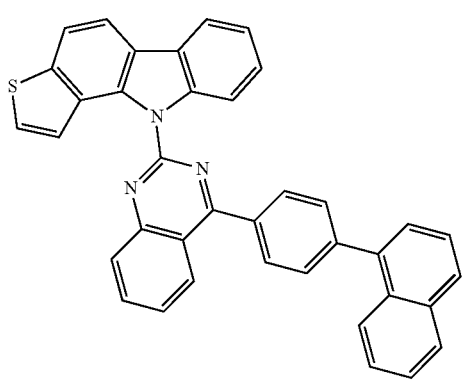
C426
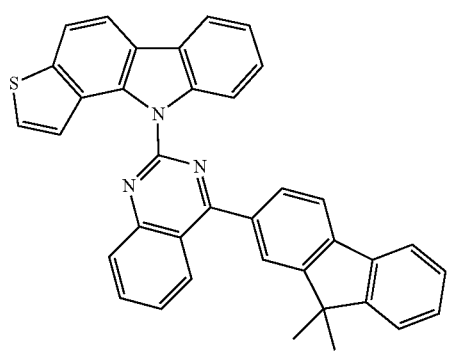
C427
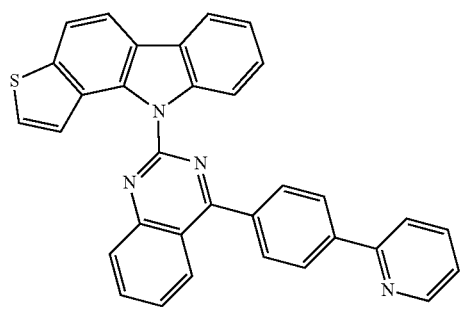
-continued
C428
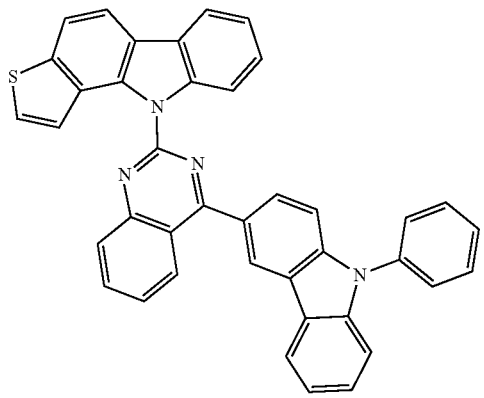
C429
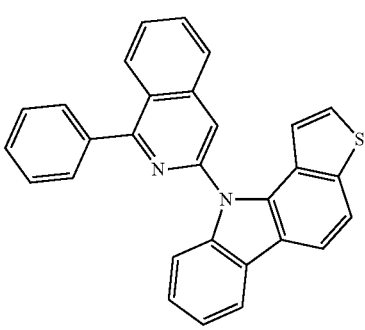
C430
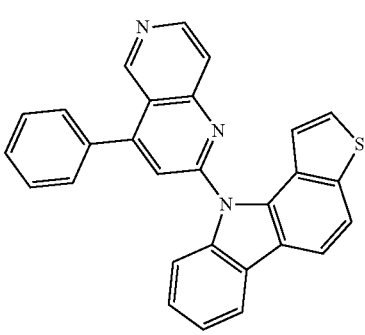
C431
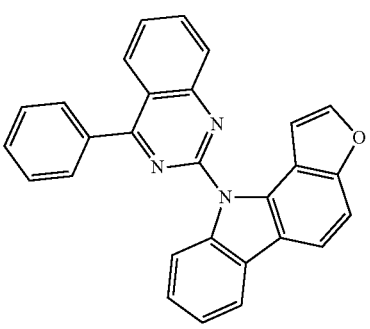

C432
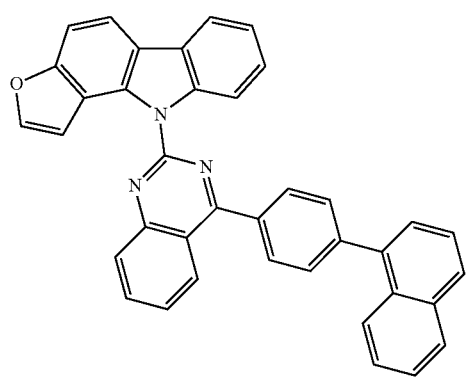
C433
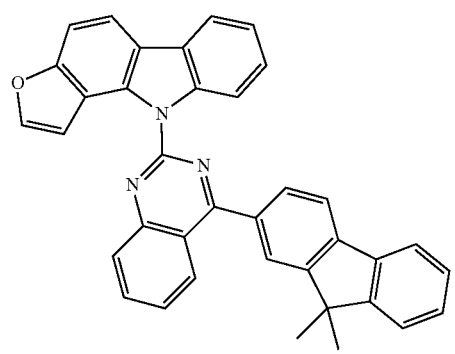
C434
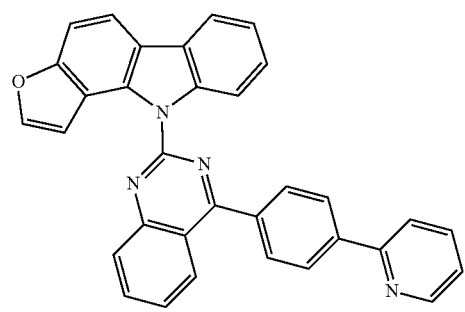
C435
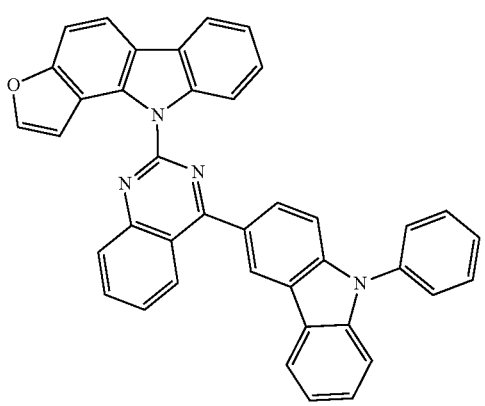
C436
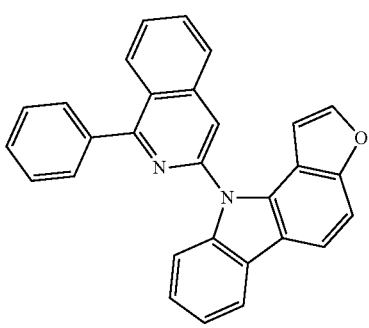
C437
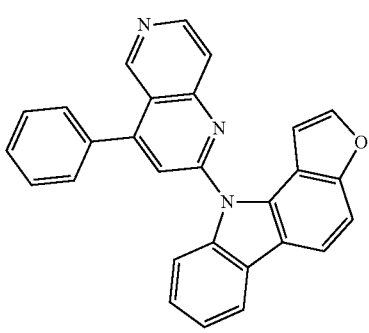
C438
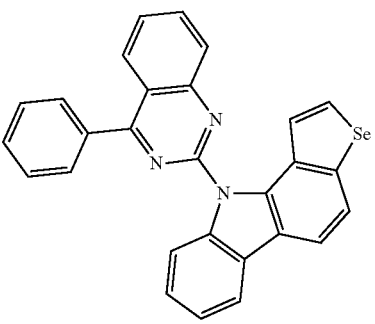
C439
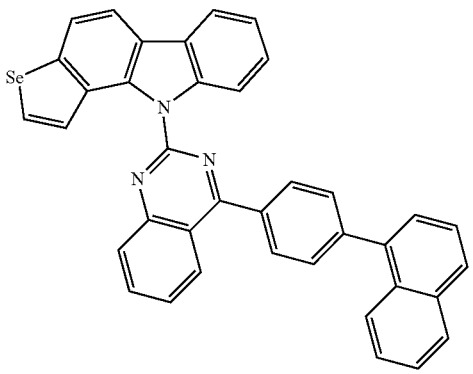

C440
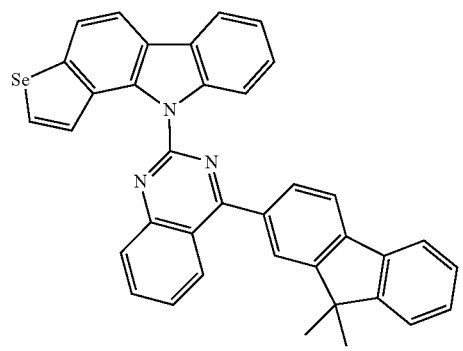
C441
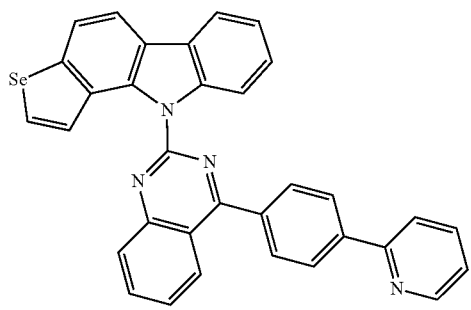
C442
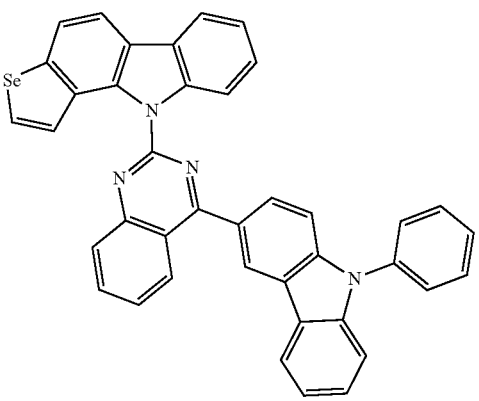
C443
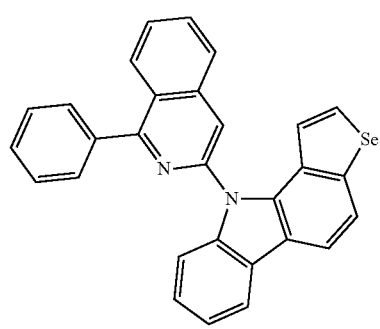
C444
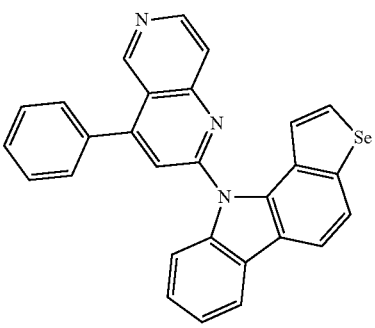
C445
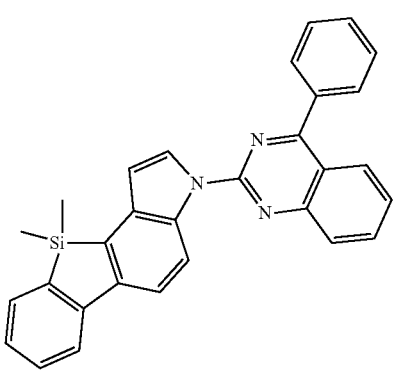
C446
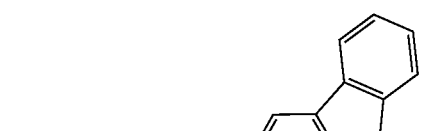
C447

-continued
C448
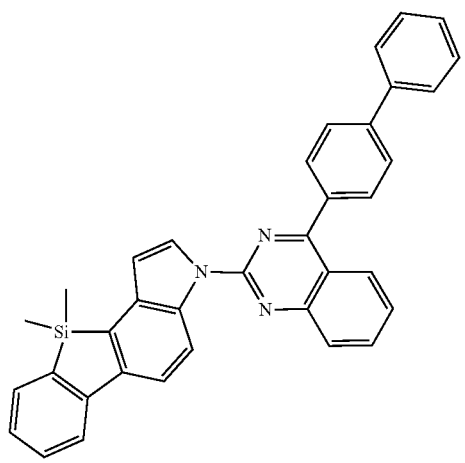
C449
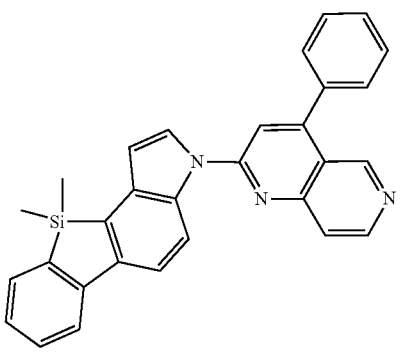
C450
-continued
C451
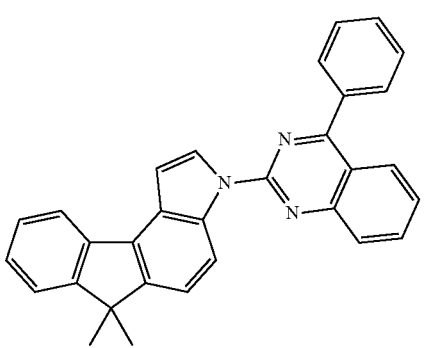
C452
C453
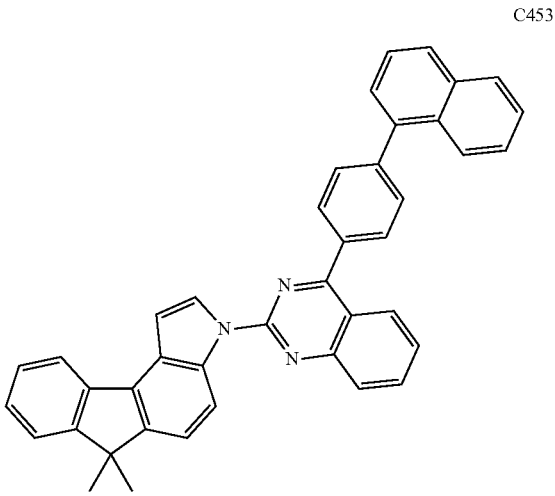
C454
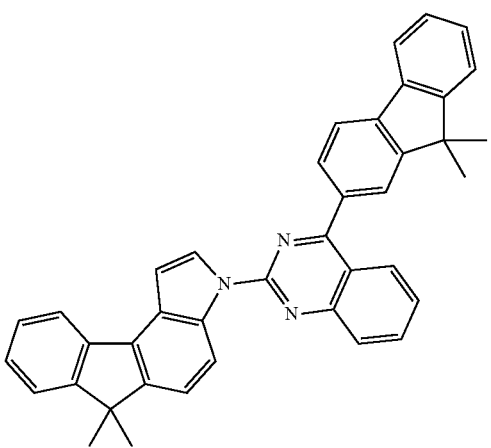

-continued

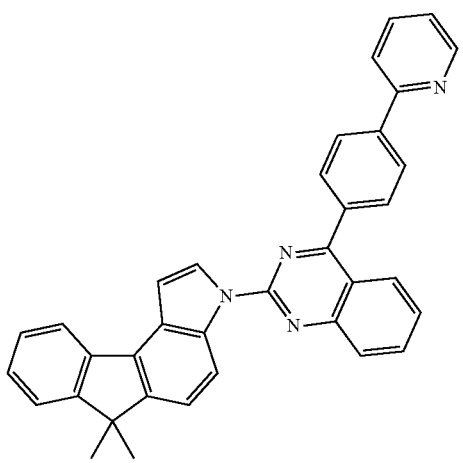
C455

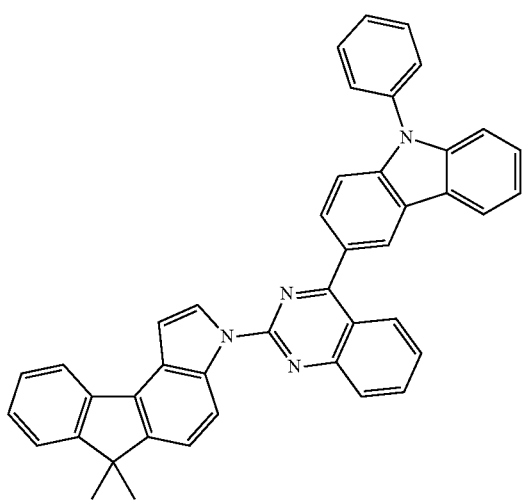
C456

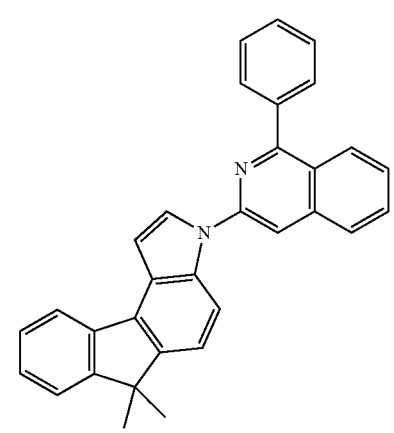
C457

-continued

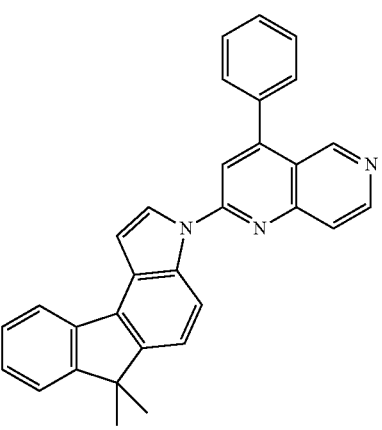
C458

The compound represented by Formula 1 according to the present invention as described above may be synthesized in various manners with reference to the synthesis procedure of the following Examples.

2. Organic Electroluminescence Device

The present invention provides an organic electroluminescence device including the compound represented by Formula 1.

Specifically, the organic electroluminescent device according to the present invention includes (i) an anode, (ii) a cathode, and (iii) an organic material layer having one or more layers interposed between the anode and the cathode, in which at least one of the organic material layer having one or more layers includes the compound represented by Formula 1.

The organic material layer including the compound represented by Formula 1 may be one or more of a hole injection layer, a hole transporting layer, a light-emitting layer, an electron transporting layer, and an electron injection layer. The organic material layer including the compound of Formula 1 may be preferably a hole injection layer, a hole transporting layer, or a light-emitting layer, and more preferably a light-emitting layer.

The light-emitting layer of the organic electroluminescence device according to the present invention may contain a host material (preferably a phosphorescent host material), and in this case, as the host material, the compound represented by Formula 1 may be used. When the light-emitting layer includes the compound represented by Formula 1 as described above, hole transporting capabilities are increased, so that the binding force of holes and electrons is increased in the light-emitting layer, thereby providing an organic electroluminescence device having excellent efficiency (light-emitting efficiency and power efficiency), lifespan, brightness, driving voltage, and the like.

The structure of the organic electroluminescence device according to the present invention is not particularly limited, but as a non-limiting example thereof, the organic electroluminescence device may have a structure in which a substrate, an anode, a hole injection layer, a hole transporting layer, a light-emitting layer, an electron transporting layer, and a cathode are sequentially laminated. Here, an electron injection layer may also be additionally laminated on the electron transporting layer. Furthermore, the organic electroluminescence device according to the present invention may have a structure in which an anode, an organic material layer including one or more layers, and a cathode are sequentially laminated and may also have a structure in which an insulating layer or an adhesive layer may be inserted into the interface between the electrode and the organic material layer.

Meanwhile, a material which may be used as the anode included in the organic electroluminescence device according to the present invention is not particularly limited, but as non-limiting examples thereof, it is possible to use: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or SnO$_2$:Sb; an electrically conductive polymer, such as polythiophene, poly(3-methylthiophene), poly[3,4-(ethylene-1, 2-dioxy)thiophene] (PEDT), polypyrrole, or polyaniline; and carbon black, and the like.

Furthermore, a material which may be used as the cathode included in the organic electroluminescence device according to the present invention is not particularly limited, but as non-limiting examples thereof, it is possible to use: a metal, such as magnesium, calcium, sodium, potassium, titanium, indium, yttrium, lithium, gadolinium, aluminum, silver, tin, and lead, or alloys thereof; and a multi-layer structured material, such as LiF/Al or LiO$_2$/Al, and the like.

The organic material layer included in the organic electroluminescence device according to the present invention may be formed by using materials and methods known in the art, except that the compound represented by Formula 1 is used in any one of a hole injection layer, a hole transporting layer, a light-emitting layer, an electron transporting layer, and an electron injection layer, preferably any one of a hole injection layer, a hole transporting layer, and a light-emitting layer, and more preferably a light-emitting layer.

A material which may be used as a substrate included in the organic electroluminescence device according to the present invention is not particularly limited, but as non-limiting examples thereof, a silicon wafer, quartz, a glass plate, a metal plate, a plastic film, a sheet, and the like may be used.

The organic electroluminescence device of the present invention as described above may be manufactured by a method publicly known in the art, and in this case, the light-emitting layer included in the organic material layer may be manufactured by a vacuum deposition method or a solution application method. Here, examples of the solution application method include spin coating, dip coating, doctor blading, inkjet printing, or a thermal transfer method, but are not limited thereto.

Hereinafter, the present invention will be described in detail as follows through Examples. However, the following Examples are only for exemplifying the present invention, and the present invention is not limited by the following Examples.

[Preparation Example 1] Synthesis of IC-1

<Step 1> Synthesis of 5-(4,4,5,5-tetramethyl-1,3,2-dioxaborolan-2-yl)-1H-indole

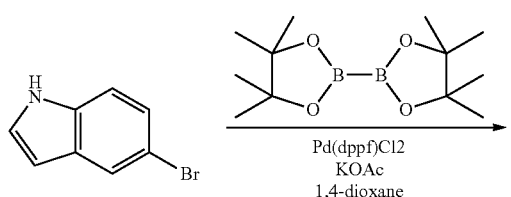

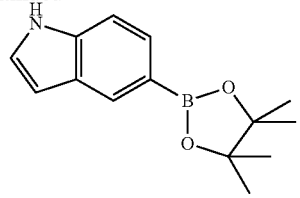

5-bromo-1H-indole (25 g, 0.128 mol), 4,4,4',4',5,5,5',5'-octamethyl-2,2'-bi(1,3,2-dioxaborolane) (48.58 g, 0.191 mol), Pd(dppf)Cl$_2$ (5.2 g, 5 mol %), KOAc (37.55 g, 0.383 mol), and 1,4-dioxane (500 ml) were mixed under nitrogen flow, and the resulting mixture was stirred at 130° C. for 12 hours.

After the reaction was terminated, 5-(4,4,5,5-tetramethyl-1,3,2-dioxaborolan-2-yl)-1H-indole (22.32 g, yield 72%) was obtained by performing extraction with ethyl acetate, removing moisture over MgSO$_4$, and refinement was performed by column chromatography (Hexane:EA=10:1 (v/v)).

<Step 2> Synthesis of 5-(5-bromo-2-nitrophenyl)-1H-indole

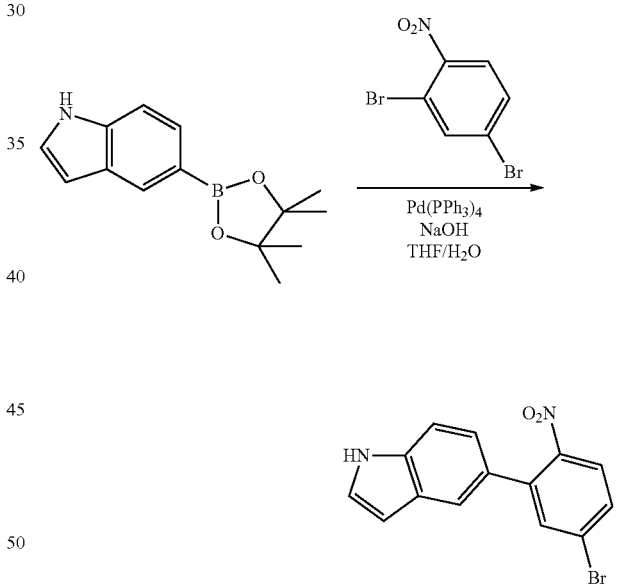

2,4-dibromo-1-nitrobenzene (21.18 g, 75.41 mmol), the product (22 g, 90.49 mmol) in <Step 1>, NaOH (9.05 g, 226.24 mmol), and THF/H$_2$O (400 ml/200 ml) were mixed under nitrogen flow, Pd(PPh$_3$)$_4$ (4.36 g, 5 mol %) was added thereto at 40° C., and the resulting mixture was stirred at 80° C. for 12 hours.

After the reaction was terminated, extraction was performed with methylene chloride, MgSO$_4$ was added thereto, and the resulting product was filtered. 5-(5-bromo-2-nitrophenyl)-1H-indole (9.6 g, yield 40%) was obtained by removing the solvent from the obtained organic layer, and refinement was performed by column chromatography (Hexane:EA=3:1 (v/v)).

<Step 3> Synthesis of 5-(5-bromo-2-nitrophenyl)-1-phenyl-1H-indole

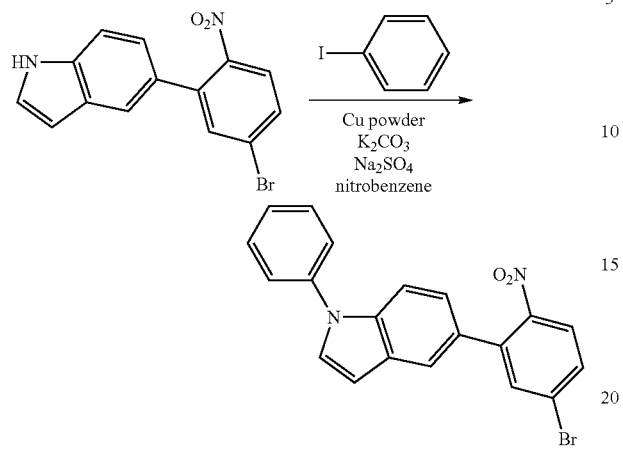

The product (14.64 g, 46.17 mmol) in <Step 2>, iodobenzene (14.13 g, 69.26 mmol), Cu powder (0.29 g, 4.62 mmol), K₂CO₃ (6.38 g, 46.17 mmol), Na₂SO₄ (6.56 g, 46.17 mmol), and nitrobenzene (200 ml) were mixed under nitrogen flow, and the resulting mixture was stirred at 190° C. for 12 hours.

After the reaction was terminated, nitrobenzene was removed, the organic layer was separated by methylene chloride, and water was removed by using MgSO₄. 545-bromo-2-nitrophenyl)-1-phenyl-1H-indole (12.89 g, yield 71%) was obtained by removing the solvent from the organic layer which water had been removed, and refinement was performed by column chromatography (Hexane:MC=3:1 (v/v)).

<Step 4> Synthesis of 7-bromo-3-phenyl-3,10-dihydropyrrolo[3,2-a]carbazole

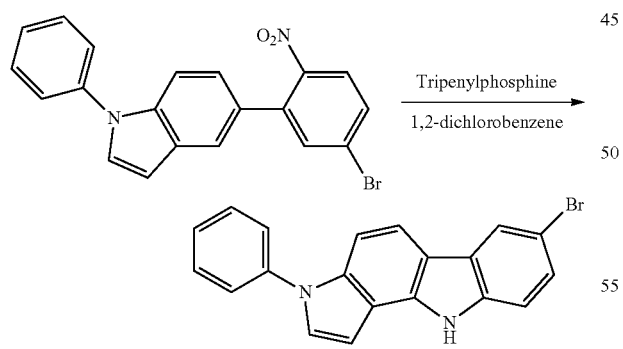

The product (6.25 g, 15.91 mmol) in <Step 3>, triphenylphosphine (10.43 g, 39.77 mmol), and 1,2-dichlorobenzene (50 ml) were mixed under nitrogen flow, and the resulting mixture was stirred for 12 hours.

After the reaction was terminated, 1,2-dichlorobenzene was removed, and extraction was performed with dichloromethane. 7-bromo-3-phenyl-3,10-dihydropyrrolo[3,2-a]carbazole (3.04 g, yield 53%) was obtained by removing water from the obtained organic layer over MgSO₄, and refinement was performed by column chromatography (Hexane:MC=3:1 (v/v)).

<Step 5> Synthesis of 7-bromo-3,10-diphenyl-3,10-dihydropyrrolo[3,2-a]carbazole

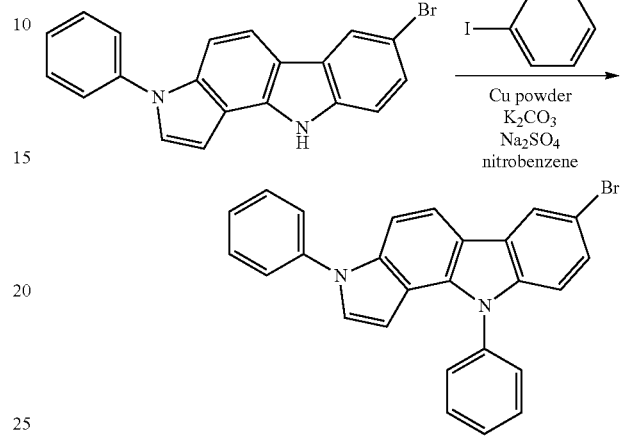

The product (5 g, 13.84 mmol) in <Step 4>, iodobenzene (4.24 g, 20.76 mmol), Cu powder (0.09 g, 1.38 mmol), K₂CO₃ (1.91 g, 13.84 mmol), Na₂SO₄ (1.97 g, 13.84 mmol), and nitrobenzene (70 ml) were mixed under nitrogen flow, and the resulting mixture was stirred at 190° C. for 12 hours.

After the reaction was terminated, nitrobenzene was removed, the organic layer was separated by methylene chloride, and water was removed by using MgSO₄. 7-bromo-3,10-diphenyl-3,10-dihydropyrrolo[3,2-a]carbazole (3.63 g, yield 60%) was obtained by removing the solvent from the organic layer which water had been removed, and refinement was performed by column chromatography (Hexane:MC=3:1 (v/v)).

<Step 6> Synthesis of IC-1

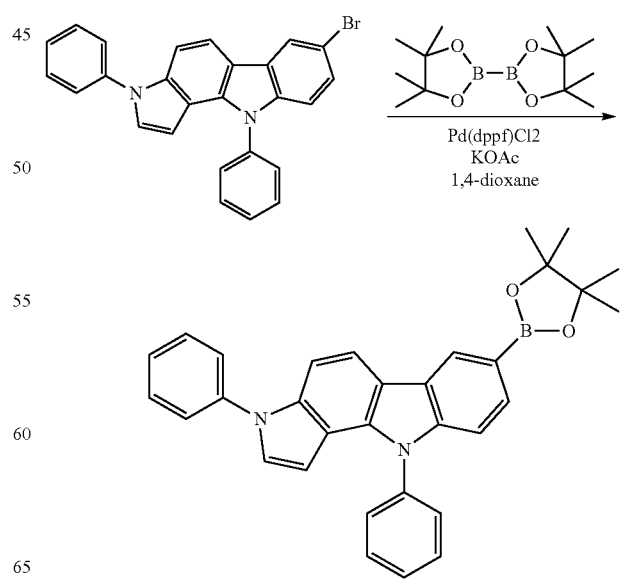

The product (10 g, 22.93 mmol) in <Step 5>, 4,4,4',4',5,5,5',5'-octamethyl-2,2'-bi(1,3,2-dioxaborolane) (7 g, 27.52 mmol), Pd(dppf)Cl₂ (0.8 g, 5 mol %), KOAc (6.75 g, 68.79 mmol), and 1,4-dioxane (250 ml) were mixed under nitrogen flow, and the resulting mixture was stirred at 130° C. for 12 hours.

After the reaction was terminated, IC-1 (7.77 g, yield 70%) was obtained by performing extraction with ethyl acetate, removing moisture over MgSO₄, and refinement was performed by column chromatography (Hexane:EA=10:1 (v/v)).

[Preparation Example 2] Synthesis of IC-2

<Step 1> Synthesis of 4-(4,4,5,5-tetramethyl-1,3,2-dioxaborolan-2-yl)-1H-indole

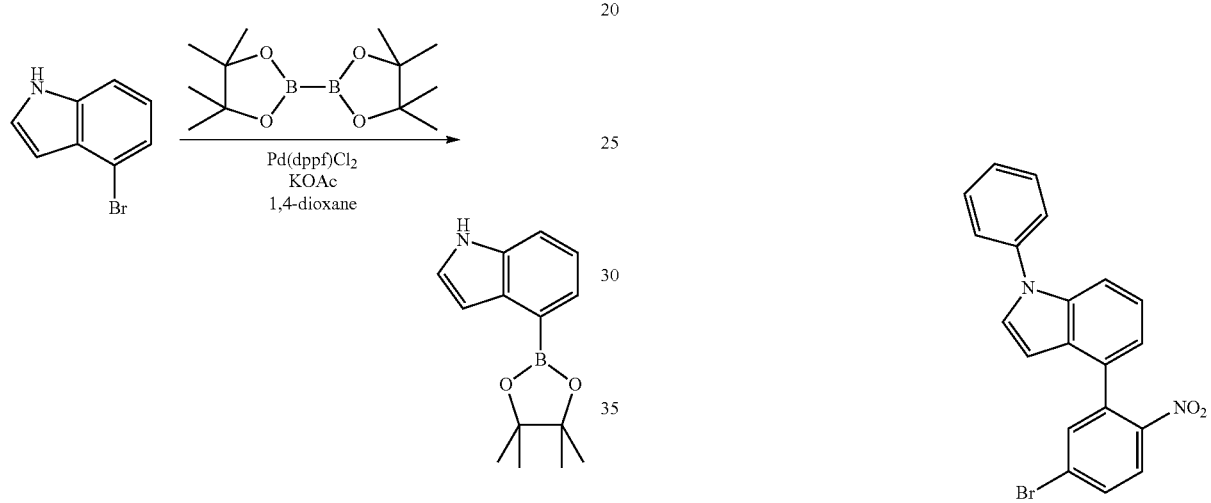

<Step 2> Synthesis of 4-(5-bromo-2-nitrophenyl)-1H-indole

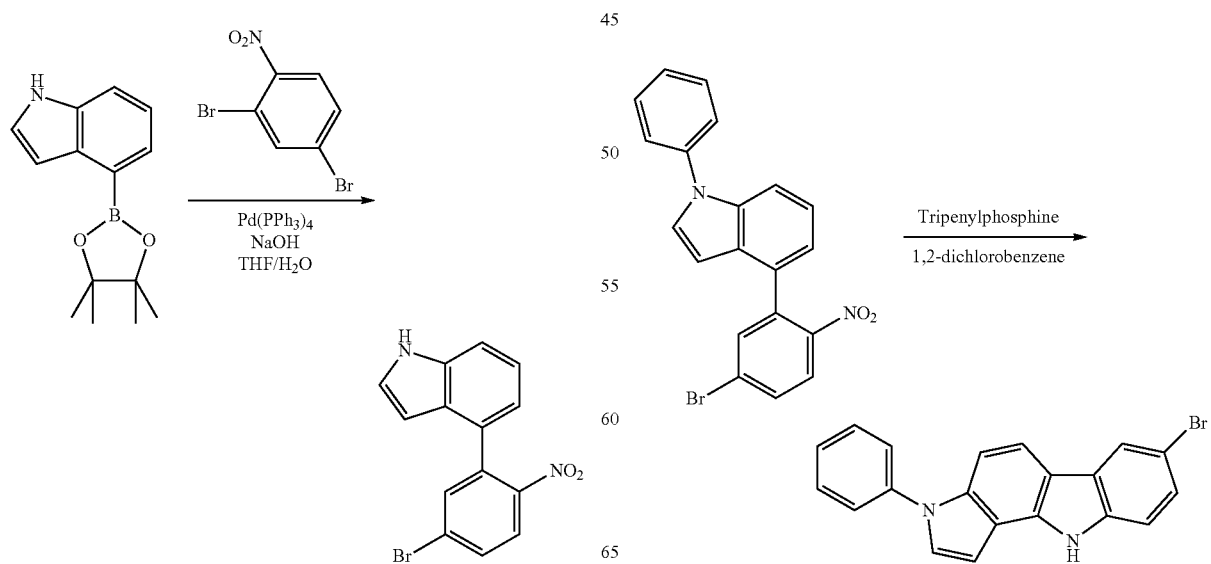

<Step 3> Synthesis of 4-(5-bromo-2-nitrophenyl)-1-phenyl-1H-indole

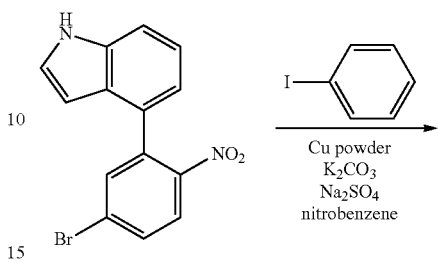

<Step 4> Synthesis of 7-bromo-3-phenyl-3,10-dihydropyrrolo[3,2-a]carbazole

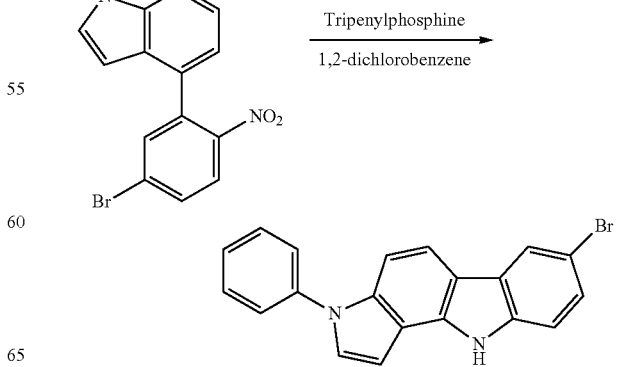

\<Step 5\> Synthesis of 3,6-diphenyl-9-(4,4,5,5-tetramethyl-1,3,2-dioxaborolan-2-yl)-3,6-dihydropyrrolo[2,3-c]carbazole

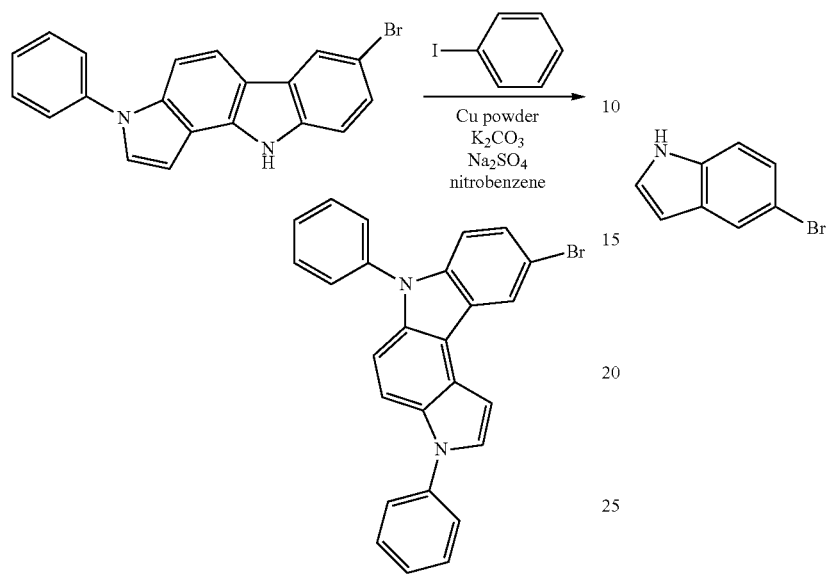

\<Step 6\> Synthesis of IC-2

IC-2 was obtained by performing the same procedure as in Preparation Example 1, except that 4-bromo-1H-indole was used instead of 5-bromo-1H-indole.

[Preparation Example 3] Synthesis of IC-3

\<Step 1\> Synthesis of 5-(4,4,5,5-tetramethyl-1,3,2-dioxaborolan-2-yl)-1H-indole

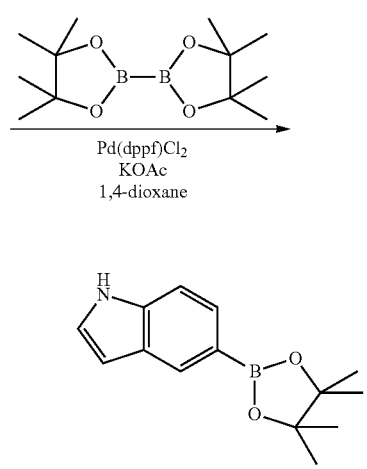

\<Step 2\> Synthesis of 5-(5-bromo-2-nitrophenyl)-1H-indole

\<Step 3\> Synthesis of 5-(5-bromo-2-nitrophenyl)-1-phenyl-1H-indole

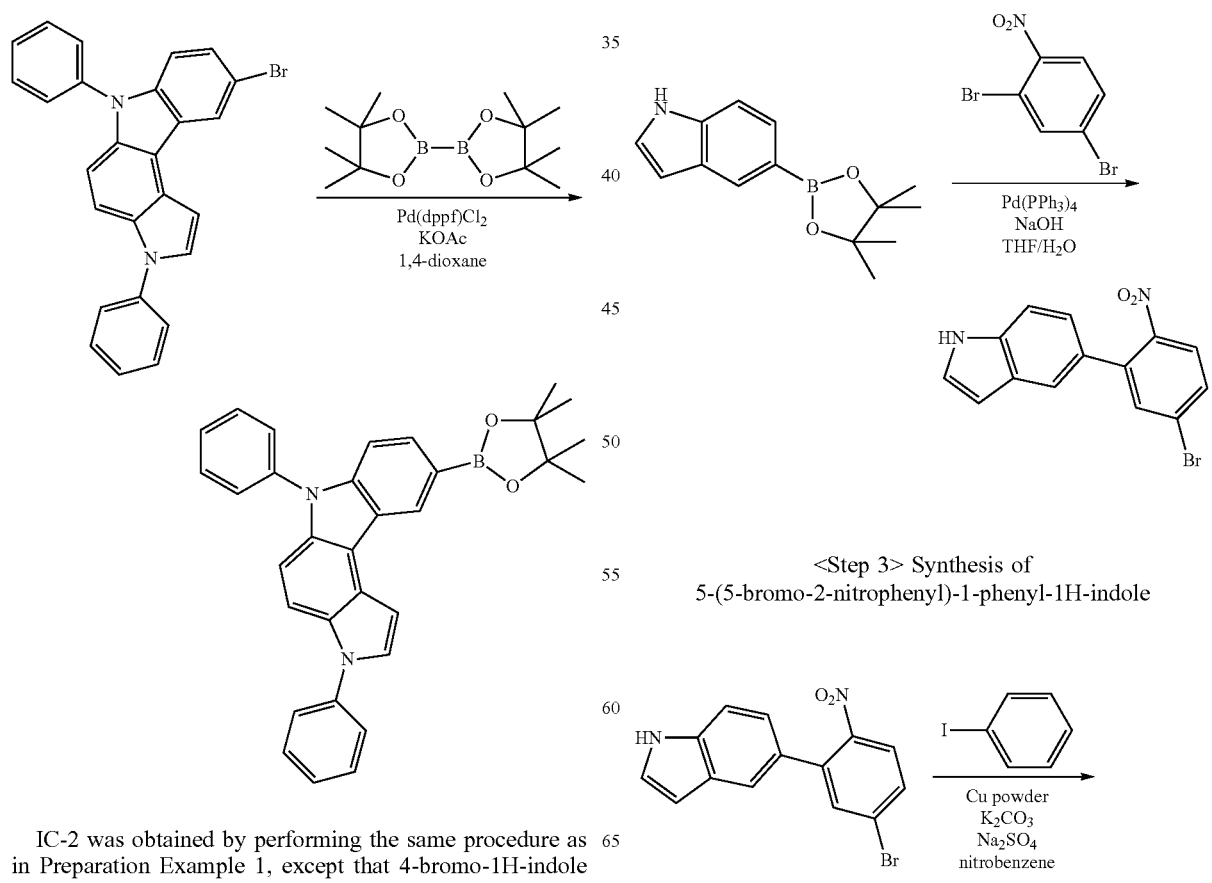

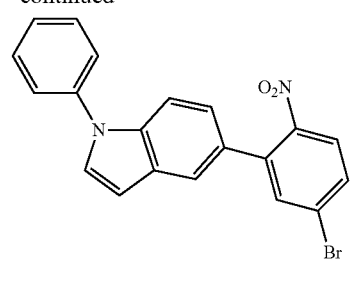

<Step 4> Synthesis of 6-bromo-1-phenyl-1,9-dihydropyrrolo[2,3-b]carbazole

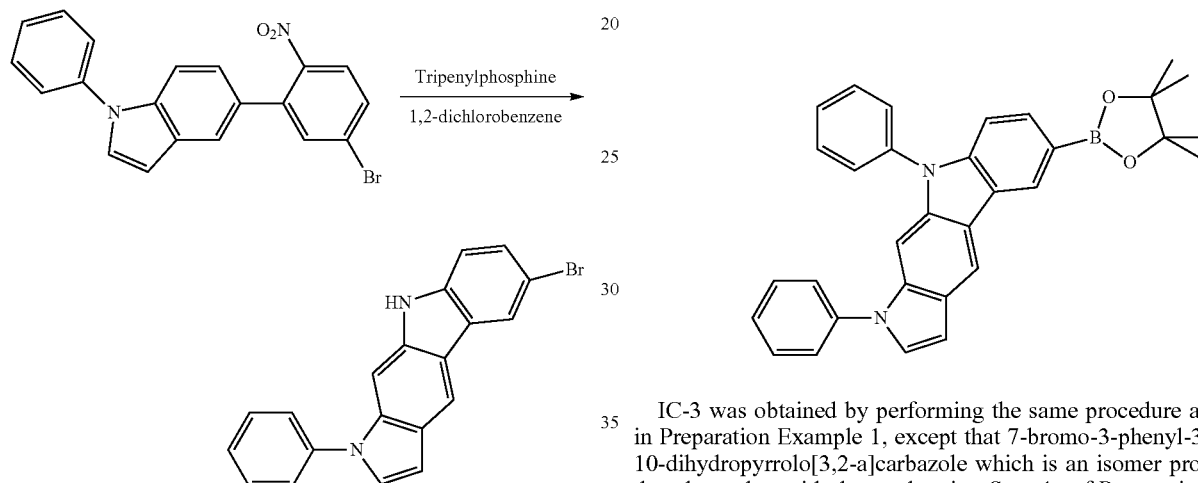

<Step 5> Synthesis of 6-bromo-1,9-diphenyl-1,9-dihydropyrrolo[2,3-b]carbazole

<Step 6> Synthesis of IC-3

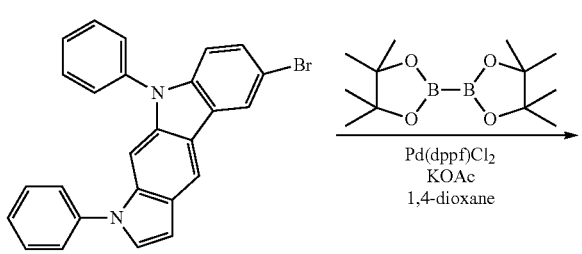

IC-3 was obtained by performing the same procedure as in Preparation Example 1, except that 7-bromo-3-phenyl-3,10-dihydropyrrolo[3,2-a]carbazole which is an isomer produced together with the product in <Step 4> of Preparation Example 1 was used.

[Preparation Example 4] Synthesis of IC-4

<Step 1> Synthesis of 6-(4,4,5,5-tetramethyl-1,3,2-dioxaborolan-2-yl)-1H-indole

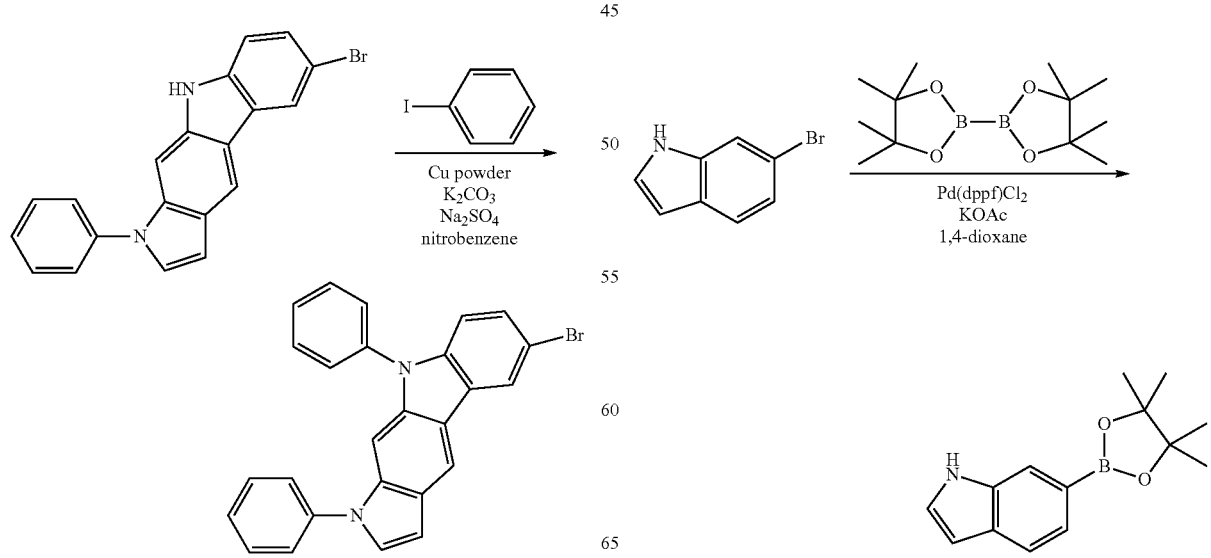

\<Step 2\> Synthesis of 6-(5-bromo-2-nitrophenyl)-1H-indole
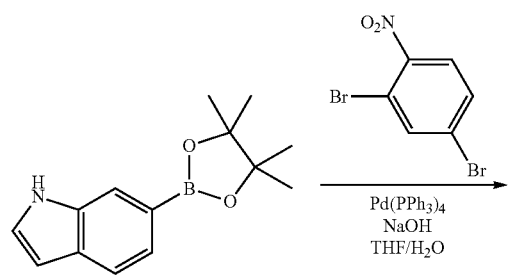
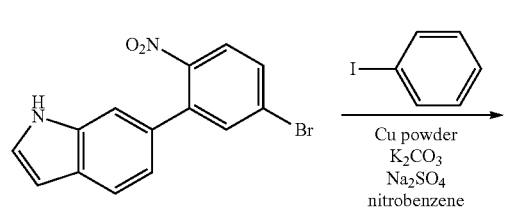
\<Step 3\> Synthesis of 6-(5-bromo-2-nitrophenyl)-1-phenyl-1H-indole
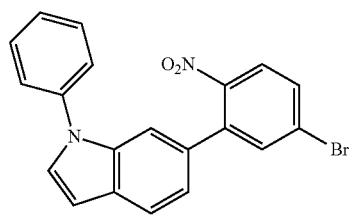
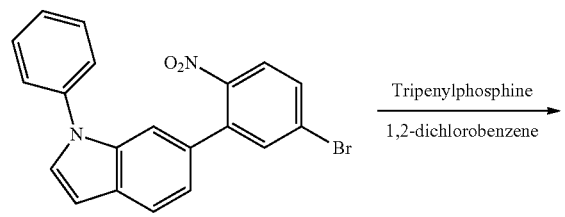
\<Step 4\> Synthesis of 8-bromo-1-phenyl-1,5-dihydropyrrolo[3,2-b]carbazole
-continued
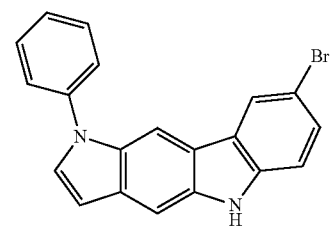
\<Step 5\> Synthesis of 8-bromo-1,5-diphenyl-1,5-dihydropyrrolo[3,2-b]carbazole
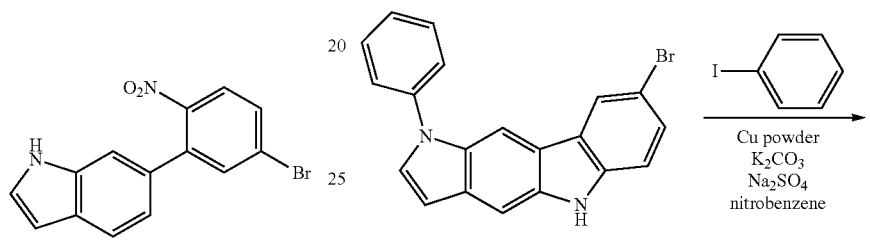
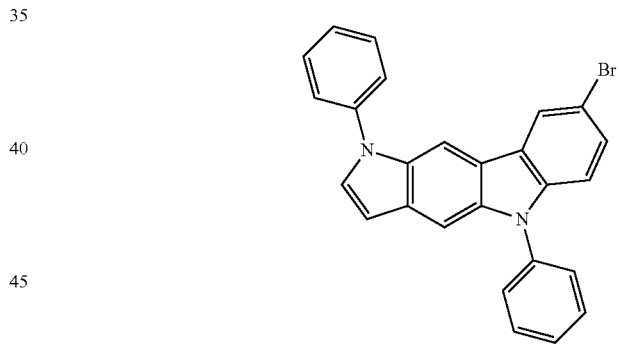
\<Step 6\> Synthesis of IC-4
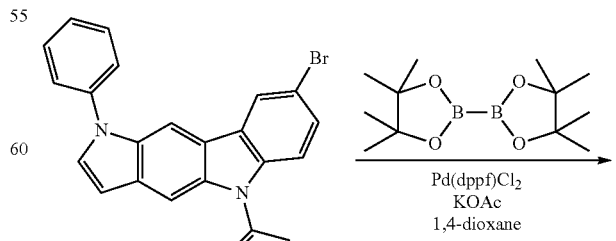

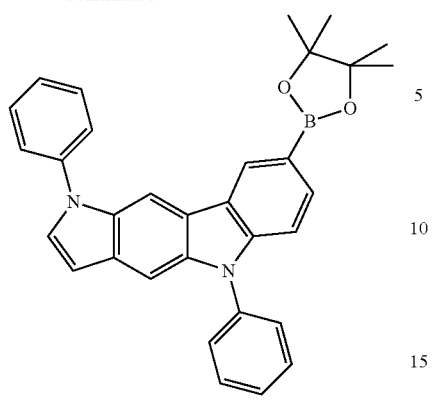

IC-4 was obtained by performing the same procedure as in Preparation Example 1, except that 6-bromo-1H-indole was used instead of 5-bromo-1H-indole, and 8-bromo-1-phenyl-1,5-dihydropyrrolo[3,2-b]carbazole of the two isomers produced in <Step 4> was used.

[Preparation Example 5] Synthesis of IC-5

<Step 1> Synthesis of 6-(4,4,5,5-tetramethyl-1,3,2-dioxaborolan-2-yl)-1H-indole

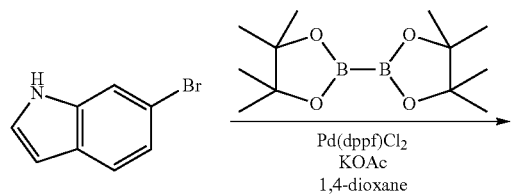

<Step 2> Synthesis of 6-(5-bromo-2-nitrophenyl)-1H-indole

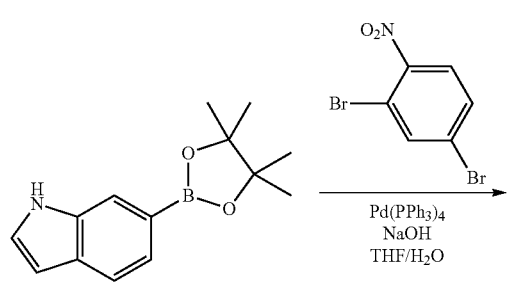

<Step 3> Synthesis of 6-(5-bromo-2-nitrophenyl)-1-phenyl-1H-indole

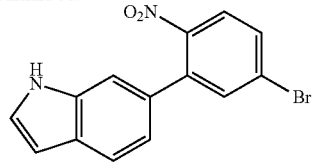

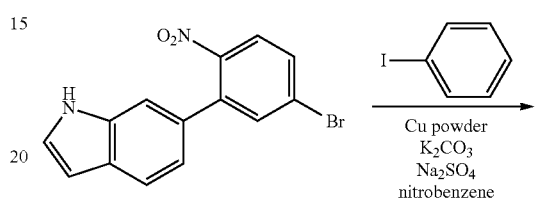

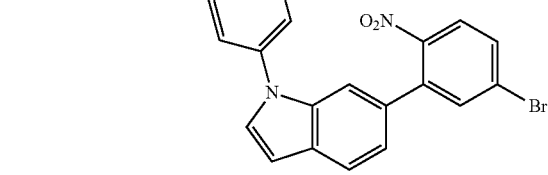

<Step 4> Synthesis of 7-bromo-1-phenyl-1,10-dihydropyrrolo[2,3-a]carbazole

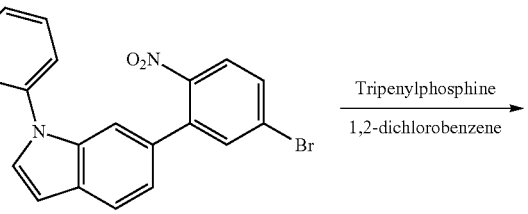

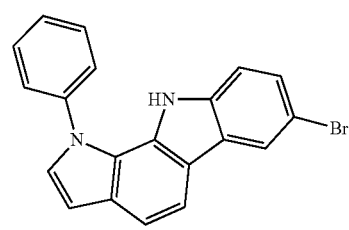

<Step 5> Synthesis of 7-bromo-1,10-diphenyl-1,10-dihydropyrrolo[2,3-a]carbazole

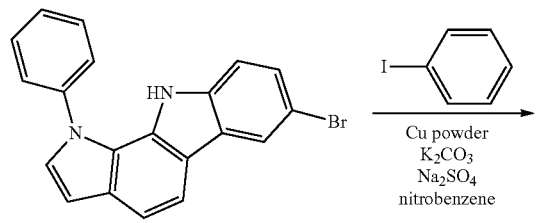

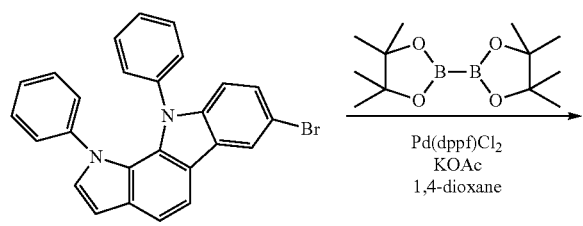

<Step 6> Synthesis of IC-5

IC-5 was obtained by performing the same procedure as in Preparation Example 1, except that 6-bromo-1H-indole was used instead of 5-bromo-1H-indole, and 7-bromo-1-phenyl-1,10-dihydropyrrolo[2,3-a]carbazole of the two isomers produced in <Step 4> was used.

[Preparation Example 6] Synthesis of IC-6

<Step 1> Synthesis of 7-(4,4,5,5-tetramethyl-1,3,2-dioxaborolan-2-yl)-1H-indole

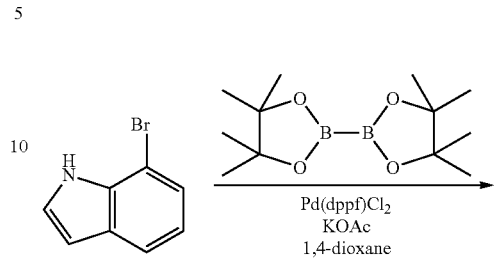

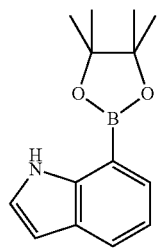

<Step 2> Synthesis of 7-(5-bromo-2-nitrophenyl)-1H-indole

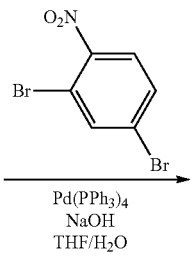

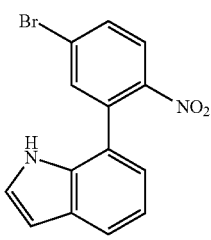

<Step 3> Synthesis of 7-(5-bromo-2-nitrophenyl)-1-phenyl-1H-indole

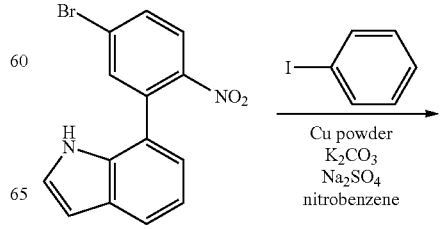

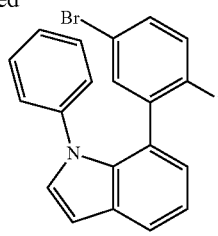

<Step 4> Synthesis of 9-bromo-1-phenyl-1,6-dihydropyrrolo[3,2-c]carbazole

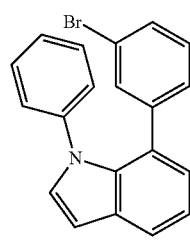 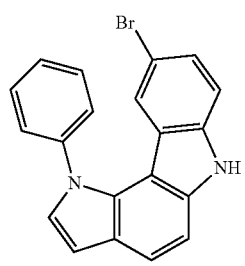

<Step 5> Synthesis of 9-bromo-1,6-diphenyl-1,6-dihydropyrrolo[3,2-c]carbazole

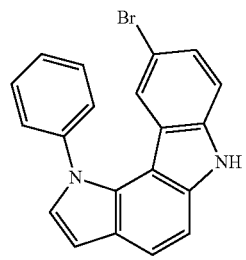 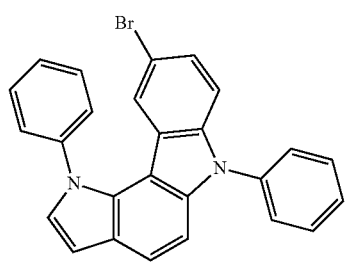

<Step 6> Synthesis of IC-6

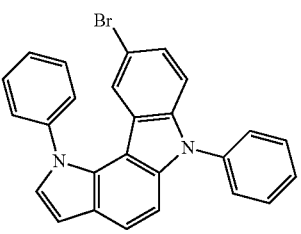 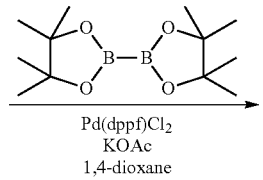

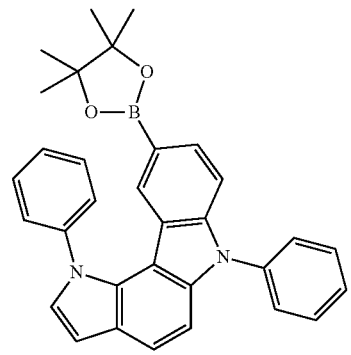

IC-6 was obtained by performing the same procedure as in Preparation Example 1, except that 7-bromo-1H-indole was used instead of 5-bromo-1H-indole.

[Preparation Example 7] Synthesis of IC-7

<Step 1> Synthesis of 5-(4,4,5,5-tetramethyl-1,3,2-dioxaborolan-2-yl)-1H-indole

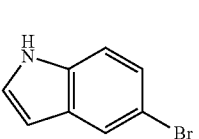 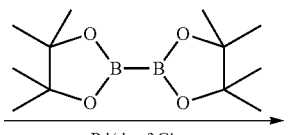

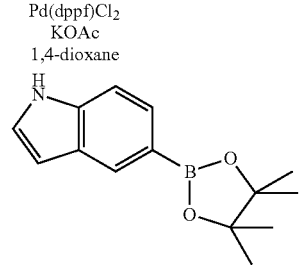

5-(4,4,5,5-tetramethyl-1,3,2-dioxaborolan-2-yl)-1H-indole was obtained by performing the same procedure as in <Step 1> of Preparation Example 1.

<Step 2> Synthesis of 5-(2-nitrophenyl)-1H-indole

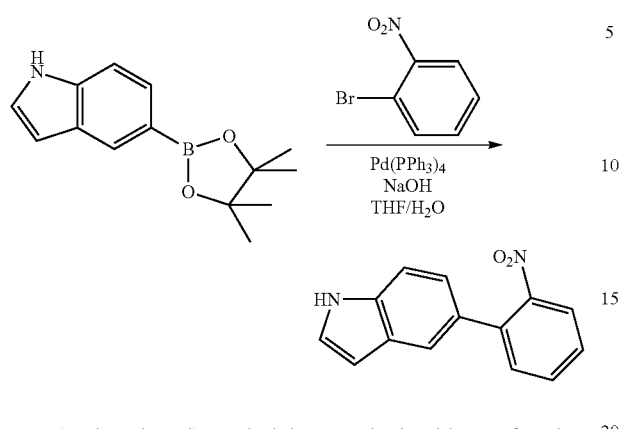

5-(2-nitrophenyl)-1H-indole was obtained by performing the same procedure as in <Step 2> of Preparation Example 1, except that 1-bromo-2-nitrobenzene was used instead of 2,4-dibromo-1-nitrobenzene.

<Step 3> Synthesis of 5-(2-nitrophenyl)-1-phenyl-1H-indole

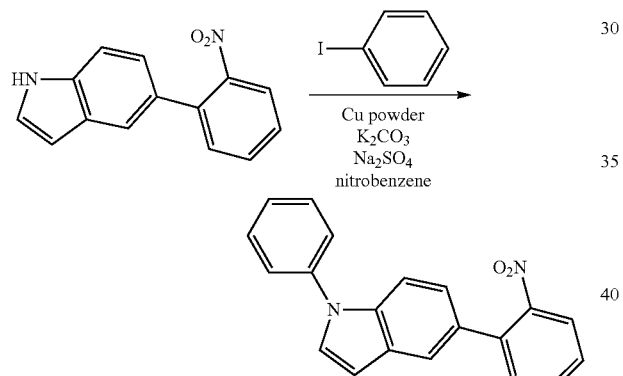

5-(2-nitrophenyl)-1-phenyl-1H-indole was obtained by performing the same procedure as in <Step 3> of Preparation Example 1, except that 5-(2-nitrophenyl)-1H-indole was used instead of 5-(5-bromo-2-nitrophenyl)-1H-indole.

<Step 4> Synthesis of IC-7

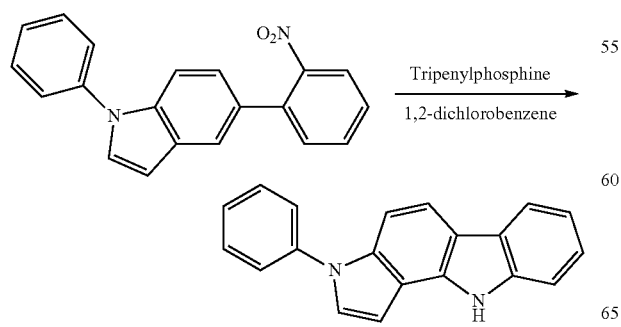

IC-7 was obtained by performing the same procedure as in <Step 4> of Preparation Example 1, except that the product in <Step 3> was used instead of 5-(5-bromo-2-nitrophenyl)-1-phenyl-1H-indole.

[Preparation Example 8] Synthesis of IC-8

<Step 1> Synthesis of 4-(4,4,5,5-tetramethyl-1,3,2-dioxaborolan-2-yl)-1H-indole

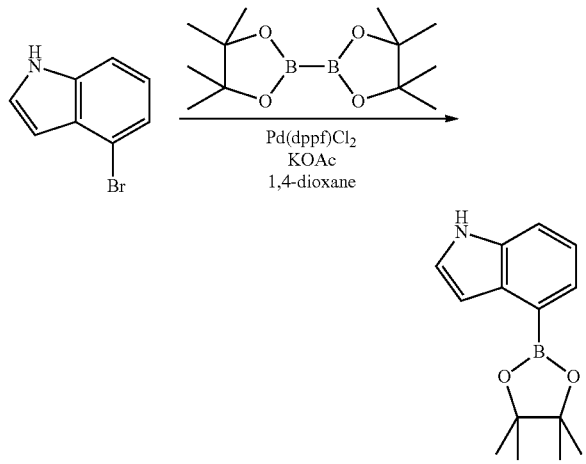

<Step 2> Synthesis of 4-(2-nitrophenyl)-1H-indole

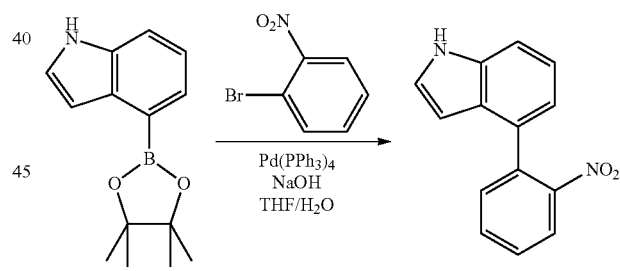

<Step 3> Synthesis of 4-(2-nitrophenyl)-1-phenyl-1H-indole

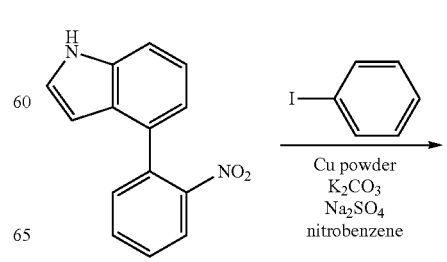

-continued

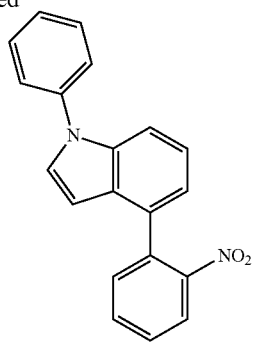

<Step 4> Synthesis of IC-8

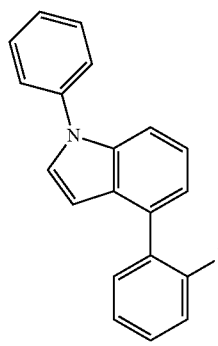

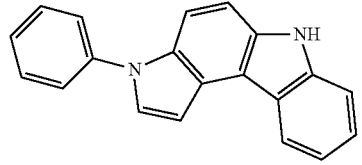

IC-8 was obtained by performing the same procedure as in Preparation Example 7, except that 4-bromo-1H-indole was used instead of 5-bromo-1H-indole.

[Preparation Example 9] Synthesis of IC-9

<Step 1> Synthesis of 5-(4,4,5,5-tetramethyl-1,3,2-dioxaborolan-2-yl)-1H-indole

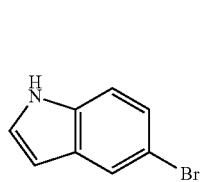

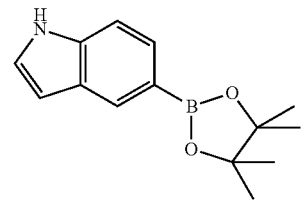

<Step 2> Synthesis of 5-(2-nitrophenyl)-1H-indole

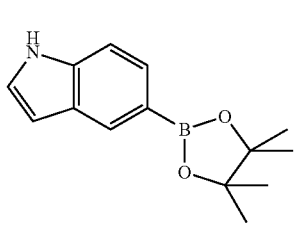

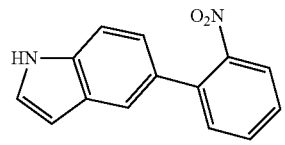

<Step 3> Synthesis of 5-(2-nitrophenyl)-1-phenyl-1H-indole

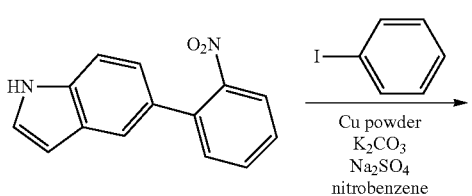

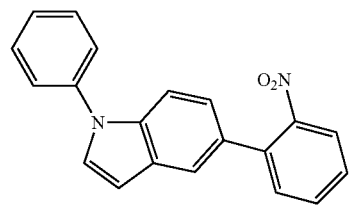

<Step 4> Synthesis of IC-9

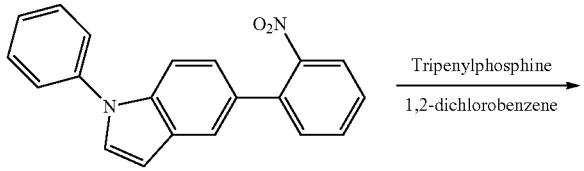

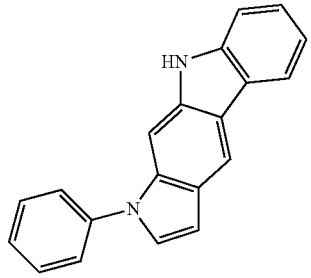

IC-9 which is the structural isomer of IC-7 was obtained by performing the same procedure as in Preparation Example 7.

[Preparation Example 10] Synthesis of IC-10

<Step 1> Synthesis of 6-(4,4,5,5-tetramethyl-1,3,2-dioxaborolan-2-yl)-1H-indole

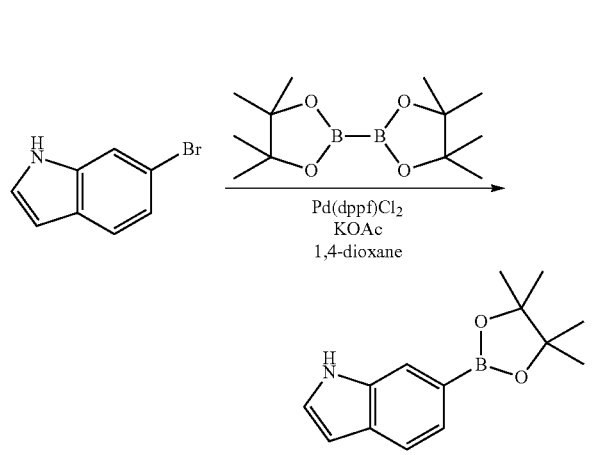

<Step 2> Synthesis of 6-(2-nitrophenyl)-1H-indole

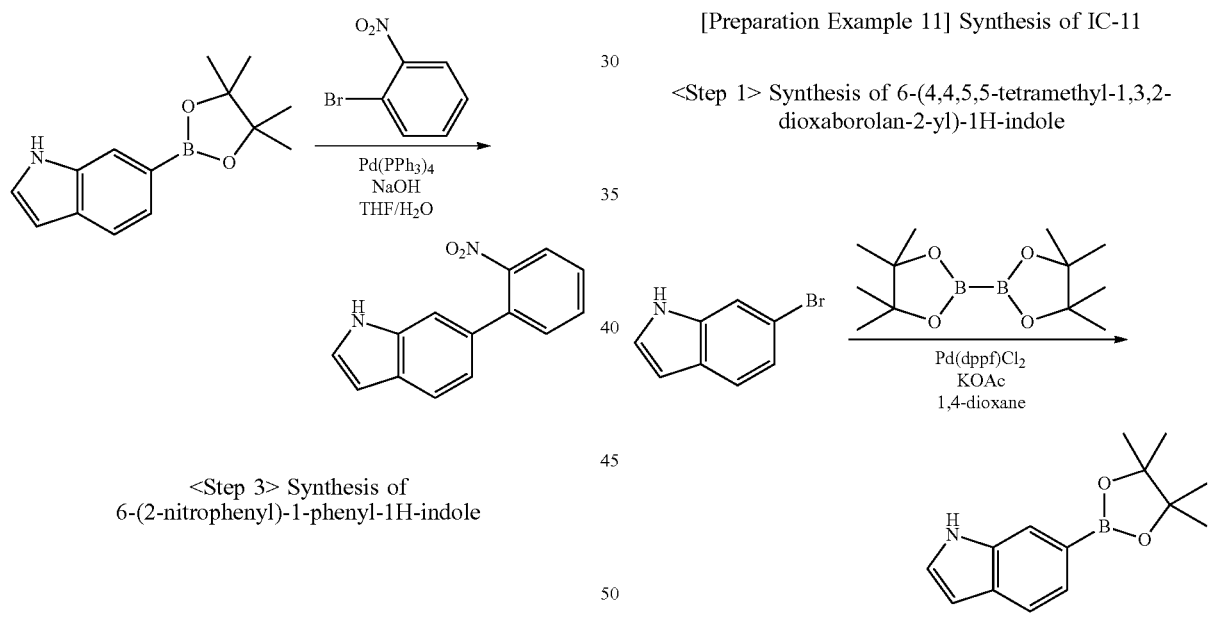

<Step 3> Synthesis of 6-(2-nitrophenyl)-1-phenyl-1H-indole

<Step 4> Synthesis of IC-10

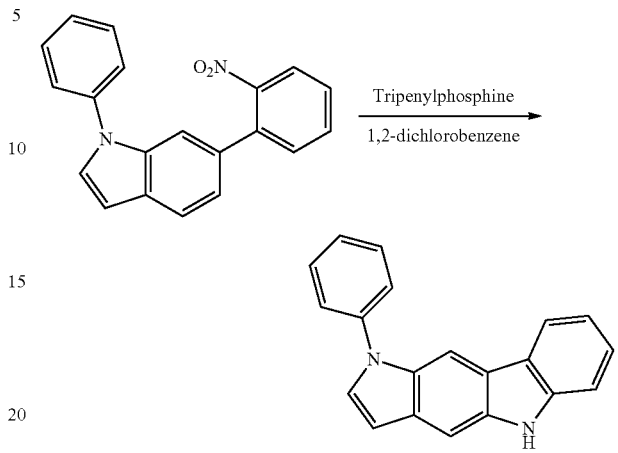

IC-10 was obtained by performing the same procedure as in Preparation Example 7, except that 6-bromo-1H-indole was used instead of 5-bromo-1H-indole.

[Preparation Example 11] Synthesis of IC-11

<Step 1> Synthesis of 6-(4,4,5,5-tetramethyl-1,3,2-dioxaborolan-2-yl)-1H-indole

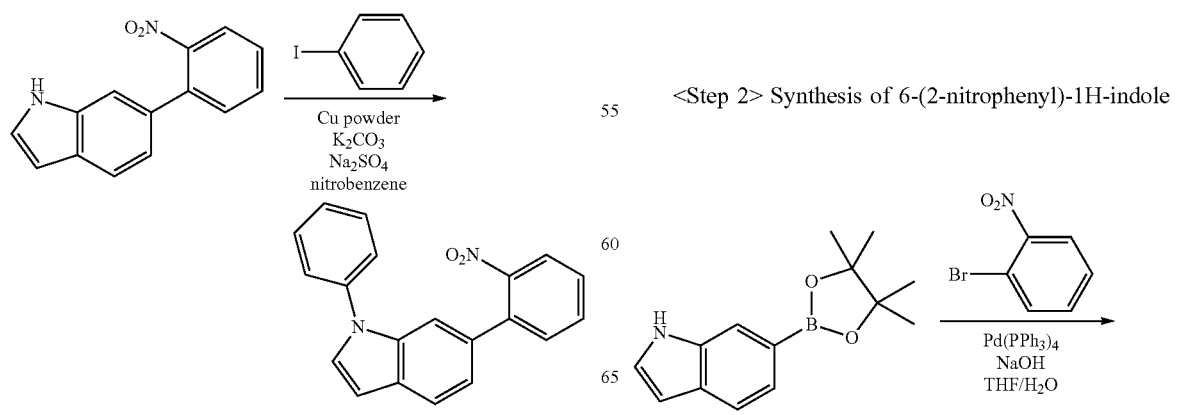

<Step 2> Synthesis of 6-(2-nitrophenyl)-1H-indole

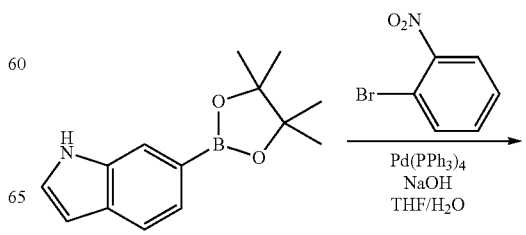

-continued

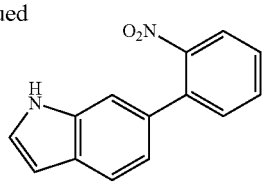

\<Step 3\> Synthesis of 6-(2-nitrophenyl)-1-phenyl-1H-indole

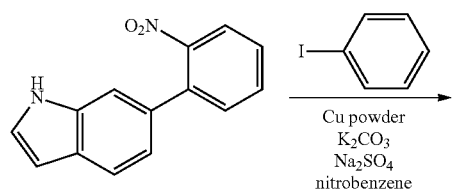

\<Step 4\> Synthesis of IC-11

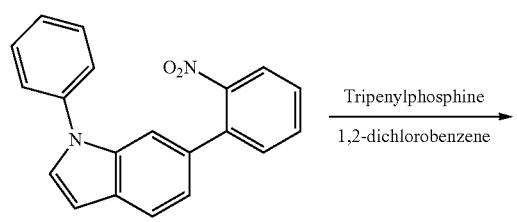

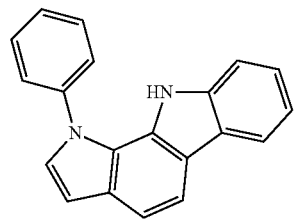

IC-11 which is the structural isomer of IC-10 was obtained by performing the same procedure as in Preparation Example 7, except that 6-bromo-1H-indole was used instead of 5-bromo-1H-indole.

[Preparation Example 12] Synthesis of IC-12

\<Step 1\> Synthesis of 7-(4,4,5,5-tetramethyl-1,3,2-dioxaborolan-2-yl)-1H-indole

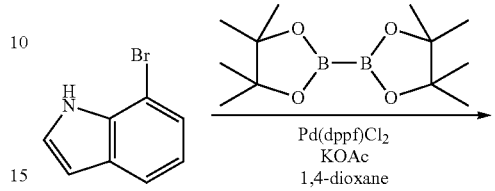

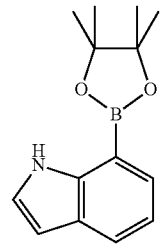

\<Step 2\> Synthesis of 7-(2-nitrophenyl)-1H-indole

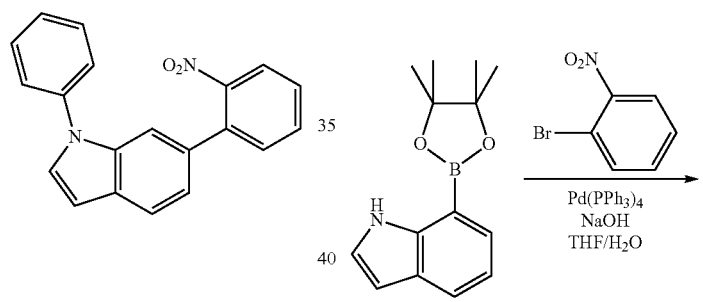

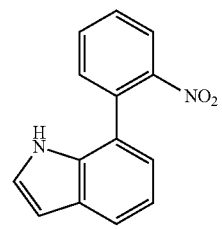

\<Step 3\> Synthesis of 7-(2-nitrophenyl)-1-phenyl-1H-indole

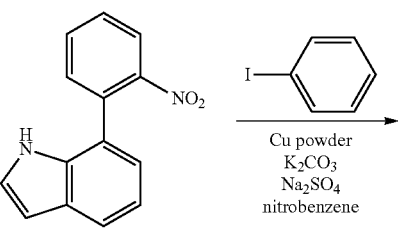

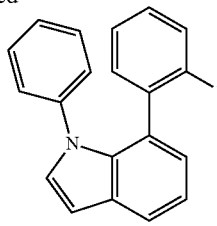

\<Step 4\> Synthesis of IC-12

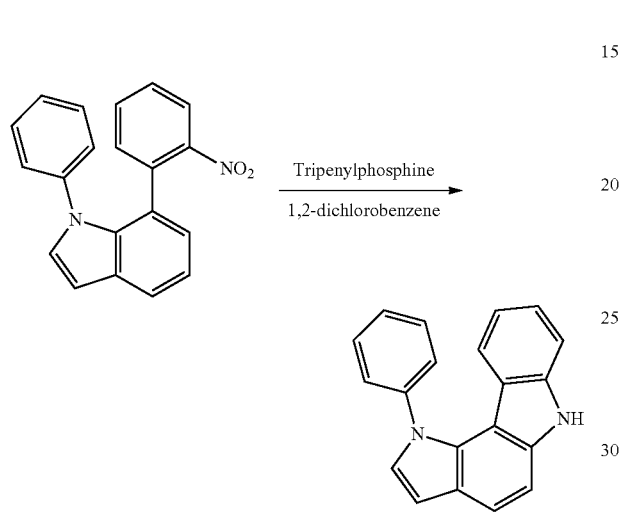

IC-12 was obtained by performing the same procedure as in Preparation Example 7, except that 7-bromo-1H-indole was used instead of 5-bromo-1H-indole.

[Preparation Example 13] Synthesis of IC-13

\<Step 1\> Synthesis of 3,10-diphenyl-7-(4,4,5,5-tetramethyl-1,3,2-dioxaborolan-2-yl)-3,10-dihydropyrrolo[3,2-a]carbazole

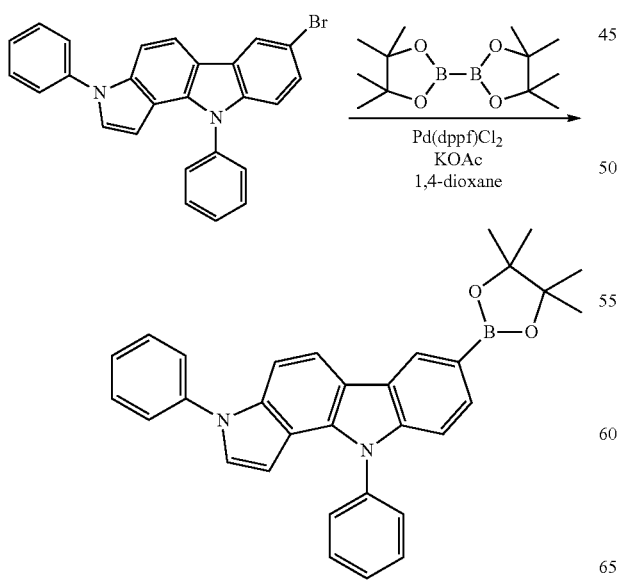

3,10-diphenyl-7-(4,4,5,5-tetramethyl-1,3,2-dioxaborolan-2-yl)-3,10-dihydropyrrolo[3,2-a]carbazole was obtained by performing the same procedure as in \<Step 1\> of Preparation Example 1, except that IC-1 was used instead of 5-bromo-1H-indole.

\<Step 2\> Synthesis of 7-(4-bromophenyl)-3,10-diphenyl-3,10-dihydropyrrolo[3,2-a]carbazole

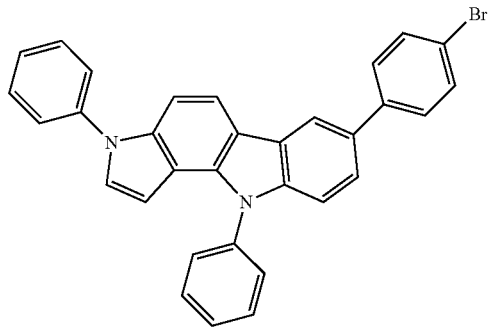

1-bromo-4-iodobenzene (6.98 g, 24.78 mmol), the product (10 g, 20.65 mmol) in \<Step 1\>, NaOH (2.48 g, 61.95 mmol), and THF/H$_2$O (200 ml/30 ml) were mixed under nitrogen flow, Pd(PPh$_3$)$_4$ (0.72 g, 0.6195 mmol) was added thereto at 40° C., and the resulting mixture was stirred at 80° C. for 12 hours.

After the reaction was terminated, extraction was performed with methylene chloride, MgSO$_4$ was added thereto, and the resulting product was filtered. 7-(4-bromophenyl)-3,10-diphenyl-3,10-dihydropyrrolo[3,2-a]carbazole (4.1 g, yield 40%) was obtained by removing the solvent from the obtained organic layer, and refinement was performed by recrystallization.

<Step 3> Synthesis of IC-13

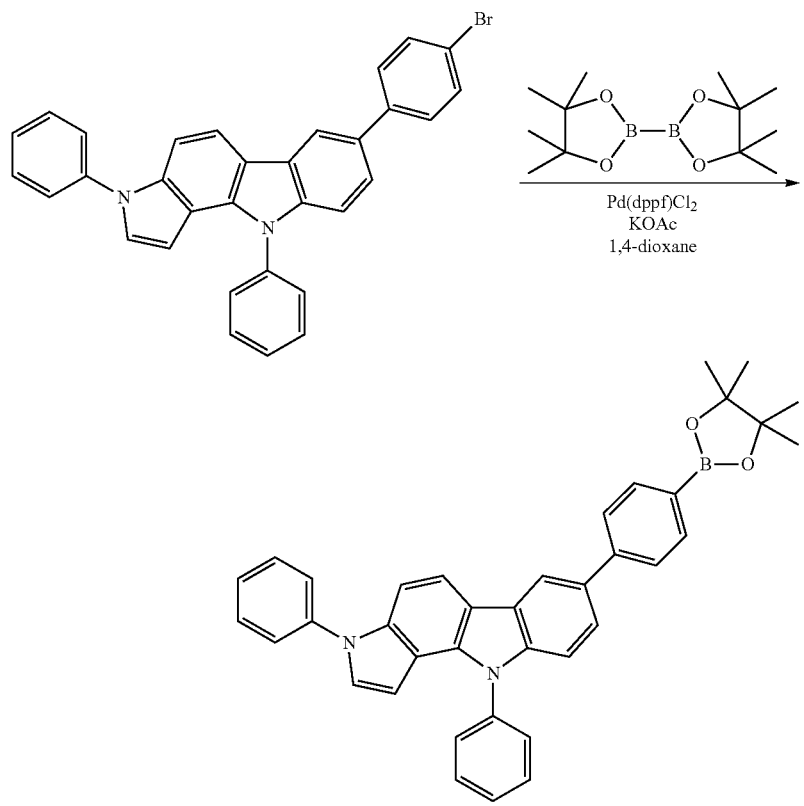

IC-13 was obtained by performing the same procedure as in <Step 1> of Preparation Example 1, except that 7-(4-bromophenyl)-3,10-diphenyl-3,10-dihydropyrrolo[3,2-a]carbazole was used instead of 5-bromo-1H-indole.

[Preparation Example 14] Synthesis of IC-14

<Step 1> Synthesis of 3,10-diphenyl-7-(4,4,5,5-tetramethyl-1,3,2-dioxaborolan-2-yl)-3,10-dihydropyrrolo[3,2-a]carbazole

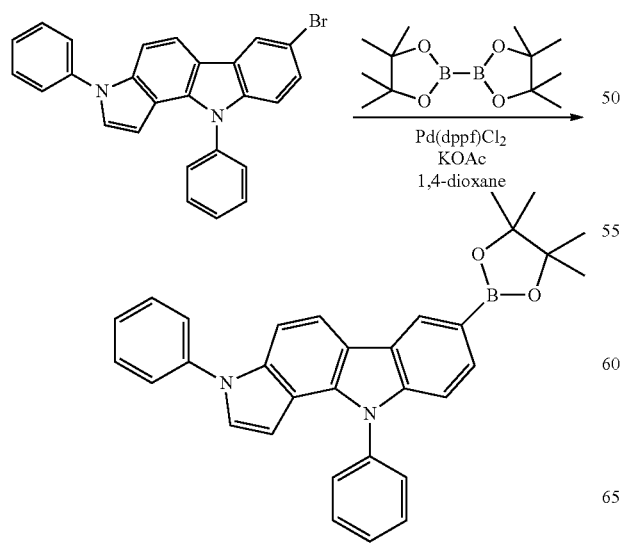

<Step 2> Synthesis of 7-(3-bromophenyl)-3,10-diphenyl-3,10-dihydropyrrolo[3,2-a]carbazole

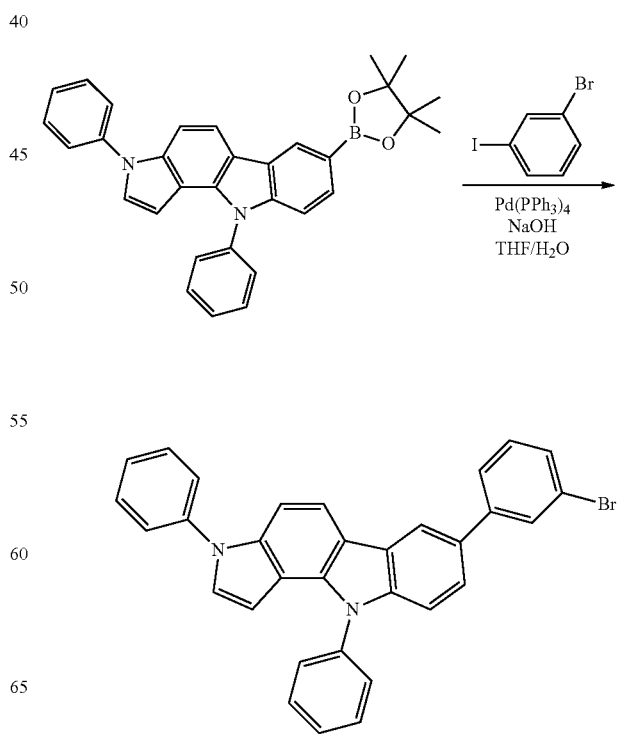

<Step 3> Synthesis of IC-14

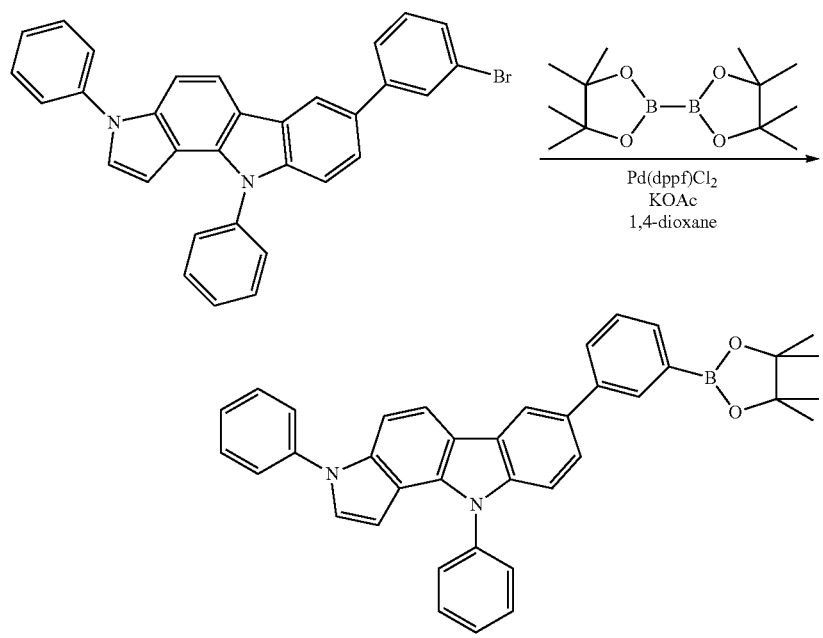

IC-14 was obtained by performing the same procedure as in Preparation Example 13, except that 1-bromo-3-iodobenzene was used instead of 1-bromo-4-iodobenzene.

[Preparation Example 15] Synthesis of IC-15

<Step 1> Synthesis of 3,10-diphenyl-7-(4,4,5,5-tetramethyl-1,3,2-dioxaborolan-2-yl)-3,10-dihydropyrrolo[3,2-a]carbazole

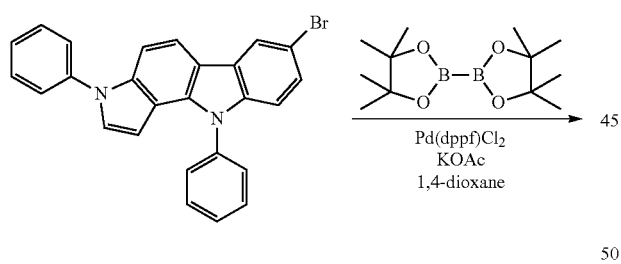

<Step 2> Synthesis of 7-(5-bromopyridin-2-yl)-3,10-diphenyl-3,10-dihydropyrrolo[3,2-a]carbazole

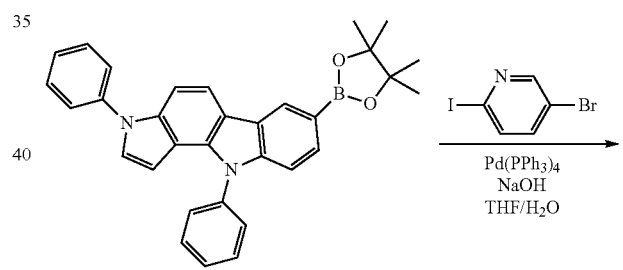

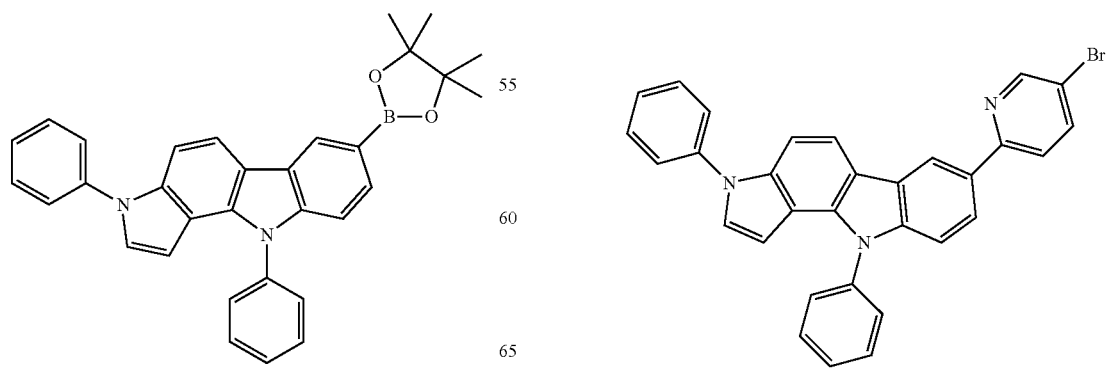

<Step 3> Synthesis of IC-15

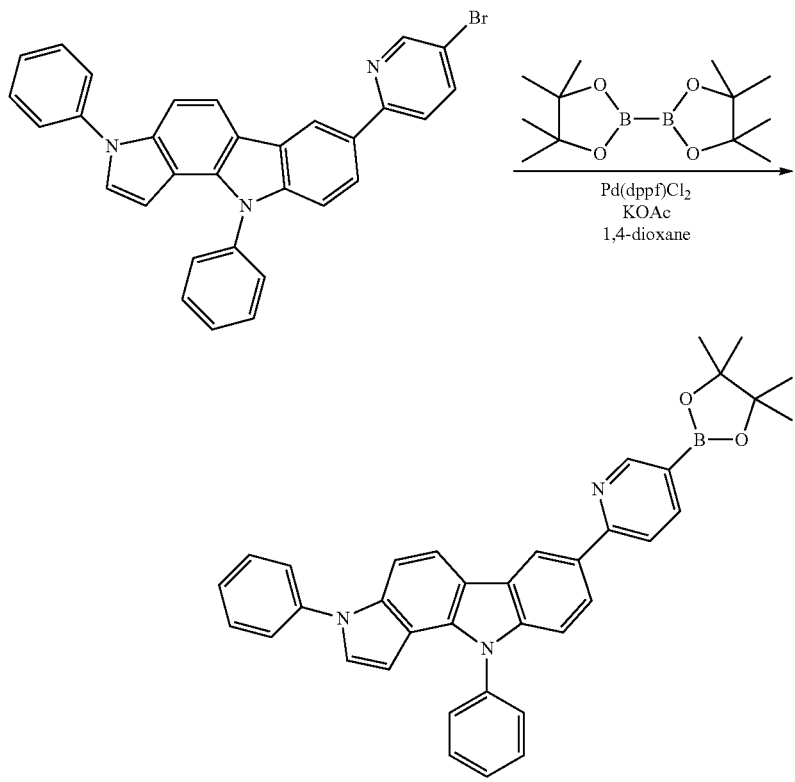

IC-15 was obtained by performing the same procedure as in Preparation Example 13, except that 5-bromo-2-iodopyridine was used instead of 1-bromo-4-iodobenzene.

[Preparation Example 16] Synthesis of IC-16

<Step 1> Synthesis of 1-(biphenyl-4-yl)-5-(5-bromo-2-nitrophenyl)-1H-indole

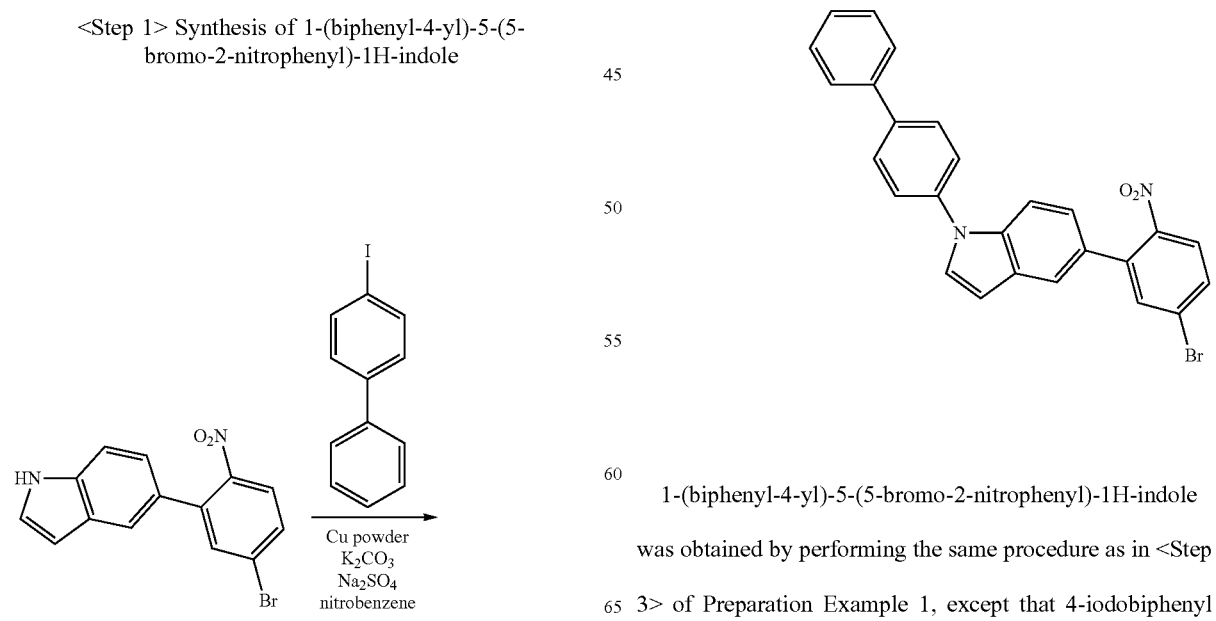

1-(biphenyl-4-yl)-5-(5-bromo-2-nitrophenyl)-1H-indole was obtained by performing the same procedure as in <Step 3> of Preparation Example 1, except that 4-iodobiphenyl was used instead of iodobenzene.

229

<Step 2> Synthesis of 3-(biphenyl-4-yl)-7-bromo-3,10-dihydropyrrolo[3,2-a]carbazole

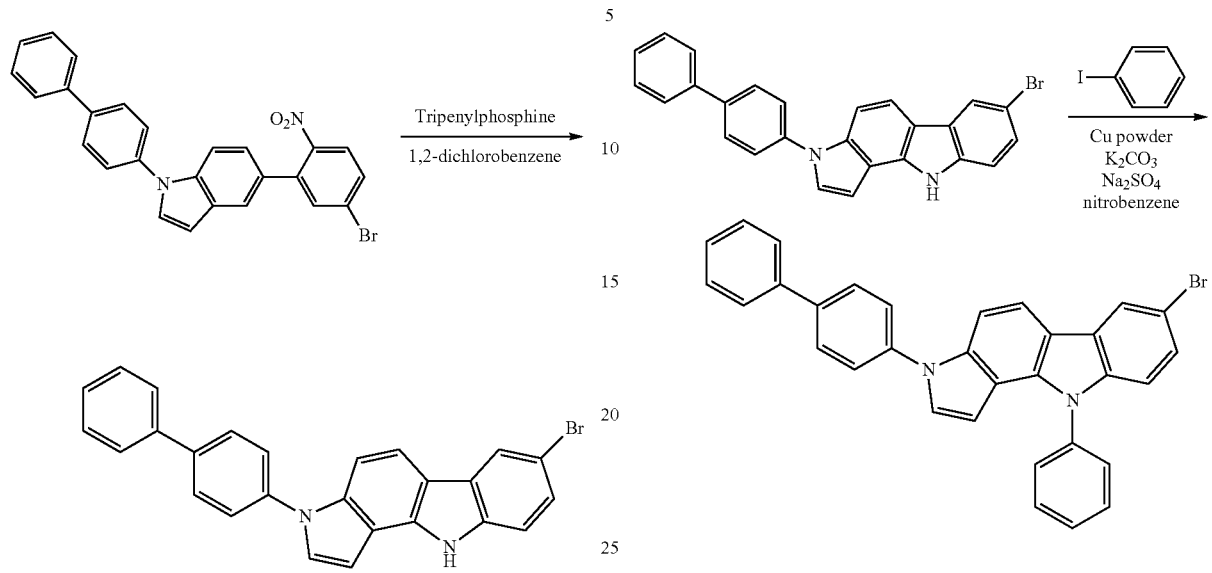

3-(biphenyl-4-yl)-7-bromo-3,10-dihydropyrrolo[3,2-a]carbazole was obtained by performing the same procedure as in <Step 4> of Preparation Example 1, except that the product in <Step 1> was used instead of 5-(5-bromo-2-nitrophenyl)-1-phenyl-1H-indole.

230

<Step 3> Synthesis of 3-(biphenyl-4-yl)-7-bromo-10-phenyl-3,10-dihydropyrrolo[3,2-a]carbazole 3-(biphenyl-4-yl)-7-bromo-10-phenyl-3,10-dihydropyrrolo[3,2-a]carbazole was obtained by performing the same procedure as in <Step 5> of Preparation Example 1, except that the product in <Step 2> was used instead of 7-bromo-3-phenyl-3,10-dihydropyrrolo[3,2-a]carbazole.

<Step 4> Synthesis of IC-16

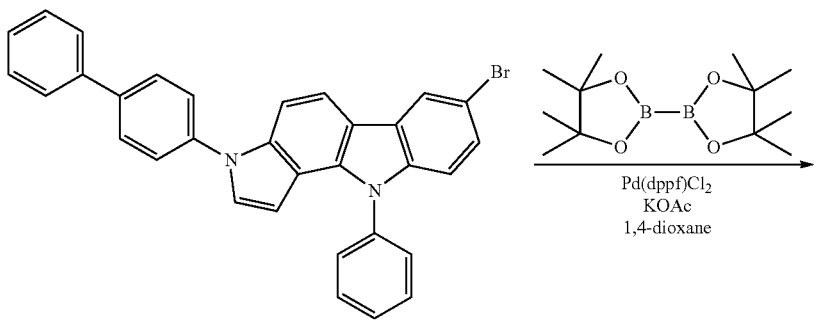

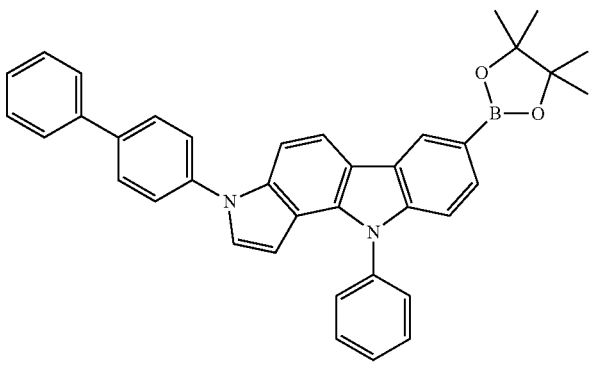

IC-16 was obtained by performing the same procedure as in <Step 6> of Preparation Example 1, except that the product in <Step 3> was used instead of 7-bromo-3,10-diphenyl-3,10-dihydropyrrolo[3,2-a]carbazole.
[Preparation Example 17] Synthesis of IC-17
<Step 1> Synthesis of 3-(biphenyl-4-yl)-7-bromo-10-(9,9-dimethyl-9H-fluoren-2-yl)-3,10-dihydropyrrolo[3,2-a]carbazole
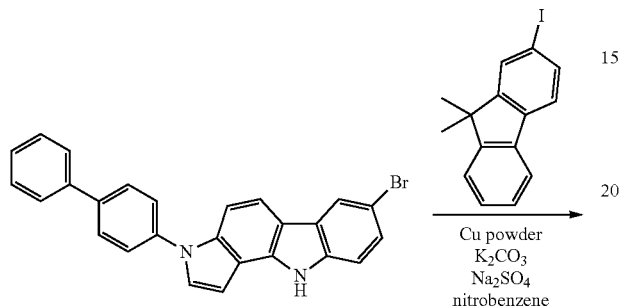
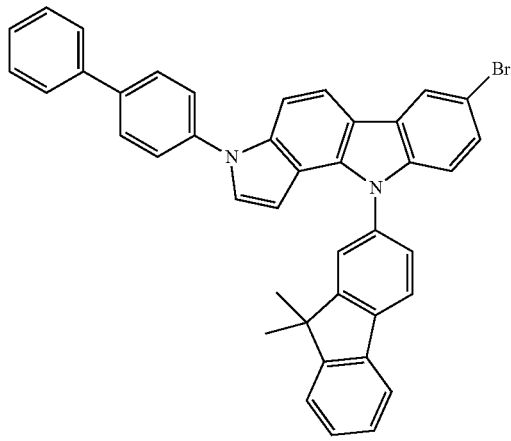
<Step 2> Synthesis of IC-17
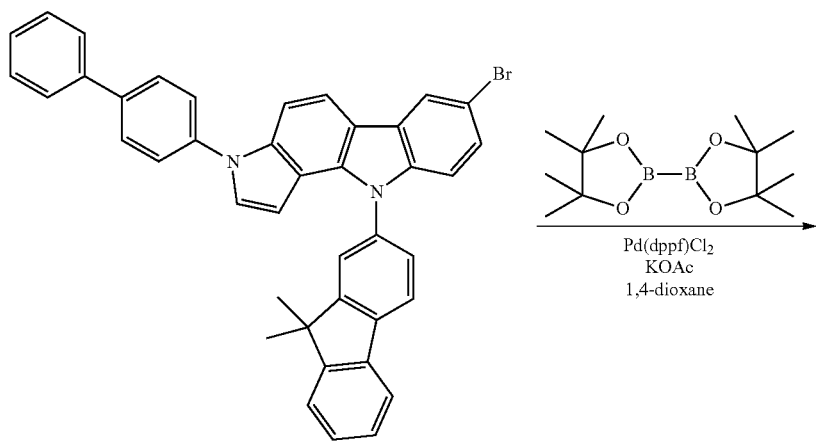
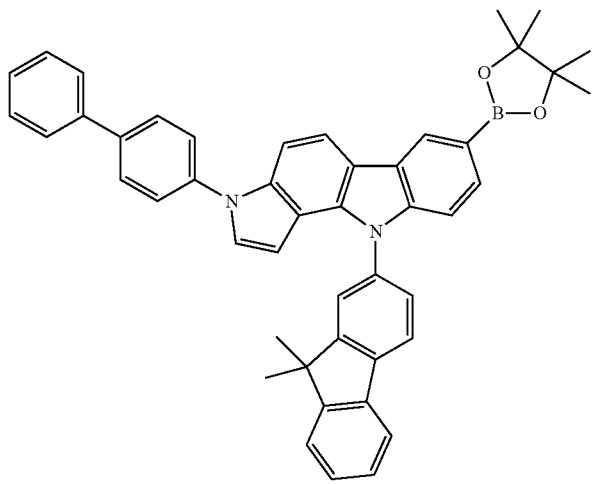

IC-17 was obtained by performing the same procedure as in Preparation Example 16, except that 2-iodo-9,9-dimethyl-9H-fluorene was used instead of iodobenzene.

[Preparation Example 18] Synthesis of IC-18

<Step 1> Synthesis of 5-(5-bromo-2-nitrophenyl)-1-(3-(pyridin-2-yl)phenyl)-1H-indole

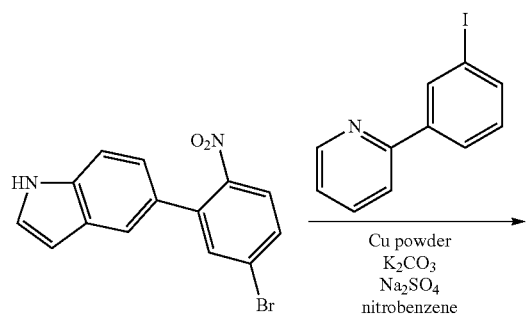

<Step 2> Synthesis of 7-bromo-3-(3-(pyridin-2-yl)phenyl)-3,10-dihydropyrrolo[3,2-a]carbazole

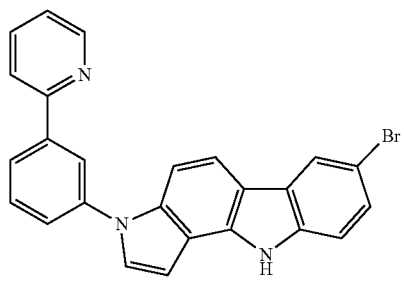

<Step 3> Synthesis of 7-bromo-10-phenyl-3-(3-(pyridin-2-yl)phenyl)-3,10-dihydropyrrolo[3,2-a]carbazole

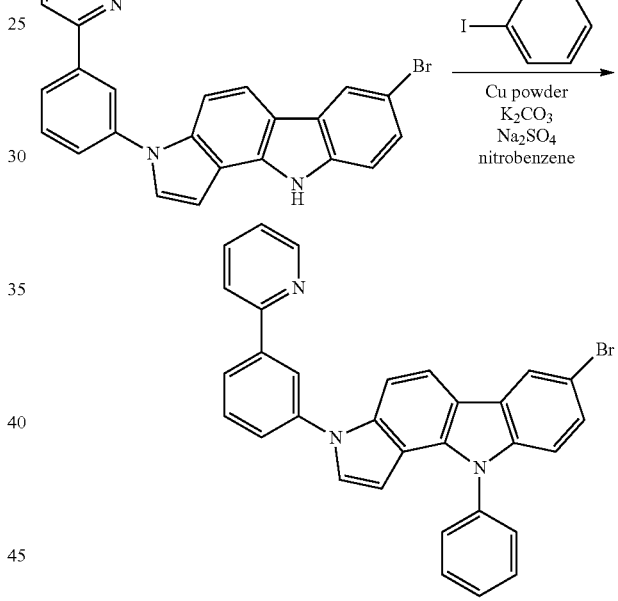

<Step 4> Synthesis of IC-18

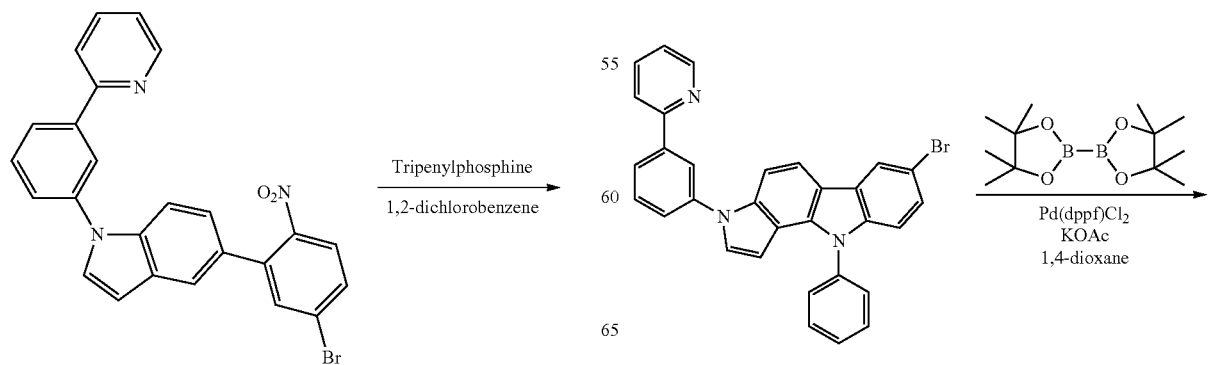

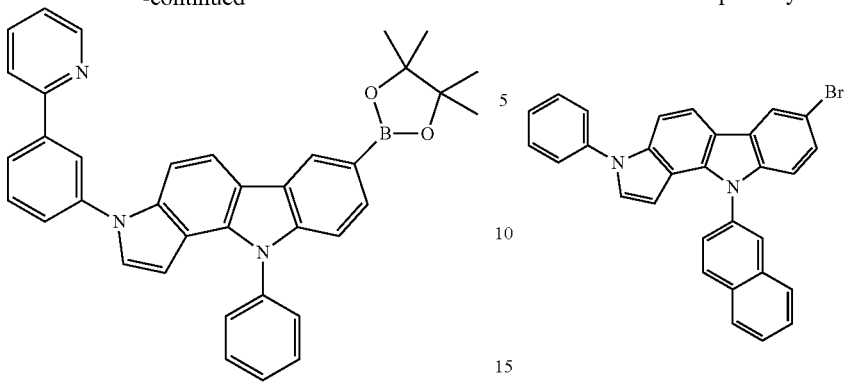

IC-18 was obtained by performing the same procedure as in Preparation Example 16, except that 2-(3-iodophenyl)pyridine was used instead of 4-iodobiphenyl.

[Preparation Example 19] Synthesis of IC-19

<Step 1> Synthesis of 7-bromo-10-(naphthalen-2-yl)-3-phenyl-3,10-dihydropyrrolo[3,2-a]carbazole

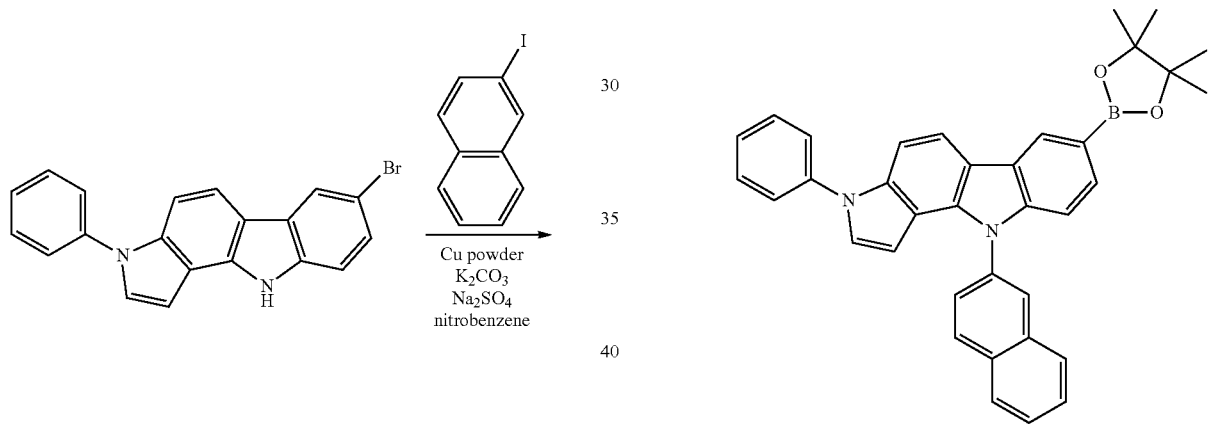

<Step 2> Synthesis of IC-19

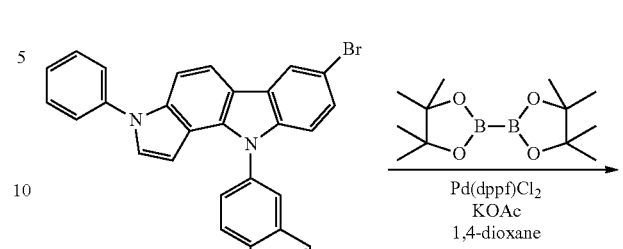

IC-19 was obtained by performing the same procedure as in Preparation Example 1, except that 2-iodonaphtalene was used instead of iodobenzene.

[Preparation Example 20] Synthesis of IC-20

<Step 1> Synthesis of 6-(biphenyl-3-yl)-9-bromo-3-phenyl-3,6-dihydropyrrolo[2,3-c]carbazole

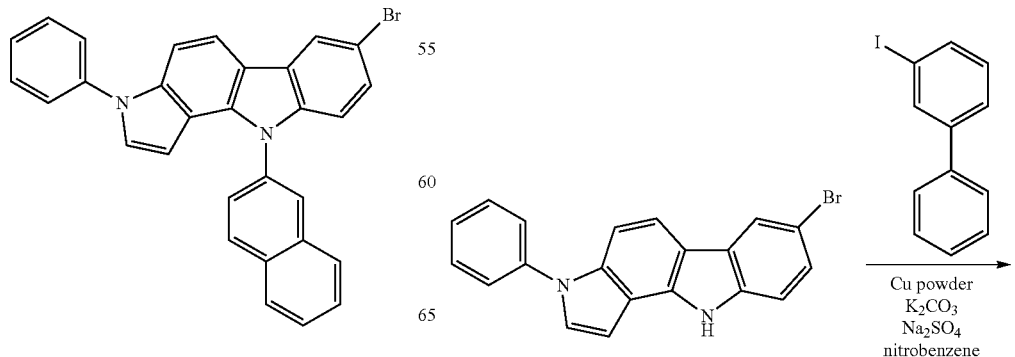

-continued

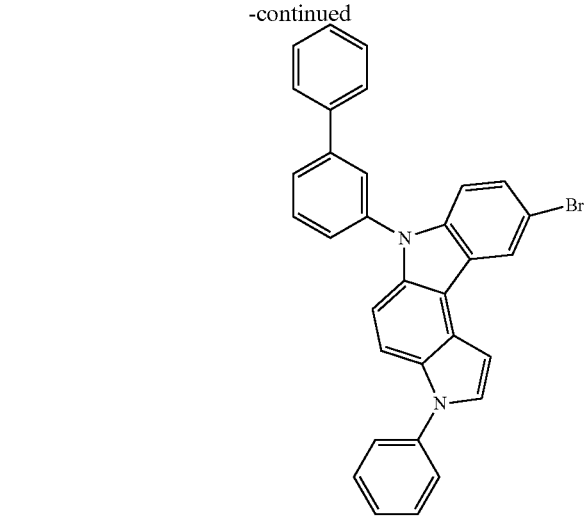

<Step 2> Synthesis of IC-20

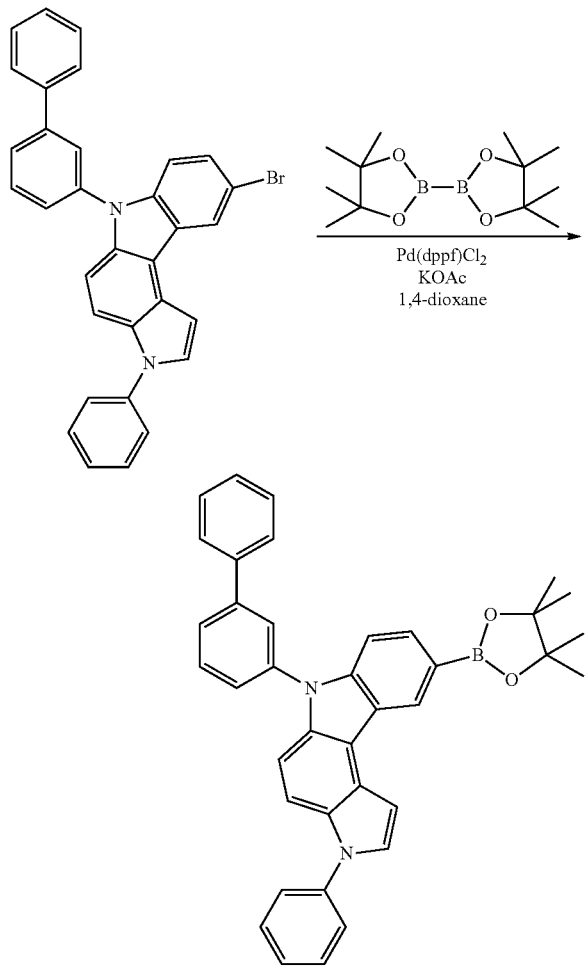

IC-20 was obtained by performing the same procedure as in Preparation Example 2, except that 3-iodobiphenyl was used instead of iodobenzene.

[Preparation Example 21] Synthesis of IC-21

<Step 1> Synthesis of 1-(4,6-diphenyl-1,3,5-triazin-2-yl)-5-(2-nitrophenyl)-1H-indole

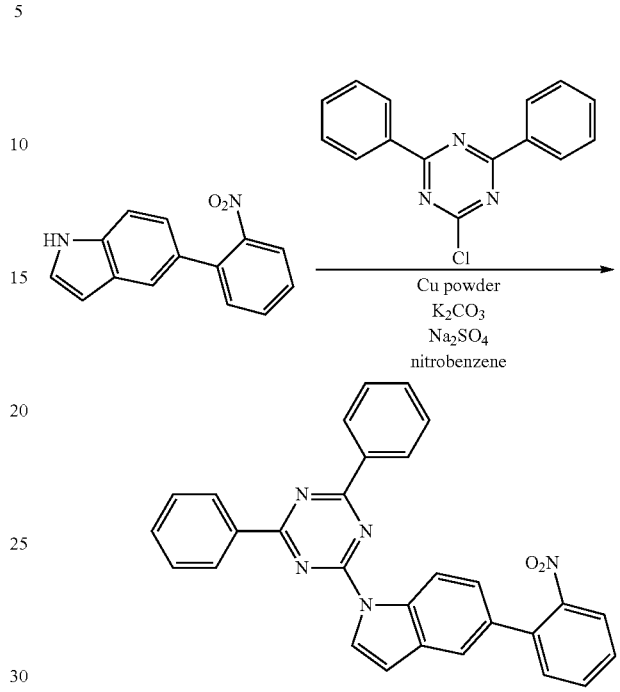

1-(4,6-diphenyl-1,3,5-triazin-2-yl)-5-(2-nitrophenyl)-1H-indole was obtained by performing the same procedure as in <Step 3> of Preparation Example 7, except that 2-chloro-4,6-diphenyl-1,3,5-triazine was used instead of iodobenzene.

<Step 2> Synthesis of IC-21

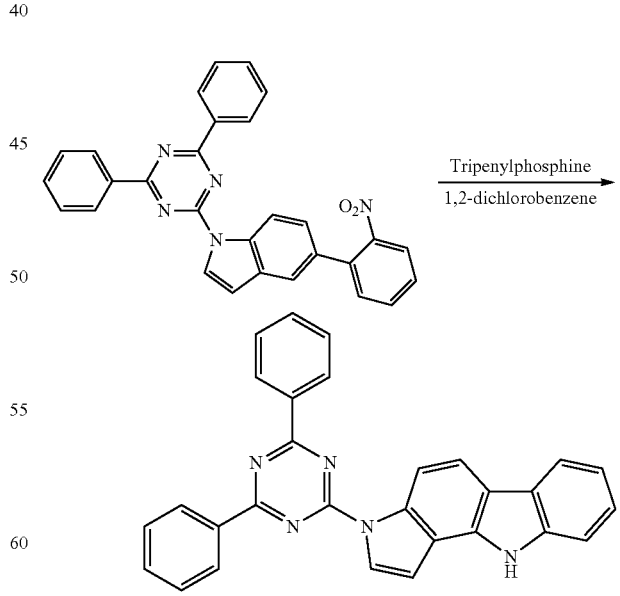

IC-21 was obtained by performing the same procedure as in <Step 4> of Preparation Example 7, except that the product in <Step 1> was used instead of 5-(2-nitrophenyl)-1-phenyl-1H-indole.

[Preparation Example 22] Synthesis of IC-22

<Step 1> Synthesis of 1-(4,6-diphenylpyrimidine-2-yl)-5-(2-nitrophenyl)-1H-indole

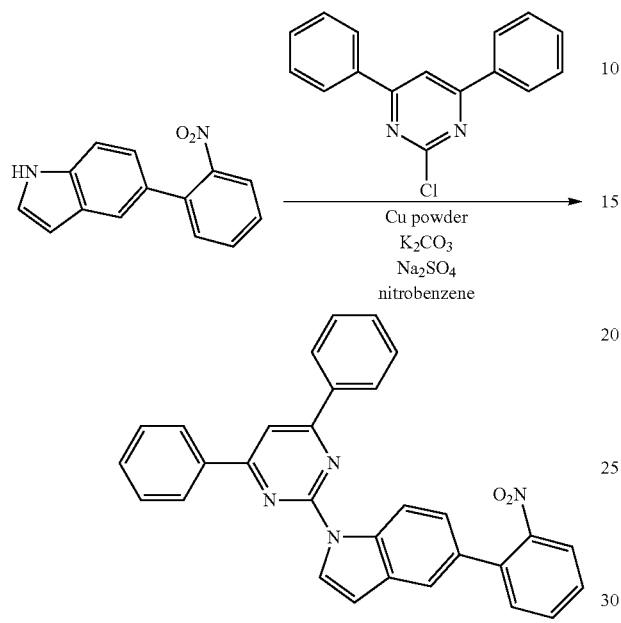

1-(4,6-diphenylpyrimidine-2-yl)-5-(2-nitrophenyl)-1H-indole was obtained by performing the same procedure as in <Step 3> of Preparation Example 7, except that 2-chloro-4,6-diphenylpyrimidine was used instead of iodobenzene.

<Step 2> Synthesis of IC-22

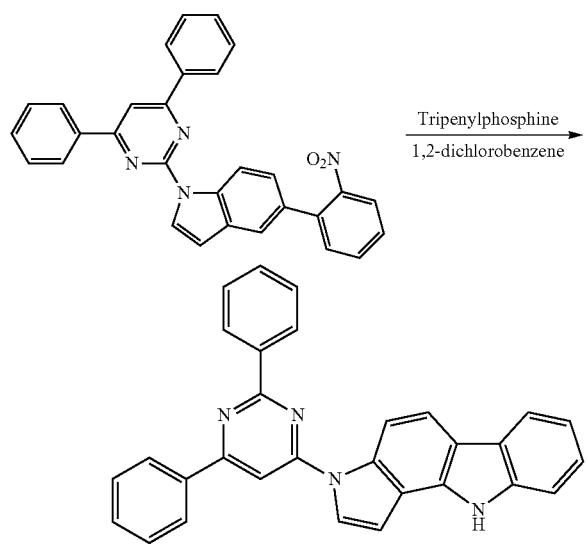

IC-22 was obtained by performing the same procedure as in <Step 4> of Preparation Example 7, except that the product in <Step 1> was used instead of 5-(2-nitrophenyl)-1-phenyl-1H-indole.

[Preparation Example 23] Synthesis of IC-23

<Step 1> Synthesis of 1-(9,9-dimethyl-9H-fluoren-2-yl)-5-(2-nitrophenyl)-1H-indole

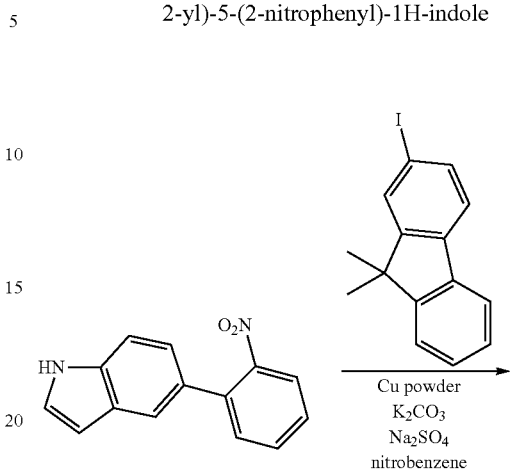

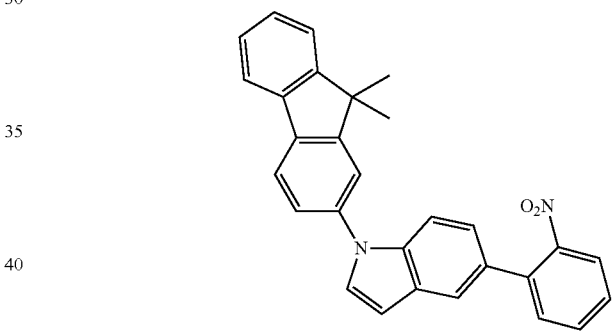

1-(9,9-dimethyl-9H-fluoren-2-yl)-5-(2-nitrophenyl)-1H-indole was obtained by performing the same procedure as in <Step 3> of Preparation Example 9, except that 2-iodo-9,9-dimethyl-9H-fluorene was used instead of iodobenzene.

<Step 2> Synthesis of IC-23

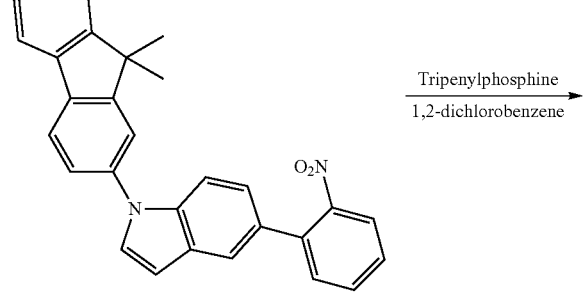

-continued

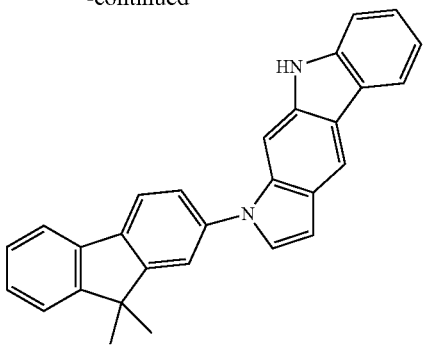

IC-23 was obtained by performing the same procedure as in <Step 4> of Preparation Example 9, except that the product in <Step 1> was used instead of 5-(2-nitrophenyl)-1-phenyl-1H-indole.

[Preparation Example 24] Synthesis of IC-24

<Step 1> Synthesis of 1-(9,9-diphenyl-9H-fluoren-2-yl)-5-(2-nitrophenyl)-1H-indole

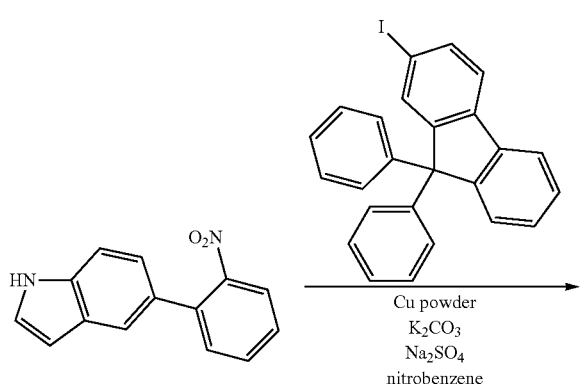

1-(9,9-diphenyl-9H-fluoren-2-yl)-5-(2-nitrophenyl)-1H-indole was obtained by performing the same procedure as in <Step 3> of Preparation Example 9, except that 2-iodo-9,9-diphenyl-9H-fluorene was used instead of iodobenzene.

<Step 2> Synthesis of IC-24

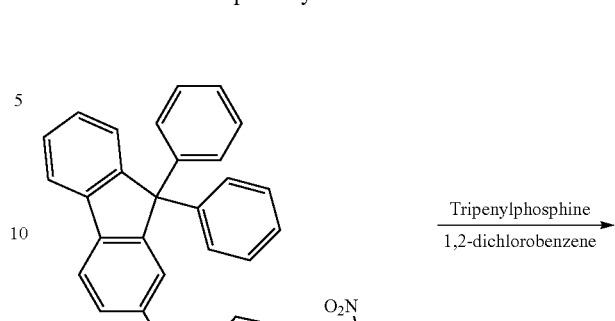

IC-24 was obtained by performing the same procedure as in <Step 4> of Preparation Example 9, except that the product in <Step 1> was used instead of 5-(2-nitrophenyl)-1-phenyl-1H-indole.

[Preparation Example 25] Synthesis of IC-25

<Step 1> Synthesis of 5-(2-nitrophenyl)-1-(3-(trifluoromethyl)phenyl)-1H-indole

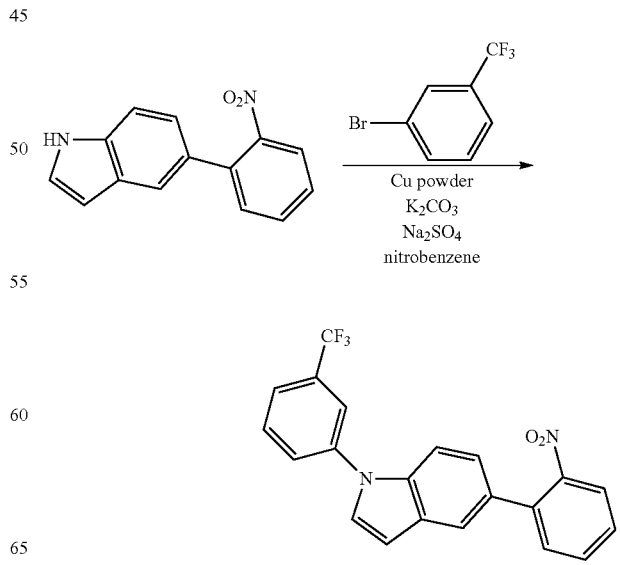

243

<Step 2> Synthesis of IC-25

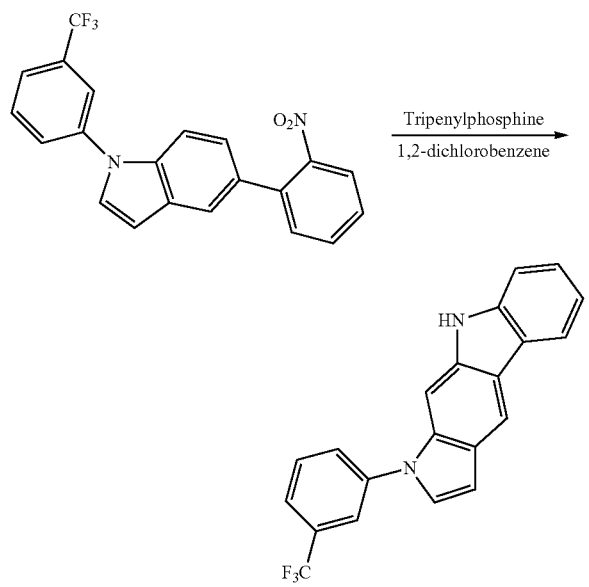

IC-25 was obtained by performing the same procedure as in Preparation Example 24, except that 1-bromo-3-(trifluoromethyl)benzene was used instead of 2-iodo-9,9-diphenyl-9H-fluorene.

[Preparation Example 26] Synthesis of IC-26

<Step 1> Synthesis of 5-bromo-2-phenyl-1H-indole

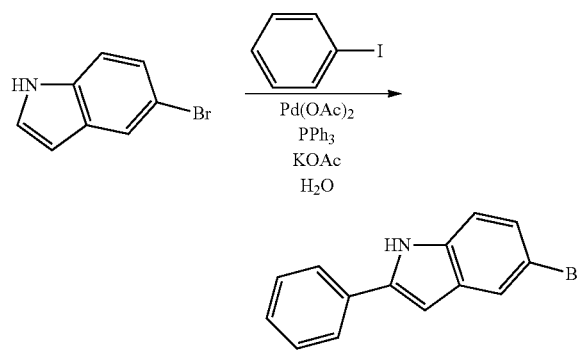

5-bromo-1H-indole (25 g, 0.13 mol), iodobenzene (31.22 g, 0.15 mol), Pd(OAc)$_2$ (1.43 g, 5 mol %), triphenylphosphine (1.67 g, 5 mol %), KOAc (37.55 g, 0.38 mol), and H$_2$O (300 ml) were mixed under nitrogen flow, and the resulting mixture was stirred at 110° C. for 24 hours.

After the reaction was terminated, 5-bromo-2-phenyl-1H-indole (16.66 g, yield 48%) was obtained by performing extraction with ethyl acetate, removing moisture over MgSO$_4$, and refinement was performed by column chromatography (Hexane:EA=10:1 (v/v)).

244

<Step 2> Synthesis of 5-(2-nitrophenyl)-2-phenyl-1H-indole

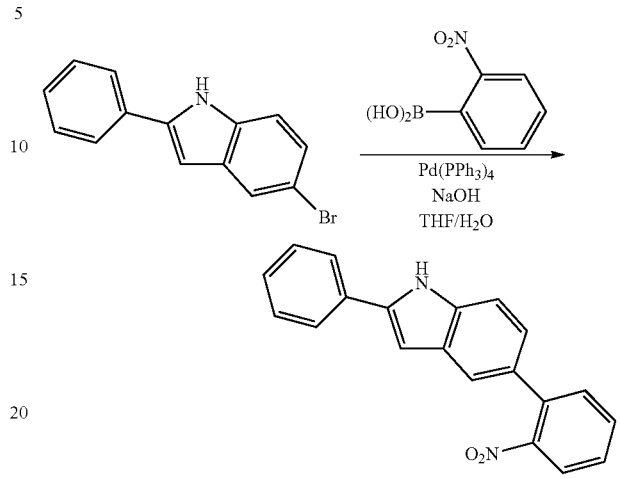

2-nitrophenylboronic acid (11.04 g, 66.14 mmol), the 5-bromo-2-phenyl-1H-indole (15 g, 55.12 mmol) obtained in <Step 1>, NaOH (6.61 g, 165.36 mmol), and THF/H$_2$O (200 ml/100 ml) were mixed under nitrogen flow, Pd(PPh$_3$)$_4$ (3.18 g, 5 mol) was added thereto at 40° C., and the resulting mixture was stirred at 80° C. for 12 hours.

After the reaction was terminated, extraction was performed with methylene chloride, MgSO$_4$ was added thereto, and the resulting product was filtered. 5-(2-nitrophenyl)-2-phenyl-1H-indole (10.74 g, yield 62%) was obtained by removing the solvent from the obtained organic layer, and refinement was performed by column chromatography (Hexane:EA=5:1 (v/v)).

<Step 3> Synthesis of 5-(2-nitrophenyl)-1,2-diphenyl-1H-indole

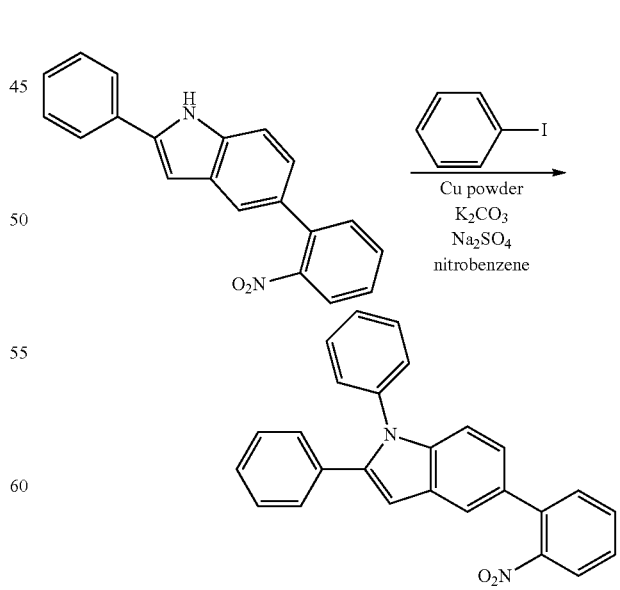

5-(2-nitrophenyl)-1,2-diphenyl-1H-indole was obtained by performing the same procedure as in <Step 3> of Preparation Example 7, except that the product in <Step 2> was used instead of 5-(2-nitrophenyl)-1H-indole.

<Step 4> Synthesis of IC-26

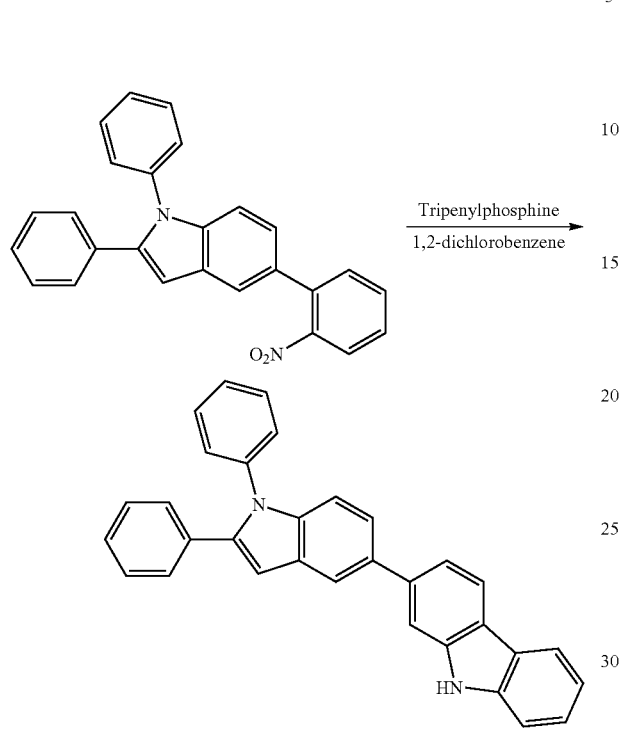

IC-26 was obtained by performing the same procedure as in <Step 4> of Preparation example 7, except that the product in <Step 3> was used instead of 5-(2-nitrophenyl)-1-phenyl-1H-indole.

[Preparation Example 27] Synthesis of IC-27

<Step 1> Synthesis of 6-bromo-2-phenyl-1H-indole

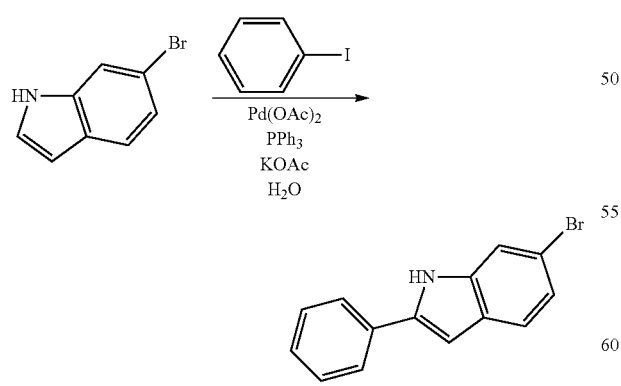

6-bromo-2-phenyl-1H-indole was obtained by performing the same procedure as in <Step 1> of Preparation Example 26, except that 6-bromo-1H-indole was used instead of 5-bromo-1H-indole.

<Step 2> Synthesis of 2-phenyl-6-(4,4,5,5-tetramethyl-1,3,2-dioxaborolan-2-yl)-1H-indole

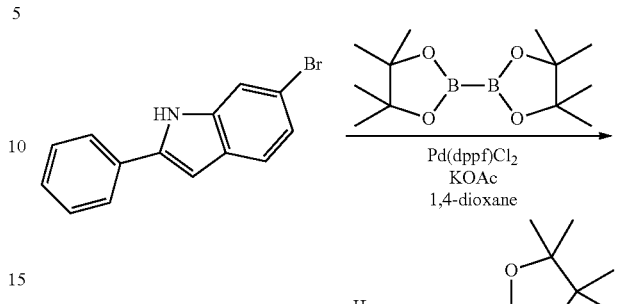

2-phenyl-6-(4,4,5,5-tetramethyl-1,3,2-dioxaborolan-2-yl)-1H-indole was obtained by performing the same procedure as in <Step 1> of Preparation Example 4, except that the product in <Step 1> was used instead of 6-bromo-1H-indole.

<Step 3> Synthesis of 6-(5-bromo-2-nitrophenyl)-2-phenyl-1H-indole

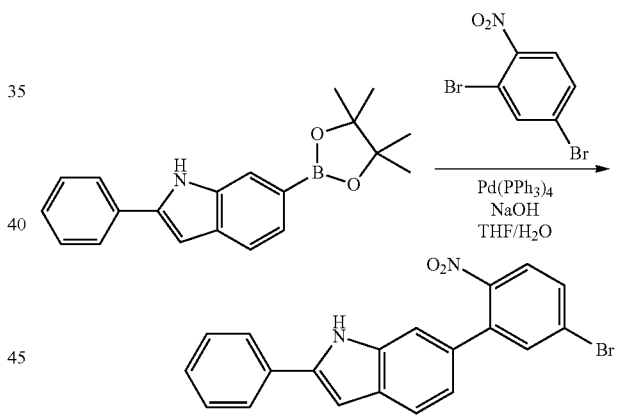

6-(5-bromo-2-nitrophenyl)-2-phenyl-1H-indole was obtained by performing the same procedure as in <Step 2> of Preparation Example 4, except that the product in <Step 2> was used instead of 6-(4,4,5,5-tetramethyl-1,3,2-dioxaborolan-2-yl)-1H-indole.

<Step 4> Synthesis of 6-(5-bromo-2-nitrophenyl)-1,2-diphenyl-1H-indole

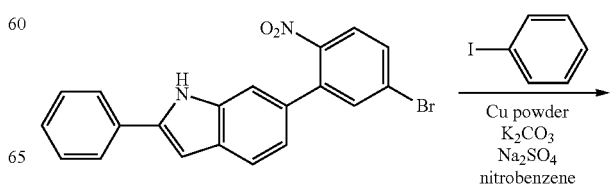

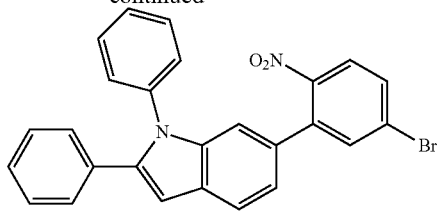

6-(5-bromo-2-nitrophenyl)-1,2-diphenyl-1H-indole was obtained by performing the same procedure as in <Step 3> of Preparation Example 4, except that the product in <Step 3> was used instead of 6-(5-bromo-2-nitrophenyl)-1H-indole.

<Step 5> Synthesis of 8-bromo-1,2-diphenyl-1,5-dihydropyrrolo[3,2-b]carbazole

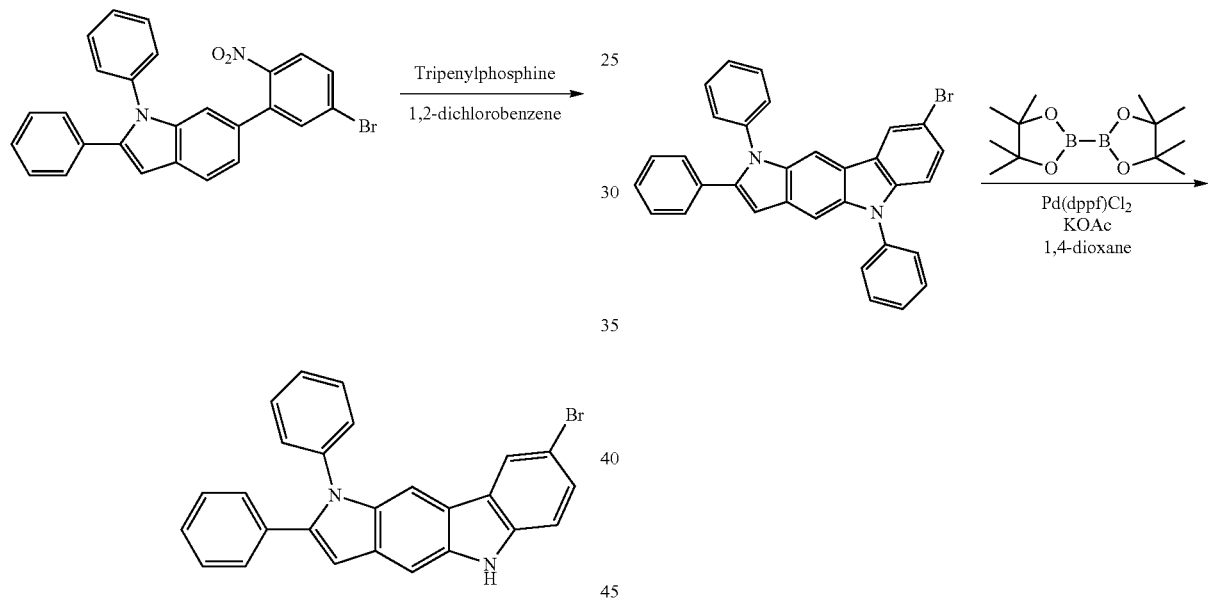

8-bromo-1,2-diphenyl-1,5-dihydropyrrolo[3,2-b]carbazole was obtained by performing the same procedure as in <Step 4> of Preparation Example 4, except that the product in <Step 4> was used instead of 6-(5-bromo-2-nitrophenyl)-1-phenyl-1H-indole.

<Step 6> Synthesis of 8-bromo-1,2,5-triphenyl-1,5-dihydropyrrolo[3,2-b]carbazole

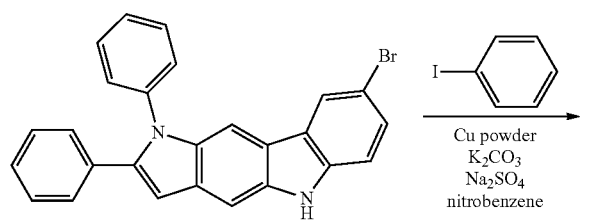

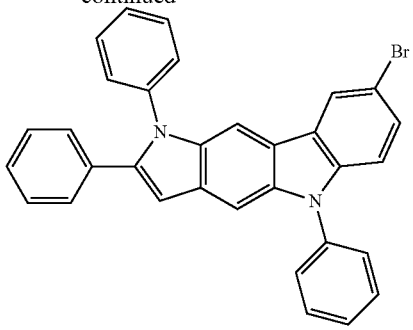

8-bromo-1,2,5-triphenyl-1,5-dihydropyrrolo[3,2-b]carbazole was obtained by performing the same procedure as in <Step 5> of Preparation Example 4, except that the product in <Step 5> was used instead of 8-bromo-1-phenyl-1,5-dihydropyrrolo[3,2-b]carbazole.

<Step 7> Synthesis of IC-27

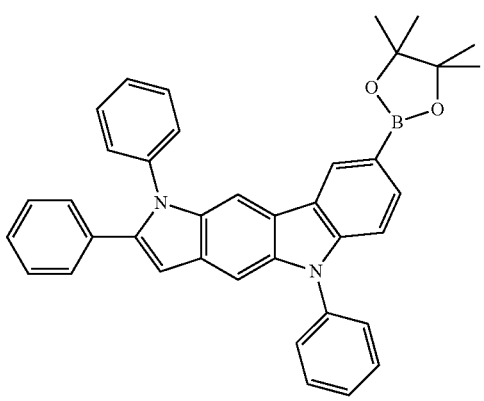

IC-27 was obtained by performing the same procedure as in <Step 6> of Preparation Example 4, except that the product in <Step 6> was used instead of 8-bromo-1,5-diphenyl-1,5-dihydropyrrolo[3,2-b]carbazole.

[Preparation Example 28] Synthesis of IC-28

<Step 1> Synthesis of 5-(biphenyl-4-yl)-8-bromo-1,2-diphenyl-1,5-dihydropyrrolo[3,2-b]carbazole

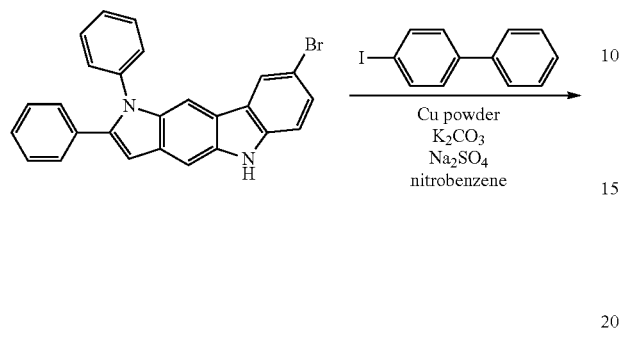

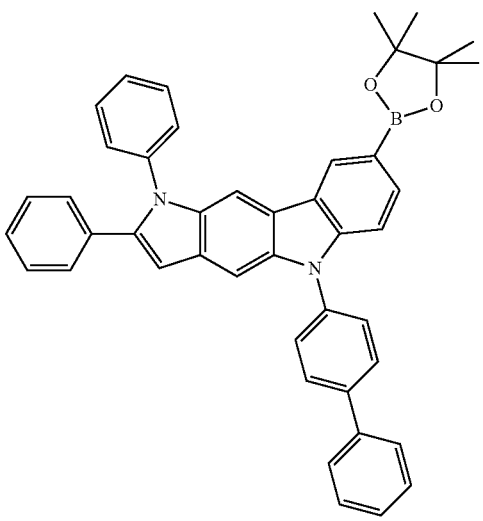

IC-28 was obtained by performing the same procedure as in Preparation Example 27, except that 4-iodobiphenyl was used instead of iodobenzene.

[Preparation Example 29] Synthesis of IC-29

<Step 1> Synthesis of 5-bromo-2,3-diphenyl-1H-indole

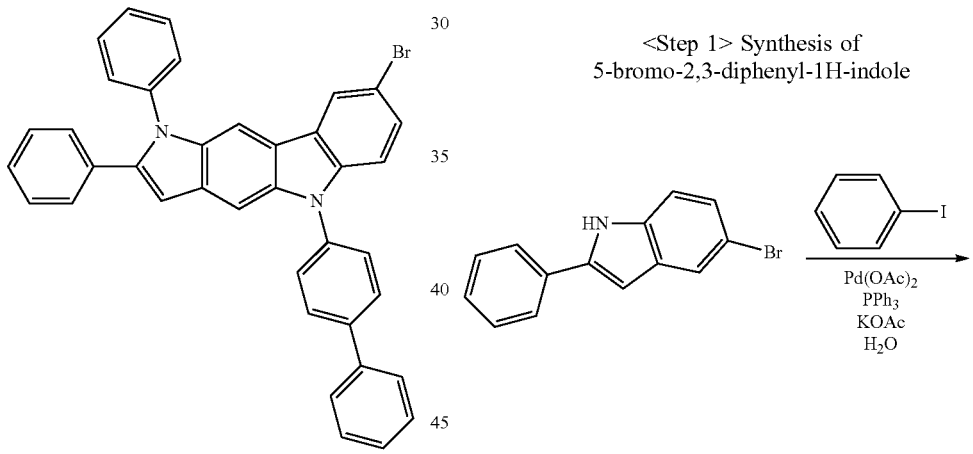

<Step 2> Synthesis of IC-28

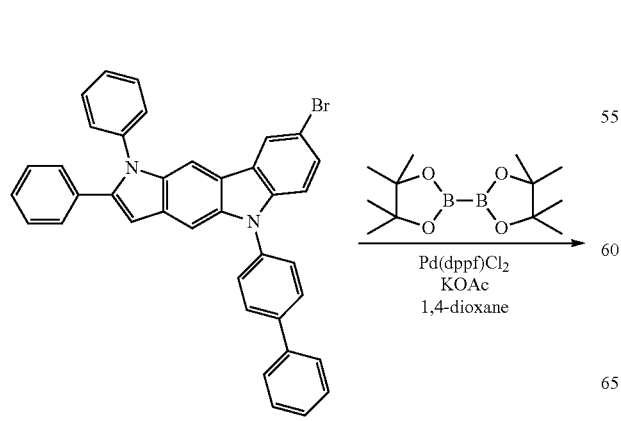

5-bromo-2,3-diphenyl-1H-indole was obtained by performing the same procedure as in <Step 1> of Preparation Example 26, except that 5-bromo-2-phenyl-1H-indole was used instead of 5-bromo-1H-indole.

<Step 2> Synthesis of 5-(2-nitrophenyl)-2,3-diphenyl-1H-indole

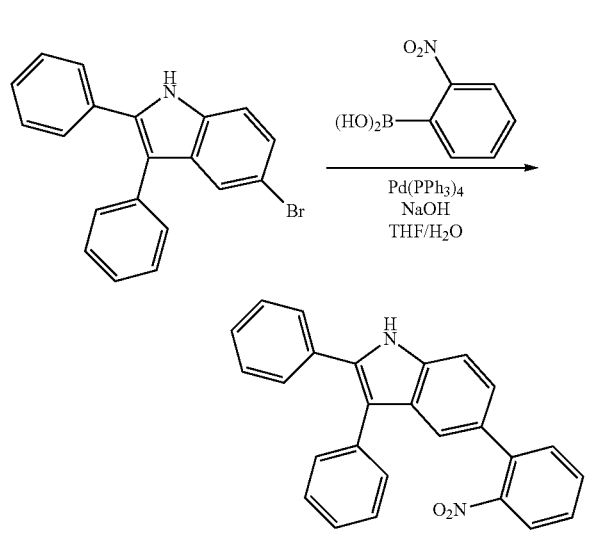

5-(2-nitrophenyl)-2,3-diphenyl-1H-indole was obtained by performing the same procedure as in <Step 2> of Preparation Example 26, except that the product in <Step 1> was used instead of 5-bromo-2-phenyl-1H-indole.

<Step 3> Synthesis of 5-(2-nitrophenyl)-1,2,3-triphenyl-1H-indole

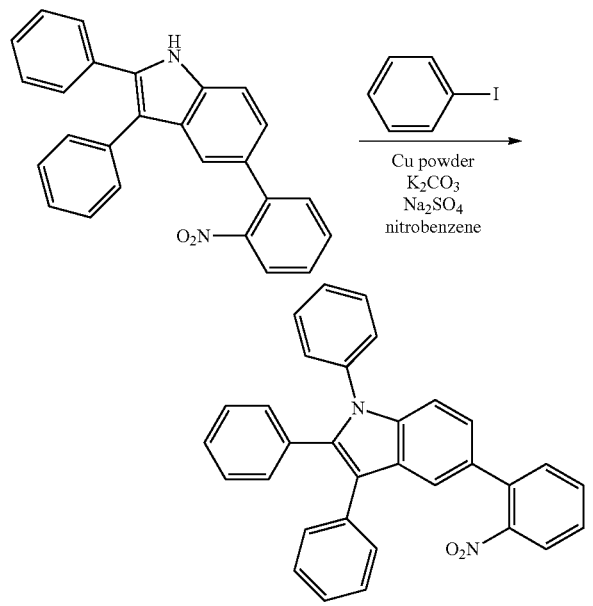

5-(2-nitrophenyl)-1,2,3-triphenyl-1H-indole was obtained by performing the same procedure as in <Step 3> of Preparation Example 26, except that the product in <Step 2> was used instead of 5-(2-nitrophenyl)-2-phenyl-1H-indole.

<Step 4> Synthesis of IC-29

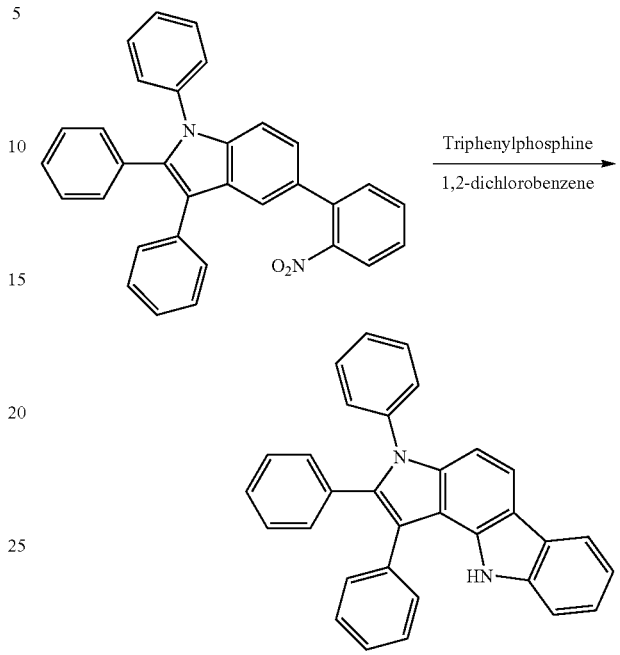

IC-29 was obtained by performing the same procedure as in <Step 4> of Preparation Example 26, except that the product in <Step 3> was used instead of 5-(2-nitrophenyl)-1,2-diphenyl-1H-indole.

[Preparation Example 30] Synthesis of IC-30

<Step 1> Synthesis of 2,3-diphenyl-5-(4,4,5,5-tetramethyl-1,3,2-dioxaborolan-2-yl)-1H-indole

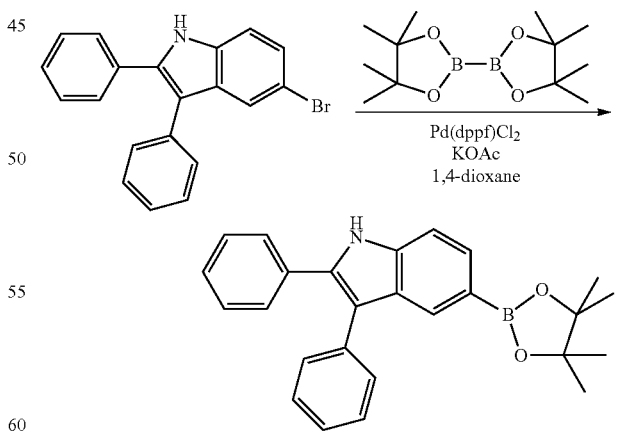

2,3-diphenyl-5-(4,4,5,5-tetramethyl-1,3,2-dioxaborolan-2-yl)-1H-indole was obtained by performing the same procedure as in <Step 1> of Preparation Example 1, except that 5-bromo-2,3-diphenyl-1H-indole was used instead of 5-bromo-1H-indole.

253

<Step 2> Synthesis of 5-(5-bromo-2-nitrophenyl)-2,3-diphenyl-1H-indole

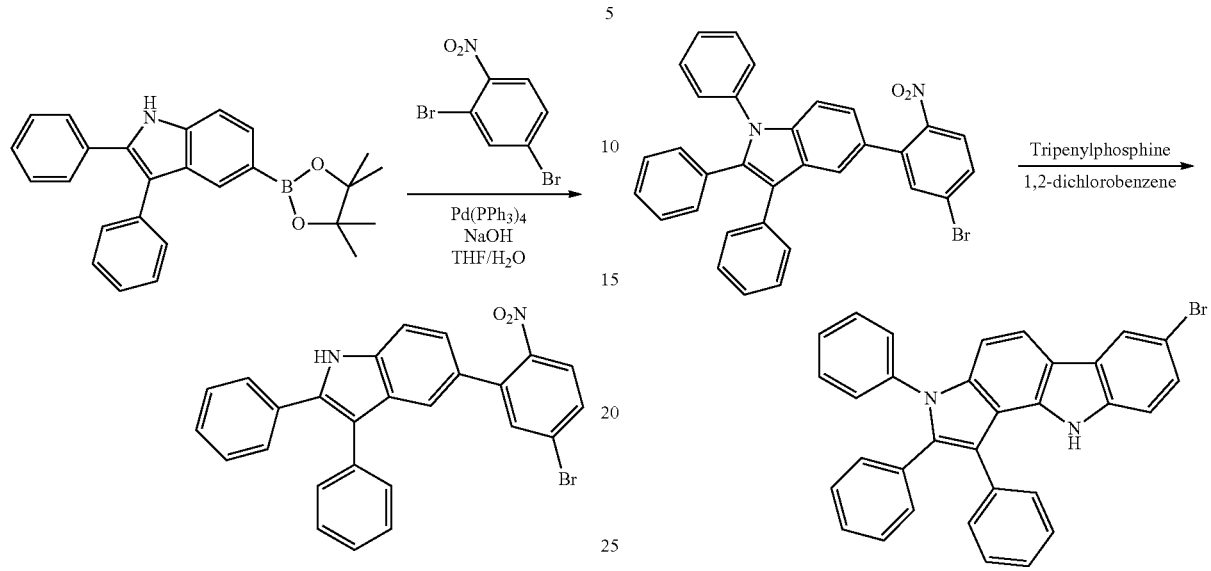

5-(5-bromo-2-nitrophenyl)-2,3-diphenyl-1H-indole was obtained by performing the same procedure as in <Step 2> of Preparation Example 1, except that the product in <Step 1> was used instead of 5-(4,4,5,5-tetramethyl-1,3,2-dioxaborolan-2-yl)-1H-indole.

<Step 3> Synthesis of 5-(5-bromo-2-nitrophenyl)-1,2,3-triphenyl-1H-indole 5-(5-bromo-2-nitrophenyl)-1,2,3-triphenyl-1H-indole was obtained by performing the same procedure as in <Step 3> of Preparation Example 1, except that the product in <Step 2> was used instead of 5-(5-bromo-2-nitrophenyl)-1H-indole.

254

<Step 4> Synthesis of 7-bromo-1,2,3-triphenyl-3,10-dihydropyrrolo[3,2-a]carbazole

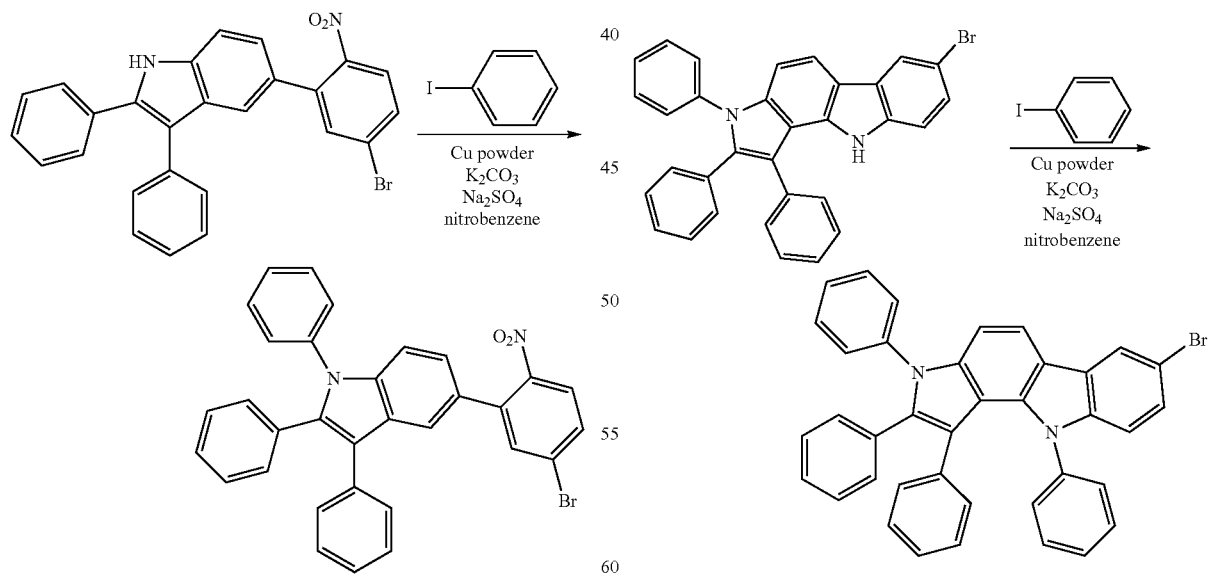

7-bromo-1,2,3-triphenyl-3,10-dihydropyrrolo[3,2-a]carbazole was obtained by performing the same procedure as in <Step 4> of Preparation Example 1, except that the product in <Step 3> was used instead of 5-(5-bromo-2-nitrophenyl)-1-phenyl-1H-indole.

<Step 5> Synthesis of 1,2,3,10-tetraphenyl-7-(4,4,5,5-tetramethyl-1,3,2-dioxaborolan-2-yl)-3,10-dihydropyrrolo[3,2-a]carbazole 1,2,3,10-tetraphenyl-7-(4,4,5,5-tetramethyl-1,3,2-dioxaborolan-2-yl)-3,10-dihydropyrrolo[3,2-a]carbazole was obtained by performing the same procedure as in <Step 5> of Preparation Example 1, except that the product in <Step 4> was used instead of 7-bromo-3-phenyl-3,10-dihydropyrrolo[3,2-a]carbazole.

\<Step 6\> Synthesis of IC-30

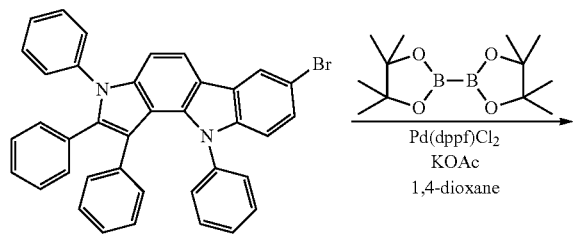

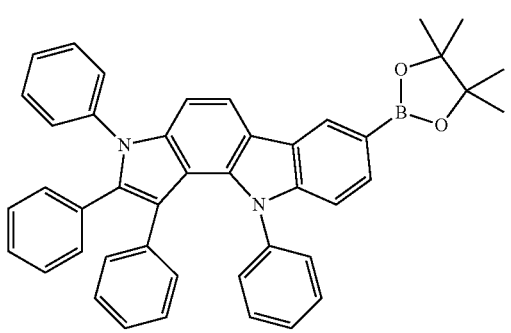

IC-30 was obtained by performing the same procedure as in \<Step 6\> of Preparation Example 1, except that the product in \<Step 5\> was used instead of 7-bromo-3,10-diphenyl-3,10-dihydropyrrolo[3,2-a]carbazole.

[Preparation Example 31] Synthesis of IC-31

\<Step 1\> Synthesis of 7-(2-nitrophenyl)benzo[b]thiophene

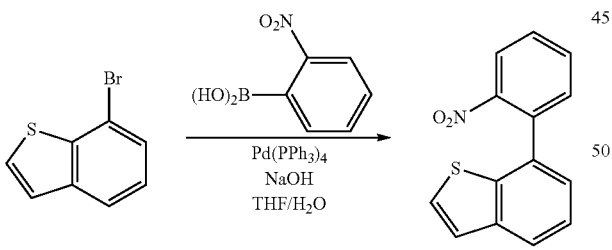

12.2 g (35.2 mmol) of 7-bromobenzo[b]thiophene, 6.44 g (38.7 mmol) of 2-nitrophenylboronic acid, 4.22 g (105.6 mmol) of NaOH, and 300 ml/150 ml of THF/H$_2$O were put thereinto under nitrogen flow, and the resulting mixture was stirred. 2.03 g (5 mol %) of Pd(PPh$_3$)$_4$ was added thereto at 40° C., and the resulting mixture was stirred at 80° C. for 12 hours. After the reaction was terminated, extraction was performed with methylene chloride, MgSO$_4$ was added thereto, and the resulting product was filtered. 7.38 g (28.9 mmol, yield 82%) of 7-(2-nitrophenyl)benzo[b]thiophene was obtained by removing the solvent from the filtered organic layer, and then using column chromatography.

\<Step 2\> Synthesis of IC-31

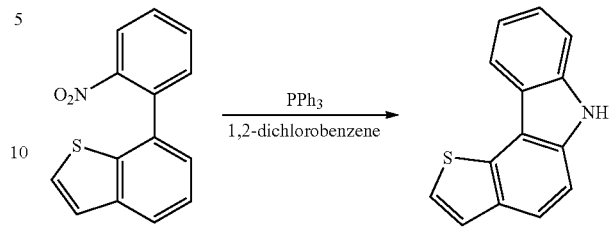

The product (5.53 g, 21.7 mmol) in \<Step 1\>, triphenylphosphine (14.2 g, 54.2 mmol), and 100 ml of 1,2-dichlorobenzene were put thereinto under nitrogen flow, and then the resulting mixture was stirred for 12 hours. After the reaction was terminated, 1,2-dichlorobenzene was removed, and extraction was performed with dichloromethane. 3.29 g (14.8 mmol, yield: 68%) of IC-31 was obtained by removing water from the extracted organic layer over MgSO$_4$ and using column chromatography.

[Preparation Example 32] Synthesis of IC-32 and IC-33

\<Step 1\> Synthesis of 6-(2-nitrophenyl)benzo[b]thiophene

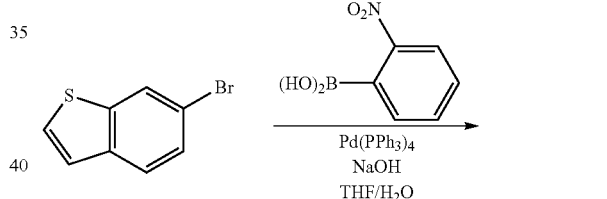

7.01 g (27.5 mmol, yield: 78%) of 6-(2-nitrophenyl)benzo[b]thiophene was obtained by performing the same procedure as in \<Step 1\> of Preparation Example 31, except that 6-bromobenzo[b]thiophene (12.2 g, 35.2 mmol) was used instead of 7-bromobenzo[b]thiophene.

<Step 2> Synthesis of IC-32 and IC-33

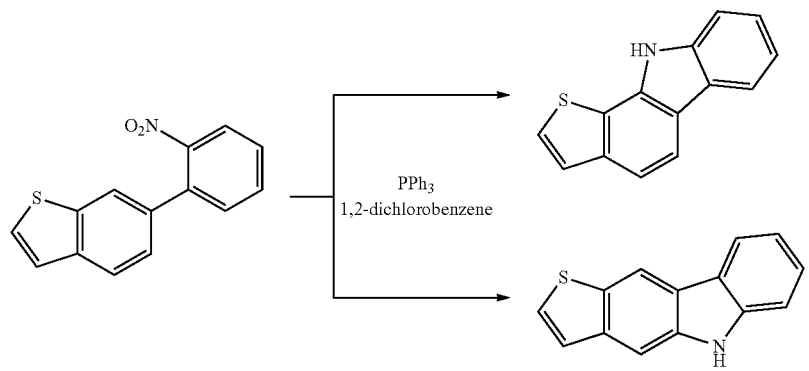

1.60 g (7.16 mmol, yield: 33%) of IC-32 and 1.79 g (8.03 mmol, yield: 37%) of IC-33 were obtained by performing the same procedure as in <Step 2> of Preparation Example 31, except that 5.53 g (21.7 mmol) of the product in <Step 1> was used instead of 7-(2-nitrophenyl)benzo[b]thiophene.

[Preparation Example 33] Synthesis of IC-34 and IC-35

<Step 1> Synthesis of 5-(2-nitrophenyl)benzo[b]thiophene

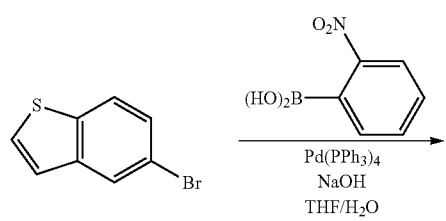

-continued

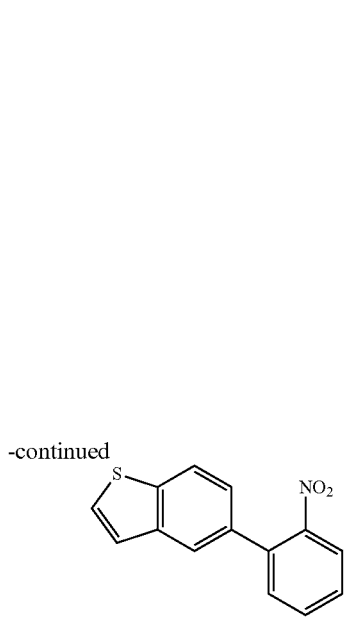

6.83 g (26.8 mmol, yield: 76%) of 5-(2-nitrophenyl)benzo[b]thiophene was obtained by performing the same procedure as in <Step 1> of Preparation Example 31, except that 5-bromobenzo[b]thiophene (12.2 g, 35.2 mmol) was used instead of 7-bromobenzo[b]thiophene.

<Step 2> Synthesis of IC-34 and IC-35

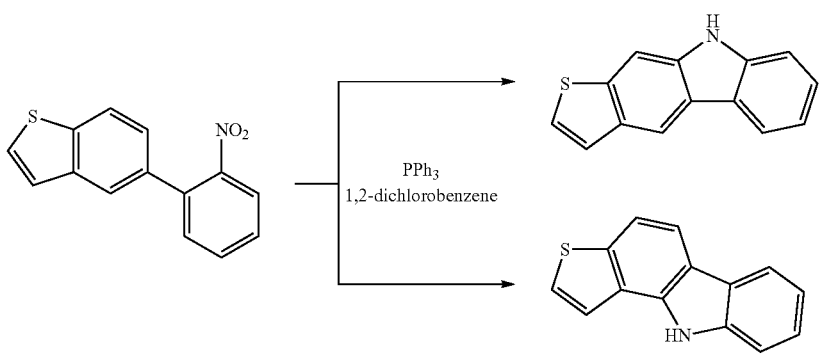

1.70 g (7.60 mmol, yield: 35%) of IC-34 and 1.89 g (8.46 mmol, yield: 39%) of IC-35 were obtained by performing the same procedure as in <Step 2> of Preparation Example 31, except that the product (5.53 g, 21.7 mmol) in <Step 1> was used instead of 7-(2-nitrophenyl)benzo[b]thiophene.

[Preparation Example 34] Synthesis of IC-36

<Step 1> Synthesis of 2-(benzofuran-5-yl)-4,4,5,5-tetramethyl-1,3,2-dioxaborolane

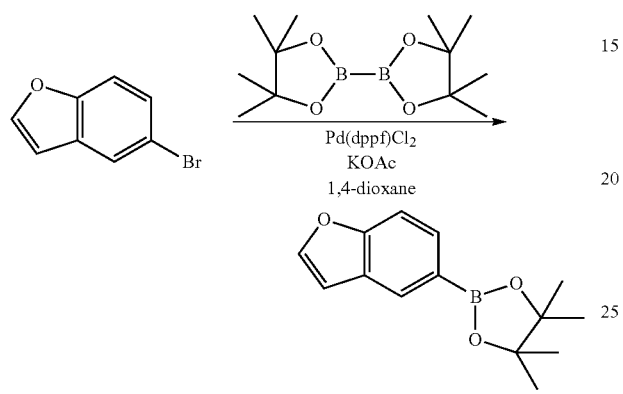

5-bromobenzofuran (25 g, 0.126 mol), 4,4,4',4',5,5,5',5'-octamethyl-2,2'-bi(1,3,2-dioxaborolane) (38.67 g, 0.152 mol), Pd(dppf)Cl$_2$ (3.11 g, 3 mol %), KOAc (37.36 g, 0.381 mol), and 1,4-dioxane (500 ml) were mixed under nitrogen flow, and the resulting mixture was stirred at 130° C. for 12 hours.

After the reaction was terminated, 2-(benzofuran-5-yl)-4,4,5,5-tetramethyl-1,3,2-dioxaborolane (23.23 g, yield 75%) was obtained by performing extraction with ethyl acetate, removing moisture over MgSO$_4$, and purifying the residue with column chromatography (Hexane:EA=10:1 (v/v)).

<Step 2> Synthesis of 5-(2-nitrophenyl)benzofuran

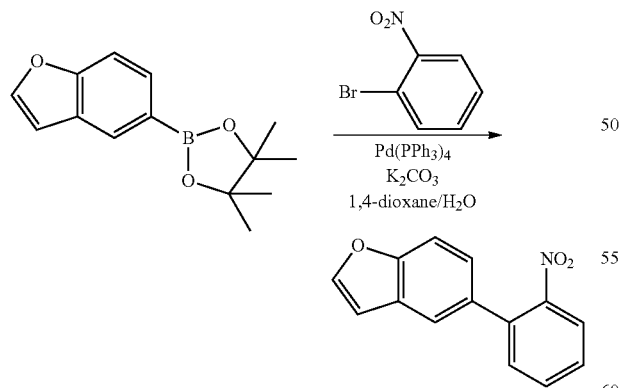

1-bromo-2-nitrobenzene (15.86 g, 78.52 mmol), the product (23 g, 94.23 mmol) in <Step 1>, K$_2$CO$_3$ (32.56 g, 235.57 mmol), and 1,4-dioxane/H$_2$O (400 ml/200 ml) were mixed under nitrogen flow, Pd(PPh$_3$)$_4$ (4.54 g, 5 mol %) was added thereto at 40° C., and the resulting mixture was stirred at 110° C. for 12 hours.

After the reaction was terminated, extraction was performed with methylene chloride, MgSO$_4$ was added thereto, and the resulting product was filtered. 5-(2-nitrophenyl)benzofuran (12.40 g, yield 66%) was obtained by removing the solvent from the obtained organic layer, and refinement was performed by column chromatography (Hexane:EA=3:1 (v/v)).

<Step 3> Synthesis of IC-36

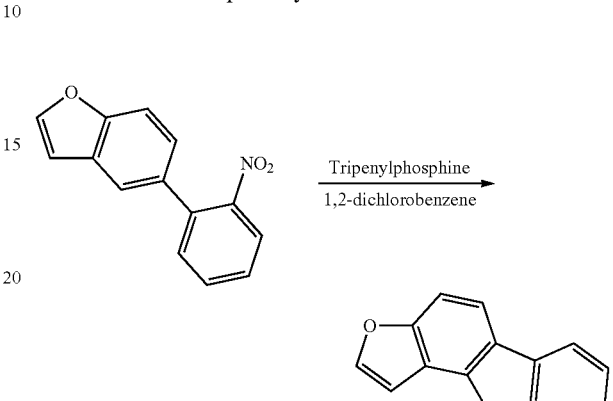

The product (10 g, 41.80 mmol) in <Step 2>, triphenylphosphine (27.41 g, 104.50 mmol), and 1,2-dichlorobenzene (150 ml) were mixed under nitrogen flow, and the resulting mixture was stirred for 12 hours.

After the reaction was terminated, 1,2-dichlorobenzene was removed, and extraction was performed with dichloromethane. IC-36 (4.76 g, yield 55%) was obtained by removing water from the obtained organic layer over MgSO$_4$, and refinement was performed by column chromatography (Hexane:MC=3:1 (v/v)).

[Preparation Example 35] Synthesis of IC-37

<Step 1> Synthesis of 5,5-dimethyl-5H-dibenzo[b,d]silole-3-amine

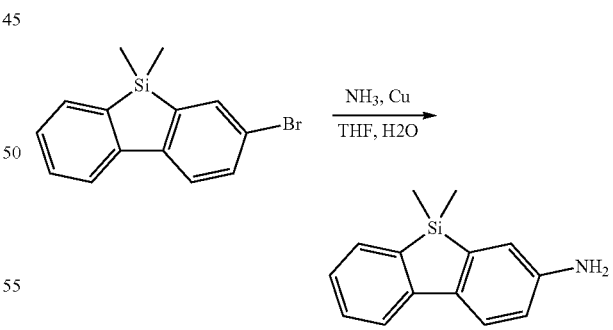

After 3-bromo-5,5-dimethyl-5H-dibenzo[b,d]silole (7.41 g, 30.0 mmol) was dissolved in 100 ml of THF under nitrogen flow, 28% aqueous ammonia (10.2 ml, 150 mmol) and Cu (0.10 g, 5 mol %) were added thereto, and the resulting mixture was stirred at 110° C. for 12 hours. After the reaction was terminated, extraction was performed with methylene chloride, MgSO$_4$ was added thereto, and the resulting product was filtered. 4.45 g (yield: 81%) of 5,5-dimethyl-5H-dibenzo[b,d]silole-3-amine was obtained by removing the solvent from the filtered organic layer, and refinement was performed by column chromatography (Hexane:EA=10:1 (v/v)).

<Step 2> Synthesis of IC-37

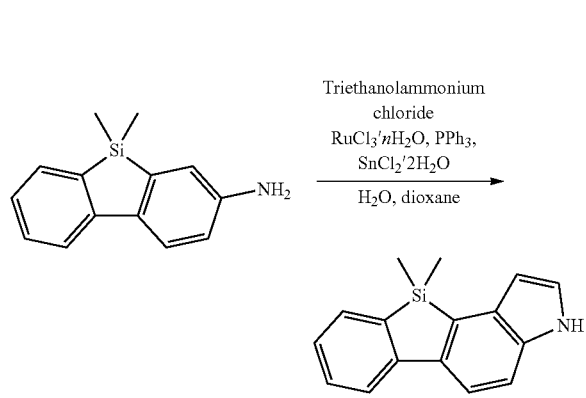

The product (4.45 g, 24.29 mmol) in <Step 1> was dissolved in H₂O/dioxane (10 ml/90 ml) under nitrogen flow, and then triethanolammonium chloride (0.45 g, 2.43 mmol), RuCl₃.H₂O (0.055 g, 0.2 mmol), PPh₃ (0.191 g, 0.7 mmol), and SnCl₂.2H₂O (0.548 g, 2.43 mmol) were added thereto, and the resulting mixture was stirred at 180° C. for 20 hours. After the reaction was terminated, the reactant was poured into aqueous 5% HCl, extraction was performed with methylene chloride, MgSO₄ was added thereto, and the resulting product was filtered. 2.7 g (yield: 53%) of IC-37 was obtained by removing the solvent from the filtered organic layer, and refinement was performed by column chromatography (Hexane:MC=1:1 (v/v)).

[Preparation Example 36] Synthesis of IC-38

<Step 1> Synthesis of 2-(benzo[b]selenophen-5-yl)-4,4,5,5-tetramethyl-1,3,2-dioxaborolane

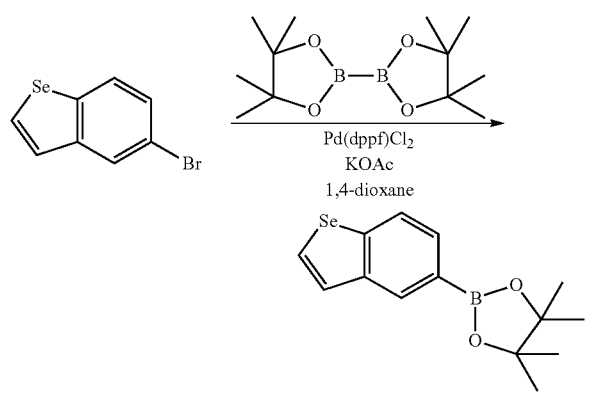

2-(benzo[b]selenophen-5-yl)-4,4,5,5-tetramethyl-1,3,2-dioxaborolane was obtained by performing the same procedure as in <Step 1> of Preparation Example 34, except that 5-bromobenzo[b]selenophene was used instead of 5-bromobenzofuran.

<Step 2> Synthesis of 5-(2-nitrophenyl)benzo[b]selenophene

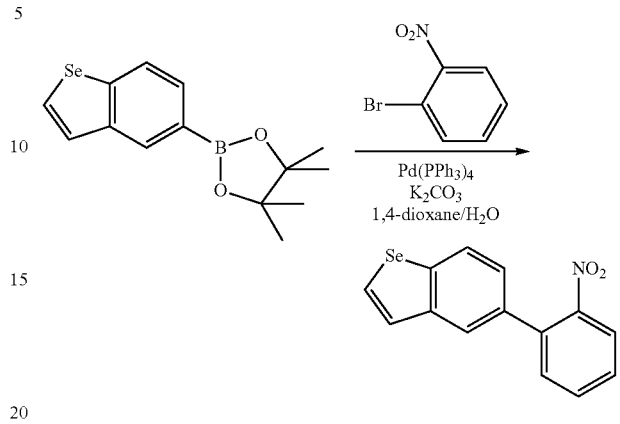

5-(2-nitrophenyl)benzo[b]selenophene was obtained by performing the same procedure as in <Step 2> of Preparation Example 34, except that the product in <Step 1> was used instead of 2-(benzofuran-5-yl)-4,4,5,5-tetramethyl-1,3,2-dioxaborolane.

<Step 3> Synthesis of IC-38

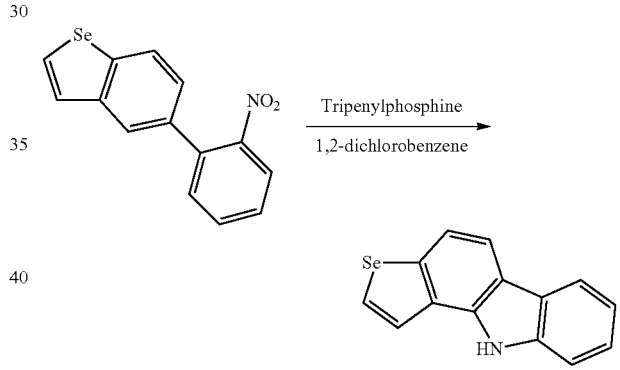

IC-38 was obtained by performing the same procedure as in <Step 3> of Preparation Example 34, except that the product in <Step 2> was used instead of 5-(2-nitrophenyl)benzofuran.

[Preparation Example 37] Synthesis of IC-39

<Step 1> Synthesis of 4-(2-isopropylphenyl)-1H-indole

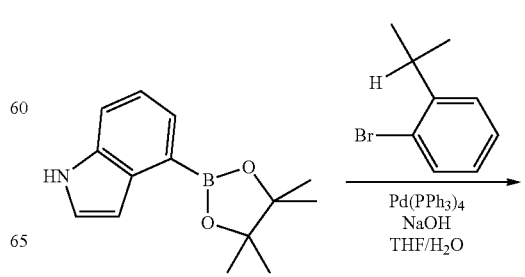

-continued

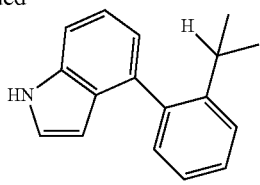

4-(2-isopropylphenyl)-1H-indole was obtained by performing the same procedure as in <Step 2> of Preparation Example 1, except that 4-(4,4,5,5-tetramethyl-1,3,2-dioxaborolan-2-yl)-1H-indole was used instead of 5-(4,4,5,5-tetramethyl-1,3,2-dioxaborolan-2-yl)-1H-indole and 1-bromo-2-isopropylbenzene was used instead of 2,4-dibromo-1-nitrobenzene.

<Step 2> Synthesis of IC-39

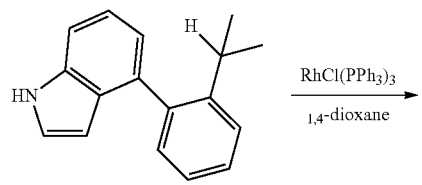

The product (5 g, 21.25 mmol) obtained in <Step 1> and RhCl(PPh₃)₃ (98.3 mg, 0.5 mol %) were dissolved in 50 ml of 1,4-dioxane under nitrogen flow, and then the resulting mixture was stirred at 135° C. for 1 hour. After the reaction was terminated, IC-39 (4 g, yield 81%) was obtained by removing the solvent and refinement was performed by column chromatography (Hexane:MC=3:1 (v:v)).

[Preparation Example 38] Synthesis of Sub-1

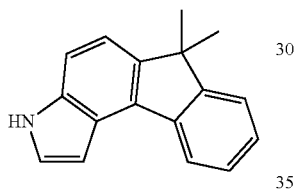

2,4-dichloroquinazoline (10 g, 50.51 mmol), phenylboronic acid (6.16 g, 50.51 mmol), tetrakis (triphenylphosphine)palladium(0) (1.75 g, 1.515 mmol), and potassium carbonate (20.6 g, 151.53 mmol) were added thereto under nitrogen flow, and then the resulting mixture was stirred in 500 ml of toluene and 75 ml of H₂O.

After the reaction was terminated, the organic layer was separated by using ethyl acetate and water was removed by using MgSO₄. Sub-1 (4.8 g, yield 40%) was obtained by removing the solvent from the organic layer which water had been removed, and refinement was performed by recrystallization.

[Preparation Example 39] Synthesis of Sub-2

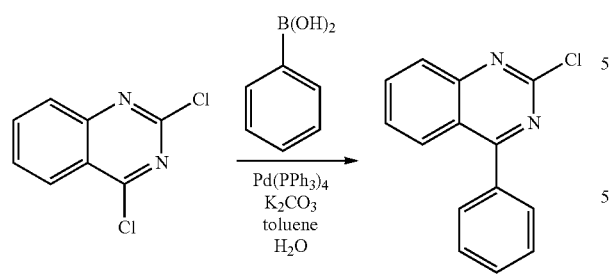

Sub-2 was obtained by performing the same procedure as in Preparation Example 38, except that 4-(naphthalen-1-yl)phenylboronic acid was used instead of phenylboronic acid.

[Preparation Example 40] Synthesis of Sub-3

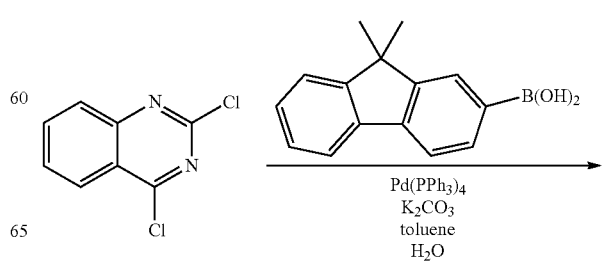

-continued

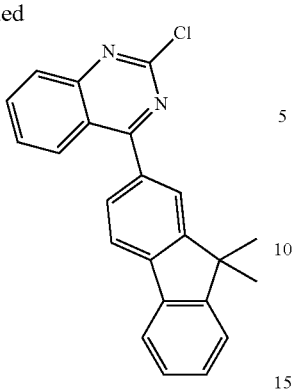

Sub-3 was obtained by performing the same procedure as in Preparation Example 38, except that 9,9-dimethyl-9H-fluoren-2-ylboronic acid was used instead of phenylboronic acid.

[Preparation Example 41] Synthesis of Sub-4

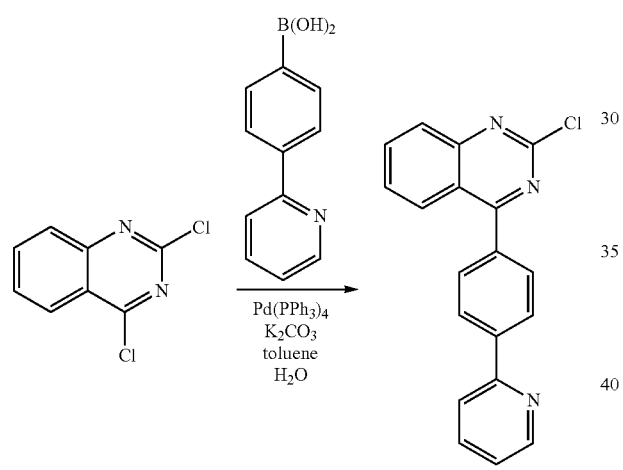

Sub-4 was obtained by performing the same procedure as in Preparation Example 38, except that 4-(pyridin-2-yl)phenylboronic acid was used instead of phenylboronic acid.

[Preparation Example 42] Synthesis of Sub-5

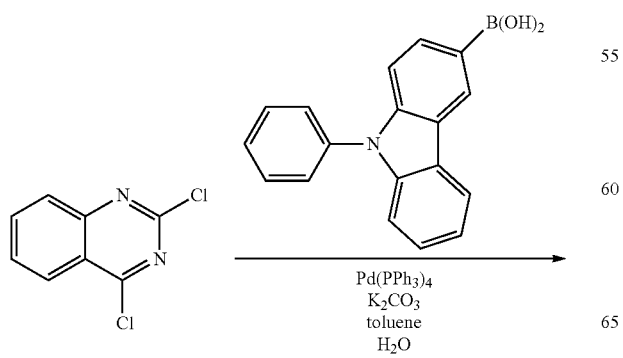

-continued

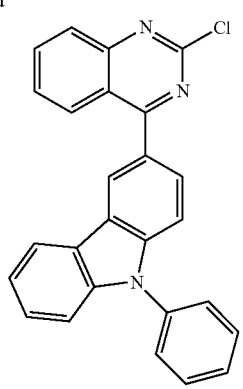

Sub-5 was obtained by performing the same procedure as in Preparation Example 38, except that 9-phenyl-9H-carbazol-3-ylboronic acid was used instead of phenylboronic acid.

[Synthesis Example 1] Synthesis of Mat-1

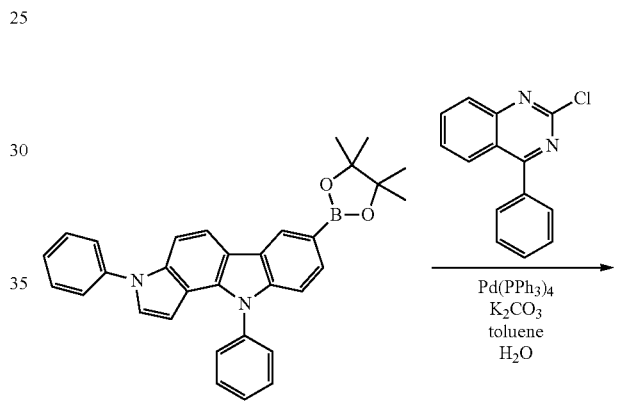

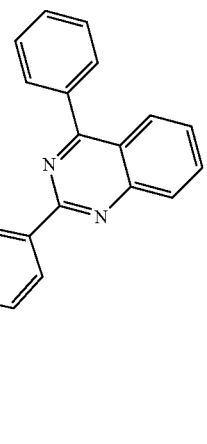

IC-1 (10 g, 20.65 mmol), sub-1 (5.9 g, 24.78 mmol), tetrakis (triphenylphosphine)palladium(0) (1.19 g, 1.03 mmol), and potassium carbonate (8.56 g, 61.95 mmol) were added thereto under nitrogen flow, and then the resulting mixture was stirred under reflux in 200 ml of toluene and 30 ml of $H_2O$.

After the reaction was terminated, the organic layer was separated with methylene chloride and water was removed by using $MgSO_4$. Mat-1 (6.96 g, yield 60%) was obtained by removing the solvent from the organic layer which water had been removed, and refinement was performed by column chromatography (Hexane:MC=3:1 (v:v)).

Elemental Analysis: C, 85.38; H, 4.66; N, 9.96/HRMS [M]$^+$: 562

[Synthesis Example 2] Synthesis of Mat-2

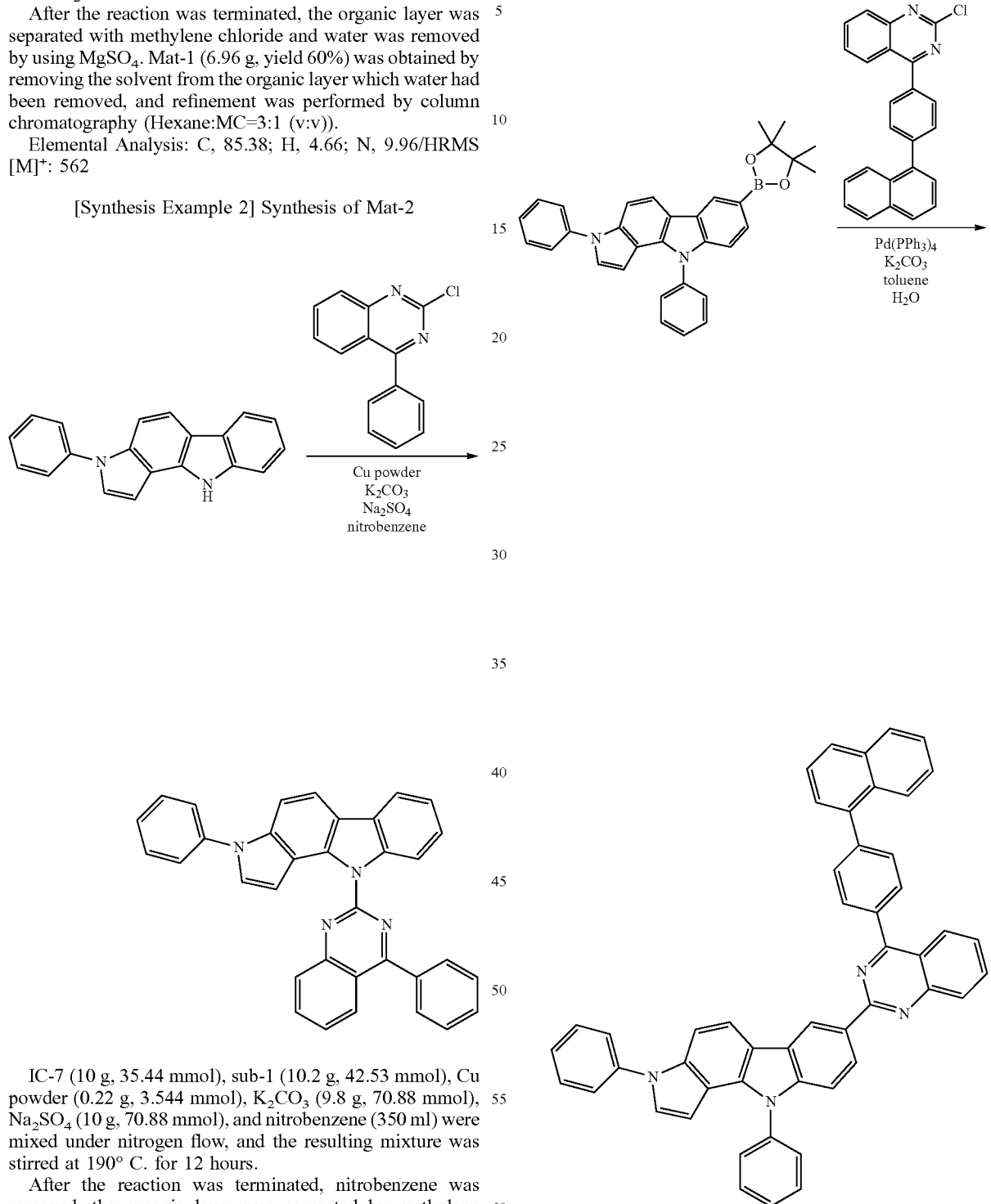

IC-7 (10 g, 35.44 mmol), sub-1 (10.2 g, 42.53 mmol), Cu powder (0.22 g, 3.544 mmol), $K_2CO_3$ (9.8 g, 70.88 mmol), $Na_2SO_4$ (10 g, 70.88 mmol), and nitrobenzene (350 ml) were mixed under nitrogen flow, and the resulting mixture was stirred at 190° C. for 12 hours.

After the reaction was terminated, nitrobenzene was removed, the organic layer was separated by methylene chloride, and water was removed by using $MgSO_4$. Mat-2 (8.6 g, yield 50%) was obtained by removing the solvent from the organic layer from which water had been removed, and refinement was performed by column chromatography (Hexane:MC=3:1 (v:v)).

Elemental Analysis: C, 83.93; H, 4.56; N, 11.51/HRMS [M]$^+$: 486

[Synthesis Example 3] Synthesis of Mat-3

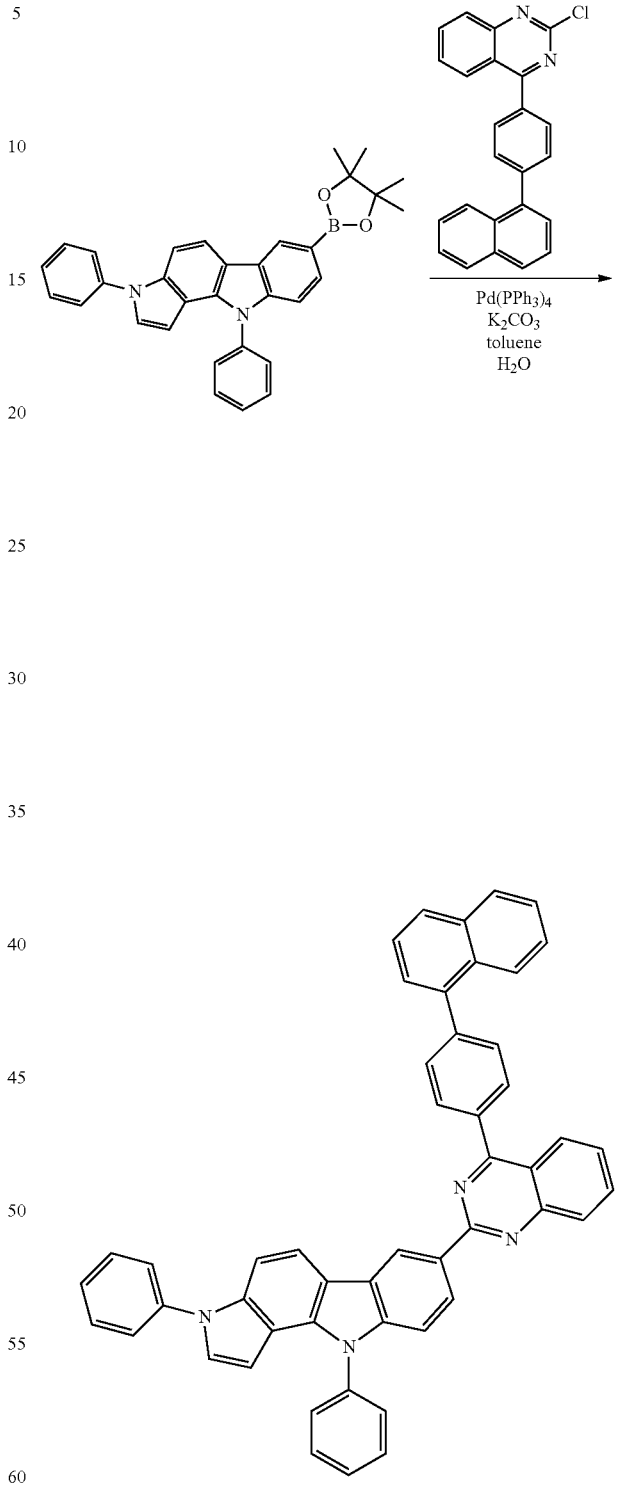

Mat-3 was obtained by performing the same procedure as in Synthesis Example 1, except that sub-2 was used instead of sub-1.

Elemental Analysis: C, 87.18; H, 4.68; N, 8.13/HRMS [M]$^+$: 688

[Synthesis Example 4] Synthesis of Mat-4
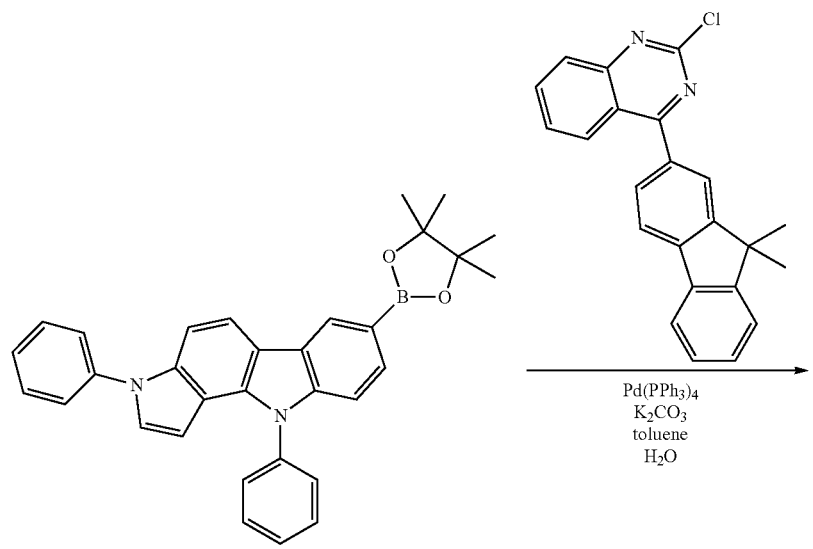
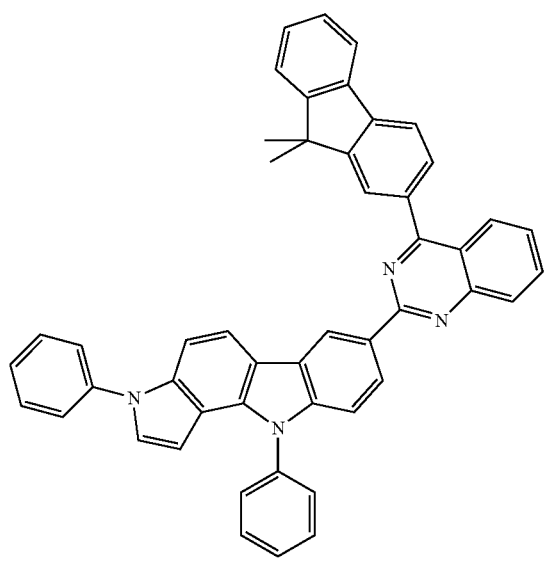

Mat-4 was obtained by performing the same procedure as in Synthesis Example 1, except that sub-3 was used instead of sub-1.

Elemental Analysis: C, 86.70; H, 5.05; N, 8.25/HRMS [M]$^+$: 678

[Synthesis Example 5] Synthesis of Mat-5

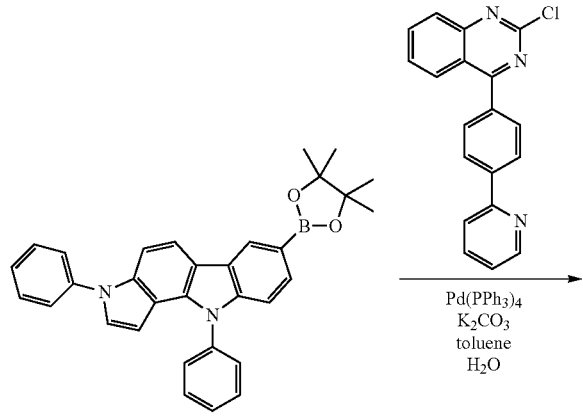
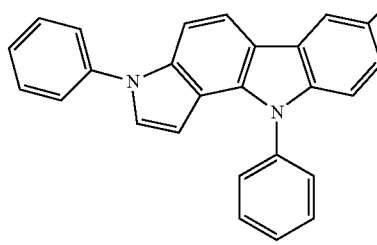
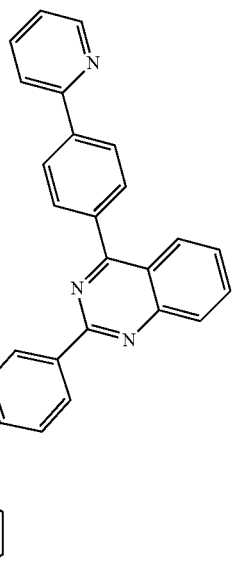

Mat-5 was obtained by performing the same procedure as in Synthesis Example 1, except that sub-4 was used instead of sub-1.

Elemental Analysis: C, 84.48; H, 4.57; N, 10.95/HRMS [M]$^+$: 639

[Synthesis Example 6] Synthesis of Mat-6

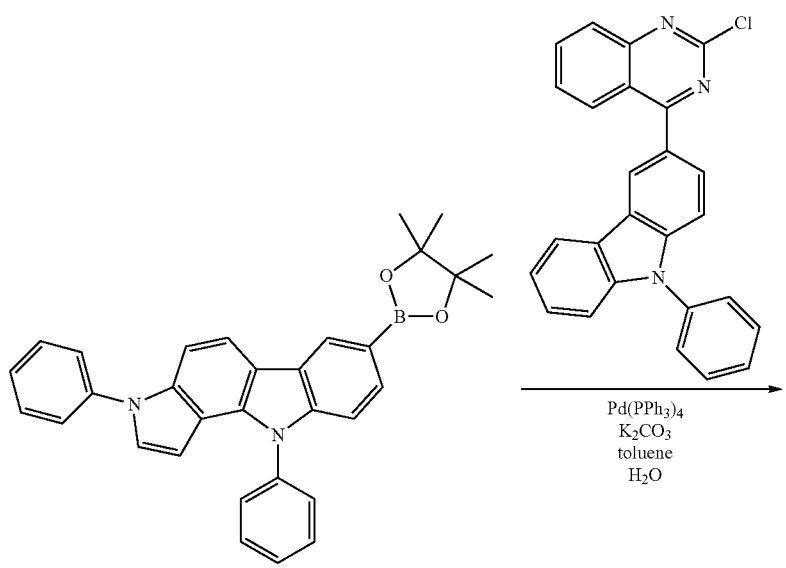

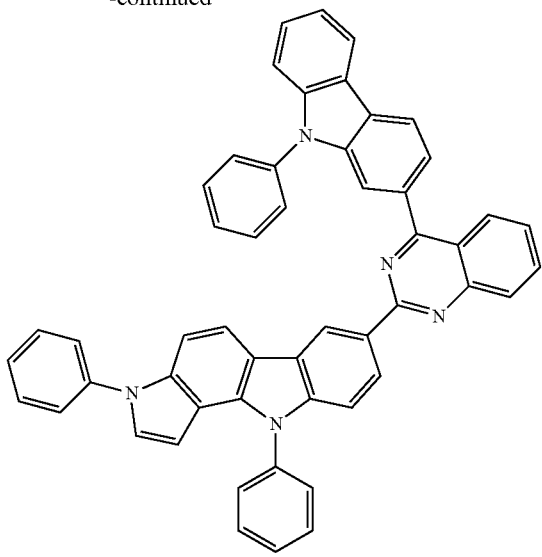

Mat-6 was obtained by performing the same procedure as in Synthesis Example 1, except that sub-5 was used instead of sub-1.

Elemental Analysis: C, 85.81; H, 4.57; N, 9.62/HRMS [M]⁺: 727

[Synthesis Example 7] Synthesis of Mat-7

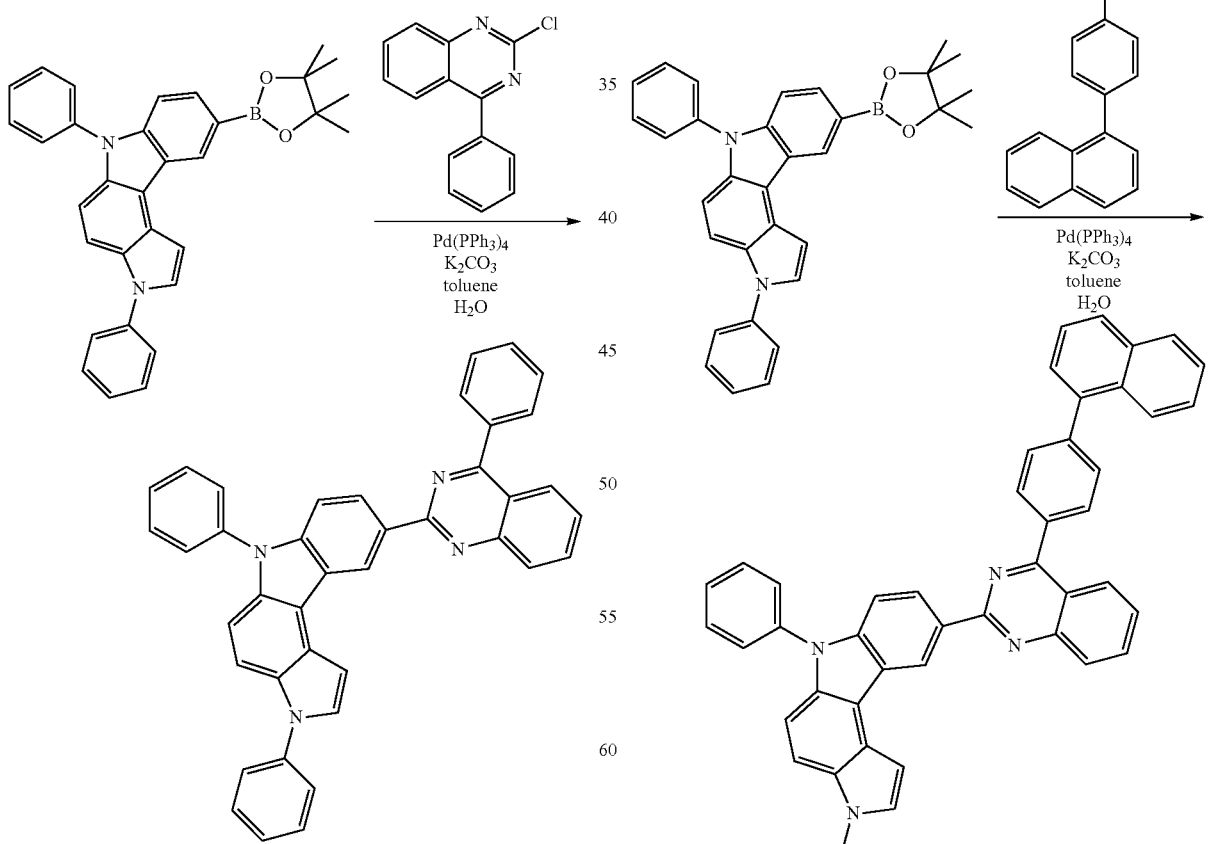

Mat-7 was obtained by performing the same procedure as in Synthesis Example 1, except that IC-2 was used instead of IC-1.

Elemental Analysis: C, 85.38; H, 4.66; N, 9.96/HRMS [M]⁺: 562

[Synthesis Example 8] Synthesis of Mat-8

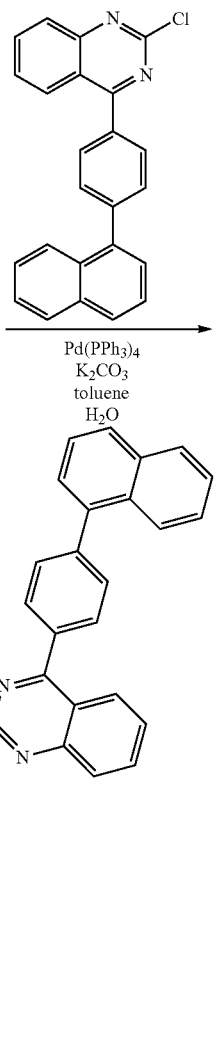

Mat-8 was obtained by performing the same procedure as in Synthesis Example 1, except that IC-2 and sub-2 were used instead of IC-1 and sub-1, respectively.
Elemental Analysis: C, 87.18; H, 4.68; N, 8.13/HRMS [M]$^+$: 688
[Synthesis Example 9] Synthesis of Mat-9
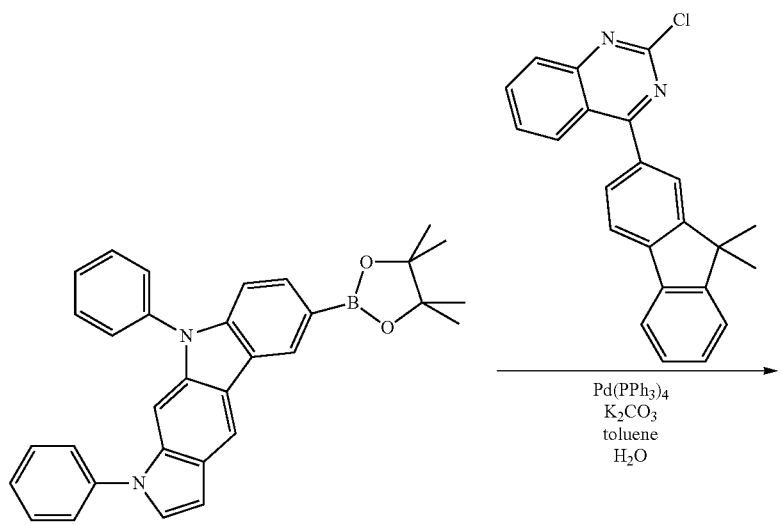
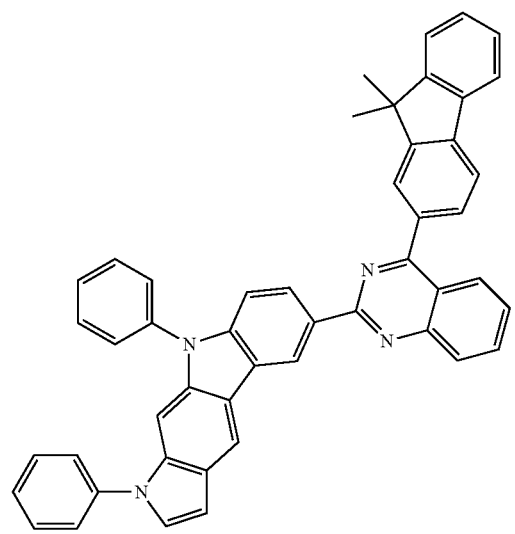

Mat-9 was obtained by performing the same procedure as in Synthesis Example 1, except that IC-3 and sub-3 were used instead of IC-1 and sub-1, respectively.

Elemental Analysis: C, 86.70; H, 5.05; N, 8.25/HRMS [M]⁺: 678

[Synthesis Example 10] Synthesis of Mat-10

Elemental Analysis: C, 84.48; H, 4.57; N, 10.95/HRMS [M]⁺: 639

[Synthesis Example 11] Synthesis of Mat-11

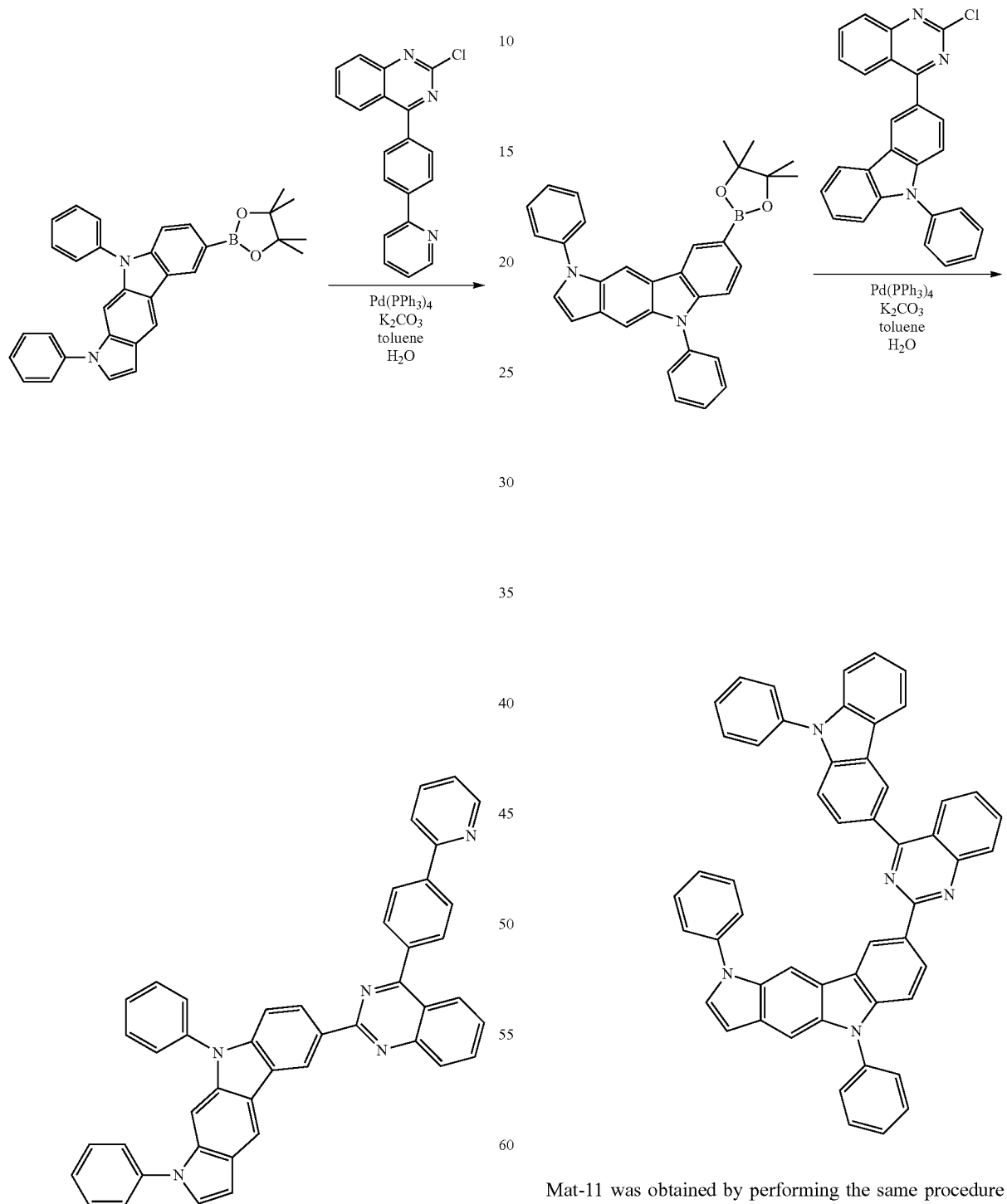

Mat-10 was obtained by performing the same procedure as in Synthesis Example 1, except that IC-3 and sub-4 were used instead of IC-1 and sub-1, respectively.

Mat-11 was obtained by performing the same procedure as in Synthesis Example 1, except that IC-4 and sub-5 were used instead of IC-1 and sub-1, respectively.

Elemental Analysis: C, 85.81; H, 4.57; N, 9.62/HRMS [M]⁺: 727

[Synthesis Example 12] Synthesis of Mat-12

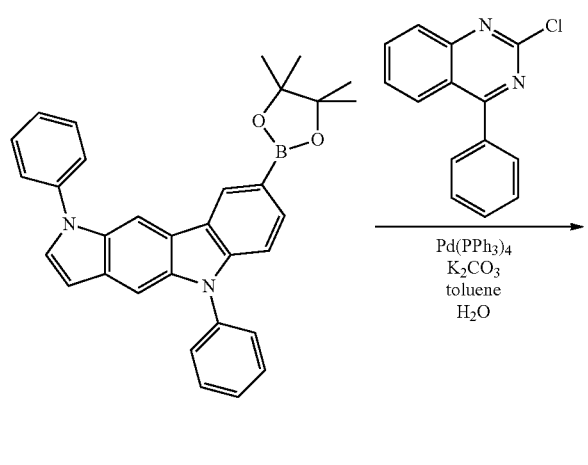
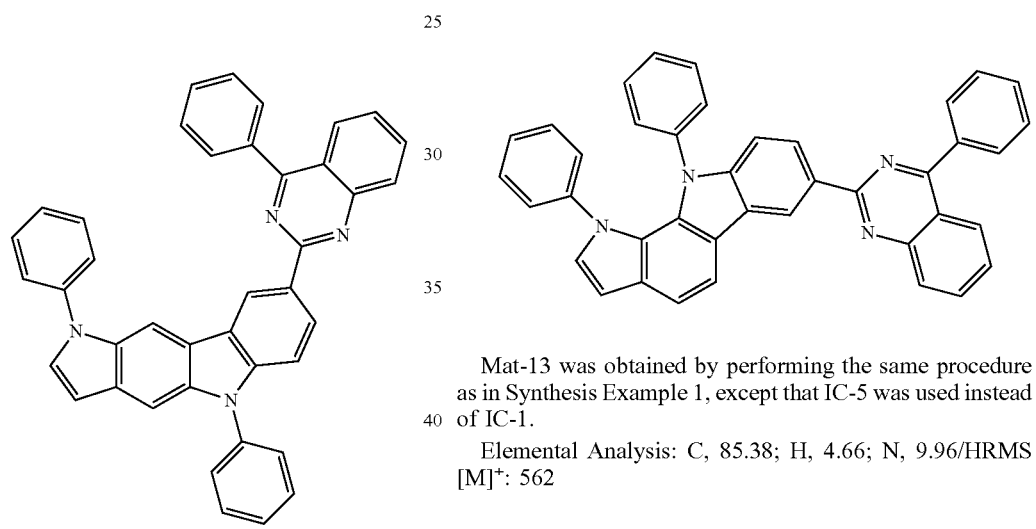

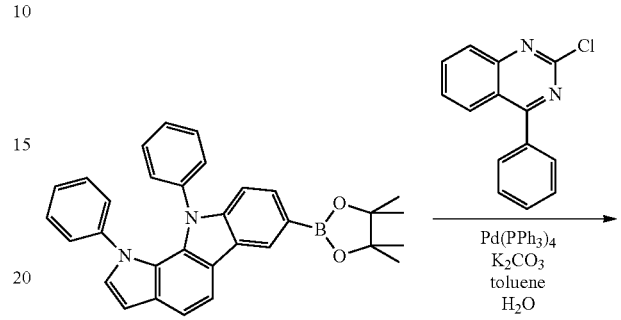

Mat-12 was obtained by performing the same procedure as in Synthesis Example 1, except that IC-4 was used instead of IC-1.

Elemental Analysis: C, 85.38; H, 4.66; N, 9.96/HRMS [M]$^+$: 562

[Synthesis Example 13] Synthesis of Mat-13

Mat-13 was obtained by performing the same procedure as in Synthesis Example 1, except that IC-5 was used instead of IC-1.

Elemental Analysis: C, 85.38; H, 4.66; N, 9.96/HRMS [M]$^+$: 562

[Synthesis Example 14] Synthesis of Mat-14

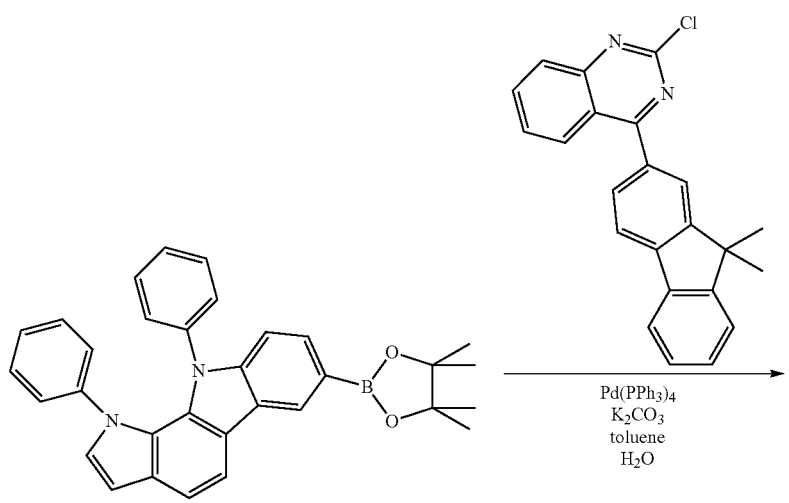

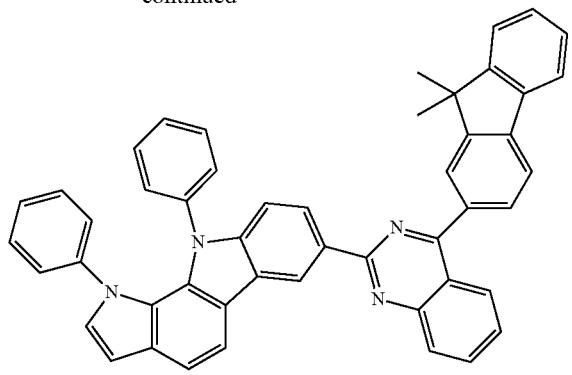

Mat-14 was obtained by performing the same procedure as in Synthesis Example 1, except that IC-5 and sub-3 were used instead of IC-1 and sub-1, respectively.

Elemental Analysis: C, 86.70; H, 5.05; N, 8.25/HRMS [M]$^+$: 678

Elemental Analysis: C, 87.18; H, 4.68; N, 8.13/HRMS [M]$^+$: 688

[Synthesis Example 16] Synthesis of Mat-16

[Synthesis Example 15] Synthesis of Mat-15

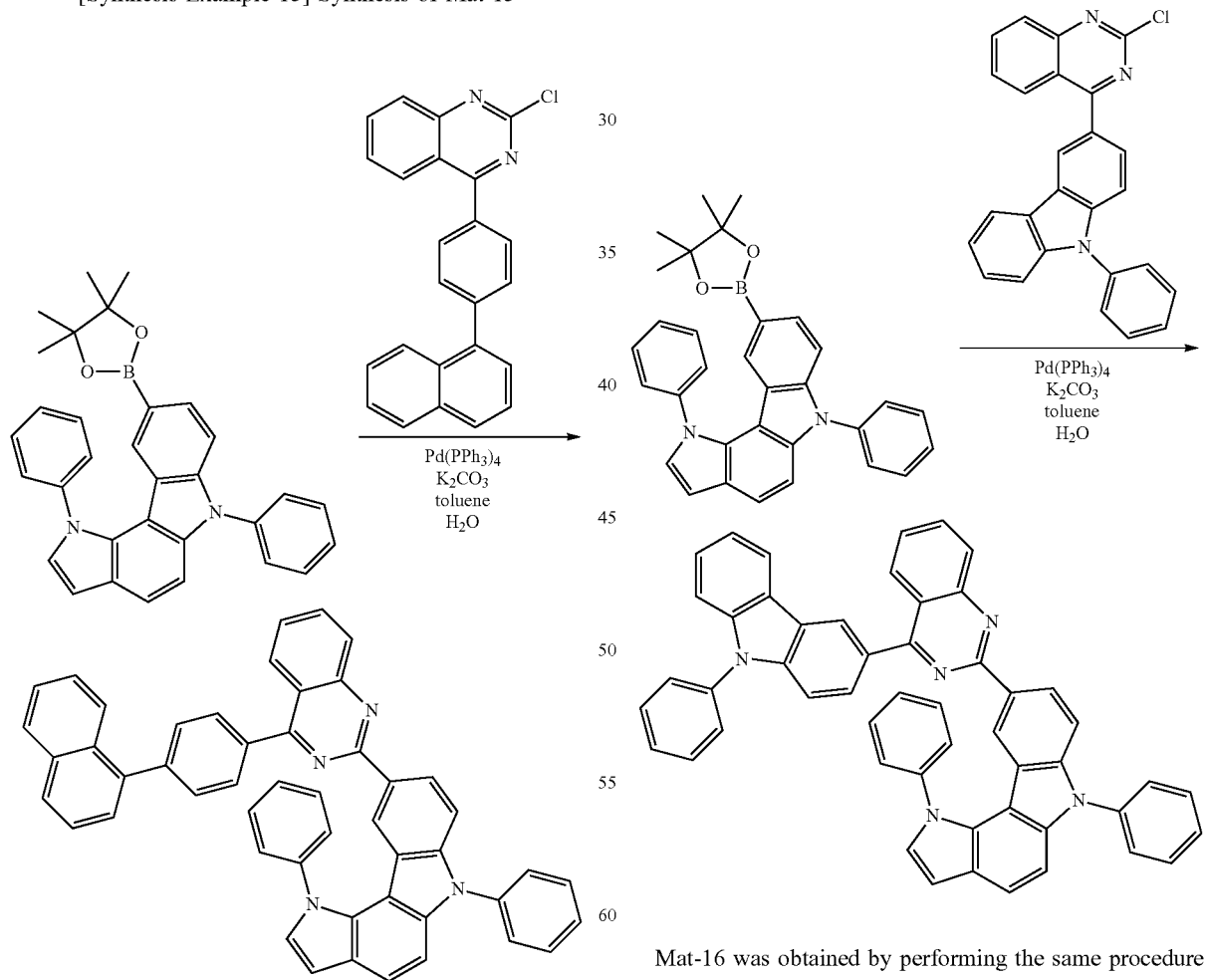

Mat-15 was obtained by performing the same procedure as in Synthesis Example 1, except that IC-6 and sub-2 were used instead of IC-1 and sub-1, respectively.

Mat-16 was obtained by performing the same procedure as in Synthesis Example 1, except that IC-6 and sub-5 were used instead of IC-1 and sub-1, respectively.

Elemental Analysis: C, 85.81; H, 4.57; N, 9.62/HRMS [M]$^+$: 727

[Synthesis Example 17] Synthesis of Mat-17

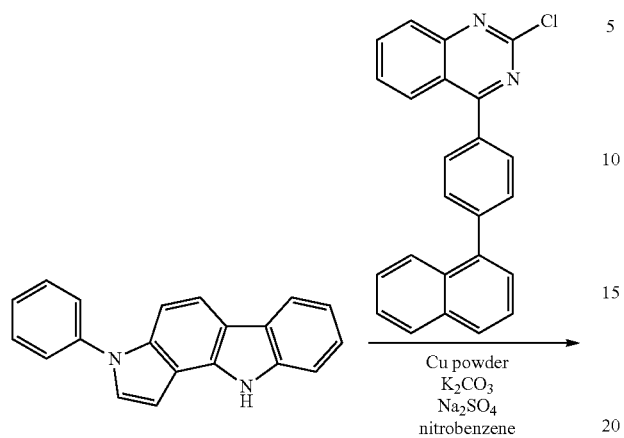

Mat-17 was obtained by performing the same procedure as in Synthesis Example 2, except that sub-2 was used instead of sub-1.

Elemental Analysis: C, 86.25; H, 4.61; N, 9.14/HRMS [M]$^+$: 612

[Synthesis Example 18] Synthesis of Mat-18

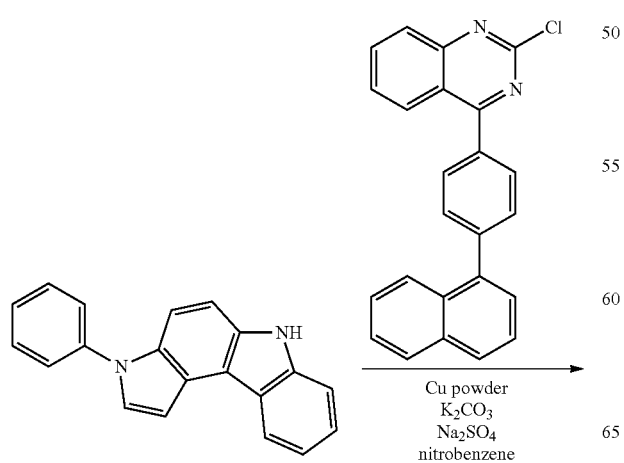

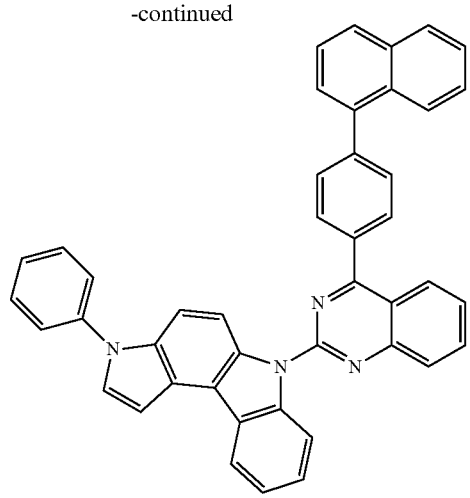

Mat-18 was obtained by performing the same procedure as in Synthesis Example 2, except that IC-8 and sub-2 were used instead of IC-7 and sub-1, respectively.

Elemental Analysis: C, 86.25; H, 4.61; N, 9.14/HRMS [M]$^+$: 612

[Synthesis Example 19] Synthesis of Mat-19

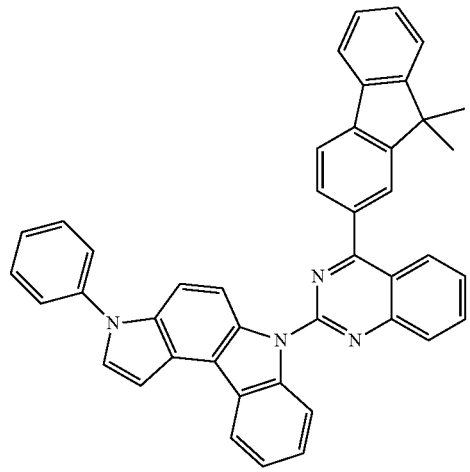

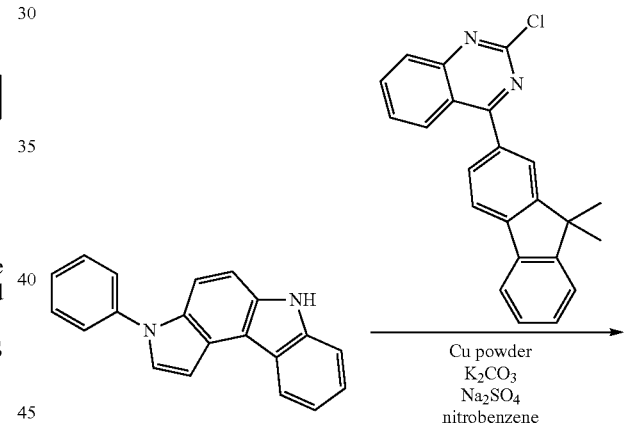

Mat-19 was obtained by performing the same procedure as in Synthesis Example 2, except that IC-8 and sub-3 were used instead of IC-7 and sub-1, respectively.

Elemental Analysis: C, 85.69; H, 5.02; N, 9.30/HRMS [M]⁺: 602

[Synthesis Example 20] Synthesis of Mat-20

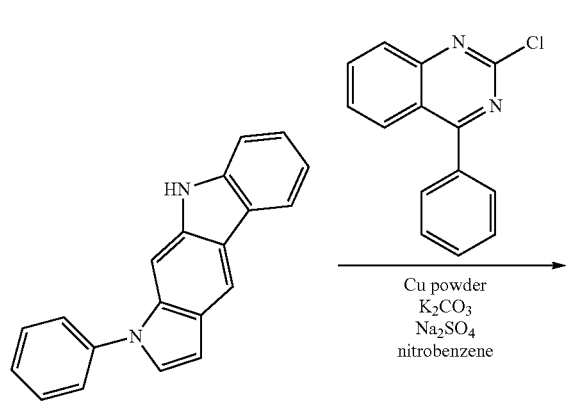

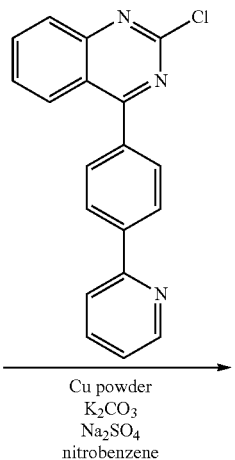

Mat-20 was obtained by performing the same procedure as in Synthesis Example 2, except that IC-9 was used instead of IC-7.

Elemental Analysis: C, 83.93; H, 4.56; N, 11.51/HRMS [M]⁺: 486

[Synthesis Example 21] Synthesis of Mat-21

Mat-21 was obtained by performing the same procedure as in Synthesis Example 2, except that IC-9 and sub-4 were used instead of IC-7 and sub-1, respectively.

Elemental Analysis: C, 83.10; H, 4.47; N, 12.43/HRMS [M]⁺: 563

[Synthesis Example 22] Synthesis of Mat-22

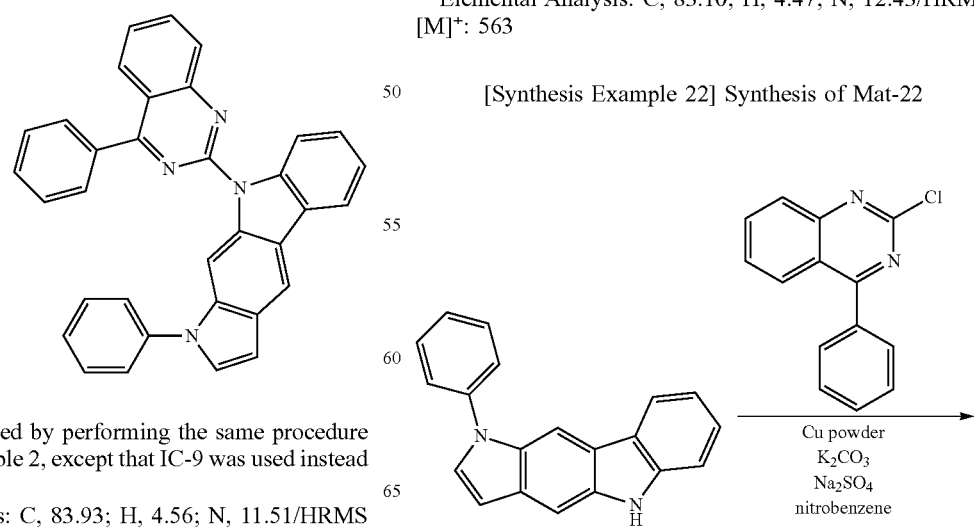

-continued

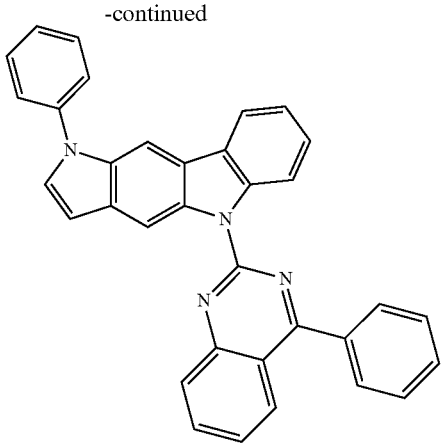

Mat-22 was obtained by performing the same procedure as in Synthesis Example 2, except that IC-10 was used instead of IC-7.

Elemental Analysis: C, 83.93; H, 4.56; N, 11.51/HRMS [M]+: 486

[Synthesis Example 23] Synthesis of Mat-23

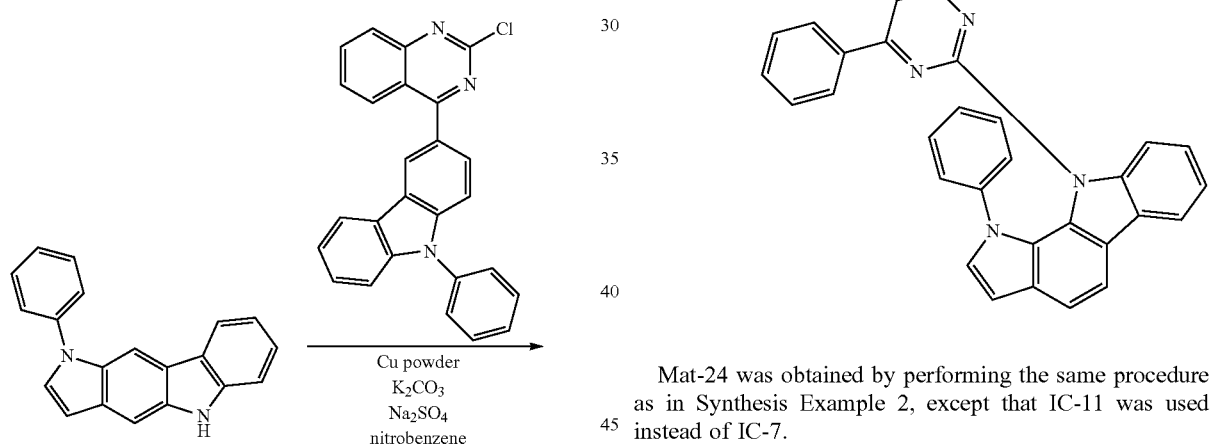

Mat-23 was obtained by performing the same procedure as in Synthesis Example 2, except that IC-10 and sub-5 were used instead of IC-7 and sub-1, respectively.

Elemental Analysis: C, 84.77; H, 4.48; N, 10.75/HRMS [M]+: 651

[Synthesis Example 24] Synthesis of Mat-24

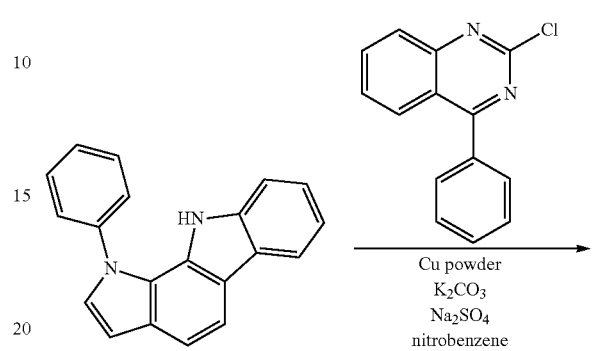

Mat-24 was obtained by performing the same procedure as in Synthesis Example 2, except that IC-11 was used instead of IC-7.

Elemental Analysis: C, 83.93; H, 4.56; N, 11.51/HRMS [M]+: 486

[Synthesis Example 25] Synthesis of Mat-25

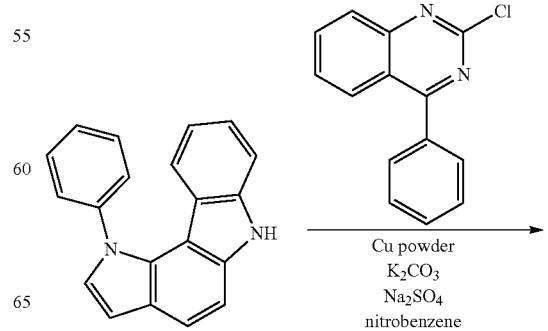

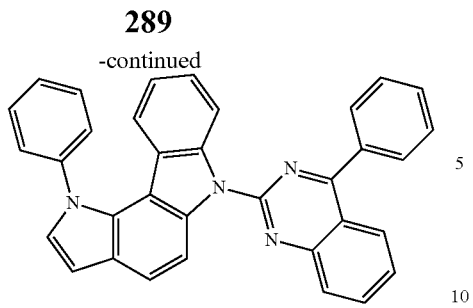

Mat-25 was obtained by performing the same procedure as in Synthesis Example 2, except that IC-12 was used instead of IC-7.

Elemental Analysis: C, 83.93; H, 4.56; N, 11.51/HRMS [M]$^+$: 486

[Synthesis Example 26] Synthesis of Mat-26

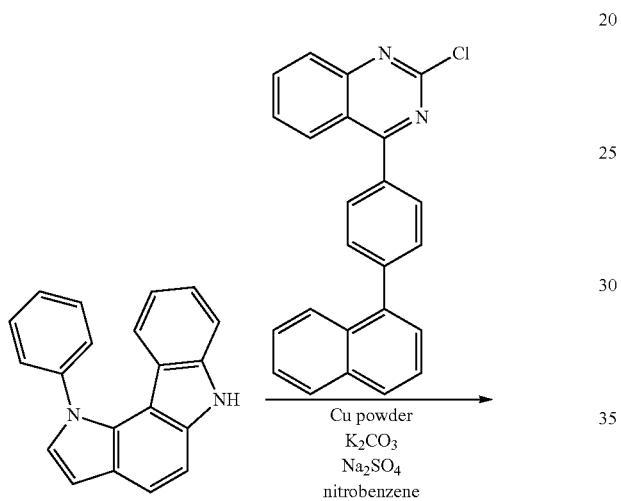

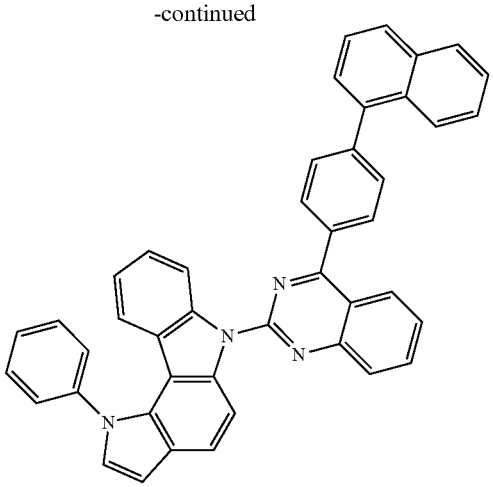

Mat-26 was obtained by performing the same procedure as in Synthesis Example 2, except that IC-12 and sub-2 were used instead of IC-7 and sub-1, respectively.

Elemental Analysis: C, 86.25; H, 4.61; N, 9.14/HRMS [M]$^+$: 616

[Synthesis Example 27] Synthesis of Mat-27

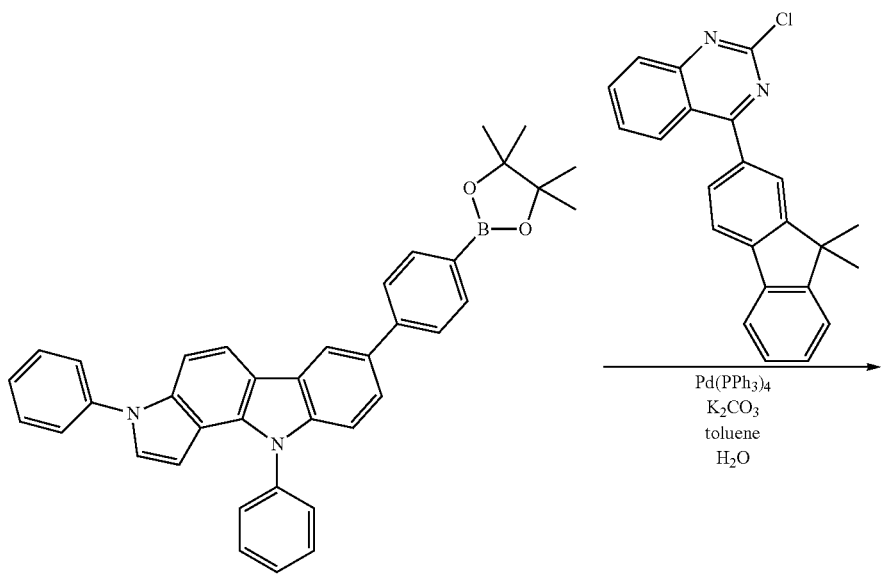

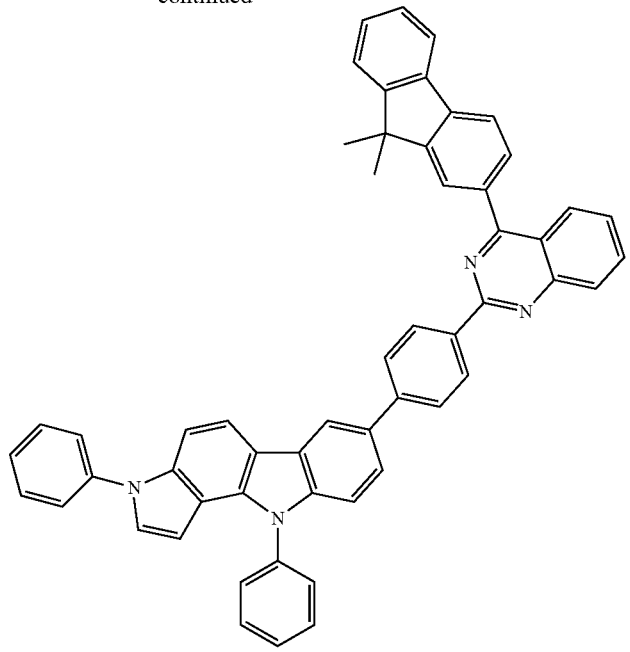
Mat-27 was obtained by performing the same procedure as in Synthesis Example 1, except that IC-13 and sub-3 were used instead of IC-1 and sub-1, respectively.
Elemental Analysis: C, 87.50; H, 5.07; N, 7.42/HRMS [M]$^+$: 754
[Synthesis Example 28] Synthesis of Mat-28
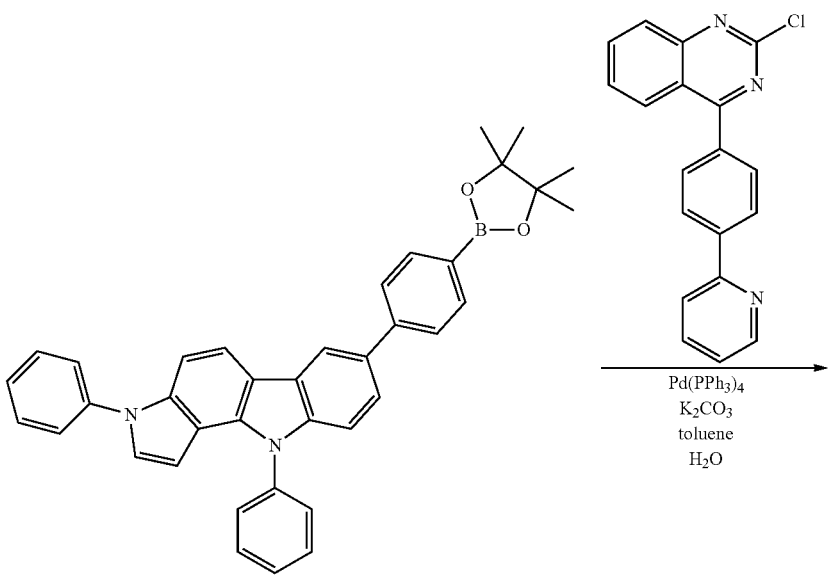

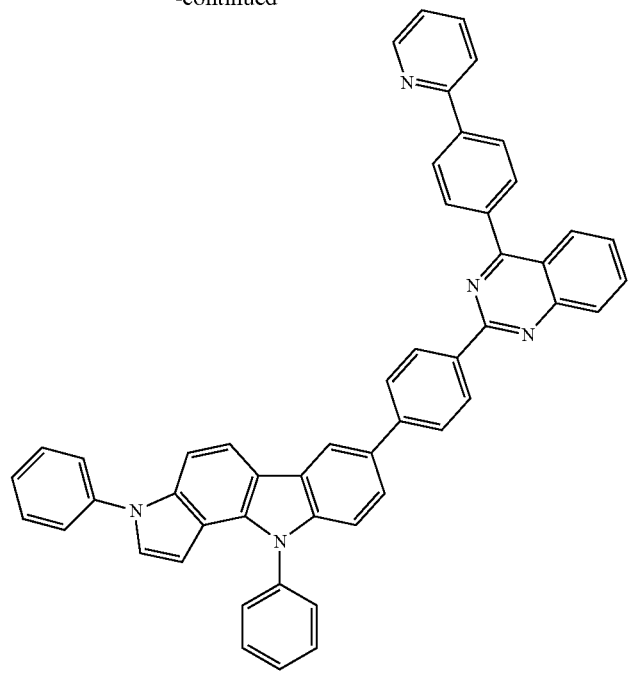
Mat-28 was obtained by performing the same procedure as in Synthesis Example 1, except that IC-13 and sub-4 were used instead of IC-1 and sub-1, respectively.
Elemental Analysis: C, 85.57; H, 4.65; N, 9.78/HRMS [M]$^+$: 715
[Synthesis Example 29] Synthesis of Mat-29

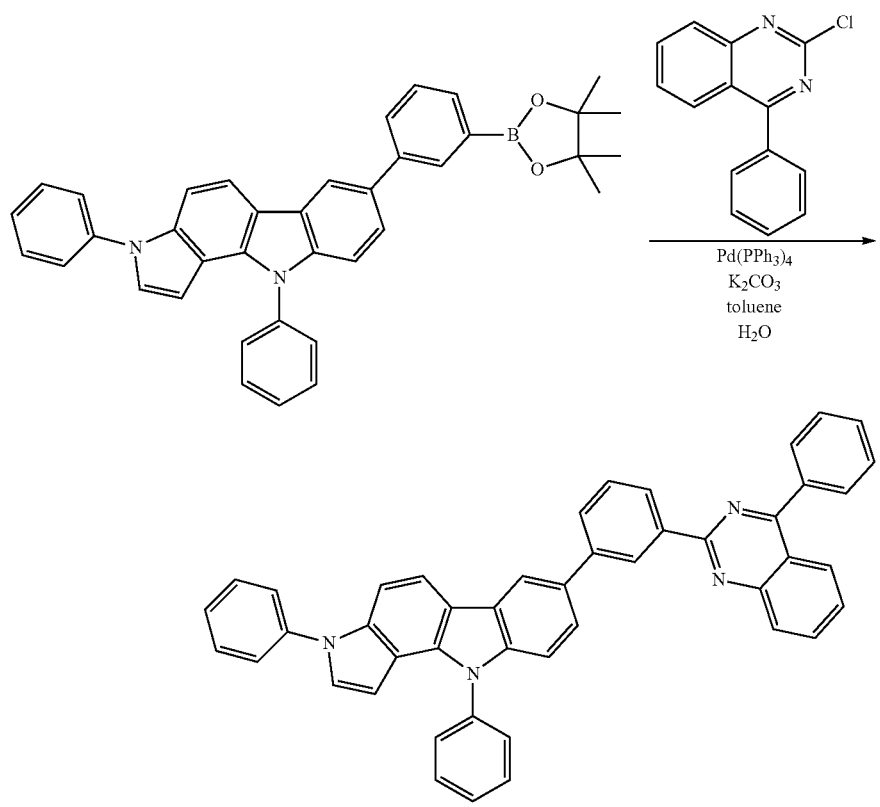
Mat-29 was obtained by performing the same procedure as in Synthesis Example 1, except that IC-14 was used instead of IC-1.
Elemental Analysis: C, 86.49; H, 4.73; N, 8.77/HRMS [M]⁺: 638
[Synthesis Example 30] Synthesis of Mat-30
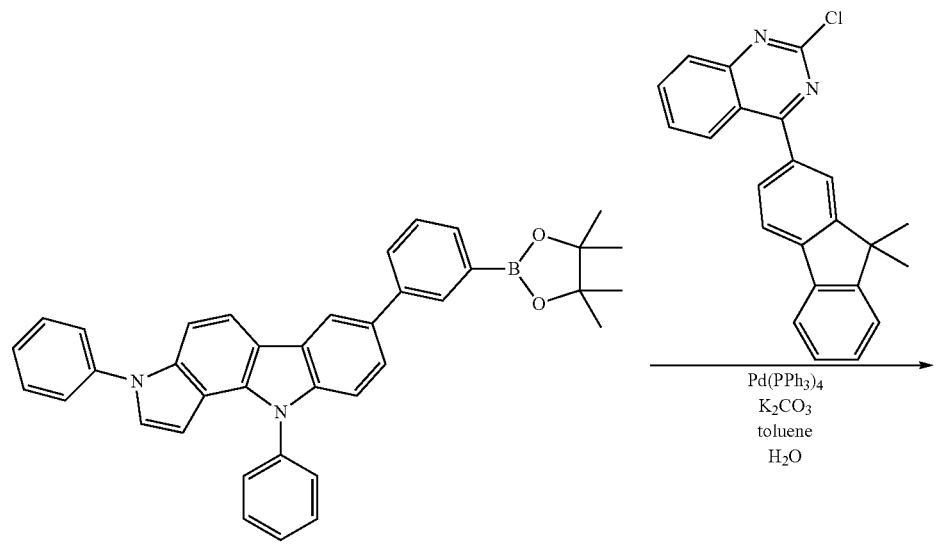

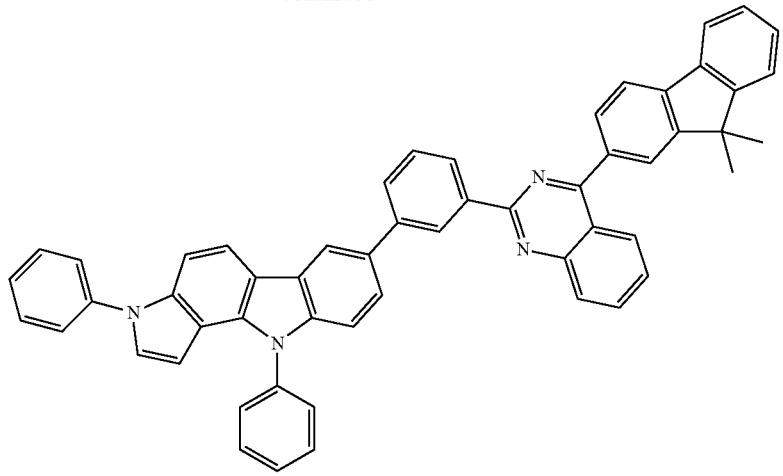
Mat-30 was obtained by performing the same procedure as in Synthesis Example 1, except that IC-14 and sub-3 were used instead of IC-1 and sub-1, respectively.
Elemental Analysis: C, 87.50; H, 5.07; N, 7.42/HRMS [M]⁺: 754
[Synthesis Example 31] Synthesis of Mat-31
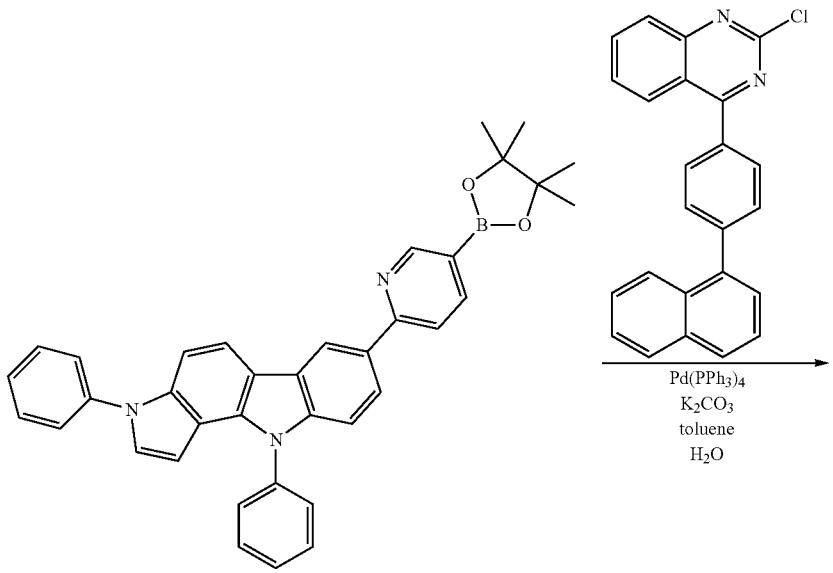

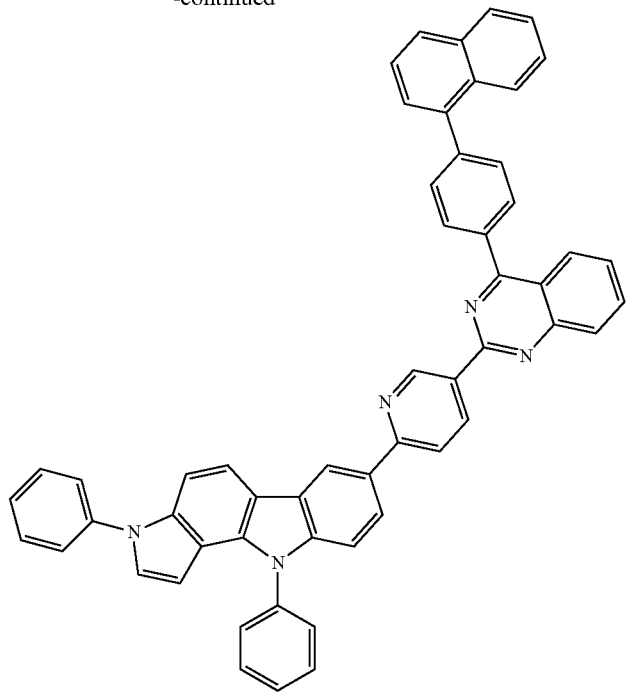
Mat-31 was obtained by performing the same procedure as in Synthesis Example 1, except that IC-15 and sub-2 were used instead of IC-1 and sub-1, respectively.
Elemental Analysis: C, 86.25; H, 4.61; N, 9.14/HRMS [M]$^+$: 765
[Synthesis Example 32] Synthesis of Mat-32
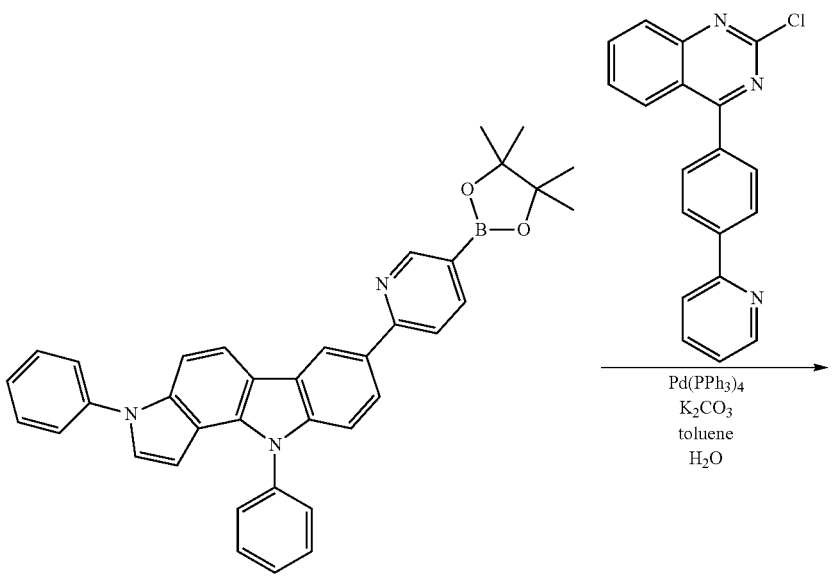

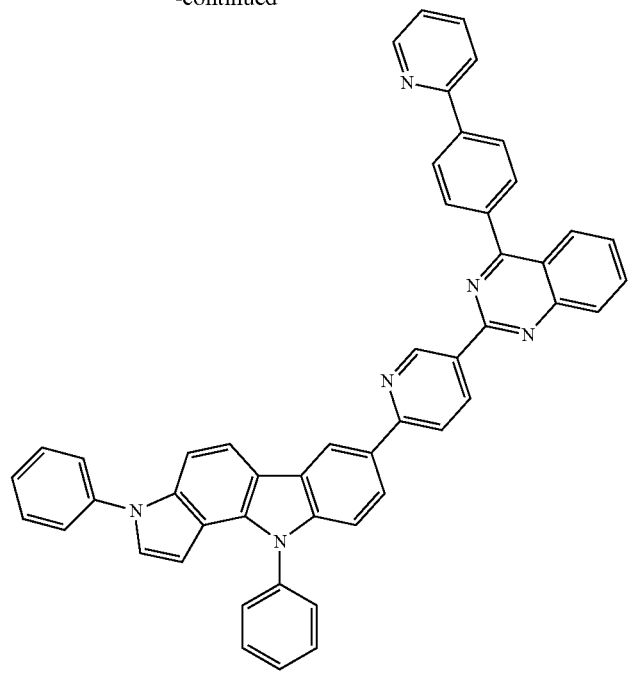
Mat-32 was obtained by performing the same procedure as in Synthesis Example 1, except that IC-15 and sub-4 were used instead of IC-1 and sub-1, respectively.
Elemental Analysis: C, 83.78; H, 4.50; N, 11.72/HRMS [M]$^+$: 716
[Synthesis Example 33] Synthesis of Mat-33
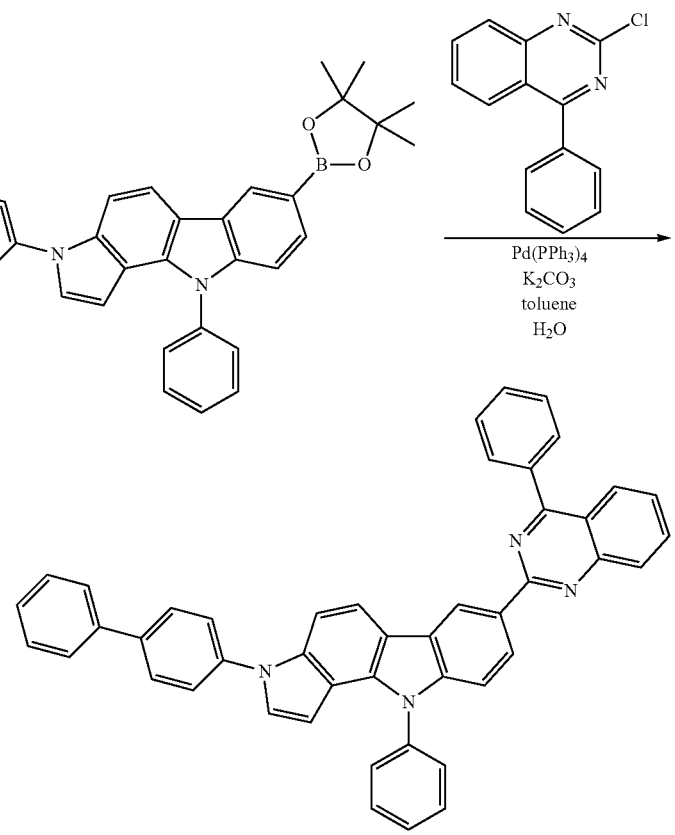

Mat-33 was obtained by performing the same procedure as in Synthesis Example 1, except that IC-16 was used instead of IC-1.
Elemental Analysis: C, 86.49; H, 4.73; N, 8.77/HRMS [M]$^+$: 638
[Synthesis Example 34] Synthesis of Mat-34
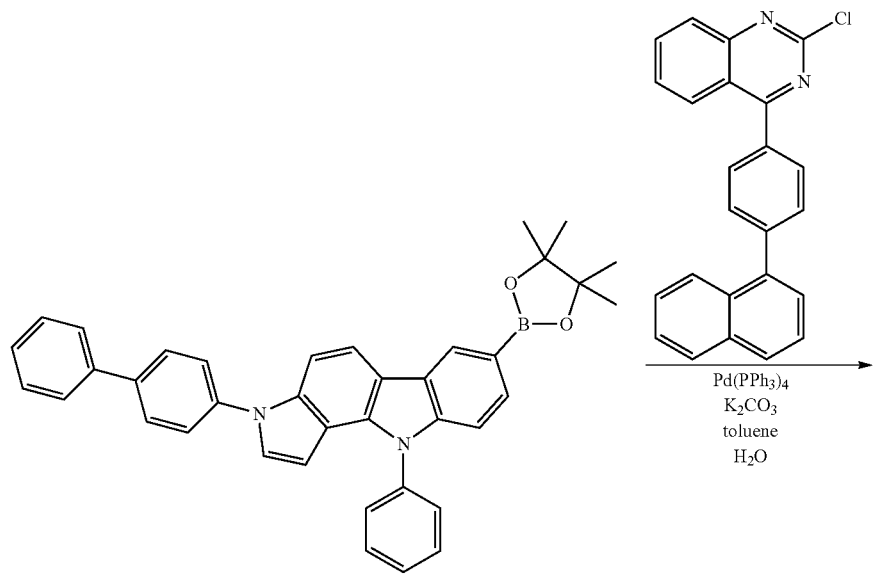
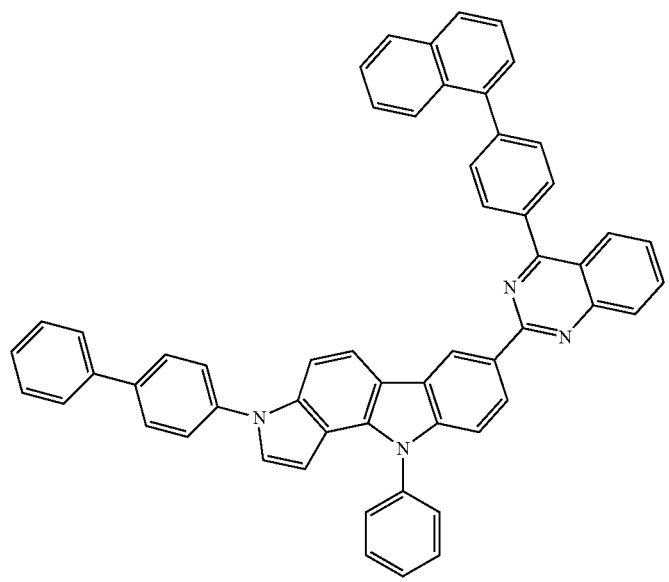

Mat-34 was obtained by performing the same procedure as in Synthesis Example 1, except that IC-16 and sub-2 were used instead of IC-1 and sub-1, respectively.
Elemental Analysis: C, 87.93; H, 4.74; N, 7.32/HRMS [M]⁺: 764
[Synthesis Example 35] Synthesis of Mat-35
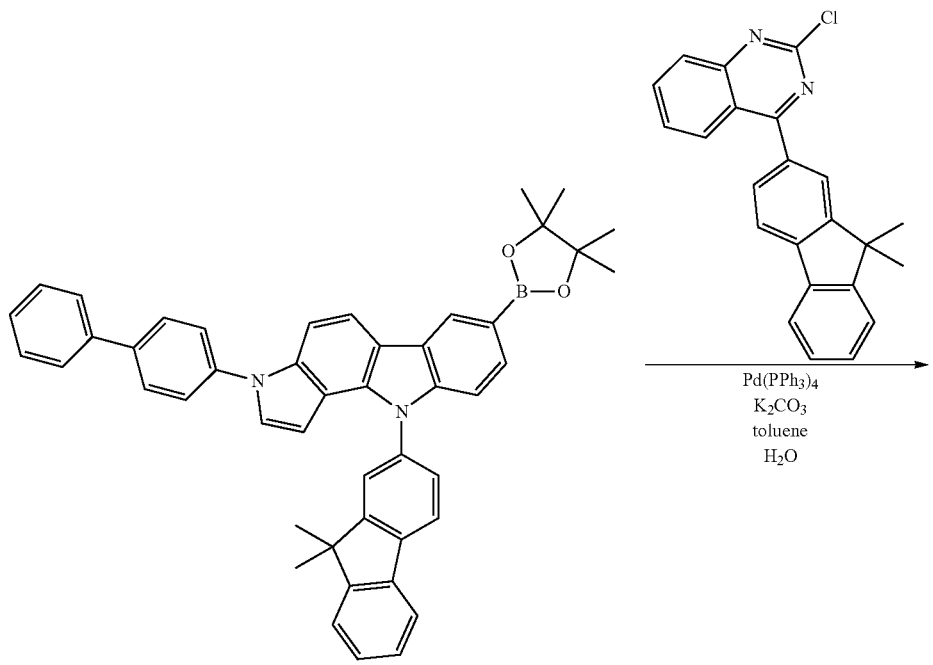
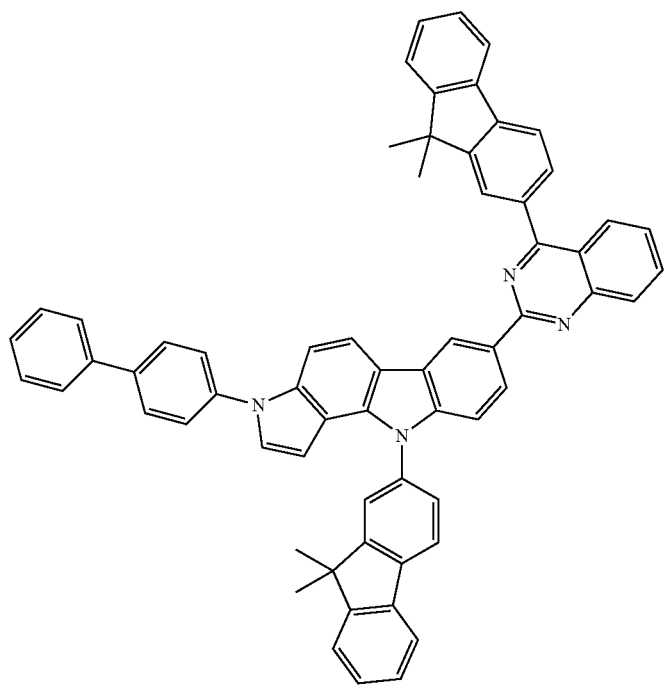

Mat-35 was obtained by performing the same procedure as in Synthesis Example 1, except that IC-17 and sub-3 were used instead of IC-1 and sub-1, respectively.
Elemental Analysis: C, 88.25; H, 5.32; N, 6.43/HRMS [M]$^+$: 870
[Synthesis Example 36] Synthesis of Mat-36
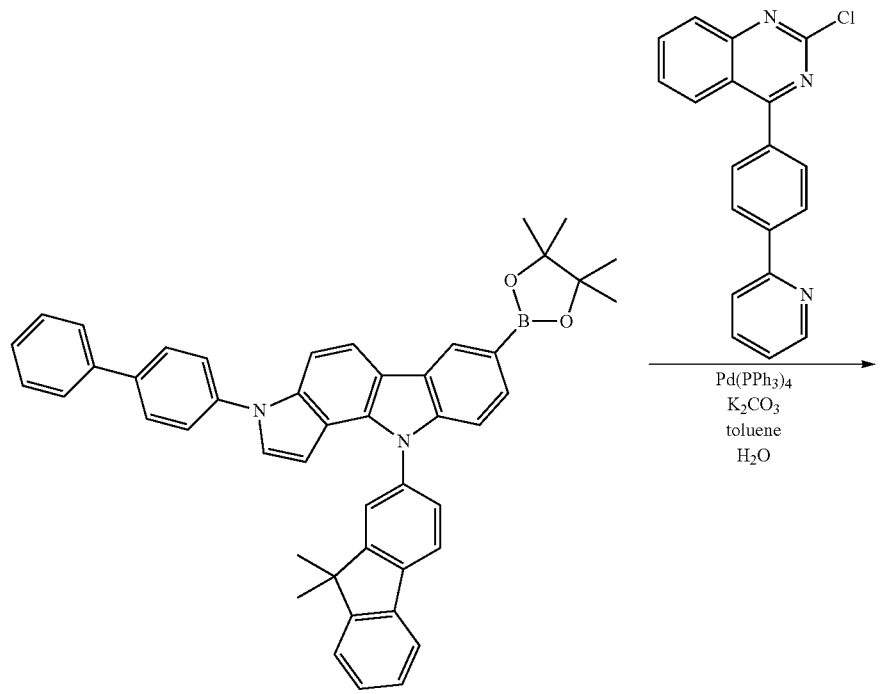
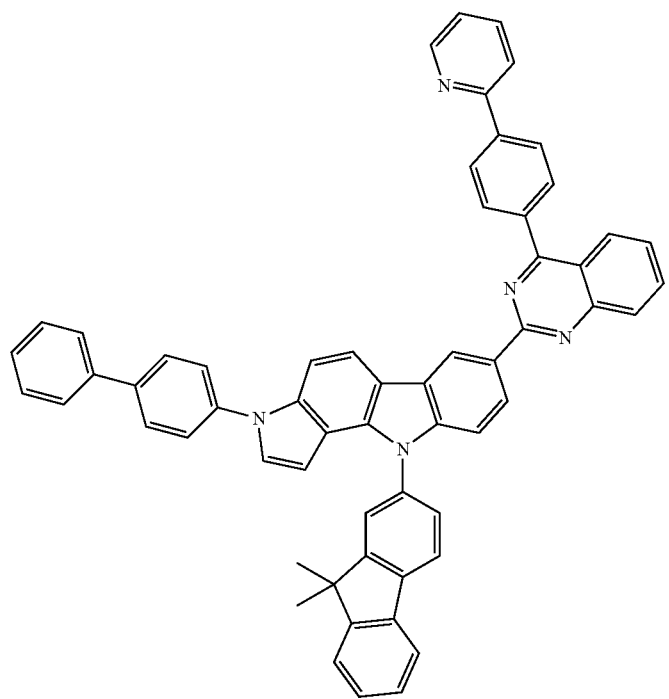

Mat-36 was obtained by performing the same procedure as in Synthesis Example 1, except that IC-17 and sub-4 were used instead of IC-1 and sub-1, respectively.

Elemental Analysis: C, 86.62; H, 4.97; N, 8.42/HRMS [M]$^+$: 831

[Synthesis Example 37] Synthesis of Mat-37

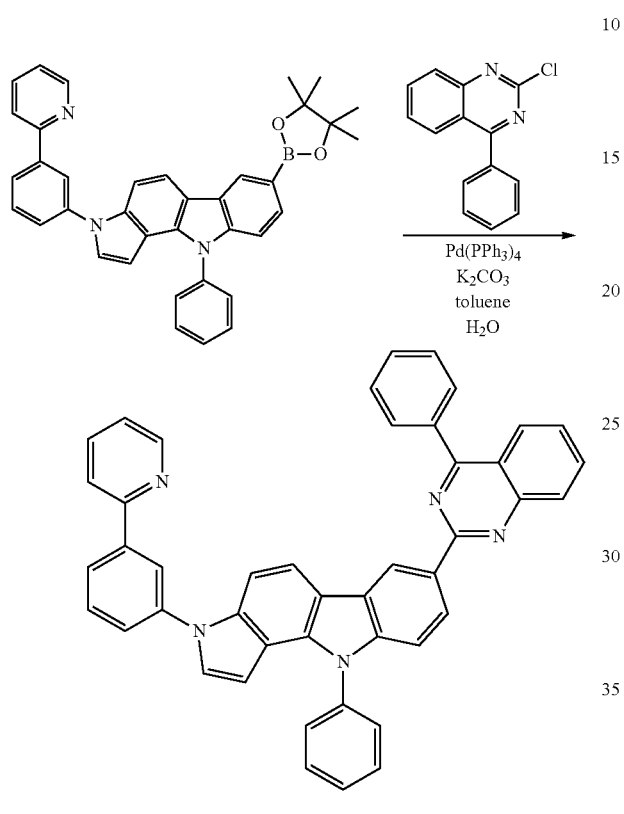

Mat-37 was obtained by performing the same procedure as in Synthesis Example 1, except that IC-18 was used instead of IC-1.

Elemental Analysis: C, 84.48; H, 4.57; N, 10.95/HRMS [M]$^+$: 639

[Synthesis Example 38] Synthesis of Mat-38

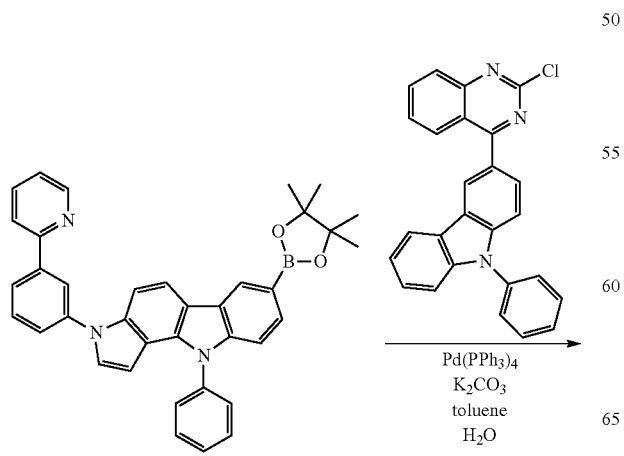

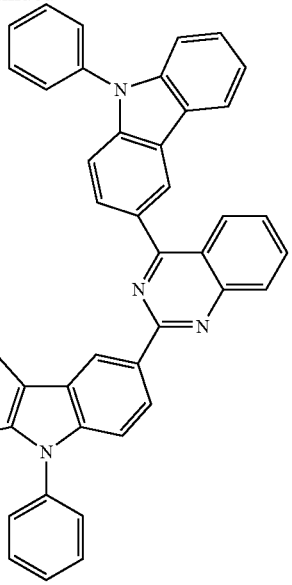

Mat-38 was obtained by performing the same procedure as in Synthesis Example 1, except that IC-18 and sub-5 were used instead of IC-1 and sub-1, respectively.

Elemental Analysis: C, 85.05; H, 4.51; N, 10.44/HRMS [M]$^+$: 804

[Synthesis Example 39] Synthesis of Mat-39

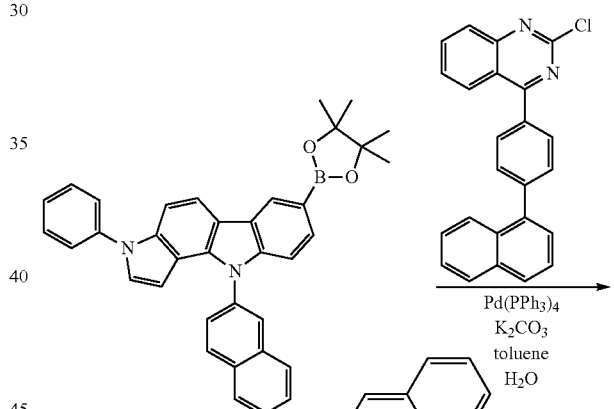

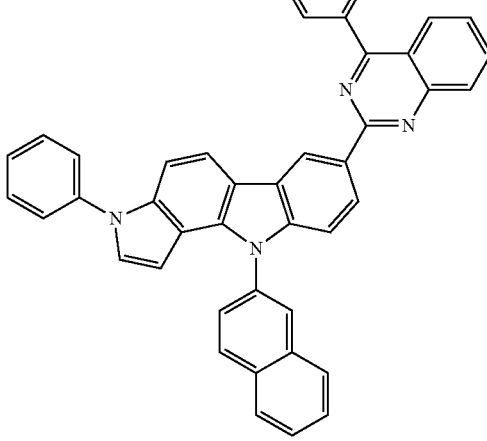

Mat-39 was obtained by performing the same procedure as in Synthesis Example 1, except that IC-19 and sub-2 were used instead of IC-1 and sub-1, respectively.

Elemental Analysis: C, 87.78; H, 4.64; N, 7.58/HRMS [M]$^+$: 738

[Synthesis Example 40] Synthesis of Mat-40

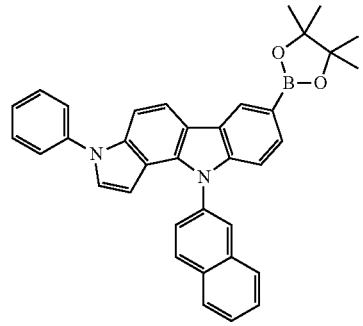 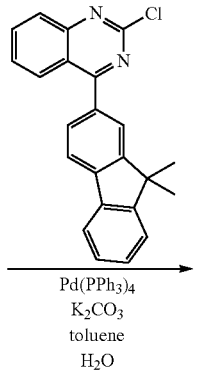

[Synthesis Example 41] Synthesis of Mat-41

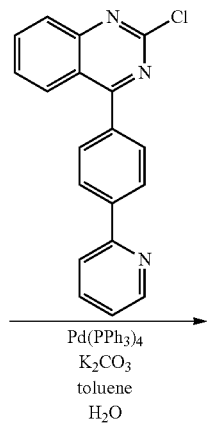

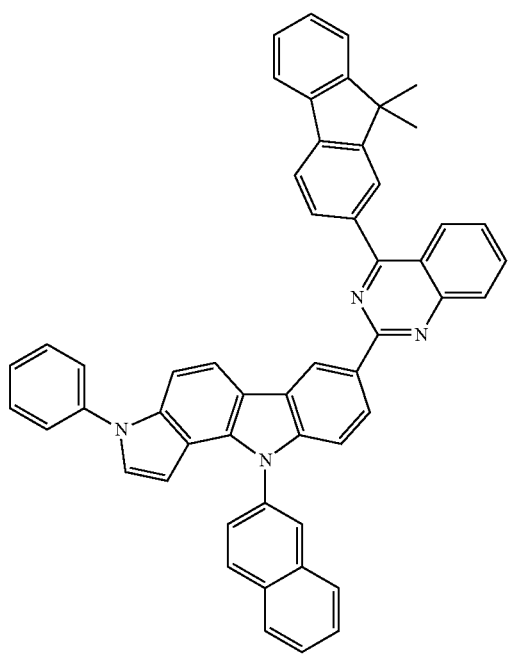

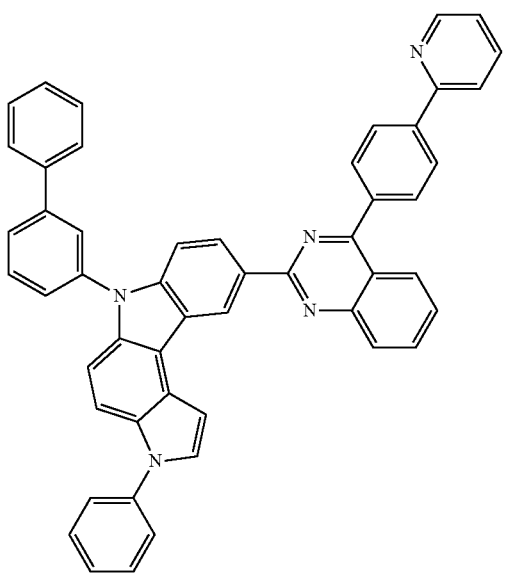

Mat-40 was obtained by performing the same procedure as in Synthesis Example 1, except that IC-19 and sub-3 were used instead of IC-1 and sub-1, respectively.

Elemental Analysis: C, 87.33; H, 4.98; N, 7.69/HRMS [M]$^+$: 728

Mat-41 was obtained by performing the same procedure as in Synthesis Example 1, except that IC-20 and sub-4 were used instead of IC-1 and sub-1, respectively.

Elemental Analysis: C, 85.57; H, 4.65; N, 9.78/HRMS [M]$^+$: 715

[Synthesis Example 42] Synthesis of Mat-42

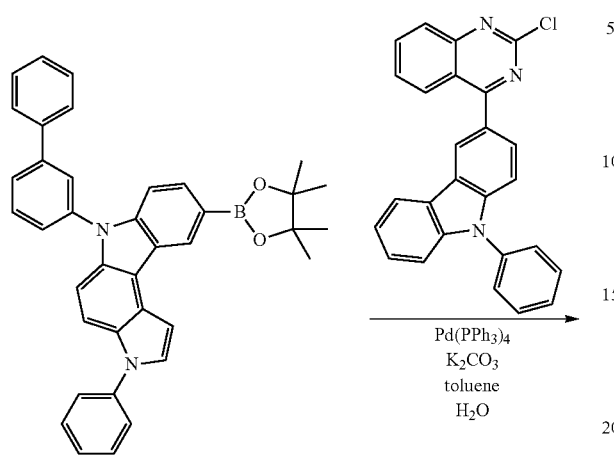

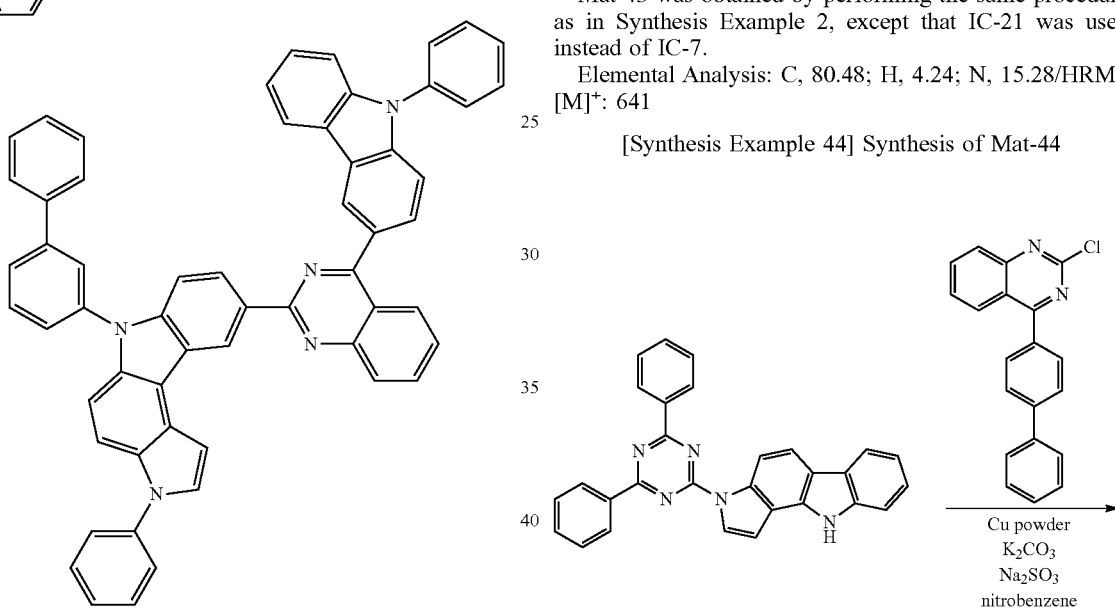

Mat-42 was obtained by performing the same procedure as in Synthesis Example 1, except that IC-20 and sub-5 were used instead of IC-1 and sub-1, respectively.

Elemental Analysis: C, 86.65; H, 4.64; N, 8.71/HRMS [M]⁺: 803

[Synthesis Example 43] Synthesis of Mat-43

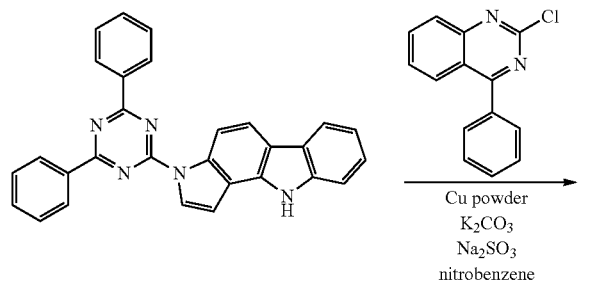

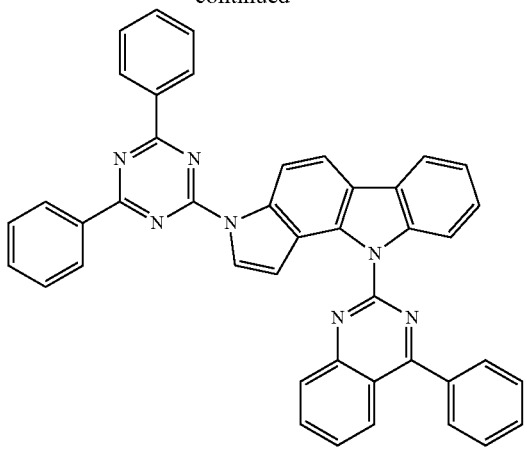

Mat-43 was obtained by performing the same procedure as in Synthesis Example 2, except that IC-21 was used instead of IC-7.

Elemental Analysis: C, 80.48; H, 4.24; N, 15.28/HRMS [M]⁺: 641

[Synthesis Example 44] Synthesis of Mat-44

Mat-44 was obtained by performing the same procedure as in Synthesis Example 2, except that IC-21 and sub-4 were used instead of IC-7 and sub-1, respectively.

Elemental Analysis: C, 80.20; H, 4.21; N, 15.59/HRMS [M]⁺: 718

[Synthesis Example 45] Synthesis of Mat-45

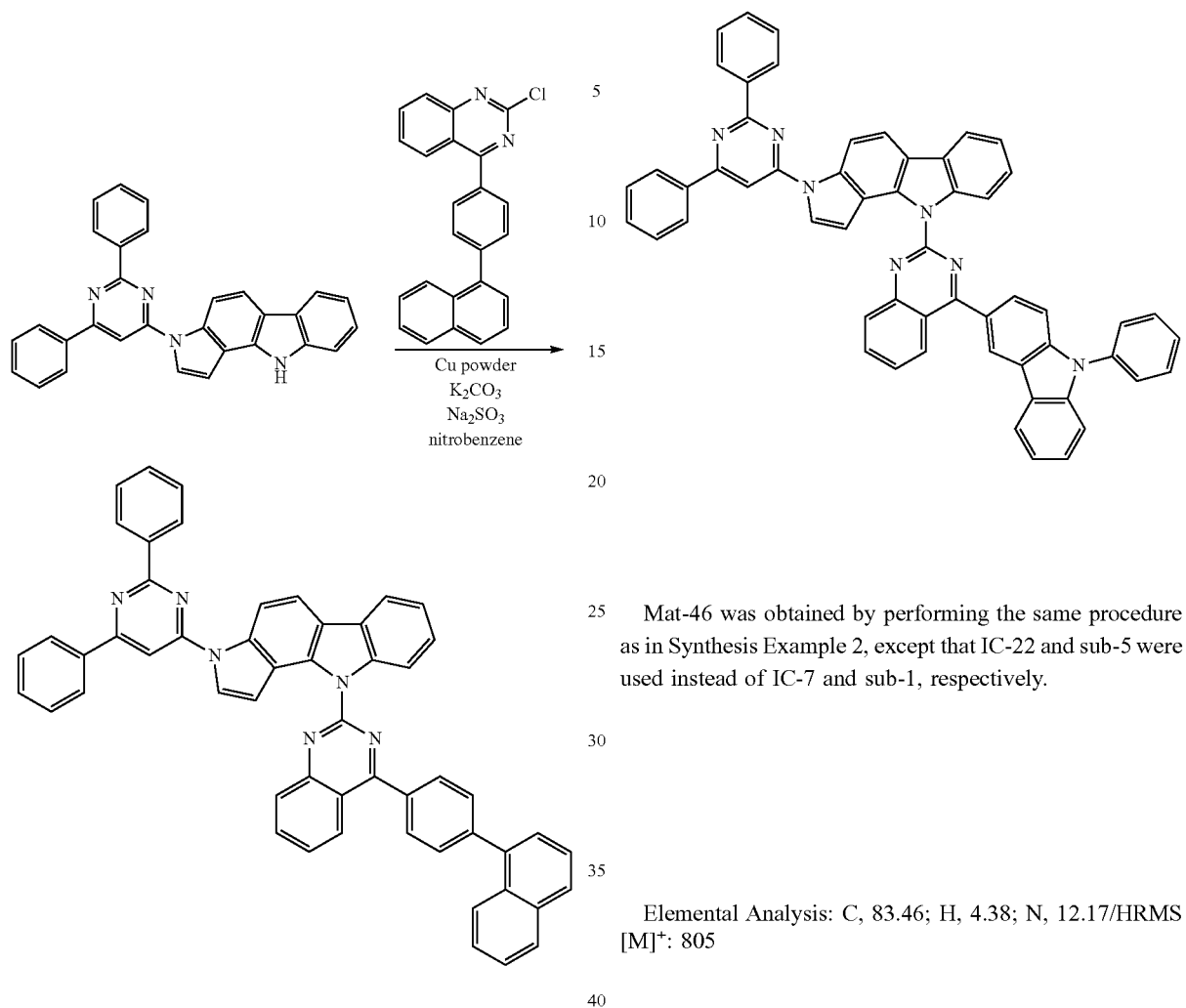

Mat-45 was obtained by performing the same procedure as in Synthesis Example 2, except that IC-22 and sub-2 were used instead of IC-7 and sub-1, respectively.

Elemental Analysis: C, 84.57; H, 4.47; N, 10.96/HRMS [M]$^+$: 766

[Synthesis Example 46] Synthesis of Mat-46

Mat-46 was obtained by performing the same procedure as in Synthesis Example 2, except that IC-22 and sub-5 were used instead of IC-7 and sub-1, respectively.

Elemental Analysis: C, 83.46; H, 4.38; N, 12.17/HRMS [M]$^+$: 805

[Synthesis Example 47] Synthesis of Mat-47

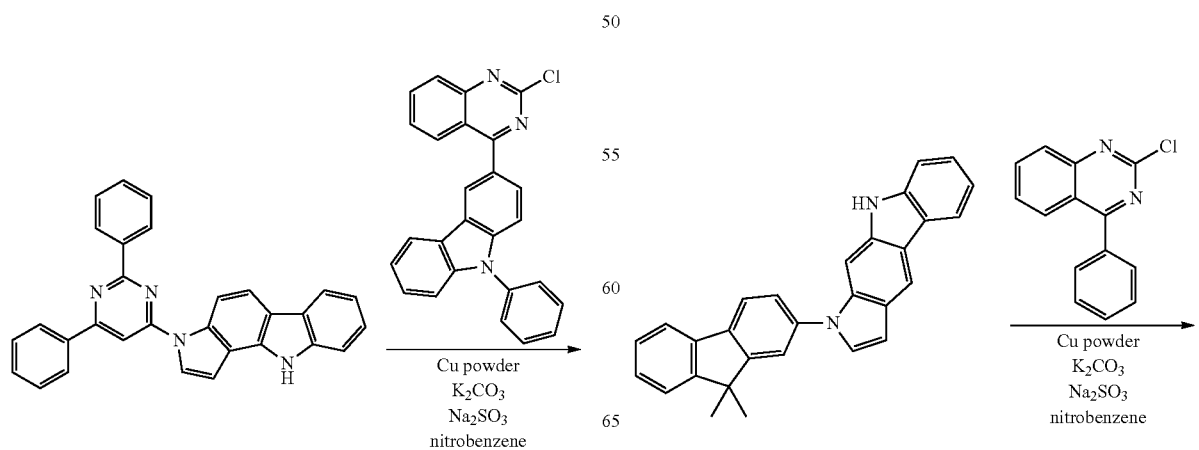

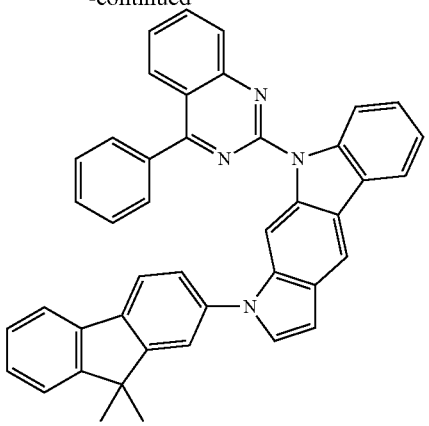

Mat-47 was obtained by performing the same procedure as in Synthesis Example 2, except that IC-23 was used instead of IC-7.

Elemental Analysis: C, 85.69; H, 5.02; N, 9.30/HRMS [M]$^+$: 602

[Synthesis Example 48] Synthesis of Mat-48

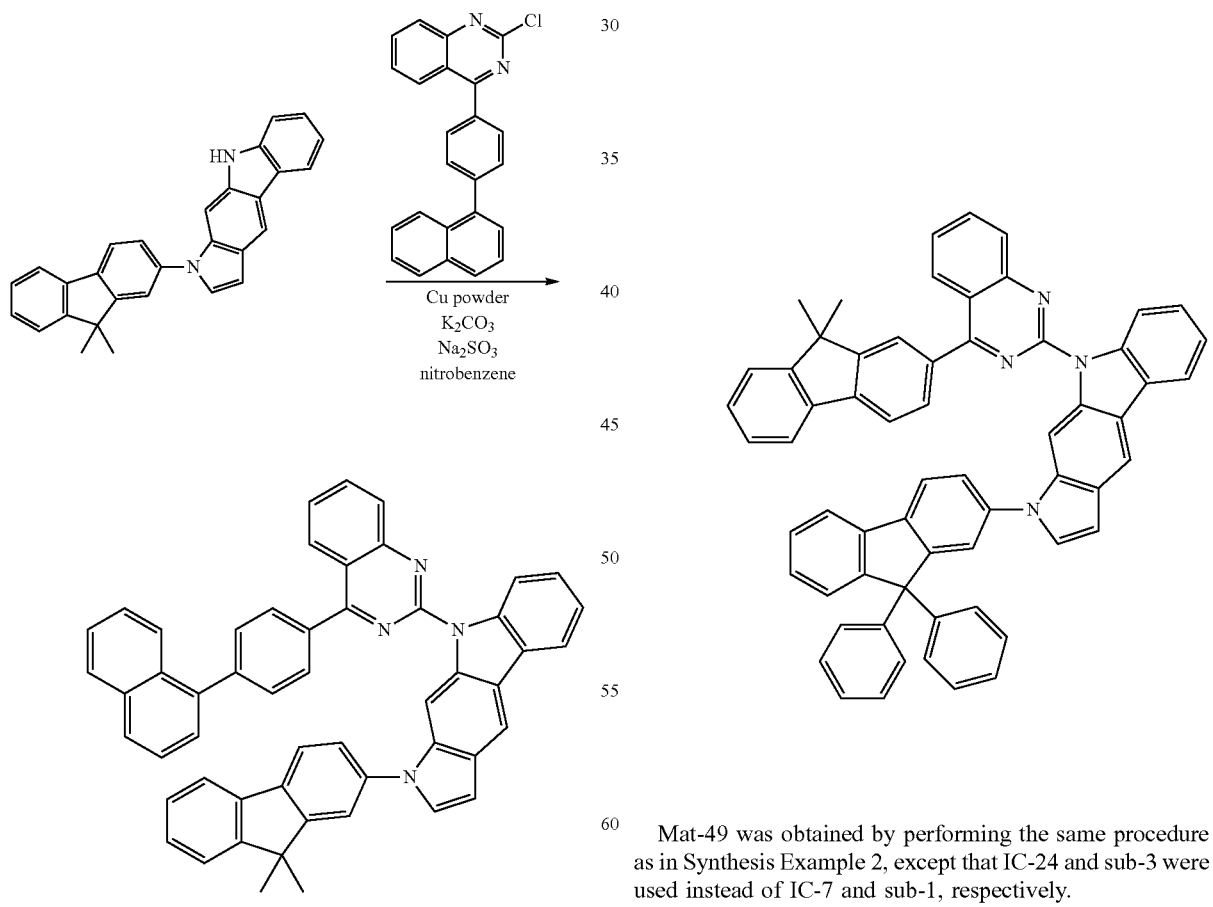

Mat-48 was obtained by performing the same procedure as in Synthesis Example 2, except that IC-23 and sub-2 were used instead of IC-7 and sub-1, respectively.

Elemental Analysis: C, 87.33; H, 4.98; N, 7.69/HRMS [M]$^+$: 728

[Synthesis Example 49] Synthesis of Mat-49

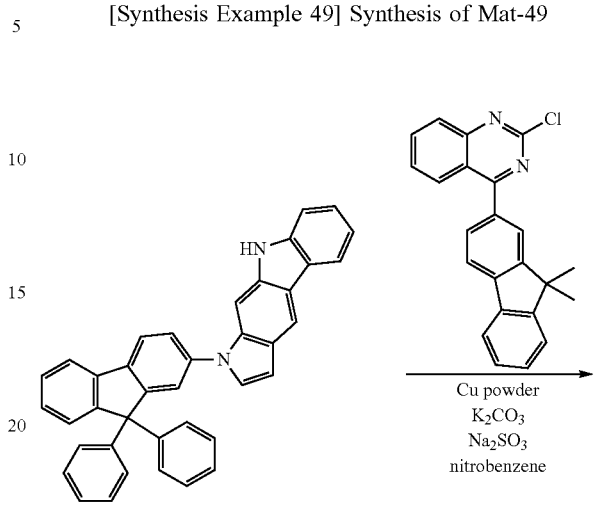

Mat-49 was obtained by performing the same procedure as in Synthesis Example 2, except that IC-24 and sub-3 were used instead of IC-7 and sub-1, respectively.

Elemental Analysis: C, 88.33; H, 5.02; N, 6.65/HRMS [M]$^+$: 842

[Synthesis Example 50] Synthesis of Mat-50

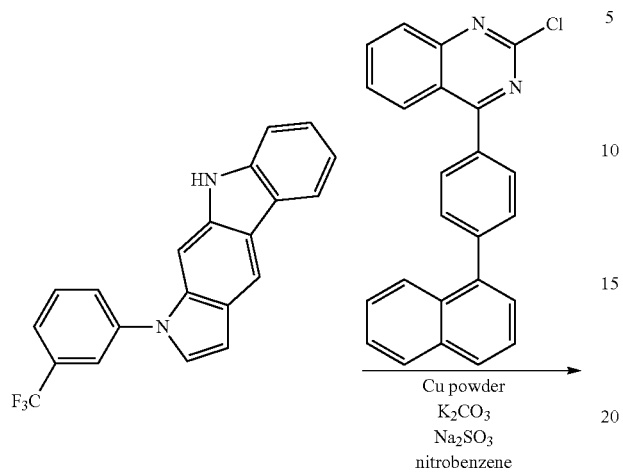

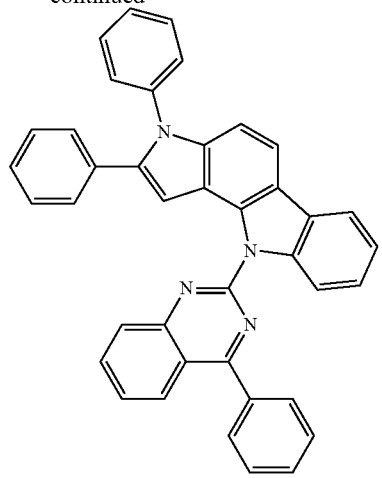

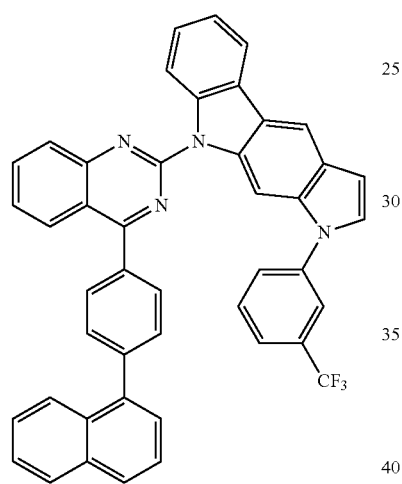

Mat-50 was obtained by performing the same procedure as in Synthesis Example 2, except that IC-25 and sub-2 were used instead of IC-7 and sub-1, respectively.

Elemental Analysis: C, 79.40; H, 4.00; N, 8.23/HRMS [M]$^+$: 680

[Synthesis Example 51] Synthesis of Mat-51

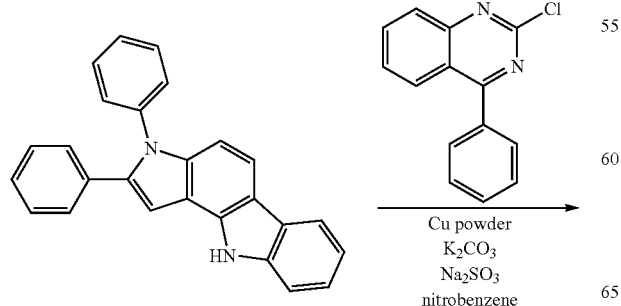

Mat-51 was obtained by performing the same procedure as in Synthesis Example 2, except that IC-26 was used instead of IC-7.

Elemental Analysis: C, 85.38; H, 4.66; N, 9.96/HRMS [M]$^+$: 562

[Synthesis Example 52] Synthesis of Mat-52

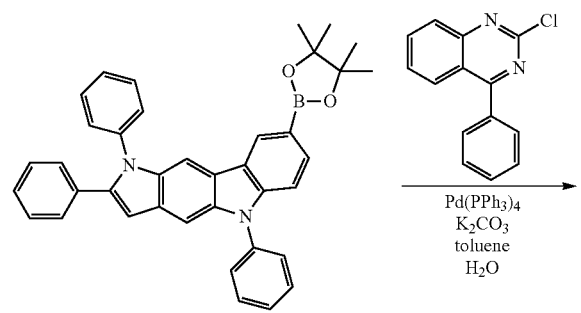

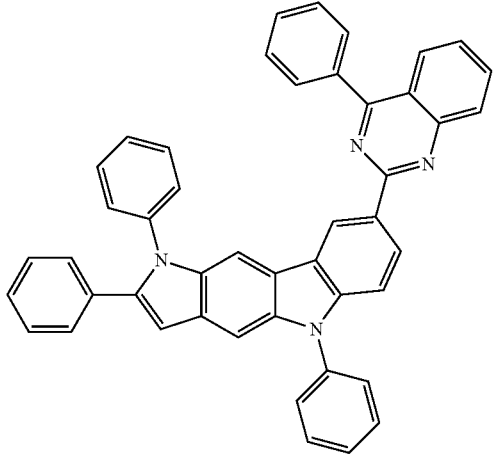

Mat-52 was obtained by performing the same procedure as in Synthesis Example 1, except that IC-27 was used instead of IC-1.

Elemental Analysis: C, 86.49; H, 4.73; N, 8.77/HRMS [M]+: 638

[Synthesis Example 53] Synthesis of Mat-53

[Synthesis Example 54] Synthesis of Mat-54

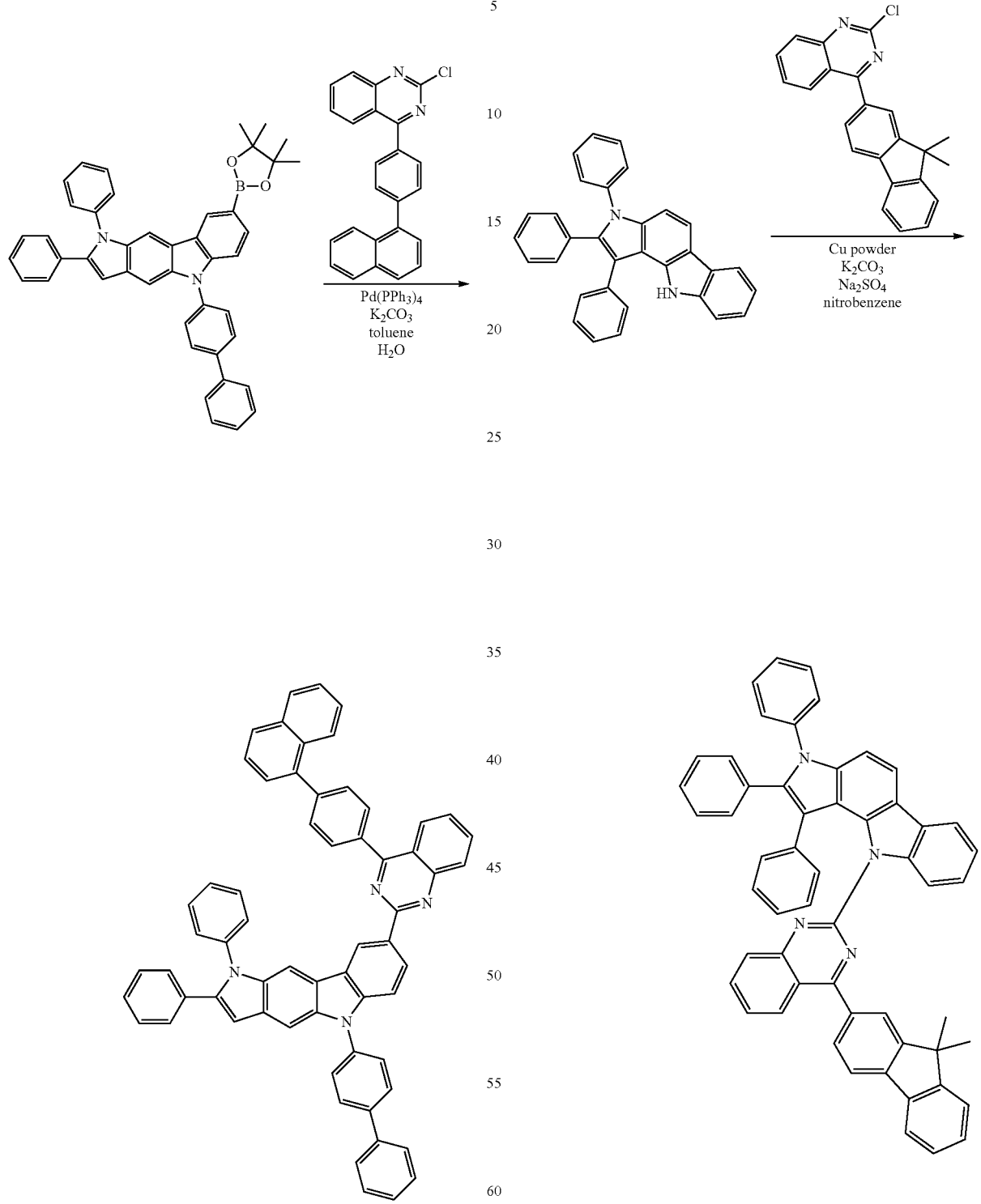

Mat-53 was obtained by performing the same procedure as in Synthesis Example 1, except that IC-28 and sub-2 were used instead of IC-1 and sub-1, respectively.

Elemental Analysis: C, 88.54; H, 4.79; N, 6.66/HRMS [M]+: 840

Mat-54 was obtained by performing the same procedure as in Synthesis Example 2, except that IC-29 and sub-3 were used instead of IC-7 and sub-1, respectively.

Elemental Analysis: C, 87.50; H, 5.07; N, 7.42/HRMS [M]+: 754

[Synthesis Example 55] Synthesis of Mat-55
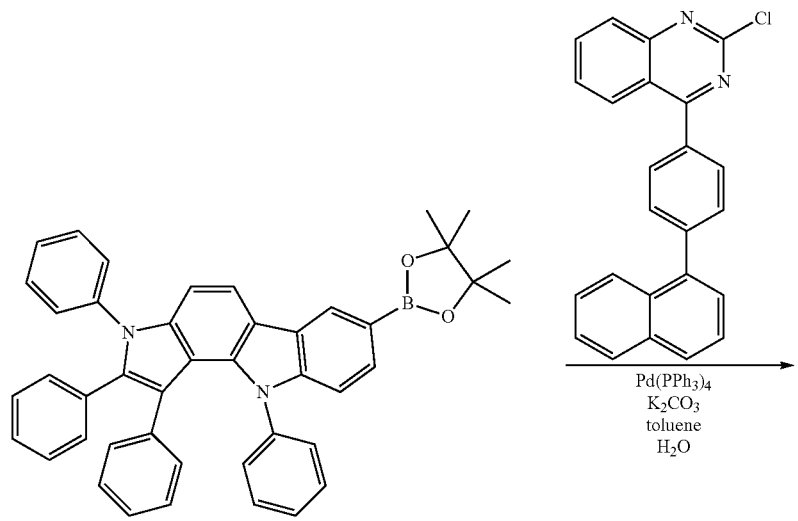
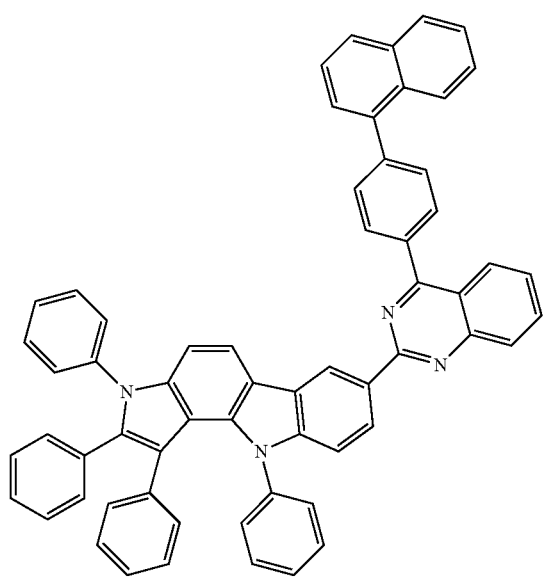

Mat-55 was obtained by performing the same procedure as in Synthesis Example 1, except that IC-30 and sub-2 were used instead of IC-1 and sub-1, respectively.

Elemental Analysis: C, 88.54; H, 4.79; N, 6.66/HRMS [M]$^+$: 840

[Synthesis Example 56] Synthesis of Mat-56

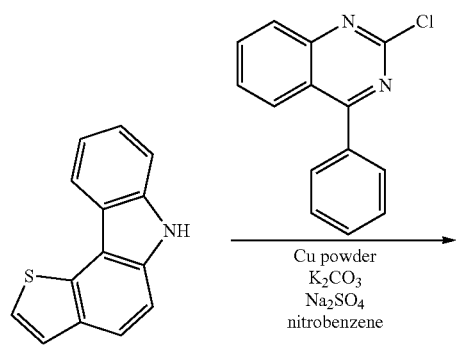

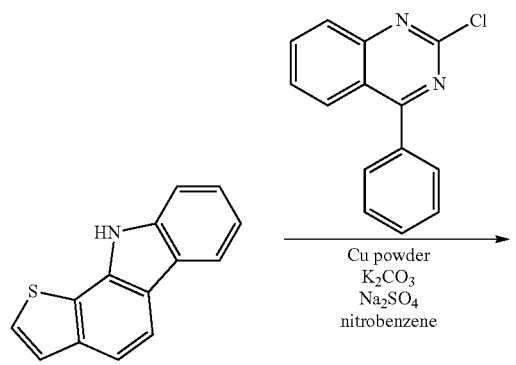

Mat-56 was obtained by performing the same procedure as in Synthesis Example 2, except that IC-31 was used instead of IC-7.

Elemental Analysis: C, 78.66; H, 4.01; N, 9.83; S, 7.50/ HRMS [M]$^+$: 427

[Synthesis Example 57] Synthesis of Mat-57

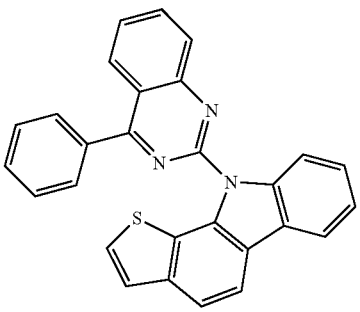

Mat-57 was obtained by performing the same procedure as in Synthesis Example 2, except that IC-32 was used instead of IC-7.

Elemental Analysis: C, 78.66; H, 4.01; N, 9.83; S, 7.50/ HRMS [M]$^+$: 427

[Synthesis Example 58] Synthesis of Mat-58

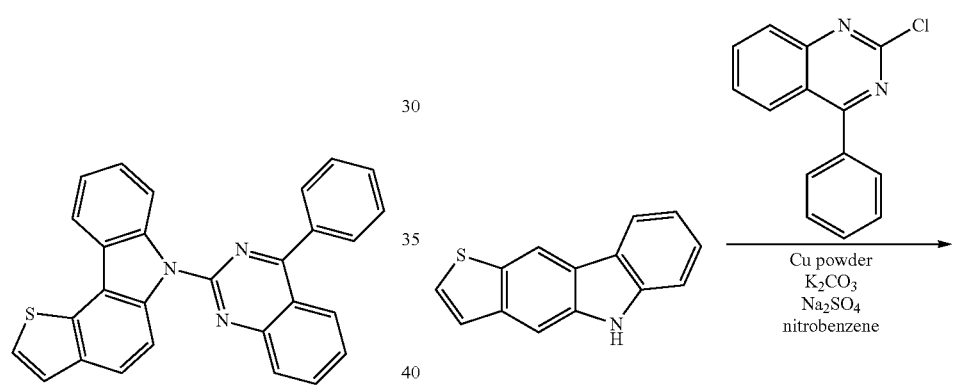

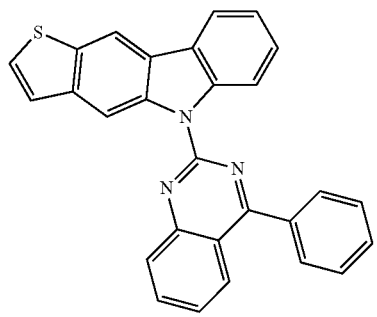

Mat-58 was obtained by performing the same procedure as in Synthesis Example 2, except that IC-33 was used instead of IC-7.

Elemental Analysis: C, 78.66; H, 4.01; N, 9.83; S, 7.50/ HRMS [M]$^+$: 427

[Synthesis Example 59] Synthesis of Mat-59

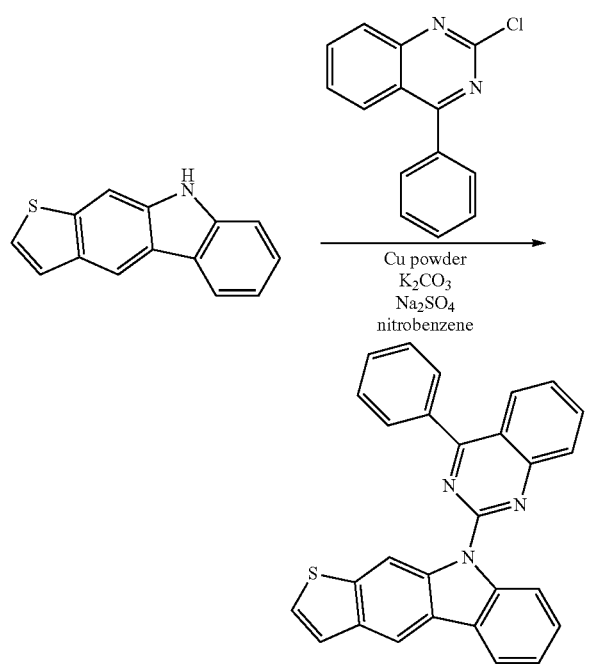

Mat-59 was obtained by performing the same procedure as in Synthesis Example 2, except that IC-34 was used instead of IC-7.

Elemental Analysis: C, 78.66; H, 4.01; N, 9.83; S, 7.50/ HRMS [M]$^+$: 427

[Synthesis Example 60] Synthesis of Mat-60

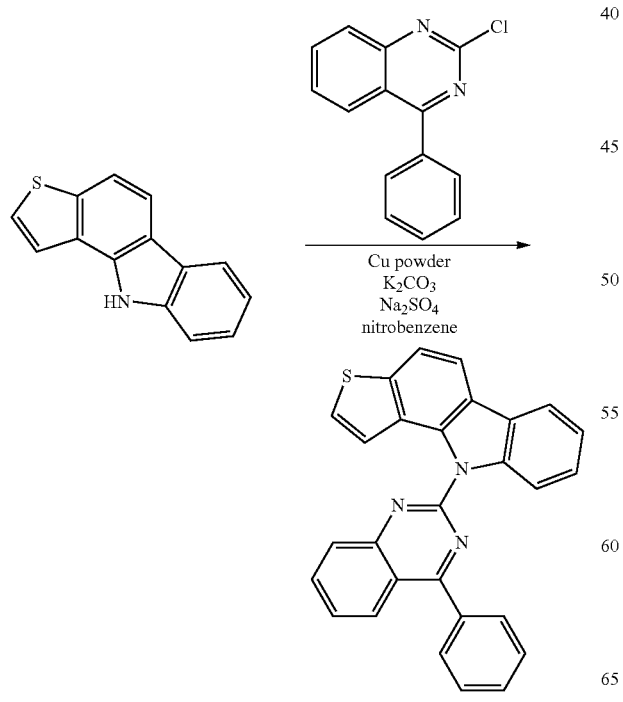

Mat-60 was obtained by performing the same procedure as in Synthesis Example 2, except that IC-35 was used instead of IC-7.

Elemental Analysis: C, 78.66; H, 4.01; N, 9.83; S, 7.50/ HRMS [M]$^+$: 427

[Synthesis Example 61] Synthesis of Mat-61

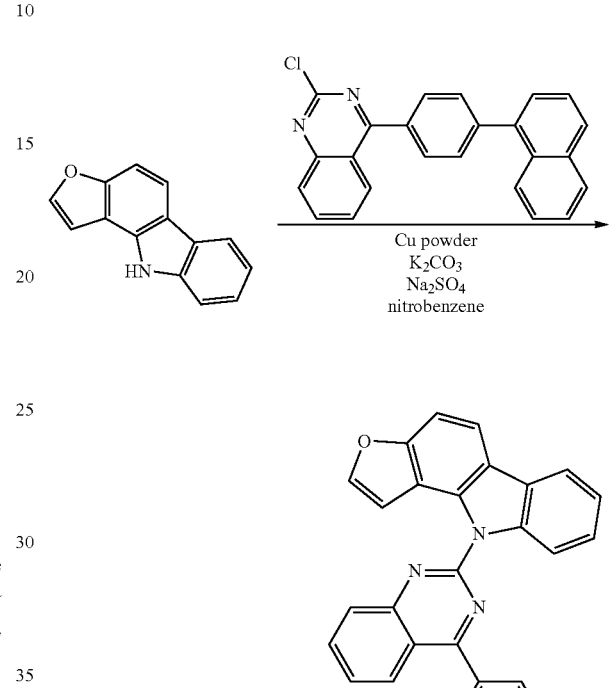

Mat-61 was obtained by performing the same procedure as in Synthesis Example 2, except that IC-36 and sub-2 were used instead of IC-7 and sub-1, respectively.

Elemental Analysis: C, 84.90; H, 4.31; N, 7.82; O, 2.98/ HRMS [M]$^+$: 537

[Synthesis Example 62] Synthesis of Mat-62

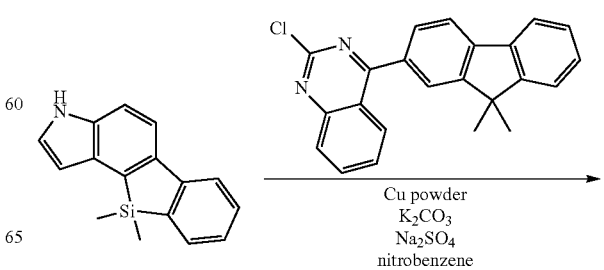

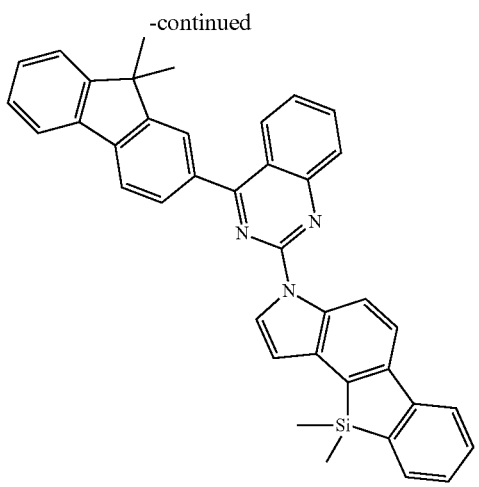

Mat-62 was obtained by performing the same procedure as in Synthesis Example 2, except that IC-37 and sub-3 were used instead of IC-7 and sub-1, respectively.

Elemental Analysis: C, 82.21; H, 5.48; N, 7.37; Si, 4.93 HRMS [M]$^+$: 569

[Synthesis Example 63] Synthesis of Mat-63

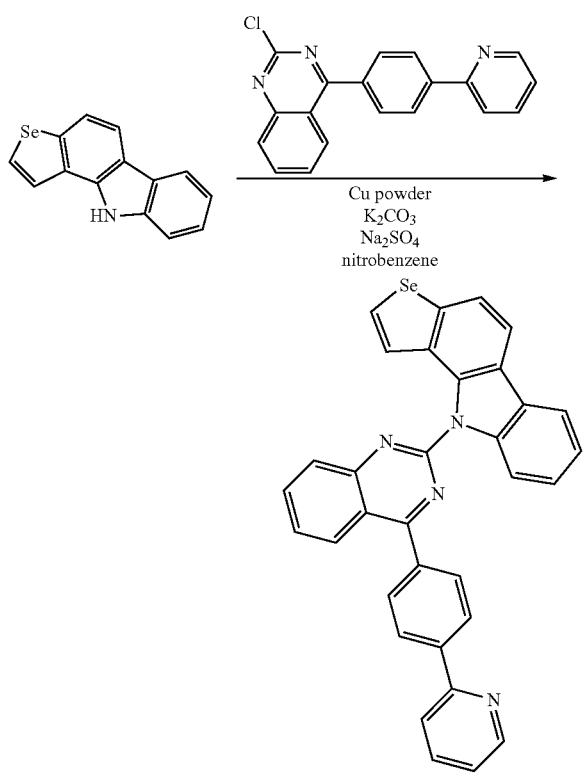

Mat-63 was obtained by performing the same procedure as in Synthesis Example 2, except that IC-38 and sub-4 were used instead of IC-7 and sub-1, respectively.

Elemental Analysis: C, 71.87; H, 3.66; N, 10.16; Se, 14.3 HRMS [M]$^+$: 552

[Synthesis Example 64] Synthesis of Mat-64

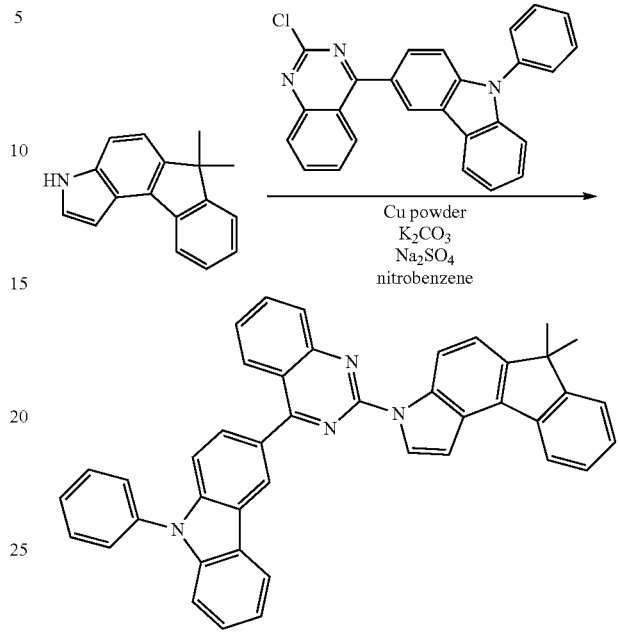

Mat-64 was obtained by performing the same procedure as in Synthesis Example 2, except that IC-39 and sub-5 were used instead of IC-7 and sub-1, respectively.

Elemental Analysis: C, 85.69; H, 5.02; N, 9.30 HRMS [M]$^+$: 602

[Examples 1 to 64] Manufacture of Red Organic Electroluminescence Device

Mat-1 to Mat-64, which are the compounds synthesized in Synthesis Examples 1 to 64, were subjected to highly-pure sublimation purification by a typically known method, and then red organic electroluminescence devices were manufactured according to the following procedure.

First, a glass substrate thinly coated with indium tin oxide (ITO) to have a thickness of 1,500 Å was ultrasonically washed with distilled water. When the ultrasonic washing with distilled water was completed, the substrate was ultrasonically washed with a solvent such as isopropyl alcohol, acetone, and methanol, dried, transferred to a UV ozone cleaner (Power sonic 405, manufactured by Hwashin Tech), washed for 5 minutes by using UV, and then transferred to a vacuum evaporator.

A red organic electroluminescence device was manufactured by laminating m-MTDATA (60 nm)/NPB (20 nm)/ each compound of Mat-1 to Mat-64+10% (piq)$_2$Ir(acac) (30 nm)/BCP (10 nm)/Alq$_3$ (30 nm)/LiF (1 nm)/Al (200 nm) on the ITO transparent substrate (electrode).

[Comparative Example] Manufacture of Red Organic Electroluminescence Device

A red organic electroluminescence device was manufactured by the same procedure as in Example 1, except that when a light-emitting layer is formed, CBP was used as a light-emitting host material instead of Compound Mat-1.

The structures of m-MTDATA, NPB, (piq)$_2$Ir(acac), BCP, and CBP used in Examples 1 to 64 and the Comparative Example are as follows.

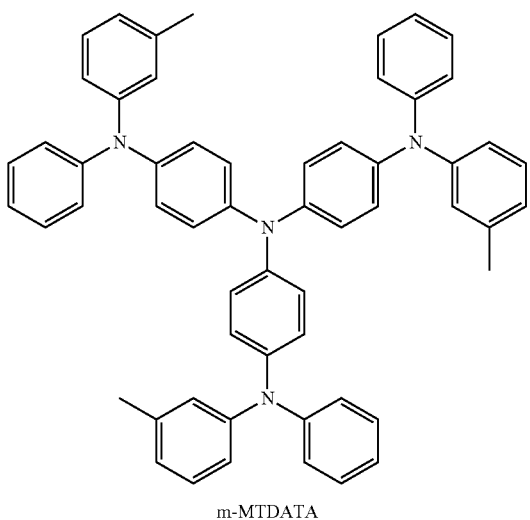

m-MTDATA

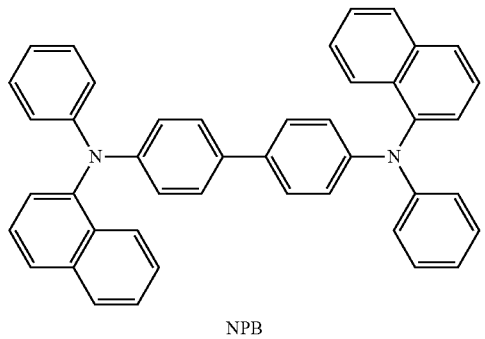

NPB

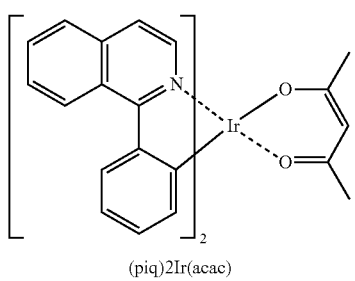

(piq)2Ir(acac)

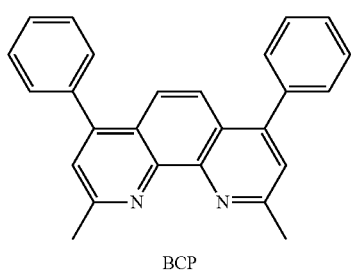

BCP

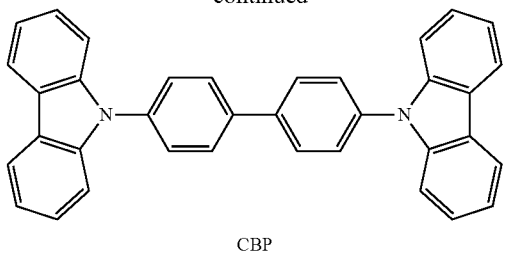

CBP

Evaluation Example

For each of the organic electroluminescence devices manufactured in Examples 1 to 64 and the Comparative Example, the driving voltage, current efficiency, and light-emitting peaks thereof were measured at a current density of 10 mA/cm², and the results are shown in the following Table 1.

TABLE 1

| Sample | Host | Driving voltage (V) | Current efficiency (cd/A) |
|---|---|---|---|
| Example 1 | Mat-1 | 4.65 | 13.5 |
| Example 2 | Mat-2 | 4.57 | 13.3 |
| Example 3 | Mat-3 | 4.60 | 12.5 |
| Example 4 | Mat-4 | 4.65 | 13.0 |
| Example 5 | Mat-5 | 4.70 | 12.6 |
| Example 6 | Mat-6 | 4.66 | 13.1 |
| Example 7 | Mat-7 | 4.72 | 13.5 |
| Example 8 | Mat-8 | 4.62 | 13.2 |
| Example 9 | Mat-9 | 4.70 | 13.3 |
| Example 10 | Mat-10 | 4.65 | 14.2 |
| Example 11 | Mat-11 | 4.71 | 13.1 |
| Example 12 | Mat-12 | 4.75 | 13.3 |
| Example 13 | Mat-13 | 4.60 | 14.2 |
| Example 14 | Mat-14 | 4.70 | 13.5 |
| Example 15 | Mat-15 | 4.80 | 13.2 |
| Example 16 | Mat-16 | 4.75 | 14.3 |
| Example 17 | Mat-17 | 4.70 | 13.5 |
| Example 18 | Mat-18 | 4.50 | 12.6 |
| Example 19 | Mat-19 | 4.55 | 13.3 |
| Example 20 | Mat-20 | 4.60 | 12.8 |
| Example 21 | Mat-21 | 4.64 | 14.2 |
| Example 22 | Mat-22 | 4.66 | 13.5 |
| Example 23 | Mat-23 | 4.71 | 13.2 |
| Example 24 | Mat-24 | 4.65 | 14.1 |
| Example 25 | Mat-25 | 4.70 | 13.9 |
| Example 26 | Mat-26 | 4.70 | 13.1 |
| Example 27 | Mat-27 | 4.65 | 14.5 |
| Example 28 | Mat-28 | 4.80 | 13.9 |
| Example 29 | Mat-29 | 4.72 | 13.4 |
| Example 30 | Mat-30 | 4.65 | 13.4 |
| Example 31 | Mat-31 | 4.71 | 12.9 |
| Example 32 | Mat-32 | 4.75 | 14.0 |
| Comparative Example | CBP | 5.25 | 8.2 |
| Example 33 | Mat-33 | 4.69 | 13.5 |
| Example 34 | Mat-34 | 4.70 | 13.3 |
| Example 35 | Mat-35 | 4.75 | 13.1 |
| Example 36 | Mat-36 | 4.70 | 14.6 |
| Example 37 | Mat-37 | 4.80 | 13.9 |
| Example 38 | Mat-38 | 4.64 | 12.9 |
| Example 39 | Mat-39 | 4.59 | 13.8 |
| Example 40 | Mat-40 | 4.55 | 13.3 |
| Example 41 | Mat-41 | 4.50 | 14.0 |
| Example 42 | Mat-42 | 4.70 | 13.5 |
| Example 43 | Mat-43 | 4.65 | 13.0 |
| Example 44 | Mat-44 | 4.60 | 14.0 |
| Example 45 | Mat-45 | 4.70 | 13.5 |
| Example 46 | Mat-46 | 4.64 | 13.8 |
| Example 47 | Mat-47 | 4.69 | 12.9 |

TABLE 1-continued

| Sample | Host | Driving voltage (V) | Current efficiency (cd/A) |
|---|---|---|---|
| Example 48 | Mat-48 | 4.70 | 13.8 |
| Example 49 | Mat-49 | 4.72 | 13.9 |
| Example 50 | Mat-50 | 4.70 | 13.3 |
| Example 51 | Mat-51 | 4.74 | 13.6 |
| Example 52 | Mat-52 | 4.60 | 14.1 |
| Example 53 | Mat-53 | 4.65 | 13.7 |
| Example 54 | Mat-54 | 4.70 | 13.5 |
| Example 55 | Mat-55 | 4.65 | 14.5 |
| Example 56 | Mat-56 | 4.60 | 14.0 |
| Example 57 | Mat-57 | 4.65 | 13.3 |
| Example 58 | Mat-58 | 4.66 | 13.9 |
| Example 59 | Mat-59 | 4.70 | 13.4 |
| Example 60 | Mat-60 | 4.75 | 13.5 |
| Example 61 | Mat-61 | 4.65 | 13.9 |
| Example 62 | Mat-62 | 4.60 | 14.3 |
| Example 63 | Mat-63 | 4.64 | 14.0 |
| Example 64 | Mat-64 | 4.71 | 13.9 |

As shown in Table 1, it can be seen that the cases where the compounds (Mat-1 to Mat-64) according to the present invention are used in a light-emitting layer of a red organic electroluminescence device (Examples 1 to 64) are excellent in efficiency and driving voltage as compared to the case (Comparative Example) where the CBP in the related art is used.

The invention claimed is:

1. A compound represented by the following Formula 1:

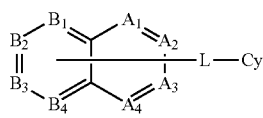

Formula 1 in Formula 1,
$A_1$ to $A_4$ are each independently $CR_1$ or N, and here, at least one or more thereof are N,
$B_1$ to $B_4$ are each independently $CR_2$ or N,
$R_1$ and $R_2$ are each independently selected from the group consisting of hydrogen, deuterium, halogen, a cyano group, a nitro group, an amino group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, or adjacent group form a fused ring,
L is a single bond, or a $C_6$ to $C_{30}$ arylene group or a heteroarylene group having 5 to 30 nuclear atoms,
Cy is selected from the group consisting of compounds of the following Formulae 2a to 2f, and

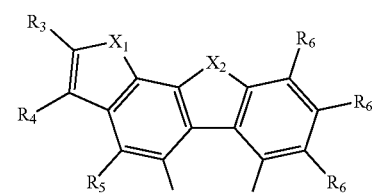

Formula 2a

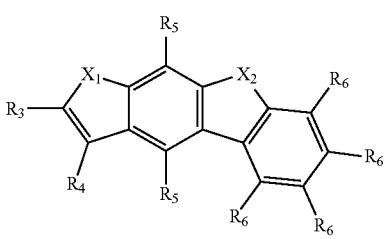

Formula 2b

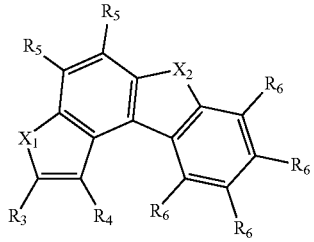

Formula 2c

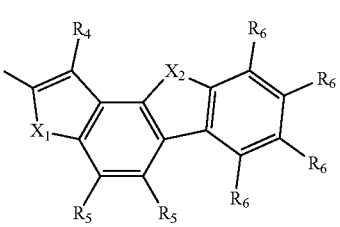

Formula 2d

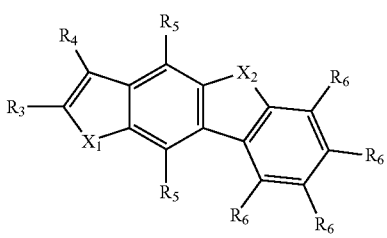

Formula 2e

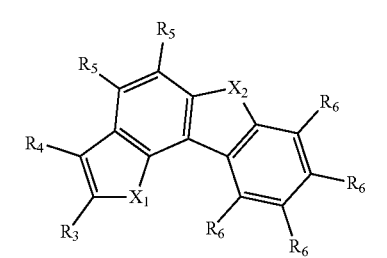

Formula 2f in Formulae 2a to 2f,
$X_1$ and $X_2$ are each independently selected from the group consisting of O, S, Se, $N(Ar_1)$, $C(Ar_2)(Ar_3)$ and $Si(Ar_4)(Ar_5)$, and here, at least one of $X_1$ and $X_2$ is $N(Ar_1)$,
a plurality of $R_5$'s is the same as or different from each other, and a plurality of $R_6$'s is the same as or different from each other, and
$R_3$ to $R_6$ are each independently selected from the group consisting of hydrogen, deuterium, halogen, a cyano group, a nitro group, an amino group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, $Ar_1$ to $Ar_5$ are each independently selected from the group consisting of hydrogen, deuterium, halogen, a cyano group, a nitro group, an amino group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, the alkyl group, the alkenyl group, the alkynyl group, the cycloalkyl group, the heterocycloalkyl group, the aryl group, the heteroaryl group, the alkyloxy group, the aryloxy group, the alkylsilyl group, the arylsilyl group, the alkylboron group, the arylboron group, the arylphosphine group, the arylphosphine oxide group and the arylamine group of $R_1$ to $R_6$ and $Ar_1$ to $Ar_5$ are each independently unsubstituted or substituted with one or more selected from the group consisting of deuterium, halogen, a cyano group, a nitro group, an amino group, a $C_1$ to $C_{40}$ alkyl group, a $C_2$ to $C_{40}$ alkenyl group, a $C_2$ to $C_{40}$ alkynyl group, a $C_3$ to $C_{40}$ cycloalkyl group, a heterocycloalkyl group having 3 to 40 nuclear atoms, a $C_6$ to $C_{40}$ aryl group, a heteroaryl group having 5 to 40 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkylboron group, a $C_6$ to $C_{60}$ arylboron group, a $C_6$ to $C_{60}$ arylphosphine group, a $C_6$ to $C_{60}$ arylphosphine oxide group and a $C_6$ to $C_{60}$ arylamine group, and L is linked to any one of $X_1$, $X_2$, $R_3$, $R_4$, $R_5$ and $R_6$ of Formulae 2a to 2f.

2. The compound of claim 1, wherein

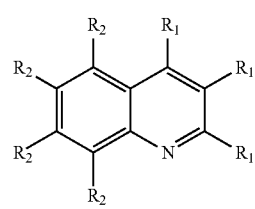

of Formula 1 is selected from the group consisting of structures represented by the following S-1 to S-30:

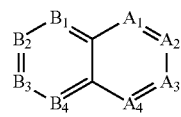
S-1

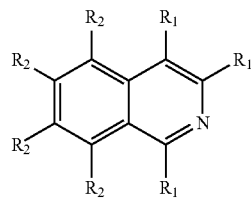
S-2

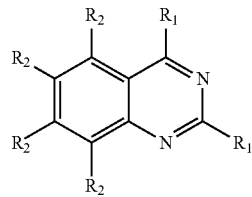
S-3

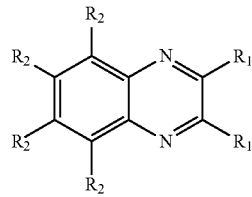
S-4

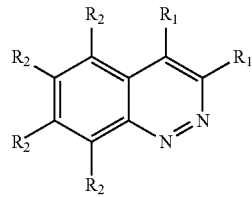
S-5

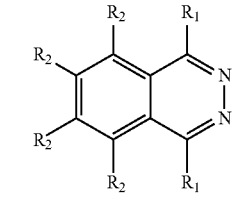
S-6

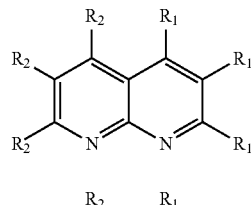
S-7

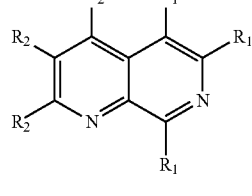
S-8

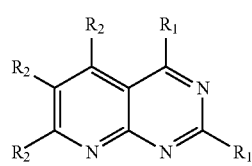
S-9

337
-continued

S-10, S-11, S-12, S-13, S-14, S-15, S-16, S-17

338
-continued

S-18, S-19, S-20, S-21, S-22, S-23, S-24

-continued

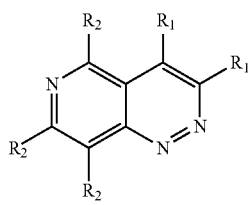 S-25

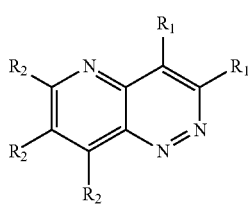 S-26

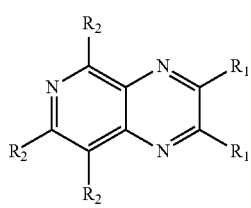 S-27

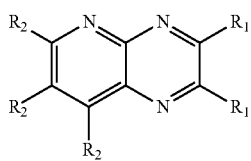 S-28

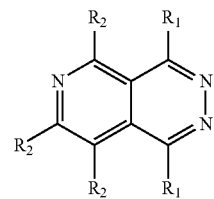 S-29

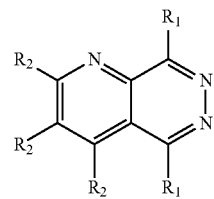 S-30 in the structures represented by S-1 to S-30, $R_1$ and $R_2$ are the same as those defined in claim 1, and a plurality of $R_1$'s is the same as or different from each other, and a plurality of $R_2$'s is the same as or different from each other.

3. The compound of claim 1, wherein $R_1$ and $R_2$ are each independently selected from the group consisting of hydrogen, a $C_6$ to $C_{60}$ aryl group, a heteroaryl group having 5 to 40 nuclear atoms and a $C_6$ to $C_{60}$ arylamine group.

4. The compound of claim 1, wherein $R_1$ and $R_2$ are each independently selected from the group consisting of hydrogen, or structures represented by the following A1 to A70:

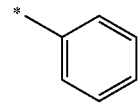 A1

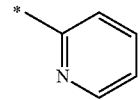 A2

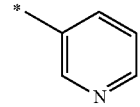 A3

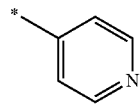 A4

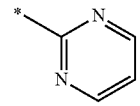 A5

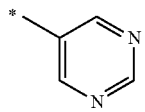 A6

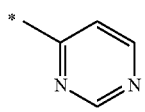 A7

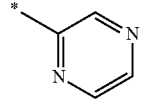 A8

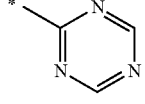 A9

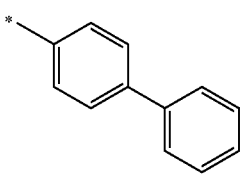 A10

 A11

-continued
A12 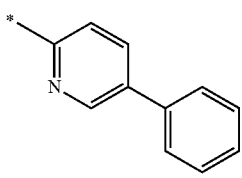
A13 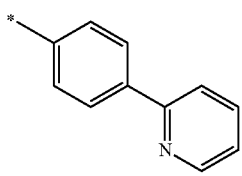
A14 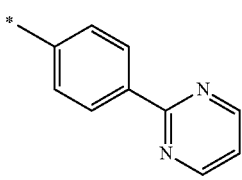
A15 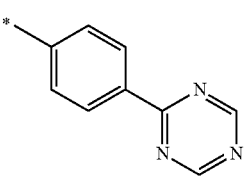
A16 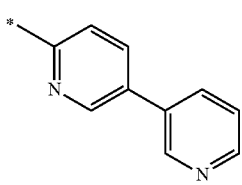
A17 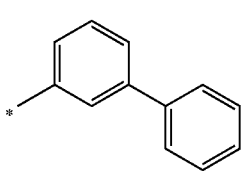
A18 
A19 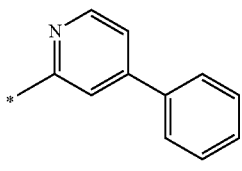
A20 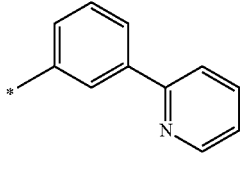
-continued
A21 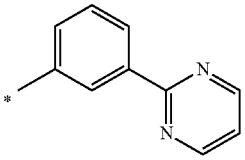
A22 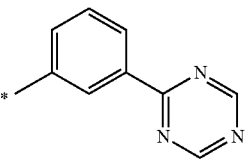
A23 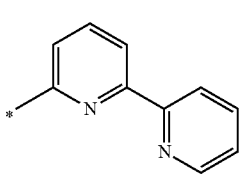
A24 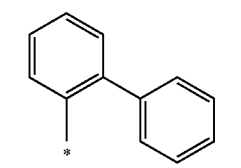
A25 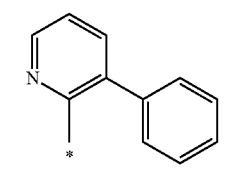
A26 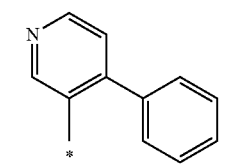
A27 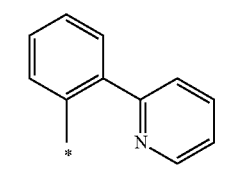
A28 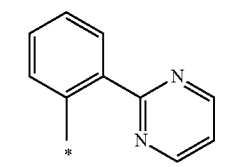
A29 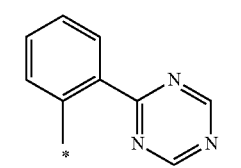

-continued
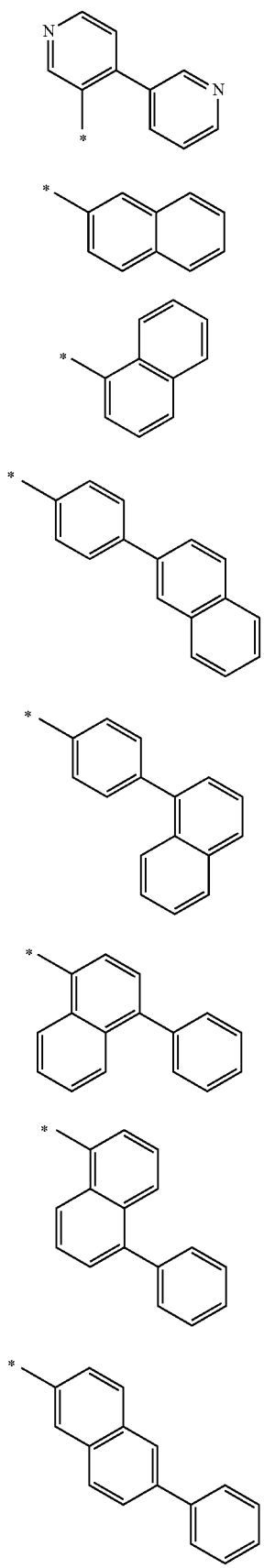
A30
A31
A32
A33
A34
A35
A36
A37
-continued
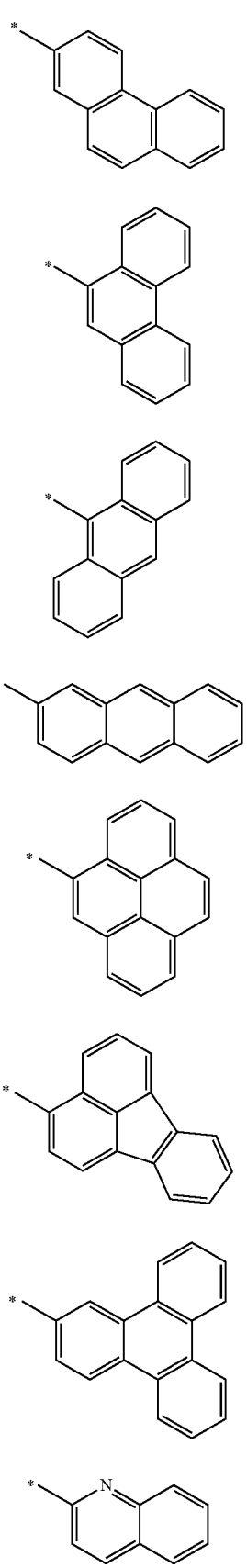
A38
A39
A40
A41
A42
A43
A44
A45

345
-continued
A46
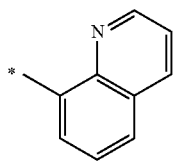
A47
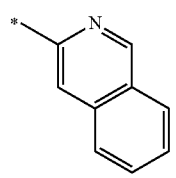
A48
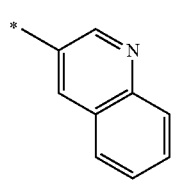
A49
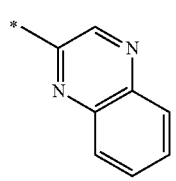
A50
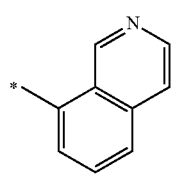
A51
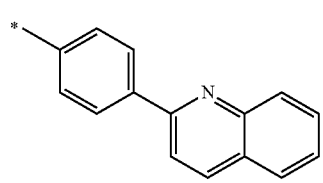
A52
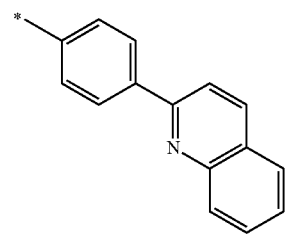
A53
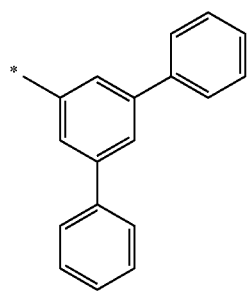
346
-continued
A54
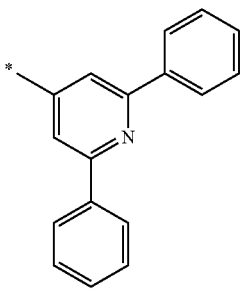
A55
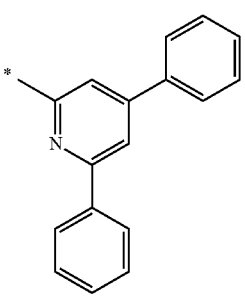
A56
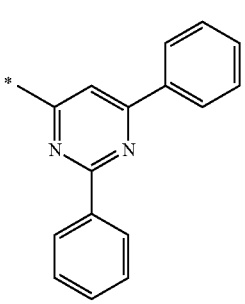
A57
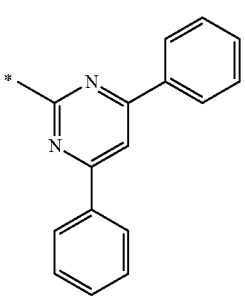
A58
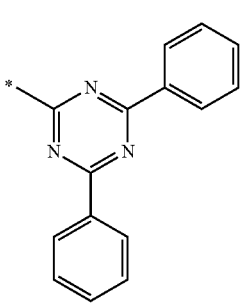
A59
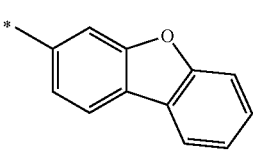

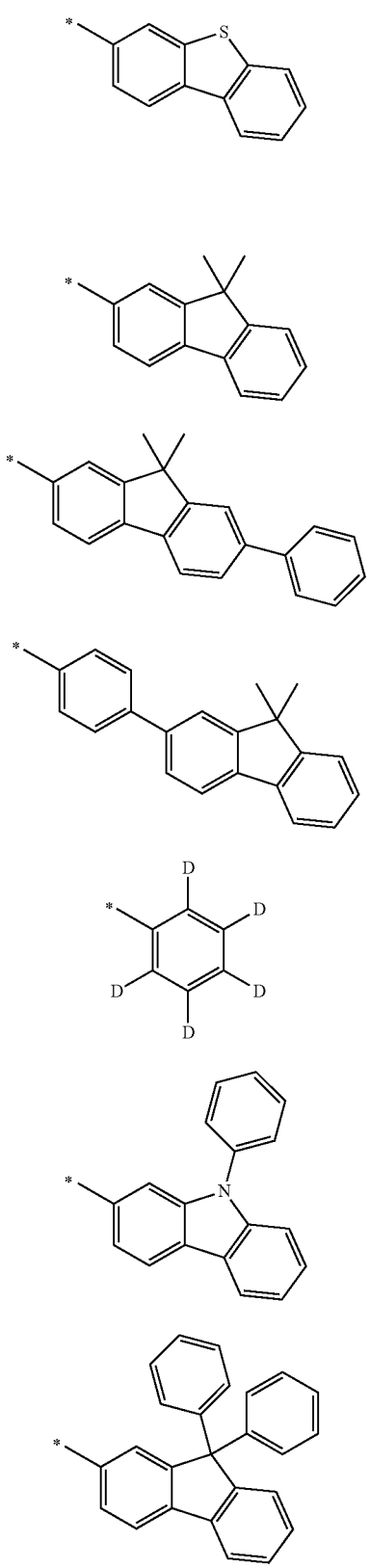

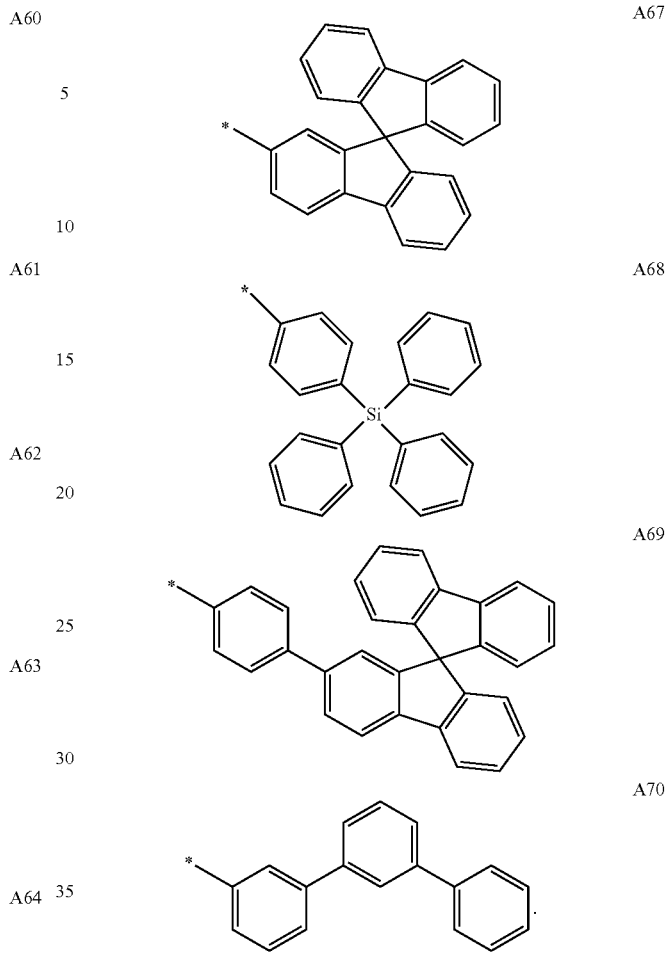

5. The compound of claim 1, wherein L of Formula 1 is a single bond or phenylene, $X_1$ and $X_2$ are $N(Ar_1)$, and here, $Ar_1$ is the same as or different from each other, and $Ar_1$ is selected from the group consisting of hydrogen, a $C_6$ to $C_{60}$ aryl group, and a heteroaryl group having 5 to 40 nuclear atoms.

6. The compound of claim 1, wherein L is linked to any one of $X_1$ and $R_6$ of Formulae 2a to 2f.

7. An organic electroluminescence device comprising:
an anode;
a cathode; and
an organic material layer having one or more layers interposed between the anode and the cathode,
wherein at least one of the organic material layer having one or more layers comprises the compound of claim 1.

8. The organic electroluminescence device of claim 7, wherein the organic material layer comprising the compound is selected from the group consisting of a hole injection layer, a hole transporting layer and a light-emitting layer.

9. The organic electroluminescence device of claim 7, wherein the organic material layer comprising the compound is a light-emitting layer, and the compound is a phosphorescent host material of the light-emitting layer.

* * * * *